US006881547B1

(12) United States Patent
Saus

(10) Patent No.: US 6,881,547 B1
(45) Date of Patent: Apr. 19, 2005

(54) METHODS AND REAGENTS FOR TREATING AUTOIMMUNE DISORDERS

(76) Inventor: Juan Saus, Fundación Valenciana de Investigaciones Biomédicas, Instituto de Investigaciones Citológicas c/Amadeo de Saboya 4, 46010 Valencia (ES)

( * ) Notice: Subject to any disclaimer, the term of this patent is extended or adjusted under 35 U.S.C. 154(b) by 286 days.

(21) Appl. No.: 10/060,607

(22) Filed: Jan. 30, 2002

Related U.S. Application Data

(60) Provisional application No. 60/265,249, filed on Jan. 31, 2001.

(51) Int. Cl.[7] .............................. C12Q 1/02; C12Q 1/48; G01N 33/68
(52) U.S. Cl. .............................. 435/7.1; 435/4; 435/7.4; 435/15; 435/25; 435/29; 436/518; 436/86
(58) Field of Search .............................. 435/4, 7.1, 15, 435/25, 29, 7.4; 436/518, 86

(56) References Cited

U.S. PATENT DOCUMENTS 5,424,408 A * 6/1995 Reeders et al. ............ 536/23.5

FOREIGN PATENT DOCUMENTS

WO        WO 00/50607        8/2000

OTHER PUBLICATIONS

Saus, J. (1998) in *Goodpasture's Syndrome: Encyclopedia of Immunology* 2nd edn. vol. 2, eds. Delves, P.J., & Roitt, J.M., (Academic Press Ltd., London),pp. 1005–1011.
Leinonen, A., Mariyama, M., Mochizuki, T., Tryggvason, K., and Reeders, S.T. (1994) *J. Biol. Chem.* 269, 26172–26177.
Quinones, S., Bernal, D., Garcia–Sogo, M., Elena, S.F., and Saus, J. (1992) *J. Biol. Chem.* 267, 19780–19784.
Revert, F., Penadés J.R., Plana, M., Bernal. D., Johansson, C., Itarte, E., Cervera, J., Wieslander, J., Quinones, S., and Saus, J. (1995) *J. Biol. Chem.* 270, 13254–13261.
Bernal, D., Quinones, S., and saus, J. (1993) *J. Biol. Chem.* 268, 12090–12094.
Feng, L., Xia, Y., and Wilson, C.B. (1994) *J. Biol. Chem.* 269, 2342–2348.
Penadés, J.R., Bernal, D., Revert, F., Johansson, C., Fresquet, V.J., Wieslander, J., Quinones, S., and Saus, J. (1995) *Eur. J. Biochem.* 229, 754–760.
Ferrel, J.E., and Martin, G.S. (1991) *Methods in Enzymology* 200, 430–435.
Boyle, W.J., van der Goer, P., and Hunter, T. (1991) *Methods in Enzymology* 201, 110–149.
Hsu, S.M., Raine, L., and Fanger, H. (1981) *J. Histochem. Cytochem.* 29, 577–580.
Altschul, S.F., Madden, T.L., Schaffer, A.A., Zhang, J., Zhang, Z., Miller, W., and Lipman, D.J. (1997) *Nucleic Acids Res.* 25, 3389–3402.

Bairoch, A., Bucher, P., and Hofmann, K. (1977) *Nucleic Acid Res.* 25, 217–221.
Lupas, A. (1996) *Trends Biochem. Sci.* 21, 375–382.
Lemmon, M.A., Falasca, M., Ferguson, K.M., and Schlessinger, J. (1997) *Trends Cell Biol.* 7, 237–242.
Boulikas, T. (1993) *Crit. Rev. Eukaryot. Gene Expr.* 3, 193–227.
Csermely, P., and Kahn, C.R. (1991) *J. Biol. Chem.* 266, 4943–4950.
Maru, Y., and Witte, O.N. (1991) *Cell* 67, 459–468.
Beeler, J.F., LaRochelle, W.J., Chedid, M., Tronick, S.R., and Aaronson, S.A. (1994) *Mol. Cell. Biol.* 14, 982–988.
Csermely, P., Miyata, Y., Schnaider, T., and Yahara, I. (1995) *J. Biol. Chem.* 270, 6381–6388.
Dikstein, R., Ruppert, S., and Tjian, R. (1996) *Cell* 84, 781–790.
Eichinger, L., Bomblies, L., Vandekerckhove, J., Schleicher, M., and Gettermans, J. (1996) *EMBO J.* 15, 5547–5556.
Côté, G.P., Luo, X., Murphy, M.B., and Egelhoff, T.T.(1997) *J. Biol. Chem.* 272, 6846–6849.
Ryazanov, A.G., Ward, M.D., Mendola, C.E., Pavur, K.S., Dorovkov, M.V., Wiedmann, M., Erdjument–Bromage, H., Tempst, P., Parmer, T.G., Prostko, C.R., Germino, F.J., and Hait, W.N. (1997) *Proc. Natl. Acad. Sci. USA* 94, 4884–4889.
Fraser, R.A., Heard, D.J., Adam, S., Lavigne, A.C., Le Douarin, B., Tora, L., Losson, R., Rochette–Egly, C., and Chambon, P., (1998) *J. Biol. Chem.* 273, 16199–16204.
Langelier, Y., Champoux, L., Hamel, M., Guilbault, C., Lamarche, N., Gaudreau, P., and Massie, B.(1998) *J. Biol. Chem.* 273, 1435–1443.
Lemmon, M.A., and Ferguson, K.M. (1998) *Curr. Top. Microbiol. Immunol.* 228, 39–74.
Rebecchi, M.J., and Scarlata, S. (1998) *Annu. Rev. Biophys. Biomol. Struct.* 27, 503–528.
Roitt, I. (1994) *Autoimmune diseases in Essential Immunology*, 383–439, 8th Ed., Blackwell Scientific, Oxford, UK.
Phelps, R.G., Turner, A.N., and Rees, A.J.(1996) *J. Biol. Chem.* 271, 18549–18553.
Henderson, R.D., Saltissi, D., and Pender, M.P.(1998) *Acta Neurol. Scand.* 98, 134–135.
Litersky, J.M., and Johnson, G.V.W. (1992) *J. Biol. Chem.* 267, 1563–1568.
Brown, K., Gerstberger, S., Carlson, L., Franzoso, G., and Siebenlist, U. (1995) *Science* 267, 1485–1488.
Chen, Z.j., Parent, L., and Maniatis, T. (1996) *Cell* 84, 853–862.
Aberle, H., Bauer, A., Stappert, J., Kispert, A., and Kemler, R. (1977) *EMBO J.* 16, 3797–3804.
Regnier, C.H., Song, H.Y., Gao, X., Goeddel, D.V., Cao, Z., and Rothe, M. (1997) *Cell* 90. 373–383.

(Continued)

*Primary Examiner*—David Saunders
(74) *Attorney, Agent, or Firm*—McDonnell Boehnen Hulbert & Berghoff LLP; David S. Harper

(57) ABSTRACT

The present invention provides methods and reagents for identifying compounds to treat autoimmune diseases.

6 Claims, 37 Drawing Sheets

OTHER PUBLICATIONS

Figure 2:
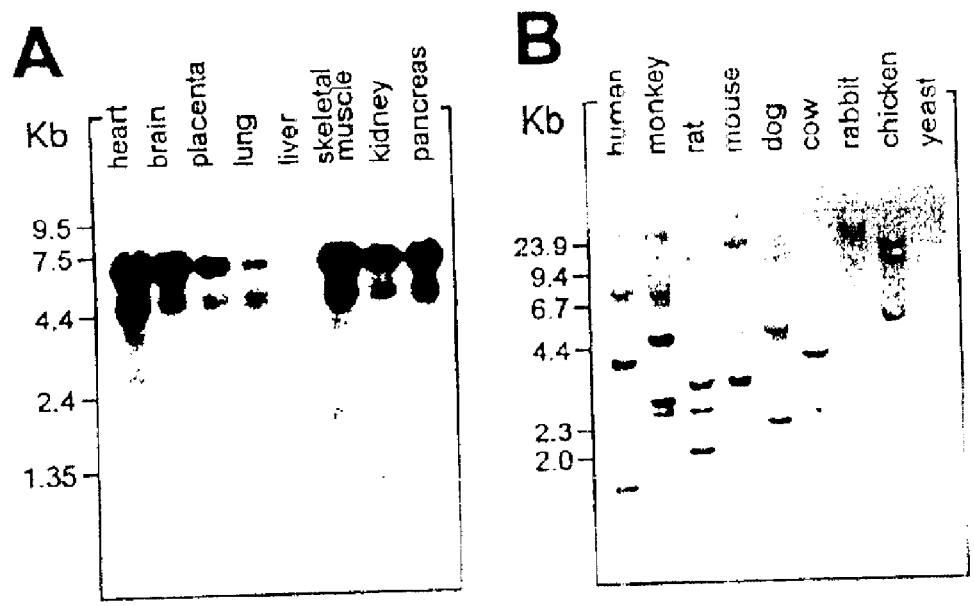

Vlach, J., Hennecke, S., and Amati, B. (1997) *EMBO J.* 16, 5334–5344.

Phelps, R.G., Jones, V.L., Coughlan, M., Turner, A.N., and Rees, A.J. (1998) *J. Biol. Chem.* 273, 11440–11447.

Raya, A., Revert, F., Navarro, S., & Saus, J. (1999) *J. Biol. Chem.* 274, 12642–12649.

Green, M.R. (1986) *Ann. Rev. Genet.* 20, 671–708.

Casciola–Rosen, L.A., Anhalt, G. & Rosen, A. (1994) *J. Exp. Med.* 179:1317–1330.

Pablos, J.L:, Santiago, B., Galindo, M., Carreira, P.E., Ballestin, C.& Gomez–Reino, J.J. (1999) *J. Pathol.* 188: 63–68.

Srinivasan, M., Edman, C.F., & Schulman, H. (1994) *J. Cell. Biol.* 126, 839–852.

Naito, Y., Watanabe, Y., Yokokura, H., Sugita, R., Nishio, M., & Hidaka, H. (1997) *J. Biol. Chem.* 272, 32704–32708.

Bayer, K.–U., Löhler, J., & Harbers, K. (1996) *Mol. Cell. Biol.* 16, 29–36.

Madaule, P., Eda, M., Watanabe, N, Fujisawa, K., Matsuoka, T., Bito, H., Ishizaki, T., & Narumiya, S. (1998) *Nature 394*, 491–494.

Papin, C., Denouel–Galy, A., Laugier, D., Calothy, G., & Eychène, A. (1998) *J. Biol. Chem.* 273, 24939–24947.

Casciola–Rosen, L.A., Anhalt, G.J,& Rosen, A.(1995) *J. Exp. Med.* 182: 1625–1634.

Casiano, C.A., Martin, S.J., Green, D.R., & Tan, E.M. (1996) *J. Exp. Med.* 184: 765–770.

Casciola–Rosen, L., & Rosen, A. (1997) *Lupus* 6: 175–180.

Bolivar, J., Guelman, S., Iglesias, C., Ortíz, M., & Valdivia, M. (1998) *J. Biol. Chem.* 273: 17122–17127.

Utz, P.J., & Anderson, P. (1998) *Arthritis Rheum.* 41: 1152–1160.

Golan, T.D., Elkon, K.B., Ghavari, A.E.,& Krueger, J.G.(1992) *J. Clin. Invest.* 90: 1067–1076.

Polalowska, R.R., Piacentini, M.,Bartlett, R., Goldsmith, L.A., & Haake, A.R. (1994) *Dev. Dinam.* 199: 176–188.

Maruoka, Y., Harada, H., Mitsuyasu et al. (1997) *Biochem. Biophys. Res. Commun.* 238: 886–890.

Xu, W., Harrison, S.C., & Eck, M.J. (1997) *Nature* 385, 595–602.

Pette, M., Fujita, K., Wilkinson, D., Altmann, D.M., Trowsdale, J., Giegerich, G., Hinkkanen, A., Epplen, J.T., Kappos, L., and Wekerle, H. (1994) *Proc. Natl. Acad. Sci. USA* 87, 7968–7972.

Tschida, T., Parker, K.C., Turner, R.V., McFarland, H.F., Coligan, J.E., and Biddison, W.E. (1994) *Proc. Natl. Acad. Sci. USA* 91, 10859–10863.

Campagnoni, A.T. (1988) *J. Neurochem.* 51, 1–14.

Hudson, B.G., Reeders, S.T. & Tryggvason, K. (1993) *J. Biol. Chem.* 268, 26033–26036.

Bachinger, H.P., Fessler, L.I. & Fessler, J.H. (1982), *J. Biol. Chem.* 257, 9796–9803.

Netzer, K., Suzuki, K., Itoh, Y., Hudson, B.G. & Khalifah, R.G. (1998), *Protein Sci* 7, 1340–1351.

Fessler, L.I. & Fessler, J.H. (1982) *J. Biol. Chem.* 257, 9804–9810.

Butkowski, R.J., Wieslander, J., Wisdom, B.J., Barr, J.F., Noelken, M.E. & Hudson, B.G.(1985) *J. Biol. Chem.* 260, 3739–3747.

Weber, S., Engel, J., Wiedemann, H., Glanville, R.W. & Timpl, R. (1984) *Eur. J. Biochem.* 139, 401–410.

Siebold, B., Deutzmann, R. & Kuhn, K. (1988) *Eur. J. Biochem* 176, 617–624.

Keppel, M.M., Fan, W.W., Cheong, H.I. & Michael, A.F. (1992) *J. Biol. Chem.* 267, 4137–4142.

Gunwar, S., Ballester, F., Noelken, M.E., Sado, Y., Ninomiya, Y.& Hudson, B.G.(1998) *J. Biol. Chem.* 273, 8767–75.

Borza , DB, Bondar, O., Ninomiya, Y., Sado, Y., Naito, I., Todd, P. & Hudson, BG (2001) *J. Biol. Chem.* 276, 28532–28540.

Boutaud, A., Borza, D., Bondar, O., Gunwar, S., Netzer, K.,Singh, N., Ninomiya, Y., Sado, Y., Noelken, M.E. & Hudson, B.G.(2000) *J. Biol. Chem.* 275, 30716–30724.

Kalluri, R.(1999) *Kidney Int.* 3, 1120–1122.

Shlomchik, M.J., Marshak–Rothstein, A., Wolfowicz, C.B., Rothsten, T.L. & Weigert, M.G. (1987) *Nature* 328, 805–811.

Borza, D.B., Netzer, K., Leinonen, A., Todd, P., Cervera, J., Saus, J. & Hudson, B.G. (2000) *J. Biol. Chem.* 275, 6030–6037.

David, M., Borza, D.B., Leinonen, A., Belmont, J.M.& Hudson, B.G.(2001) *J. Biol. Chem.* 276, 6370–6377.

Hellmark, T., Johansson, C. & Wieslander, J. (1994) *Kidney Int.* 46, 823–829.

Sado, Y., Boutaud, A., Kagawa, M., Naito, I., Ninomiya, Y. & Hudson, B.G. (1998) *Kidney Int.* 53, 664–671.

Riddles, P.W., Robert, L.B. & Zerner, B. (1983), *Methods Enzymol.* 91, 49–60.

Johansson, C., Butkowski, R. & Wieslander, J. (1991) *Connect. Tissue Res.* 25, 229–241.

Saxena, R., Bygren, P., Butkowski, R. & Wieslander, J. (1989) *Clin. Exp. Immunol.*78,31–36.

Kalluri, R., Wilson, C.B., Weber, M., Gunwar, S., Chonko, A.M., Neilson, E.G. & Hudson, B.G.(1995) *J. Am. Soc. Nephrol.* 4, 1178–1185.

Creighton, T.E. (1997) *Biol. Chem.* 378, 731–744.

Braakman, I., Helenius, J., and Helenius, A. (1992) *Nature* 356, 260–262.

Raya , A., Revert–Ros, F., Martinez–Martinez, P., Navarro, S., Roselló, E., Vieites, B., Granero, F., Forteza, J., and Saus, J. (2000) *J. Biol. Chem*275, 40392–40399.

Reddy, G.K., Hudson, B.G., Bailey, A.J., and Noelken, M.E. (1993) *Biochem. Biophys. Res. Commun.* 190: 277–282.

Ries, A., Engel, J., Lusting, A., and Kuhn, K. (1995) *J. Biol. Chem.* 270, 23790–23794.

Kahsai, T.Z, Enders, G.C., Gunwar, S., Brunmark, C., Wieslander, J., Kalluri, R., Zhou, J., Noelken, M., and Hudson, B.G.(1997) *J. Biol. Chem.* 272, 17023–17032.

Ghohestani, R.F., Hudson, B.G., Claudy, A., and Uitto, J. (2000) *J. Biol. Chem.* 275, 16002–16006.

Hellmark, T., Burkhardt, H., and Wieslander, J. (1999) *J. Biol. Chem.* 274, 25862–25868.

Johansson, C., Butkowski, R., Swedenborg, P., Alm, P., and Wieslander, J. (1993) *Nephrol. Dial. Transplant.* 8, 1205–1210.

Merkel, F., Kalluri, R., Marx, M., Enders, U., Stevanovic, S., Giegerich, G., Neilson, E., Rammensee, H., Hudson, B.G., and Weber, M., (1996) *Kidney Int.* 49, 1127–1133.

Netzer, K., Leinonen, A., Boutaud, A., Borza, D., Todd, P., Gunwar, S., Langeveld, J.P.M., and Hudson, B.G. (1999) *J. Biol. Chem.* 274, 11267–11274.

Plemper, R.K., and Wolf, D.H.(1999) *TIBS* 24, 266–270.

Prusiner, S. (1998) *Proc. Natl. Acad. Sci. USA* 95, 13363–13383.

Saus, J., Wieslander, J., Langeveld, J.P., Quinones, S., and Hudson, B.G. (1988) *J. Biol. Chem.* 263, 13374–13380.

* cited by examiner

```
   1 GCAGGAAGATGGCGGCGGTAGCGGAGGTGTGAGTGGACGCGGGACTCAGCGGCGGATTTTCTCTTCCCTTCTTTCCCTTTTCCTTCCCTATTTGAAA
 100 TTGGCATCGAGGGGGCTAAGTTCGGGTGGCAGCGCCGGGCGCAACGCAGGGGTCACGGCGACGGCGGCGGCGGCTGACGGCTGGAAGGGTAGGCTTCAT
 199 TCACCGCTCGTCCTCCTTCCTCGCTCCGCTCGGTGTCAGGCGCGGCGGCGGCGGGCGGGGCGGACTTCGTCCCTCCTCCTGCTCCCCCCCACACCGGAG
 298 CGGGCACTCTTCGCTTCGCCATCCCCCGACCCTTCACCCGCGAGGACTGGGCGCCTCCCTCCGCGGCAGCTGAGGGAGCGGGGGCCGGTCTCCTGCTCGGT

M  S  D  N  Q  S  W  N  S  S  G  S  E  E  D  P  E  T  E  S  G  F  P  V  E  R  C  G  V    29
 397 TGTCGAGCCTCCATGTCGGATAATCAGAGCTGGAACTCGTCGGGCTCGGAGGAGGATCCAGAGACGGAGTCTGGGCCGCCTGTGGAGCGCTGCGGGGTC

L  S  K  W  T  N  Y  I  H  G  W  Q  D  R  W  V  V  L  K  N  N  A  L  S  Y  Y  K  S  E  D  E  T  E    62
 496 CTCAGTAAGTGGACAAACTACATTCATGGGTGGCAGGATCGTTGGGTAGTTTTGAAAAATAATGCTCTGAGTTACTACAAATCTGAAGATGAAACAGAG

Y  G  C  R  G  S  I  C  L  S  K  A  V  I  T  P  H  D  F  D  E  C  R  F  D  I  S  V  N  D  S  V  W    95
 595 TATGGCTGCAGAGGATCCATCTGTCTTAGCAAGGCTGTCATCACACCTCACGATTTTGATGAATGTCGATTTGATATTAGTGTAAATGATAGTGTTTGG

Y  L  R  A  Q  D  P  D  H  R  Q  Q  W  I  D  A  I  E  Q  H  F  T  E  S  G  Y  G  S  E  S  S  L  R   128
 694 TATCTTCGTGCTCAGGATCCACATCATAGACAGCAATGGATAGATGCCATTGAACAGCACAAGACTGAATCTGGATATGGATCTGAATCCAGCTTGCGT

R  H  G  S  M  V  S  L  V  S  G  A  S  G  Y  S  A  T  S  T  S  S  F  K  K  G  H  S  L  R  E  K  L   161
 793 CGACATGGCTCAATGGTGTCCCTGGTGTCTGGAGCAAGTGGCTACTCTGCAACATCCACCTCTTCATTCAAGAAGGCCACAGTTTACGTGAGAAGTTG

A  E  M  E  T  F  R  D  I  L  C  R  Q  V  D  T  L  Q  K  Y  F  D  A  C  A  D  A  V  S  K  D  E  L   194
 892 GCTGAAATGGAAACATTTAGACACATCTTATGTAGACAAGTTGACACGCTACAGAAGTACTTTGATGCCTGTCTGATGCTGTCTCTAAGGATGAACTT

Q  R  D  K  V  V  E  D  D  E  D  D  F  P  T  T  R  S  D  G  L  F  I  H  S  T  N  G  N  K  E  K  L   227
 991 CAAAGGGATAAAGTGGTAGAAGATGATGAAGATGACTTTCCTACAACGCGTTCTGATGGTGACTTCTTGCATAGTACCAACGGCAATAAAGAAAAGTTA

F  P  H  V  T  P  K  G  I  N  G  I  D  F  K  G  E  A  I  T  F  K  A  T  T  A  G  I  L  A  T  L  S   260
1090 TTTCCACATGTGACACCAAAAGGAATTAATGGTATAGACTTTAAAGGGGAAGCGATAACTTTTAAAGCAACTACTGCTGGAATCCTTGCAACACTTTCT

H  C  I  E  L  M  V  K  R  E  D  S  W  Q  K  R  L  D  K  E  T  E  R  K  R  R  T  E  E  A  Y  K  N   293
1189 CATTGTATTGAACTAATGGTTAAACGTGAGGACAGCTGGCAGAAGAGACTGGATAAGGAAACTGAGAAGAAAAGAAGAACAGAGGAAGCATATAAAAAT

A  M  T  E  L  K  K  K  S  H  F  G  G  P  D  Y  E  E  G  P  N  S  L  I  N  E  E  F  F  D  A  V   326
1288 GCAATGACAGAACTTAAGAAAAAATCCCACTTTGGAGGACCAGATTATGAAGAAGGCCCCTAACAGTCTGATTAATGAAGAAGAGTTCTTTGATGCTGTT

E  A  A  L  D  R  Q  D  K  I  E  E  Q  S  Q  S  E  K  V  R  L  H  W  P  T  S  L  P  S  G  D  A  F   359
1387 GAAGCTGCTCTTGACAGACAAGATAAAATAGAAGAACAGTCACAGAGTGAAAAGGTGAGATTACATTGGCCTACATCCTTGCCCTCTGGAGATGCCTTT

S  S  V  G  T  H  R  F  V  Q  K  P  Y  S  R  S  S  S  M  S  G  I  D  L  V  S  A  S  D  D  V  H  R   392
1486 TCTTCTGTGGGACACATAGATTTGTCCAAAAGCCCTATAGTCGCTCTTCCTCCATGTCTTCCATTGATCTAGTCAGTGCCTCTGATGATGTTCACAGA

F  S  S  Q  V  E  E  M  V  Q  N  H  M  T  Y  S  L  Q  D  V  T  G  D  A  N  W  Q  L  V  V  E  E  G   425
1585 TTCAGCTCCCACGTTGAAGAGATGGTGCAGAACCACATGACTTACTCATTACAGGATGTAGGCGGAGATGCCAATTGGCAGTTGGTTGTAGAAGAAGGA

E  M  K  V  Y  R  R  E  V  E  E  N  G  I  V  L  D  P  L  K  A  T  H  A  V  K  G  V  T  G  H  E  V   458
1684 GAAATGAAGGTATACAGAAGAGAAGTAGAAGAAAATGGGATTGTTCTGGATCCTTTAAAGGCTACCCATGCAGTTAAGGGCGTCACAGGACATGAAGTC

C  N  Y  F  W  N  V  D  V  R  N  D  W  E  T  T  I  E  N  F  H  V  V  E  T  L  A  D  N  A  I  I  I   491
1783 TGCAATTATTTCTGGAATGTTGACGTTCGCAATGACTGGGAAACAACTATAGAAAACTTTCATGTGGTGGAAACATAGCTGATAATGCAATCATCATT

Y  Q  T  H  K  R  V  W  P  A  S  Q  R  D  V  L  Y  L  S  V  I  R  K  I  P  A  L  T  E  N  D  P  E   524
1882 TATCAAACACACAAGAGGGTGTGGCCTGCTTCTCAGCGAGACGTATTATATCTTTCTGTCATTCGAAAGATACCAGCCTTGACTGAAAATGACCCTGAA

T  W  I  V  C  N  P  S  V  D  H  D  S  A  P  L  N  N  R  C  V  R  A  K  I  N  V  A  M  I  C  Q  T   557
1981 ACTTGGATAGTTTGTAATTTTTCTGTGGATCATGACAGTGCTCCTCTAAACAACCGATGTGTCCGTGCCAAAATAAATGTTGCTATGATTTGTCAAACC

L  V  S  P  P  E  G  N  Q  E  I  S  R  D  N  I  L  C  K  I  T  Y  V  A  N  V  P  G  G  W  A  P   590
2080 TTGGTAAGCCCACCAGAGGGAAACCAGGAAATTAGCAGGGACAACATTCTATGCAAGATTACATATGTAGCTAATGTGAACCCTGGAGGATGGGCACCA

A  S  V  L  R  A  V  A  K  R  E  Y  P  K  F  L  K  R  F  T  S  Y  V  Q  E  K  T  A  G  K  P  I  L   623
2179 GCCTCAGTGTTAAGGGCAGTGGCAAAGCGAGAGTATCCTAAATTTCTAAAACGTTTTACTTCTTACGTCCAAGAAAAACTGCAGGAAAGCCTATTTTG

F  .
2278 TTCTAGTATTAACAGGTACTAGAAGATATGTTTTATCTTTTTTTAACTTTATTTGACTAATATGACTGTCAATACTAAATTTAGTTGTTGAAAGTATT
2377 TACTATGTTTTT
```

FIG. 1

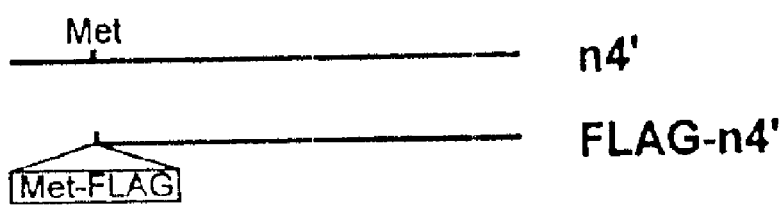
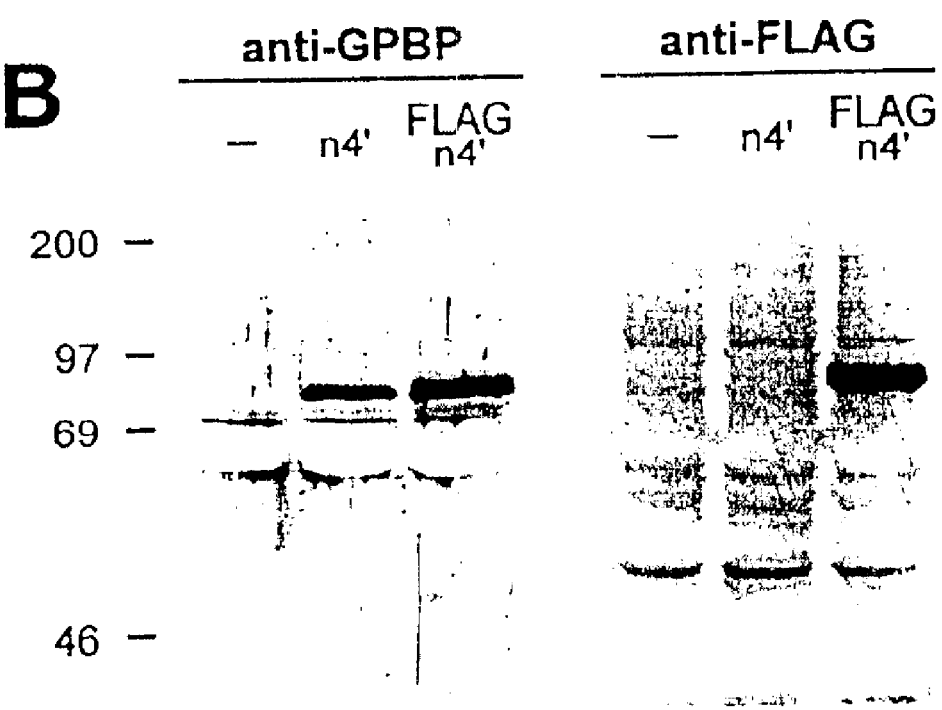
FIG. 3

```
GPΔIII    GLKGKRGDSGSPATWTTRGFVFTRHSQTTAI
          | |    |
MBP       MASQKRP-SQRHGSKYLATASTMDHARHGFL

GPΔIII    PSCPEGPVPLYSGFSFLFVQGNQRAHGQDLD
MBP       PRHRDTGILDSIGRFFGGDRGAPKRGSGK--

GPΔIII    ALFVKVLRSP
          . . . . |  . . | | |
MBP       VPWLKPGRSP
```

FIG. 17

SEQUENCE LISTING

```
<160> NUMBER OF SEQ ID NOS: 84

<210> SEQ ID NO 1
<211> LENGTH: 2389
<212> TYPE: DNA
<213> ORGANISM: Homo sapiens
<220> FEATURE:
<221> NAME/KEY: CDS
<222> LOCATION: (409)..(2280)

<400> SEQUENCE: 1
gcaggaagat ggcggcggta gcggaggtgt gagtggacgc gggactcagc ggccggattt      60
tctcttccct tcttttccct tttccttccc tatttgaaat tggcatcgag ggggctaagt     120
tcgggtggca gcgccgggcg caacgcaggg gtcacggcga cggcggcggc ggctgacggc     180
tggaagggta ggcttcattc accgctcgtc ctccttcctc gctccgctcg gtgtcaggcg     240
cggcggcggc gcggcgggcg gacttcgtcc ctcctcctgc tcccccccac accggagcgg     300
gcactcttcg cttcgccatc ccccgaccct tcaccccgag gactgggcgc ctcctccggc     360
gcagctgagg gagcgggggc cggtctcctg ctcggttgtc gagcctcc atg tcg gat     417
                                                    Met Ser Asp
                                                     1
```

```
aat cag agc tgg aac tcg tcg ggc tcg gag gag gat cca gag acg gag      465
Asn Gln Ser Trp Asn Ser Ser Gly Ser Glu Glu Asp Pro Glu Thr Glu
      5                  10                  15 tct ggg ccg cct gtg gag cgc tgc ggg gtc ctc agt aag tgg aca aac      513
Ser Gly Pro Pro Val Glu Arg Cys Gly Val Leu Ser Lys Trp Thr Asn
 20                  25                  30                  35 tac att cat ggg tgg cag gat cgt tgg gta gtt ttg aaa aat aat gct      561
Tyr Ile His Gly Trp Gln Asp Arg Trp Val Val Leu Lys Asn Asn Ala
                 40                  45                  50 ctg agt tac tac aaa tct gaa gat gaa aca gag tat ggc tgc aga gga      609
Leu Ser Tyr Tyr Lys Ser Glu Asp Glu Thr Glu Tyr Gly Cys Arg Gly
             55                  60                  65 tcc atc tgt ctt agc aag gct gtc atc aca cct cac gat ttt gat gaa      657
Ser Ile Cys Leu Ser Lys Ala Val Ile Thr Pro His Asp Phe Asp Glu
         70                  75                  80 tgt cga ttt gat att agt gta aat gat agt gtt tgg tat ctt cgt gct      705
Cys Arg Phe Asp Ile Ser Val Asn Asp Ser Val Trp Tyr Leu Arg Ala
     85                  90                  95 cag gat cca gat cat aga cag caa tgg ata gat gcc att gaa cag cac      753
Gln Asp Pro Asp His Arg Gln Gln Trp Ile Asp Ala Ile Glu Gln His
100                 105                 110                 115 aag act gaa tct gga tat gga tct gaa tcc agc ttg cgt cga cat ggc      801
Lys Thr Glu Ser Gly Tyr Gly Ser Glu Ser Ser Leu Arg Arg His Gly
                120                 125                 130 tca atg gtg tcc ctg gtg tct gga gca agt ggc tac tct gca aca tcc      849
Ser Met Val Ser Leu Val Ser Gly Ala Ser Gly Tyr Ser Ala Thr Ser
            135                 140                 145 acc tct tca ttc aag aaa ggc cac agt tta cgt gag aag ttg gct gaa      897
Thr Ser Ser Phe Lys Lys Gly His Ser Leu Arg Glu Lys Leu Ala Glu
        150                 155                 160 atg gaa aca ttt aga gac atc tta tgt aga caa gtt gac acg cta cag      945
Met Glu Thr Phe Arg Asp Ile Leu Cys Arg Gln Val Asp Thr Leu Gln
    165                 170                 175 aag tac ttt gat gcc tgt gct gat gct gtc tct aag gat gaa ctt caa      993
Lys Tyr Phe Asp Ala Cys Ala Asp Ala Val Ser Lys Asp Glu Leu Gln
180                 185                 190                 195 agg gat aaa gtg gta gaa gat gat gaa gat gac ttt cct aca acg cgt     1041
Arg Asp Lys Val Val Glu Asp Asp Glu Asp Asp Phe Pro Thr Thr Arg
                200                 205                 210 tct gat ggt gac ttc ttg cat agt acc aac ggc aat aaa gaa aag tta     1089
Ser Asp Gly Asp Phe Leu His Ser Thr Asn Gly Asn Lys Glu Lys Leu
            215                 220                 225 ttt cca cat gtg aca cca aaa gga att aat ggt ata gac ttt aaa ggg     1137
Phe Pro His Val Thr Pro Lys Gly Ile Asn Gly Ile Asp Phe Lys Gly
        230                 235                 240 gaa gcg ata act ttt aaa gca act act gct gga atc ctt gca aca ctt     1185
Glu Ala Ile Thr Phe Lys Ala Thr Thr Ala Gly Ile Leu Ala Thr Leu
    245                 250                 255 tct cat tgt att gaa cta atg gtt aaa cgt gag gac agc tgg cag aag     1233
Ser His Cys Ile Glu Leu Met Val Lys Arg Glu Asp Ser Trp Gln Lys
260                 265                 270                 275 aga ctg gat aag gaa act gag aag aaa aga aga aca gag gaa gca tat     1281
Arg Leu Asp Lys Glu Thr Glu Lys Lys Arg Arg Thr Glu Glu Ala Tyr
                280                 285                 290 aaa aat gca atg aca gaa ctt aag aaa aaa tcc cac ttt gga gga cca     1329
Lys Asn Ala Met Thr Glu Leu Lys Lys Lys Ser His Phe Gly Gly Pro
            295                 300                 305 gat tat gaa gaa ggc cct aac agt ctg att aat gaa gaa gag ttc ttt     1377
Asp Tyr Glu Glu Gly Pro Asn Ser Leu Ile Asn Glu Glu Glu Phe Phe
        310                 315                 320
```

```
gat gct gtt gaa gct gct ctt gac aga caa gat aaa ata gaa gaa cag       1425
Asp Ala Val Glu Ala Ala Leu Asp Arg Gln Asp Lys Ile Glu Glu Gln
    325                 330                 335 tca cag agt gaa aag gtg aga tta cat tgg cct aca tcc ttg ccc tct       1473
Ser Gln Ser Glu Lys Val Arg Leu His Trp Pro Thr Ser Leu Pro Ser
340                 345                 350                 355 gga gat gcc ttt tct tct gtg ggg aca cat aga ttt gtc caa aag ccc       1521
Gly Asp Ala Phe Ser Ser Val Gly Thr His Arg Phe Val Gln Lys Pro
                360                 365                 370 tat agt cgc tct tcc tcc atg tct tcc att gat cta gtc agt gcc tct       1569
Tyr Ser Arg Ser Ser Ser Met Ser Ser Ile Asp Leu Val Ser Ala Ser
            375                 380                 385 gat gat gtt cac aga ttc agc tcc cag gtt gaa gag atg gtg cag aac       1617
Asp Asp Val His Arg Phe Ser Ser Gln Val Glu Glu Met Val Gln Asn
        390                 395                 400 cac atg act tac tca tta cag gat gta ggc gga gat gcc aat tgg cag       1665
His Met Thr Tyr Ser Leu Gln Asp Val Gly Gly Asp Ala Asn Trp Gln
    405                 410                 415 ttg gtt gta gaa gaa gga gaa atg aag gta tac aga aga gaa gta gaa       1713
Leu Val Val Glu Glu Gly Glu Met Lys Val Tyr Arg Arg Glu Val Glu
420                 425                 430                 435 gaa aat ggg att gtt ctg gat cct tta aaa gct acc cat gca gtt aaa       1761
Glu Asn Gly Ile Val Leu Asp Pro Leu Lys Ala Thr His Ala Val Lys
                440                 445                 450 ggc gtc aca gga cat gaa gtc tgc aat tat ttc tgg aat gtt gac gtt       1809
Gly Val Thr Gly His Glu Val Cys Asn Tyr Phe Trp Asn Val Asp Val
            455                 460                 465 cgc aat gac tgg gaa aca act ata gaa aac ttt cat gtg gtg gaa aca       1857
Arg Asn Asp Trp Glu Thr Thr Ile Glu Asn Phe His Val Val Glu Thr
        470                 475                 480 tta gct gat aat gca atc atc att tat caa aca cac aag agg gtg tgg       1905
Leu Ala Asp Asn Ala Ile Ile Ile Tyr Gln Thr His Lys Arg Val Trp
    485                 490                 495 cct gct tct cag cga gac gta tta tat ctt tct gtc att cga aag ata       1953
Pro Ala Ser Gln Arg Asp Val Leu Tyr Leu Ser Val Ile Arg Lys Ile
500                 505                 510                 515 cca gcc ttg act gaa aat gac cct gaa act tgg ata gtt tgt aat ttt       2001
Pro Ala Leu Thr Glu Asn Asp Pro Glu Thr Trp Ile Val Cys Asn Phe
                520                 525                 530 tct gtg gat cat gac agt gct cct cta aac aac cga tgt gtc cgt gcc       2049
Ser Val Asp His Asp Ser Ala Pro Leu Asn Asn Arg Cys Val Arg Ala
            535                 540                 545 aaa ata aat gtt gct atg att tgt caa acc ttg gta agc cca cca gag       2097
Lys Ile Asn Val Ala Met Ile Cys Gln Thr Leu Val Ser Pro Pro Glu
        550                 555                 560 gga aac cag gaa att agc agg gac aac att cta tgc aag att aca tat       2145
Gly Asn Gln Glu Ile Ser Arg Asp Asn Ile Leu Cys Lys Ile Thr Tyr
    565                 570                 575 gta gct aat gtg aac cct gga gga tgg gca cca gcc tca gtg tta agg       2193
Val Ala Asn Val Asn Pro Gly Gly Trp Ala Pro Ala Ser Val Leu Arg
580                 585                 590                 595 gca gtg gca aag cga gag tat cct aaa ttt cta aaa cgt ttt act tct       2241
Ala Val Ala Lys Arg Glu Tyr Pro Lys Phe Leu Lys Arg Phe Thr Ser
                600                 605                 610 tac gtc caa gaa aaa act gca gga aag cct att ttg ttc tagtattaac       2290
Tyr Val Gln Glu Lys Thr Ala Gly Lys Pro Ile Leu Phe
            615                 620 aggtactaga agatatgttt tatctttttt taactttatt tgactaatat gactgtcaat   2350
```
actaaaattt agttgttgaa agtatttact atgttttt    2389

<210> SEQ ID NO 2
<211> LENGTH: 624
<212> TYPE: PRT
<213> ORGANISM: Homo sapiens

<400> SEQUENCE: 2

```
Met Ser Asp Asn Gln Ser Trp Asn Ser Ser Gly Ser Glu Glu Asp Pro
  1               5                  10                  15

Glu Thr Glu Ser Gly Pro Pro Val Glu Arg Cys Gly Val Leu Ser Lys
             20                  25                  30

Trp Thr Asn Tyr Ile His Gly Trp Gln Asp Arg Trp Val Val Leu Lys
         35                  40                  45

Asn Asn Ala Leu Ser Tyr Tyr Lys Ser Glu Asp Glu Thr Glu Tyr Gly
     50                  55                  60

Cys Arg Gly Ser Ile Cys Leu Ser Lys Ala Val Ile Thr Pro His Asp
 65                  70                  75                  80

Phe Asp Glu Cys Arg Phe Asp Ile Ser Val Asn Asp Ser Val Trp Tyr
                 85                  90                  95

Leu Arg Ala Gln Asp Pro Asp His Arg Gln Gln Trp Ile Asp Ala Ile
            100                 105                 110

Glu Gln His Lys Thr Glu Ser Gly Tyr Gly Ser Glu Ser Ser Leu Arg
        115                 120                 125

Arg His Gly Ser Met Val Ser Leu Val Ser Gly Ala Ser Gly Tyr Ser
    130                 135                 140

Ala Thr Ser Thr Ser Ser Phe Lys Lys Gly His Ser Leu Arg Glu Lys
145                 150                 155                 160

Leu Ala Glu Met Glu Thr Phe Arg Asp Ile Leu Cys Arg Gln Val Asp
                165                 170                 175

Thr Leu Gln Lys Tyr Phe Asp Ala Cys Ala Asp Ala Val Ser Lys Asp
            180                 185                 190

Glu Leu Gln Arg Asp Lys Val Val Glu Asp Asp Glu Asp Asp Phe Pro
        195                 200                 205

Thr Thr Arg Ser Asp Gly Asp Phe Leu His Ser Thr Asn Gly Asn Lys
    210                 215                 220

Glu Lys Leu Phe Pro His Val Thr Pro Lys Gly Ile Asn Gly Ile Asp
225                 230                 235                 240

Phe Lys Gly Glu Ala Ile Thr Phe Lys Ala Thr Thr Ala Gly Ile Leu
                245                 250                 255

Ala Thr Leu Ser His Cys Ile Glu Leu Met Val Lys Arg Glu Asp Ser
            260                 265                 270

Trp Gln Lys Arg Leu Asp Lys Glu Thr Glu Lys Lys Arg Arg Thr Glu
        275                 280                 285

Glu Ala Tyr Lys Asn Ala Met Thr Glu Leu Lys Lys Lys Ser His Phe
    290                 295                 300

Gly Gly Pro Asp Tyr Glu Glu Gly Pro Asn Ser Leu Ile Asn Glu Glu
305                 310                 315                 320

Glu Phe Phe Asp Ala Val Glu Ala Ala Leu Asp Arg Gln Asp Lys Ile
                325                 330                 335

Glu Glu Gln Ser Gln Ser Glu Lys Val Arg Leu His Trp Pro Thr Ser
            340                 345                 350

Leu Pro Ser Gly Asp Ala Phe Ser Ser Val Gly Thr His Arg Phe Val
        355                 360                 365
```

```
Gln Lys Pro Tyr Ser Arg Ser Ser Met Ser Ser Ile Asp Leu Val
    370                 375                 380
Ser Ala Ser Asp Asp Val His Arg Phe Ser Ser Gln Val Glu Glu Met
385                 390                 395                 400
Val Gln Asn His Met Thr Tyr Ser Leu Gln Asp Val Gly Gly Asp Ala
                405                 410                 415
Asn Trp Gln Leu Val Val Glu Glu Gly Glu Met Lys Val Tyr Arg Arg
            420                 425                 430
Glu Val Glu Glu Asn Gly Ile Val Leu Asp Pro Leu Lys Ala Thr His
        435                 440                 445
Ala Val Lys Gly Val Thr Gly His Glu Val Cys Asn Tyr Phe Trp Asn
    450                 455                 460
Val Asp Val Arg Asn Asp Trp Glu Thr Thr Ile Glu Asn Phe His Val
465                 470                 475                 480
Val Glu Thr Leu Ala Asp Asn Ala Ile Ile Ile Tyr Gln Thr His Lys
                485                 490                 495
Arg Val Trp Pro Ala Ser Gln Arg Asp Val Leu Tyr Leu Ser Val Ile
            500                 505                 510
Arg Lys Ile Pro Ala Leu Thr Glu Asn Asp Pro Glu Thr Trp Ile Val
        515                 520                 525
Cys Asn Phe Ser Val Asp His Asp Ser Ala Pro Leu Asn Asn Arg Cys
    530                 535                 540
Val Arg Ala Lys Ile Asn Val Ala Met Ile Cys Gln Thr Leu Val Ser
545                 550                 555                 560
Pro Pro Glu Gly Asn Gln Glu Ile Ser Arg Asp Asn Ile Leu Cys Lys
                565                 570                 575
Ile Thr Tyr Val Ala Asn Val Asn Pro Gly Gly Trp Ala Pro Ala Ser
            580                 585                 590
Val Leu Arg Ala Val Ala Lys Arg Glu Tyr Pro Lys Phe Leu Lys Arg
        595                 600                 605
Phe Thr Ser Tyr Val Gln Glu Lys Thr Ala Gly Lys Pro Ile Leu Phe
    610                 615                 620

<210> SEQ ID NO 3
<211> LENGTH: 2762
<212> TYPE: DNA
<213> ORGANISM: Mus musculus
<220> FEATURE:
<221> NAME/KEY: CDS
<222> LOCATION: (444)..(2315)

<400> SEQUENCE: 3
cgggccacca cgtgtaaata gtatcggacc cggcaggaag atggcggctg tagcggaggt      60
gtgagtgagt ggatctgggt ctctgccgtt ggcttggctc ttcccgtctt cctcccctcc     120
tccctccctg actgaggttg gcatctaggg ggccgagttc aggtggcggc gccgggcgca     180 gcgcagggt cacggccacg gcggctgacg gctggaaggg caggctttct tcgccgctcg      240
tcctccttcc ccggtccgct cggtgtcagg cgcggcggcg gcggcgcggc gggcgcgctt     300
cgtccctctt cctgttccct cactccccgg agcgggctct cttggcggtg ccatccccg      360 acccttcacc ccaggggacta ggcgcctgca ctggcgcagc tcgcggagcg ggggccggtc    420
tcctgctcgg ctgtcgcgtc tcc atg tcg gat aac cag agc tgg aac tcg tcg    473
                           Met Ser Asp Asn Gln Ser Trp Asn Ser Ser
                             1               5                  10 ggc tcg gag gag gat ccg gag acg gag tcc ggg ccg cct gtg gag cgc      521
Gly Ser Glu Glu Asp Pro Glu Thr Glu Ser Gly Pro Pro Val Glu Arg
```

```
                  15                    20                      25
tgc ggg gtc ctc agc aag tgg aca aac tat att cat gga tgg cag gat       569
Cys Gly Val Leu Ser Lys Trp Thr Asn Tyr Ile His Gly Trp Gln Asp
             30                      35                      40 cgt tgg gta gtt ttg aaa aat aat act ttg agt tac tac aaa tct gaa       617
Arg Trp Val Val Leu Lys Asn Asn Thr Leu Ser Tyr Tyr Lys Ser Glu
         45                      50                      55 gat gaa aca gaa tat ggc tgt agg gga tcc atc tgt ctt agc aag gct       665
Asp Glu Thr Glu Tyr Gly Cys Arg Gly Ser Ile Cys Leu Ser Lys Ala
     60                      65                      70 gtg atc acg cct cac gat ttt gat gaa tgc cgg ttt gat atc agt gta       713
Val Ile Thr Pro His Asp Phe Asp Glu Cys Arg Phe Asp Ile Ser Val
 75                      80                      85                      90 aat gat agt gtt tgg tac ctt cga gct cag gac ccg gag cac aga cag       761
Asn Asp Ser Val Trp Tyr Leu Arg Ala Gln Asp Pro Glu His Arg Gln
                     95                     100                     105 caa tgg gta gac gcc att gaa cag cac aag act gaa tcg gga tat gga       809
Gln Trp Val Asp Ala Ile Glu Gln His Lys Thr Glu Ser Gly Tyr Gly
                110                     115                     120 tct gag tcc agc ttg cgt aga cat ggc tca atg gtg tca ctg gtg tct       857
Ser Glu Ser Ser Leu Arg Arg His Gly Ser Met Val Ser Leu Val Ser
            125                     130                     135 gga gcg agt ggc tat tct gct acg tcc acc tct tct ttc aag aaa ggc       905
Gly Ala Ser Gly Tyr Ser Ala Thr Ser Thr Ser Ser Phe Lys Lys Gly
        140                     145                     150 cac agt tta cgt gag aaa ctg gct gaa atg gag aca ttt cgg gac atc       953
His Ser Leu Arg Glu Lys Leu Ala Glu Met Glu Thr Phe Arg Asp Ile
155                     160                     165                     170 ctg tgc cgg cag gtt gat act ctc cag aag tac ttt gat gtc tgt gct      1001
Leu Cys Arg Gln Val Asp Thr Leu Gln Lys Tyr Phe Asp Val Cys Ala
                175                     180                     185 gac gct gtc tcc aag gat gag ctt cag agg gat aaa gtc gta gaa gat      1049
Asp Ala Val Ser Lys Asp Glu Leu Gln Arg Asp Lys Val Val Glu Asp
            190                     195                     200 gat gaa gat gac ttc cct aca act cgt tct gat gga gac ttt ttg cac      1097
Asp Glu Asp Asp Phe Pro Thr Thr Arg Ser Asp Gly Asp Phe Leu His
        205                     210                     215 aat acc aat ggt aat aaa gaa aaa tta ttt cca cat gta aca cca aaa      1145
Asn Thr Asn Gly Asn Lys Glu Lys Leu Phe Pro His Val Thr Pro Lys
    220                     225                     230 gga att aat ggc ata gac ttt aaa ggg gaa gca ata act ttt aaa gca      1193
Gly Ile Asn Gly Ile Asp Phe Lys Gly Glu Ala Ile Thr Phe Lys Ala
235                     240                     245                     250 act act gct gga atc ctt gct aca ctt tct cat tgt att gaa tta atg      1241
Thr Thr Ala Gly Ile Leu Ala Thr Leu Ser His Cys Ile Glu Leu Met
                255                     260                     265 gta aaa cgg gaa gag agc tgg caa aaa aga cac gat agg gaa gtg gaa      1289
Val Lys Arg Glu Glu Ser Trp Gln Lys Arg His Asp Arg Glu Val Glu
            270                     275                     280 aag agg aga cga gtg gag gaa gcg tac aag aat gtg atg gaa gaa ctt      1337
Lys Arg Arg Arg Val Glu Glu Ala Tyr Lys Asn Val Met Glu Glu Leu
        285                     290                     295 aag aag aaa ccc cgt ttc gga ggg ccg gat tat gaa gaa ggt cca aac      1385
Lys Lys Lys Pro Arg Phe Gly Gly Pro Asp Tyr Glu Glu Gly Pro Asn
    300                     305                     310 agt ctg att aat gag gaa gag ttc ttt gat gct gtt gaa gct gct ctt      1433
Ser Leu Ile Asn Glu Glu Glu Phe Phe Asp Ala Val Glu Ala Ala Leu
315                     320                     325                     330 gac aga caa gat aaa ata gag gaa cag tca cag agt gaa aag gtc agg      1481
```

```
                            -continued

Asp Arg Gln Asp Lys Ile Glu Glu Gln Ser Gln Ser Glu Lys Val Arg
            335                 340                 345 tta cac tgg ccc aca tca ttg cca tct gga gac acc ttt tct tct gtc    1529
Leu His Trp Pro Thr Ser Leu Pro Ser Gly Asp Thr Phe Ser Ser Val
        350                 355                 360 ggg acg cat aga ttt gta caa aag ccc tat agt cgc tct tcc tcc atg    1577
Gly Thr His Arg Phe Val Gln Lys Pro Tyr Ser Arg Ser Ser Ser Met
    365                 370                 375 tct tcc att gat cta gtc agt gcc tct gac gat gtt cac aga ttc agc    1625
Ser Ser Ile Asp Leu Val Ser Ala Ser Asp Asp Val His Arg Phe Ser
380                 385                 390 tcc cag gtt gaa gaa atg gta cag aac cac atg aac tat tca tta cag    1673
Ser Gln Val Glu Glu Met Val Gln Asn His Met Asn Tyr Ser Leu Gln
395                 400                 405                 410 gat gta ggt ggt gat gca aat tgg caa ctg gtt gtt gaa gaa gga gaa    1721
Asp Val Gly Gly Asp Ala Asn Trp Gln Leu Val Val Glu Glu Gly Glu
                415                 420                 425 atg aag gta tac aga aga gaa gtg gaa gaa aat gga att gtt ctg gat    1769
Met Lys Val Tyr Arg Arg Glu Val Glu Glu Asn Gly Ile Val Leu Asp
            430                 435                 440 cct ttg aaa gct act cat gca gtt aaa ggt gtt aca gga cat gag gtc    1817
Pro Leu Lys Ala Thr His Ala Val Lys Gly Val Thr Gly His Glu Val
        445                 450                 455 tgc aat tac ttt tgg aat gtt gat gtt cgc aat gac tgg gaa act act    1865
Cys Asn Tyr Phe Trp Asn Val Asp Val Arg Asn Asp Trp Glu Thr Thr
    460                 465                 470 ata gaa aac ttt cat gtg gtg gaa aca tta gct gat aat gca atc atc    1913
Ile Glu Asn Phe His Val Val Glu Thr Leu Ala Asp Asn Ala Ile Ile
475                 480                 485                 490 gtt tat caa acg cac aag aga gta tgg ccc gct tct cag aga gac gta    1961
Val Tyr Gln Thr His Lys Arg Val Trp Pro Ala Ser Gln Arg Asp Val
                495                 500                 505 ctg tat ctt tct gct att cga aag atc cca gcc ttg act gaa aat gat    2009
Leu Tyr Leu Ser Ala Ile Arg Lys Ile Pro Ala Leu Thr Glu Asn Asp
            510                 515                 520 cct gaa act tgg ata gtt tgt aat ttt tct gtg gat cat gat agt gct    2057
Pro Glu Thr Trp Ile Val Cys Asn Phe Ser Val Asp His Asp Ser Ala
        525                 530                 535 cct ctg aac aat cga tgt gtc cgt gcc aaa atc aat att gct atg att    2105
Pro Leu Asn Asn Arg Cys Val Arg Ala Lys Ile Asn Ile Ala Met Ile
    540                 545                 550 tgt caa act tta gta agc cca cca gag gga gac cag gag ata agc aga    2153
Cys Gln Thr Leu Val Ser Pro Pro Glu Gly Asp Gln Glu Ile Ser Arg
555                 560                 565                 570 gac aac att ctg tgc aag atc acg tat gta gct aat gtg aac cca gga    2201
Asp Asn Ile Leu Cys Lys Ile Thr Tyr Val Ala Asn Val Asn Pro Gly
                575                 580                 585 gga tgg gcg cca gct tcg gtc tta aga gca gtg gca aag cga gaa tac    2249
Gly Trp Ala Pro Ala Ser Val Leu Arg Ala Val Ala Lys Arg Glu Tyr
            590                 595                 600 cct aag ttt cta aaa cgt ttt act tct tat gtc caa gaa aaa act gca    2297
Pro Lys Phe Leu Lys Arg Phe Thr Ser Tyr Val Gln Glu Lys Thr Ala
        605                 610                 615 gga aaa cca att ttg ttt tagtattaac agtgactgaa gcaaggctgc           2345
Gly Lys Pro Ile Leu Phe
    620 gtgacgttcc atgttggaga aaggagggaa aaataaaaa gaatcctcta agctggaacg   2405 taggatctac agccttgtct gtggcccaag aagaaacatt gcaatcgtaa agctgggtat  2465
```

-continued

```
ccagcactag ccatctcctg ctaggcctcc tcgctcagcg tgtaactata aatacatgta    2525
gaatcacatg gatatggcta tattttatt tgcttgctcc ttggagtgaa acaaataac     2585 tttgaattac aactaggaat taaccgatgc tttaattttg aggaactttt tcagaatttt    2645
ttatttacca tggtccaacc taagatcctc agttgtatca agttttgtg cacaaaagaa     2705 aagcacaaaa gttgaacgca cctgaaggca tgtgctctct gtgcaacaaa tactcag      2762
```

<210> SEQ ID NO 4
<211> LENGTH: 624
<212> TYPE: PRT
<213> ORGANISM: Mus musculus

<400> SEQUENCE: 4

```
Met Ser Asp Asn Gln Ser Trp Asn Ser Gly Ser Glu Glu Asp Pro
  1               5                  10                  15

Glu Thr Glu Ser Gly Pro Pro Val Glu Arg Cys Gly Val Leu Ser Lys
                 20                  25                  30

Trp Thr Asn Tyr Ile His Gly Trp Gln Asp Arg Trp Val Val Leu Lys
             35                  40                  45

Asn Asn Thr Leu Ser Tyr Tyr Lys Ser Glu Asp Glu Thr Glu Tyr Gly
         50                  55                  60

Cys Arg Gly Ser Ile Cys Leu Ser Lys Ala Val Ile Thr Pro His Asp
 65                  70                  75                  80

Phe Asp Glu Cys Arg Phe Asp Ile Ser Val Asn Asp Ser Val Trp Tyr
                 85                  90                  95

Leu Arg Ala Gln Asp Pro Glu His Arg Gln Gln Trp Val Asp Ala Ile
             100                 105                 110

Glu Gln His Lys Thr Glu Ser Gly Tyr Gly Ser Glu Ser Ser Leu Arg
         115                 120                 125

Arg His Gly Ser Met Val Ser Leu Val Ser Gly Ala Ser Gly Tyr Ser
 130                 135                 140

Ala Thr Ser Thr Ser Ser Phe Lys Lys Gly His Ser Leu Arg Glu Lys
145                 150                 155                 160

Leu Ala Glu Met Glu Thr Phe Arg Asp Ile Leu Cys Arg Gln Val Asp
                 165                 170                 175

Thr Leu Gln Lys Tyr Phe Asp Val Cys Ala Asp Ala Val Ser Lys Asp
             180                 185                 190

Glu Leu Gln Arg Asp Lys Val Val Glu Asp Asp Glu Asp Asp Phe Pro
         195                 200                 205

Thr Thr Arg Ser Asp Gly Asp Phe Leu His Asn Thr Asn Gly Asn Lys
 210                 215                 220

Glu Lys Leu Phe Pro His Val Thr Pro Lys Gly Ile Asn Gly Ile Asp
225                 230                 235                 240

Phe Lys Gly Glu Ala Ile Thr Phe Lys Ala Thr Thr Ala Gly Ile Leu
                 245                 250                 255

Ala Thr Leu Ser His Cys Ile Glu Leu Met Val Lys Arg Glu Glu Ser
             260                 265                 270

Trp Gln Lys Arg His Asp Arg Glu Val Glu Lys Arg Arg Arg Val Glu
         275                 280                 285

Glu Ala Tyr Lys Asn Val Met Glu Glu Leu Lys Lys Lys Pro Arg Phe
 290                 295                 300

Gly Gly Pro Asp Tyr Glu Glu Gly Pro Asn Ser Leu Ile Asn Glu Glu
305                 310                 315                 320

Glu Phe Phe Asp Ala Val Glu Ala Ala Leu Asp Arg Gln Asp Lys Ile
```

```
                    325                 330                 335
Glu Glu Gln Ser Gln Ser Glu Lys Val Arg Leu His Trp Pro Thr Ser
                340                 345                 350
Leu Pro Ser Gly Asp Thr Phe Ser Ser Val Gly Thr His Arg Phe Val
                355                 360                 365
Gln Lys Pro Tyr Ser Arg Ser Ser Met Ser Ser Ile Asp Leu Val
            370                 375                 380
Ser Ala Ser Asp Asp Val His Arg Phe Ser Ser Gln Val Glu Glu Met
385                 390                 395                 400
Val Gln Asn His Met Asn Tyr Ser Leu Gln Asp Val Gly Gly Asp Ala
                405                 410                 415
Asn Trp Gln Leu Val Val Glu Glu Gly Glu Met Lys Val Tyr Arg Arg
                420                 425                 430
Glu Val Glu Glu Asn Gly Ile Val Leu Asp Pro Leu Lys Ala Thr His
                435                 440                 445
Ala Val Lys Gly Val Thr Gly His Glu Val Cys Asn Tyr Phe Trp Asn
                450                 455                 460
Val Asp Val Arg Asn Asp Trp Glu Thr Thr Ile Glu Asn Phe His Val
465                 470                 475                 480
Val Glu Thr Leu Ala Asp Asn Ala Ile Ile Val Tyr Gln Thr His Lys
                485                 490                 495
Arg Val Trp Pro Ala Ser Gln Arg Asp Val Leu Tyr Leu Ser Ala Ile
                500                 505                 510
Arg Lys Ile Pro Ala Leu Thr Glu Asn Asp Pro Glu Thr Trp Ile Val
                515                 520                 525
Cys Asn Phe Ser Val Asp His Asp Ser Ala Pro Leu Asn Asn Arg Cys
                530                 535                 540
Val Arg Ala Lys Ile Asn Ile Ala Met Ile Cys Gln Thr Leu Val Ser
545                 550                 555                 560
Pro Pro Glu Gly Asp Gln Glu Ile Ser Arg Asp Asn Ile Leu Cys Lys
                565                 570                 575
Ile Thr Tyr Val Ala Asn Val Asn Pro Gly Gly Trp Ala Pro Ala Ser
                580                 585                 590
Val Leu Arg Ala Val Ala Lys Arg Glu Tyr Pro Lys Phe Leu Lys Arg
                595                 600                 605
Phe Thr Ser Tyr Val Gln Glu Lys Thr Ala Gly Lys Pro Ile Leu Phe
            610                 615                 620

<210> SEQ ID NO 5
<211> LENGTH: 2361
<212> TYPE: DNA
<213> ORGANISM: Bos taurus
<220> FEATURE:
<221> NAME/KEY: CDS
<222> LOCATION: (421)..(2292)

<400> SEQUENCE: 5
cggcaggaag atggcggcct agcggaggtg tgagtggacc tgggtctctg cagctgggtt      60
ttccctcttc ccgtctttct cctctttcc  tctcccccga ggttggcatc gagggggcca    120
aattcgggcg gcggcgccgg gcgcagcgca ggggtcacaa cgacggcgac ggctgacggt    180
tggaagggca ggcttccttc gcccctcgac ctccttcccc ggtccgcttg gtgtcaggcg    240
cggcggcggc ggcggcggcg gcgcggcggg cggactccat ccctcctccc gctccctcct    300
gcaccggagc gggcactcct tccttcgcca tcccccgacc cttcacccc gggactgggc    360
```

-continued

| | |
|---|---|
| gcctccaccg gcgcagctca gggagcgggg gccggtctcc tgctcggctg tcgcgcctcc | 420 |

| | | |
|---|---|---|
| atg tcg gat aac cag agc tgg aac tcg tcg ggc tcg gag gag gat ccg<br>Met Ser Asp Asn Gln Ser Trp Asn Ser Ser Gly Ser Glu Glu Asp Pro<br>1                5                  10              15 | 468 |
| gag acg gag tcc ggg ccg ccg gtg gag cgc tgc gga gtc ctc aac aag<br>Glu Thr Glu Ser Gly Pro Pro Val Glu Arg Cys Gly Val Leu Asn Lys<br>                20                  25                30 | 516 |
| tgg aca aac tat att cat ggg tgg cag gat cgc tgg gta gtt ttg aaa<br>Trp Thr Asn Tyr Ile His Gly Trp Gln Asp Arg Trp Val Val Leu Lys<br>          35                  40                45 | 564 |
| aat aac act ctg agt tac tac aaa tct gaa gat gag aca gag tat ggc<br>Asn Asn Thr Leu Ser Tyr Tyr Lys Ser Glu Asp Glu Thr Glu Tyr Gly<br>50                  55                  60 | 612 |
| tgc aga gga tcc atc tgt ctt agc aag gct gtc atc acg cct cat gat<br>Cys Arg Gly Ser Ile Cys Leu Ser Lys Ala Val Ile Thr Pro His Asp<br>65                  70                75              80 | 660 |
| ttt gat gaa tgc cga ttt gat att agt gta aat gat agt gtt tgg tat<br>Phe Asp Glu Cys Arg Phe Asp Ile Ser Val Asn Asp Ser Val Trp Tyr<br>                  85                  90                95 | 708 |
| ctt cgt gct caa gat cca gat cac aga cag cag tgg ata gat gcc att<br>Leu Arg Ala Gln Asp Pro Asp His Arg Gln Gln Trp Ile Asp Ala Ile<br>          100                  105                110 | 756 |
| gaa cag cac aag act gaa tct gga tat gga tct gaa tcc agc ttg cgt<br>Glu Gln His Lys Thr Glu Ser Gly Tyr Gly Ser Glu Ser Ser Leu Arg<br>115                 120                125 | 804 |
| cga cat ggc tcc atg gta tca ttg gta tcc gga gca agt ggc tat tct<br>Arg His Gly Ser Met Val Ser Leu Val Ser Gly Ala Ser Gly Tyr Ser<br>130                 135                140 | 852 |
| gca aca tcc acc tcc tca ttc aag aag ggc cac agt tta cgt gag aaa<br>Ala Thr Ser Thr Ser Ser Phe Lys Lys Gly His Ser Leu Arg Glu Lys<br>145                 150                155              160 | 900 |
| ctg gct gaa atg gaa acc ttt aga gat ata ctg tgt aga caa gtt gat<br>Leu Ala Glu Met Glu Thr Phe Arg Asp Ile Leu Cys Arg Gln Val Asp<br>                 165                170                175 | 948 |
| acc cta cag aag ttc ttt gat gcc tgt gct gat gct gtc tcc aag gat<br>Thr Leu Gln Lys Phe Phe Asp Ala Cys Ala Asp Ala Val Ser Lys Asp<br>          180                  185                190 | 996 |
| gaa ttt caa agg gat aaa gtg gta gaa gat gat gaa gat gac ttt cct<br>Glu Phe Gln Arg Asp Lys Val Val Glu Asp Asp Glu Asp Asp Phe Pro<br>195                 200                205 | 1044 |
| acg aca cgt tct gat gga gac ttc ttg cat aat acc aat ggc aat aag<br>Thr Thr Arg Ser Asp Gly Asp Phe Leu His Asn Thr Asn Gly Asn Lys<br>210                 215                220 | 1092 |
| gaa aag gta ttt cca cat gta aca cca aaa gga att aat ggt ata gac<br>Glu Lys Val Phe Pro His Val Thr Pro Lys Gly Ile Asn Gly Ile Asp<br>225                 230                235              240 | 1140 |
| ttt aaa ggt gag gcg ata act ttt aaa gca act act gcc gga atc ctt<br>Phe Lys Gly Glu Ala Ile Thr Phe Lys Ala Thr Thr Ala Gly Ile Leu<br>                 245                250                255 | 1188 |
| gct aca ctt tct cat tgt att gag ctg atg gta aaa cgt gag gac agc<br>Ala Thr Leu Ser His Cys Ile Glu Leu Met Val Lys Arg Glu Asp Ser<br>          260                  265                270 | 1236 |
| tgg caa aag aga atg gac aag gaa act gag aag aga aga aga gtg gag<br>Trp Gln Lys Arg Met Asp Lys Glu Thr Glu Lys Arg Arg Arg Val Glu<br>275                 280                285 | 1284 |
| gaa gca tac aaa aat gcc atg aca gaa ctt aag aaa tcc cac ttt<br>Glu Ala Tyr Lys Asn Ala Met Thr Glu Leu Lys Lys Ser His Phe<br>290                 295                300 | 1332 |
| gga gga cca gat tat gag gaa ggc cca aac agt ttg att aat gaa gag<br>Gly Gly Pro Asp Tyr Glu Glu Gly Pro Asn Ser Leu Ile Asn Glu Glu | 1380 |

```
                305                 310                 315                 320
gag ttc ttt gat gct gtt gaa gct gct ctt gac aga caa gat aaa ata            1428
Glu Phe Phe Asp Ala Val Glu Ala Ala Leu Asp Arg Gln Asp Lys Ile
                    325                 330                 335 gaa gaa cag tcg cag agt gaa aag gtc agg tta cat tgg tct act tca            1476
Glu Glu Gln Ser Gln Ser Glu Lys Val Arg Leu His Trp Ser Thr Ser
                340                 345                 350 atg cca tct gga gat gcc ttt tct tct gtg ggg act cat aga ttt gtc            1524
Met Pro Ser Gly Asp Ala Phe Ser Ser Val Gly Thr His Arg Phe Val
            355                 360                 365 caa aag ccc tat agt cgc tct tcc tcc atg tct tcc att gat cta gtc            1572
Gln Lys Pro Tyr Ser Arg Ser Ser Ser Met Ser Ser Ile Asp Leu Val
        370                 375                 380 agt gcc tct gac ggt gtt cac aga ttc agc tcc cag gtt gaa gag atg            1620
Ser Ala Ser Asp Gly Val His Arg Phe Ser Ser Gln Val Glu Glu Met
385                 390                 395                 400 gtg cag aac cac atg acc tat tca ttg cag gat gta ggt ggg gac gcc            1668
Val Gln Asn His Met Thr Tyr Ser Leu Gln Asp Val Gly Gly Asp Ala
                    405                 410                 415 aac tgg cag ttg gtt gta gaa gaa ggg gag atg aag gta tat aga aga            1716
Asn Trp Gln Leu Val Val Glu Glu Gly Glu Met Lys Val Tyr Arg Arg
                420                 425                 430 gaa gta gaa gaa aat ggg att gtt ctg gat cct ttg aaa gct acc cat            1764
Glu Val Glu Glu Asn Gly Ile Val Leu Asp Pro Leu Lys Ala Thr His
            435                 440                 445 gca gtt aaa ggc gtt aca gga cac gag gtc tgc aat tac ttc tgg aat            1812
Ala Val Lys Gly Val Thr Gly His Glu Val Cys Asn Tyr Phe Trp Asn
        450                 455                 460 gtt gat gtt cgc aat gat tgg gaa aca act ata gaa aac ttt cat gtg            1860
Val Asp Val Arg Asn Asp Trp Glu Thr Thr Ile Glu Asn Phe His Val
465                 470                 475                 480 gtg gaa aca tta gct gat aat gca atc atc att tat caa acg cac aag            1908
Val Glu Thr Leu Ala Asp Asn Ala Ile Ile Ile Tyr Gln Thr His Lys
                    485                 490                 495 aga gtg tgg cca gcc tct cag cgg gat gtc tta tat ctg tct gcc att            1956
Arg Val Trp Pro Ala Ser Gln Arg Asp Val Leu Tyr Leu Ser Ala Ile
                500                 505                 510 cga aag ata cca gct ttg aat gaa aat gac ccg gag act tgg ata gtt            2004
Arg Lys Ile Pro Ala Leu Asn Glu Asn Asp Pro Glu Thr Trp Ile Val
            515                 520                 525 tgt aat ttt tct gta gat cac agc agt gct cct cta aac aat cga tgt            2052
Cys Asn Phe Ser Val Asp His Ser Ser Ala Pro Leu Asn Asn Arg Cys
        530                 535                 540 gtc cgt gcc aaa ata aac gtt gct atg att tgt cag acc ttg gtg agc            2100
Val Arg Ala Lys Ile Asn Val Ala Met Ile Cys Gln Thr Leu Val Ser
545                 550                 555                 560 ccc cca gag gga aac cag gag att agc agg gac aac att cta tgc aag            2148
Pro Pro Glu Gly Asn Gln Glu Ile Ser Arg Asp Asn Ile Leu Cys Lys
                    565                 570                 575 att aca tac gtg gcc aat gta aac cct gga gga tgg gcc cca gcc tca            2196
Ile Thr Tyr Val Ala Asn Val Asn Pro Gly Gly Trp Ala Pro Ala Ser
                580                 585                 590 gtg tta cgg gca gtg gca aag cga gaa tat cca aag ttt cta aag cgt            2244
Val Leu Arg Ala Val Ala Lys Arg Glu Tyr Pro Lys Phe Leu Lys Arg
            595                 600                 605 ttt act tct tac gta caa gaa aaa act gca gga aaa cct att ttg ttc            2292
Phe Thr Ser Tyr Val Gln Glu Lys Thr Ala Gly Lys Pro Ile Leu Phe
        610                 615                 620 tagtattaac agtgactgaa gcaaggctgt gtgacattcc atgttggagg aaaaaaaaaa         2352
``` aaaaaaaa                                                    2361

<210> SEQ ID NO 6
<211> LENGTH: 624
<212> TYPE: PRT
<213> ORGANISM: Bos taurus

<400> SEQUENCE: 6

Met Ser Asp Asn Gln Ser Trp Asn Ser Ser Gly Ser Glu Glu Asp Pro
 1               5                  10                  15

Glu Thr Glu Ser Gly Pro Pro Val Glu Arg Cys Gly Val Leu Asn Lys
            20                  25                  30

Trp Thr Asn Tyr Ile His Gly Trp Gln Asp Arg Trp Val Val Leu Lys
        35                  40                  45

Asn Asn Thr Leu Ser Tyr Tyr Lys Ser Glu Asp Glu Thr Glu Tyr Gly
    50                  55                  60

Cys Arg Gly Ser Ile Cys Leu Ser Lys Ala Val Ile Thr Pro His Asp
65                  70                  75                  80

Phe Asp Glu Cys Arg Phe Asp Ile Ser Val Asn Asp Ser Val Trp Tyr
                85                  90                  95

Leu Arg Ala Gln Asp Pro Asp His Arg Gln Gln Trp Ile Asp Ala Ile
           100                 105                 110

Glu Gln His Lys Thr Glu Ser Gly Tyr Gly Ser Glu Ser Ser Leu Arg
       115                 120                 125

Arg His Gly Ser Met Val Ser Leu Val Ser Gly Ala Ser Gly Tyr Ser
   130                 135                 140

Ala Thr Ser Thr Ser Ser Phe Lys Lys Gly His Ser Leu Arg Glu Lys
145                 150                 155                 160

Leu Ala Glu Met Glu Thr Phe Arg Asp Ile Leu Cys Arg Gln Val Asp
               165                 170                 175

Thr Leu Gln Lys Phe Phe Asp Ala Cys Ala Asp Ala Val Ser Lys Asp
           180                 185                 190

Glu Phe Gln Arg Asp Lys Val Val Glu Asp Asp Glu Asp Asp Phe Pro
       195                 200                 205

Thr Thr Arg Ser Asp Gly Asp Phe Leu His Asn Thr Asn Gly Asn Lys
   210                 215                 220

Glu Lys Val Phe Pro His Val Thr Pro Lys Gly Ile Asn Gly Ile Asp
225                 230                 235                 240

Phe Lys Gly Glu Ala Ile Thr Phe Lys Ala Thr Thr Ala Gly Ile Leu
               245                 250                 255

Ala Thr Leu Ser His Cys Ile Glu Leu Met Val Lys Arg Glu Asp Ser
           260                 265                 270

Trp Gln Lys Arg Met Asp Lys Glu Thr Glu Lys Arg Arg Arg Val Glu
       275                 280                 285

Glu Ala Tyr Lys Asn Ala Met Thr Glu Leu Lys Lys Lys Ser His Phe
   290                 295                 300

Gly Gly Pro Asp Tyr Glu Glu Gly Pro Asn Ser Leu Ile Asn Glu Glu
305                 310                 315                 320

Glu Phe Phe Asp Ala Val Glu Ala Ala Leu Asp Arg Gln Asp Lys Ile
               325                 330                 335

Glu Glu Gln Ser Gln Ser Glu Lys Val Arg Leu His Trp Ser Thr Ser
           340                 345                 350

Met Pro Ser Gly Asp Ala Phe Ser Val Gly Thr His Arg Phe Val
       355                 360                 365

```
Gln Lys Pro Tyr Ser Arg Ser Ser Met Ser Ser Ile Asp Leu Val
    370                 375                 380

Ser Ala Ser Asp Gly Val His Arg Phe Ser Ser Gln Val Glu Glu Met
385                 390                 395                 400

Val Gln Asn His Met Thr Tyr Ser Leu Gln Asp Val Gly Gly Asp Ala
                405                 410                 415

Asn Trp Gln Leu Val Val Glu Glu Gly Glu Met Lys Val Tyr Arg Arg
            420                 425                 430

Glu Val Glu Glu Asn Gly Ile Val Leu Asp Pro Leu Lys Ala Thr His
                435                 440                 445

Ala Val Lys Gly Val Thr Gly His Glu Val Cys Asn Tyr Phe Trp Asn
    450                 455                 460

Val Asp Val Arg Asn Asp Trp Glu Thr Thr Ile Glu Asn Phe His Val
465                 470                 475                 480

Val Glu Thr Leu Ala Asp Asn Ala Ile Ile Tyr Gln Thr His Lys
                485                 490                 495

Arg Val Trp Pro Ala Ser Gln Arg Asp Val Leu Tyr Leu Ser Ala Ile
                500                 505                 510

Arg Lys Ile Pro Ala Leu Asn Glu Asn Asp Pro Glu Thr Trp Ile Val
    515                 520                 525

Cys Asn Phe Ser Val Asp His Ser Ser Ala Pro Leu Asn Asn Arg Cys
530                 535                 540

Val Arg Ala Lys Ile Asn Val Ala Met Ile Cys Gln Thr Leu Val Ser
545                 550                 555                 560

Pro Pro Glu Gly Asn Gln Gly Ile Ser Arg Asp Asn Ile Leu Cys Lys
                565                 570                 575

Ile Thr Tyr Val Ala Asn Val Asn Pro Gly Gly Trp Ala Pro Ala Ser
                580                 585                 590

Val Leu Arg Ala Val Ala Lys Arg Glu Tyr Pro Lys Phe Leu Lys Arg
    595                 600                 605

Phe Thr Ser Tyr Val Gln Glu Lys Thr Ala Gly Lys Pro Ile Leu Phe
    610                 615                 620

<210> SEQ ID NO 7
<211> LENGTH: 2187
<212> TYPE: DNA
<213> ORGANISM: Artificial Sequence
<220> FEATURE:
<223> OTHER INFORMATION: Description of Artificial Sequence: Human
      GPBP26
<220> FEATURE:
<221> NAME/KEY: CDS
<222> LOCATION: (391)..(2184)

<400> SEQUENCE: 7
tagcggaggt gtgagtggac gcgggactca gcggccggat tttctcttcc cttcttttcc      60
cttttccttc cctatttgaa attggcatcg aggggctaa  gttcgggtgg cagcgccggg     120
cgcaacgcag gggtcacggc gacggcggcg gcggctgacg gctggaaggg taggcttcat     180
tcaccgctcg tcctccttcc tcgctccgct cggtgtcagg cgcggcggcg gcgcggcggg     240
cggacttcgt ccctcctcct gctcccccc  acaccggagc gggcactctt cgcttcgcca     300
tcccccgacc cttcaccccg aggactgggc gcctcctccg gcgcagctga gggagcgggg     360
gccggtctcc tgctcggttg tcgagcctcc atg tcg gat aat cag agc tgg aac     414
                                 Met Ser Asp Asn Gln Ser Trp Asn
                                  1                   5
```

-continued

| | | |
|---|---|---|
| tcg tcg ggc tcg gag gag gat cca gag acg gag tct ggg ccg cct gtg<br>Ser Ser Gly Ser Glu Glu Asp Pro Glu Thr Glu Ser Gly Pro Pro Val<br>10                       15                      20 | 462 |
| gag cgc tgc ggg gtc ctc agt aag tgg aca aac tac att cat ggg tgg<br>Glu Arg Cys Gly Val Leu Ser Lys Trp Thr Asn Tyr Ile His Gly Trp<br>25                       30                      35                      40 | 510 |
| cag gat cgt tgg gta gtt ttg aaa aat aat gct ctg agt tac tac aaa<br>Gln Asp Arg Trp Val Val Leu Lys Asn Asn Ala Leu Ser Tyr Tyr Lys<br>                 45                      50                      55 | 558 |
| tct gaa gat gaa aca gag tat ggc tgc aga gga tcc atc tgt ctt agc<br>Ser Glu Asp Glu Thr Glu Tyr Gly Cys Arg Gly Ser Ile Cys Leu Ser<br>                    60                      65                      70 | 606 |
| aag gct gtc atc aca cct cac gat ttt gat gaa tgt cga ttt gat att<br>Lys Ala Val Ile Thr Pro His Asp Phe Asp Glu Cys Arg Phe Asp Ile<br>75                       80                      85 | 654 |
| agt gta aat gat agt gtt tgg tat ctt cgt gct cag gat cca gat cat<br>Ser Val Asn Asp Ser Val Trp Tyr Leu Arg Ala Gln Asp Pro Asp His<br>90                       95                      100 | 702 |
| aga cag caa tgg ata gat gcc att gaa cag cac aag act gaa tct gga<br>Arg Gln Gln Trp Ile Asp Ala Ile Glu Gln His Lys Thr Glu Ser Gly<br>105                     110                    115                    120 | 750 |
| tat gga tct gaa tcc agc ttg cgt cga cat ggc tca atg gtg tcc ctg<br>Tyr Gly Ser Glu Ser Ser Leu Arg Arg His Gly Ser Met Val Ser Leu<br>                   125                    130                    135 | 798 |
| gtg tct gga gca agt ggc tac tct gca aca tcc acc tct tca ttc aag<br>Val Ser Gly Ala Ser Gly Tyr Ser Ala Thr Ser Thr Ser Ser Phe Lys<br>               140                    145                    150 | 846 |
| aaa ggc cac agt tta cgt gag aag ttg gct gaa atg gaa aca ttt aga<br>Lys Gly His Ser Leu Arg Glu Lys Leu Ala Glu Met Glu Thr Phe Arg<br>            155                    160                    165 | 894 |
| gac atc tta tgt aga caa gtt gac acg cta cag aag tac ttt gat gcc<br>Asp Ile Leu Cys Arg Gln Val Asp Thr Leu Gln Lys Tyr Phe Asp Ala<br>170                     175                    180 | 942 |
| tgt gct gat gct gtc tct aag gat gaa ctt caa agg gat aaa gtg gta<br>Cys Ala Asp Ala Val Ser Lys Asp Glu Leu Gln Arg Asp Lys Val Val<br>185                     190                    195                    200 | 990 |
| gaa gat gat gaa gat gac ttt cct aca acg cgt tct gat ggt gac ttc<br>Glu Asp Asp Glu Asp Asp Phe Pro Thr Thr Arg Ser Asp Gly Asp Phe<br>               205                    210                    215 | 1038 |
| ttg cat agt acc aac ggc aat aaa gaa aag tta ttt cca cat gtg aca<br>Leu His Ser Thr Asn Gly Asn Lys Glu Lys Leu Phe Pro His Val Thr<br>            220                    225                    230 | 1086 |
| cca aaa gga att aat ggt ata gac ttt aaa ggg gaa gcg ata act ttt<br>Pro Lys Gly Ile Asn Gly Ile Asp Phe Lys Gly Glu Ala Ile Thr Phe<br>235                     240                    245 | 1134 |
| aaa gca act act gct gga atc ctt gca aca ctt tct cat tgt att gaa<br>Lys Ala Thr Thr Ala Gly Ile Leu Ala Thr Leu Ser His Cys Ile Glu<br>250                     255                    260 | 1182 |
| cta atg gtt aaa cgt gag gac agc tgg cag aag aga ctg gat aag gaa<br>Leu Met Val Lys Arg Glu Asp Ser Trp Gln Lys Arg Leu Asp Lys Glu<br>265                     270                    275                    280 | 1230 |
| act gag aag aaa aga aga aca gag gaa gca tat aaa aat gca atg aca<br>Thr Glu Lys Lys Arg Arg Thr Glu Glu Ala Tyr Lys Asn Ala Met Thr<br>               285                    290                    295 | 1278 |
| gaa ctt aag aaa aaa tcc cac ttt gga gga cca gat tat gaa gaa ggc<br>Glu Leu Lys Lys Lys Ser His Phe Gly Gly Pro Asp Tyr Glu Glu Gly<br>            300                    305                    310 | 1326 |
| cct aac agt ctg att aat gaa gaa gag ttc ttt gat gct gtt gaa gct<br>Pro Asn Ser Leu Ile Asn Glu Glu Glu Phe Phe Asp Ala Val Glu Ala<br>315                     320                    325 | 1374 |

-continued

```
gct ctt gac aga caa gat aaa ata gaa gaa cag tca cag agt gaa aag       1422
Ala Leu Asp Arg Gln Asp Lys Ile Glu Glu Gln Ser Gln Ser Glu Lys
    330                 335                 340 gtg aga tta cat tgg cct aca tcc ttg ccc tct gga gat gcc ttt tct       1470
Val Arg Leu His Trp Pro Thr Ser Leu Pro Ser Gly Asp Ala Phe Ser
345                 350                 355                 360 tct gtg ggg aca cat aga ttt gtc caa aag gtt gaa gag atg gtg cag       1518
Ser Val Gly Thr His Arg Phe Val Gln Lys Val Glu Glu Met Val Gln
                365                 370                 375 aac cac atg act tac tca tta cag gat gta ggc gga gat gcc aat tgg       1566
Asn His Met Thr Tyr Ser Leu Gln Asp Val Gly Gly Asp Ala Asn Trp
            380                 385                 390 cag ttg gtt gta gaa gaa gga gaa atg aag gta tac aga aga gaa gta       1614
Gln Leu Val Val Glu Glu Gly Glu Met Lys Val Tyr Arg Arg Glu Val
        395                 400                 405 gaa gaa aat ggg att gtt ctg gat cct tta aaa gct acc cat gca gtt       1662
Glu Glu Asn Gly Ile Val Leu Asp Pro Leu Lys Ala Thr His Ala Val
    410                 415                 420 aaa ggc gtc aca gga cat gaa gtc tgc aat tat ttc tgg aat gtt gac       1710
Lys Gly Val Thr Gly His Glu Val Cys Asn Tyr Phe Trp Asn Val Asp
425                 430                 435                 440 gtt cgc aat gac tgg gaa aca act ata gaa aac ttt cat gtg gtg gaa       1758
Val Arg Asn Asp Trp Glu Thr Thr Ile Glu Asn Phe His Val Val Glu
                445                 450                 455 aca tta gct gat aat gca atc atc att tat caa aca cac aag agg gtg       1806
Thr Leu Ala Asp Asn Ala Ile Ile Ile Tyr Gln Thr His Lys Arg Val
            460                 465                 470 tgg cct gct tct cag cga gac gta tta tat ctt tct gtc att cga aag       1854
Trp Pro Ala Ser Gln Arg Asp Val Leu Tyr Leu Ser Val Ile Arg Lys
        475                 480                 485 ata cca gcc ttg act gaa aat gac cct gaa act tgg ata gtt tgt aat       1902
Ile Pro Ala Leu Thr Glu Asn Asp Pro Glu Thr Trp Ile Val Cys Asn
    490                 495                 500 ttt tct gtg gat cat gac agt gct cct cta aac aac cga tgt gtc cgt       1950
Phe Ser Val Asp His Asp Ser Ala Pro Leu Asn Asn Arg Cys Val Arg
505                 510                 515                 520 gcc aaa ata aat gtt gct atg att tgt caa acc ttg gta agc cca cca       1998
Ala Lys Ile Asn Val Ala Met Ile Cys Gln Thr Leu Val Ser Pro Pro
                525                 530                 535 gag gga aac cag gaa att agc agg gac aac att cta tgc aag att aca       2046
Glu Gly Asn Gln Glu Ile Ser Arg Asp Asn Ile Leu Cys Lys Ile Thr
            540                 545                 550 tat gta gct aat gtg aac cct gga gga tgg gca cca gcc tca gtg tta       2094
Tyr Val Ala Asn Val Asn Pro Gly Gly Trp Ala Pro Ala Ser Val Leu
        555                 560                 565 agg gca gtg gca aag cga gag tat cct aaa ttt cta aaa cgt ttt act       2142
Arg Ala Val Ala Lys Arg Glu Tyr Pro Lys Phe Leu Lys Arg Phe Thr
    570                 575                 580 tct tac gtc caa gaa aaa act gca gga aag cct att ttg ttc tag           2187
Ser Tyr Val Gln Glu Lys Thr Ala Gly Lys Pro Ile Leu Phe
585                 590                 595

<210> SEQ ID NO 8
<211> LENGTH: 598
<212> TYPE: PRT
<213> ORGANISM: Artificial Sequence
<220> FEATURE:
<223> OTHER INFORMATION: Description of Artificial Sequence: Human
      GPBP26

<400> SEQUENCE: 8
```

```
Met Ser Asp Asn Gln Ser Trp Asn Ser Gly Ser Glu Glu Asp Pro
 1               5                  10                  15

Glu Thr Glu Ser Gly Pro Pro Val Glu Arg Cys Gly Val Leu Ser Lys
             20                  25                  30

Trp Thr Asn Tyr Ile His Gly Trp Gln Asp Arg Trp Val Val Leu Lys
             35                  40                  45

Asn Asn Ala Leu Ser Tyr Tyr Lys Ser Glu Asp Glu Thr Glu Tyr Gly
 50                  55                  60

Cys Arg Gly Ser Ile Cys Leu Ser Lys Ala Val Ile Thr Pro His Asp
 65                  70                  75                  80

Phe Asp Glu Cys Arg Phe Asp Ile Ser Val Asn Asp Ser Val Trp Tyr
                 85                  90                  95

Leu Arg Ala Gln Asp Pro Asp His Arg Gln Gln Trp Ile Asp Ala Ile
             100                 105                 110

Glu Gln His Lys Thr Glu Ser Gly Tyr Gly Ser Glu Ser Ser Leu Arg
             115                 120                 125

Arg His Gly Ser Met Val Ser Leu Val Ser Gly Ala Ser Gly Tyr Ser
 130                 135                 140

Ala Thr Ser Thr Ser Ser Phe Lys Lys Gly His Ser Leu Arg Glu Lys
145                 150                 155                 160

Leu Ala Glu Met Glu Thr Phe Arg Asp Ile Leu Cys Arg Gln Val Asp
                 165                 170                 175

Thr Leu Gln Lys Tyr Phe Asp Ala Cys Ala Asp Ala Val Ser Lys Asp
             180                 185                 190

Glu Leu Gln Arg Asp Lys Val Val Glu Asp Asp Glu Asp Phe Pro
             195                 200                 205

Thr Thr Arg Ser Asp Gly Asp Phe Leu His Ser Thr Asn Gly Asn Lys
             210                 215                 220

Glu Lys Leu Phe Pro His Val Thr Pro Lys Gly Ile Asn Gly Ile Asp
225                 230                 235                 240

Phe Lys Gly Glu Ala Ile Thr Phe Lys Ala Thr Thr Ala Gly Ile Leu
                 245                 250                 255

Ala Thr Leu Ser His Cys Ile Glu Leu Met Val Lys Arg Glu Asp Ser
             260                 265                 270

Trp Gln Lys Arg Leu Asp Lys Thr Glu Lys Lys Arg Arg Thr Glu
             275                 280                 285

Glu Ala Tyr Lys Asn Ala Met Thr Glu Leu Lys Lys Lys Ser His Phe
290                 295                 300

Gly Gly Pro Asp Tyr Glu Glu Gly Pro Asn Ser Leu Ile Asn Glu Glu
305                 310                 315                 320

Glu Phe Phe Asp Ala Val Glu Ala Ala Leu Asp Arg Gln Asp Lys Ile
                 325                 330                 335

Glu Glu Gln Ser Gln Ser Glu Lys Val Arg Leu His Trp Pro Thr Ser
             340                 345                 350

Leu Pro Ser Gly Asp Ala Phe Ser Ser Val Gly Thr His Arg Phe Val
             355                 360                 365

Gln Lys Val Glu Glu Met Val Gln Asn His Met Thr Tyr Ser Leu Gln
             370                 375                 380

Asp Val Gly Gly Asp Ala Asn Trp Gln Leu Val Val Glu Glu Gly Glu
385                 390                 395                 400

Met Lys Val Tyr Arg Arg Glu Val Glu Glu Asn Gly Ile Val Leu Asp
                 405                 410                 415
```

```
Pro Leu Lys Ala Thr His Ala Val Lys Gly Val Thr Gly His Glu Val
        420                 425                 430

Cys Asn Tyr Phe Trp Asn Val Asp Val Arg Asn Asp Trp Glu Thr Thr
        435                 440                 445

Ile Glu Asn Phe His Val Val Glu Thr Leu Ala Asp Asn Ala Ile Ile
        450                 455                 460

Ile Tyr Gln Thr His Lys Arg Val Trp Pro Ala Ser Gln Arg Asp Val
465                 470                 475                 480

Leu Tyr Leu Ser Val Ile Arg Lys Ile Pro Ala Leu Thr Glu Asn Asp
                485                 490                 495

Pro Glu Thr Trp Ile Val Cys Asn Phe Ser Val Asp His Asp Ser Ala
        500                 505                 510

Pro Leu Asn Asn Arg Cys Val Arg Ala Lys Ile Asn Val Ala Met Ile
        515                 520                 525

Cys Gln Thr Leu Val Ser Pro Pro Glu Gly Asn Gln Glu Ile Ser Arg
        530                 535                 540

Asp Asn Ile Leu Cys Lys Ile Thr Tyr Val Ala Asn Val Asn Pro Gly
545                 550                 555                 560

Gly Trp Ala Pro Ala Ser Val Leu Arg Ala Val Ala Lys Arg Glu Tyr
                565                 570                 575

Pro Lys Phe Leu Lys Arg Phe Thr Ser Tyr Val Gln Glu Lys Thr Ala
        580                 585                 590

Gly Lys Pro Ile Leu Phe
        595

<210> SEQ ID NO 9
<211> LENGTH: 2684
<212> TYPE: DNA
<213> ORGANISM: Artificial Sequence
<220> FEATURE:
<223> OTHER INFORMATION: Description of Artificial Sequence: Murine
      GPBP26
<220> FEATURE:
<221> NAME/KEY: CDS
<222> LOCATION: (444)..(2237)

<400> SEQUENCE: 9
cgggccacca cgtgtaaata gtatcggacc cggcaggaag atggcggctg tagcggaggt      60
gtgagtgagt ggatctgggt ctctgccgtt ggcttggctc ttcccgtctt cctcccctcc    120
tccctccctg actgaggttg gcatctaggg ggccgagttc aggtggcggc gccgggcgca    180 gcgcagggt cacggccacg gcggctgacg gctggaaggg caggctttct tcgccgctcg    240
tcctccttcc ccggtccgct cggtgtcagg cgcggcggcg gcggcgcggc gggcgcgctt    300
cgtccctctt cctgttccct cactccccgg agcgggctct cttggcggtg ccatcccccg    360 accccttcacc ccagggacta ggcgcctgca ctggcgcagc tcgcggagcg ggggccggtc    420
tcctgctcgg ctgtcgcgtc tcc atg tcg gat aac cag agc tgg aac tcg tcg      473
                        Met Ser Asp Asn Gln Ser Trp Asn Ser Ser
                          1               5                  10 ggc tcg gag gag gat ccg gag acg gag tcc ggg ccg cct gtg gag cgc      521
Gly Ser Glu Glu Asp Pro Glu Thr Glu Ser Gly Pro Pro Val Glu Arg
                 15                  20                  25 tgc ggg gtc ctc agc aag tgg aca aac tat att cat gga tgg cag gat      569
Cys Gly Val Leu Ser Lys Trp Thr Asn Tyr Ile His Gly Trp Gln Asp
             30                  35                  40 cgt tgg gta gtt ttg aaa aat aat act ttg agt tac tac aaa tct gaa      617
Arg Trp Val Val Leu Lys Asn Asn Thr Leu Ser Tyr Tyr Lys Ser Glu
 45                  50                  55
```

-continued

| | |
|---|---|
| gat gaa aca gaa tat ggc tgt agg gga tcc atc tgt ctt agc aag gct<br>Asp Glu Thr Glu Tyr Gly Cys Arg Gly Ser Ile Cys Leu Ser Lys Ala<br>60                          65                   70 | 665 |
| gtg atc acg cct cac gat ttt gat gaa tgc cgg ttt gat atc agt gta<br>Val Ile Thr Pro His Asp Phe Asp Glu Cys Arg Phe Asp Ile Ser Val<br>75                     80                    85                    90 | 713 |
| aat gat agt gtt tgg tac ctt cga gct cag gac ccg gag cac aga cag<br>Asn Asp Ser Val Trp Tyr Leu Arg Ala Gln Asp Pro Glu His Arg Gln<br>                95                         100                    105 | 761 |
| caa tgg gta gac gcc att gaa cag cac aag act gaa tcg gga tat gga<br>Gln Trp Val Asp Ala Ile Glu Gln His Lys Thr Glu Ser Gly Tyr Gly<br>            110                      115                    120 | 809 |
| tct gag tcc agc ttg cgt aga cat ggc tca atg gtg tca ctg gtg tct<br>Ser Glu Ser Ser Leu Arg Arg His Gly Ser Met Val Ser Leu Val Ser<br>                125                    130                    135 | 857 |
| gga gcg agt ggc tat tct gct acg tcc acc tct tct ttc aag aaa ggc<br>Gly Ala Ser Gly Tyr Ser Ala Thr Ser Thr Ser Ser Phe Lys Lys Gly<br>140                       145                    150 | 905 |
| cac agt tta cgt gag aaa ctg gct gaa atg gag aca ttt cgg gac atc<br>His Ser Leu Arg Glu Lys Leu Ala Glu Met Glu Thr Phe Arg Asp Ile<br>155                     160                    165                   170 | 953 |
| ctg tgc cgg cag gtt gat act ctc cag aag tac ttt gat gtc tgt gct<br>Leu Cys Arg Gln Val Asp Thr Leu Gln Lys Tyr Phe Asp Val Cys Ala<br>                    175                    180                    185 | 1001 |
| gac gct gtc tcc aag gat gag ctt cag agg gat aaa gtc gta gaa gat<br>Asp Ala Val Ser Lys Asp Glu Leu Gln Arg Asp Lys Val Val Glu Asp<br>            190                      195                    200 | 1049 |
| gat gaa gat gac ttc cct aca act cgt tct gat gga gac ttt ttg cac<br>Asp Glu Asp Asp Phe Pro Thr Thr Arg Ser Asp Gly Asp Phe Leu His<br>205                       210                    215 | 1097 |
| aat acc aat ggt aat aaa gaa aaa tta ttt cca cat gta aca cca aaa<br>Asn Thr Asn Gly Asn Lys Glu Lys Leu Phe Pro His Val Thr Pro Lys<br>220                       225                    230 | 1145 |
| gga att aat ggc ata gac ttt aaa ggg gaa gca ata act ttt aaa gca<br>Gly Ile Asn Gly Ile Asp Phe Lys Gly Glu Ala Ile Thr Phe Lys Ala<br>235                       240                    245                    250 | 1193 |
| act act gct gga atc ctt gct aca ctt tct cat tgt att gaa tta atg<br>Thr Thr Ala Gly Ile Leu Ala Thr Leu Ser His Cys Ile Glu Leu Met<br>                    255                    260                    265 | 1241 |
| gta aaa cgg gaa gag agc tgg caa aaa aga cac gat agg gaa gtg gaa<br>Val Lys Arg Glu Glu Ser Trp Gln Lys Arg His Asp Arg Glu Val Glu<br>            270                      275                    280 | 1289 |
| aag agg aga cga gtg gag gaa gcg tac aag aat gtg atg gaa gaa ctt<br>Lys Arg Arg Arg Val Glu Glu Ala Tyr Lys Asn Val Met Glu Glu Leu<br>285                       290                    295 | 1337 |
| aag aag aaa ccc cgt ttc gga ggg ccg gat tat gaa gaa ggt cca aac<br>Lys Lys Lys Pro Arg Phe Gly Gly Pro Asp Tyr Glu Glu Gly Pro Asn<br>300                       305                    310 | 1385 |
| agt ctg att aat gag gaa gag ttc ttt gat gct gtt gaa gct gct ctt<br>Ser Leu Ile Asn Glu Glu Glu Phe Phe Asp Ala Val Glu Ala Ala Leu<br>315                       320                    325                    330 | 1433 |
| gac aga caa gat aaa ata gag gaa cag tca cag agt gaa aag gtc agg<br>Asp Arg Gln Asp Lys Ile Glu Glu Gln Ser Gln Ser Glu Lys Val Arg<br>                    335                    340                    345 | 1481 |
| tta cac tgg ccc aca tca ttg cca tct gga gac acc ttt tct tct gtc<br>Leu His Trp Pro Thr Ser Leu Pro Ser Gly Asp Thr Phe Ser Ser Val<br>            350                      355                    360 | 1529 |
| ggg acg cat aga ttt gta caa aag gtt gaa gaa atg gta cag aac cac<br>Gly Thr His Arg Phe Val Gln Lys Val Glu Glu Met Val Gln Asn His | 1577 |

```
                365                 370                 375
atg aac tat tca tta cag gat gta ggt ggt gat gca aat tgg caa ctg         1625
Met Asn Tyr Ser Leu Gln Asp Val Gly Gly Asp Ala Asn Trp Gln Leu
        380                 385                 390 gtt gtt gaa gaa gga gaa atg aag gta tac aga aga gaa gtg gaa gaa         1673
Val Val Glu Glu Gly Glu Met Lys Val Tyr Arg Arg Glu Val Glu Glu
395                 400                 405                 410 aat gga att gtt ctg gat cct ttg aaa gct act cat gca gtt aaa ggt         1721
Asn Gly Ile Val Leu Asp Pro Leu Lys Ala Thr His Ala Val Lys Gly
                415                 420                 425 gtt aca gga cat gag gtc tgc aat tac ttt tgg aat gtt gat gtt cgc         1769
Val Thr Gly His Glu Val Cys Asn Tyr Phe Trp Asn Val Asp Val Arg
            430                 435                 440 aat gac tgg gaa act act ata gaa aac ttt cat gtg gtg gaa aca tta         1817
Asn Asp Trp Glu Thr Thr Ile Glu Asn Phe His Val Val Glu Thr Leu
        445                 450                 455 gct gat aat gca atc atc gtt tat caa acg cac aag aga gta tgg ccc         1865
Ala Asp Asn Ala Ile Ile Val Tyr Gln Thr His Lys Arg Val Trp Pro
    460                 465                 470 gct tct cag aga gac gta ctg tat ctt tct gct att cga aag atc cca         1913
Ala Ser Gln Arg Asp Val Leu Tyr Leu Ser Ala Ile Arg Lys Ile Pro
475                 480                 485                 490 gcc ttg act gaa aat gat cct gaa act tgg ata gtt tgt aat ttt tct         1961
Ala Leu Thr Glu Asn Asp Pro Glu Thr Trp Ile Val Cys Asn Phe Ser
                495                 500                 505 gtg gat cat gat agt gct cct ctg aac aat cga tgt gtc cgt gcc aaa         2009
Val Asp His Asp Ser Ala Pro Leu Asn Asn Arg Cys Val Arg Ala Lys
            510                 515                 520 atc aat att gct atg att tgt caa act tta gta agc cca cca gag gga         2057
Ile Asn Ile Ala Met Ile Cys Gln Thr Leu Val Ser Pro Pro Glu Gly
        525                 530                 535 gac cag gag ata agc aga gac aac att ctg tgc aag atc acg tat gta         2105
Asp Gln Glu Ile Ser Arg Asp Asn Ile Leu Cys Lys Ile Thr Tyr Val
    540                 545                 550 gct aat gtg aac cca gga gga tgg gcg cca gct tcg gtc tta aga gca         2153
Ala Asn Val Asn Pro Gly Gly Trp Ala Pro Ala Ser Val Leu Arg Ala
555                 560                 565                 570 gtg gca aag cga gaa tac cct aag ttt cta aaa cgt ttt act tct tat         2201
Val Ala Lys Arg Glu Tyr Pro Lys Phe Leu Lys Arg Phe Thr Ser Tyr
                575                 580                 585 gtc caa gaa aaa act gca gga aaa cca att ttg ttt tagtattaac              2247
Val Gln Glu Lys Thr Ala Gly Lys Pro Ile Leu Phe
            590                 595 agtgactgaa gcaaggctgc gtgacgttcc atgttggaga aaggagggaa aaaataaaaa       2307
gaatcctcta agctggaacg taggatctac agccttgtct gtggcccaag aagaaacatt       2367
gcaatcgtaa agctgggtat ccagcactag ccatctcctg ctaggcctcc tcgctcagcg       2427
tgtaactata aatacatgta gaatcacatg gatatggcta tattttattt tgcttgctcc       2487
ttggagtgaa aacaaataac tttgaattac aactaggaat taaccgatgc tttaattttg       2547
aggaactttt tcagaatttt ttatttacca tggtccaacc taagatcctc agttgtatca       2607 agttttgtg cacaaaagaa aagcacaaaa gttgaacgca cctgaaggca tgtgctctct        2667
gtgcaacaaa tactcag                                                      2684

<210> SEQ ID NO 10
<211> LENGTH: 598
<212> TYPE: PRT
<213> ORGANISM: Artificial Sequence
```

```
<220> FEATURE:
<223> OTHER INFORMATION: Description of Artificial Sequence: Murine
      GPBP26

<400> SEQUENCE: 10

Met Ser Asp Asn Gln Ser Trp Asn Ser Ser Gly Ser Glu Glu Asp Pro
  1               5                  10                  15

Glu Thr Glu Ser Gly Pro Pro Val Glu Arg Cys Gly Val Leu Ser Lys
             20                  25                  30

Trp Thr Asn Tyr Ile His Gly Trp Gln Asp Arg Trp Val Val Leu Lys
         35                  40                  45

Asn Asn Thr Leu Ser Tyr Tyr Lys Ser Glu Asp Thr Glu Tyr Gly
     50                  55                  60

Cys Arg Gly Ser Ile Cys Leu Ser Lys Ala Val Ile Thr Pro His Asp
 65                  70                  75                  80

Phe Asp Glu Cys Arg Phe Asp Ile Ser Val Asn Asp Ser Val Trp Tyr
                 85                  90                  95

Leu Arg Ala Gln Asp Pro Glu His Arg Gln Gln Trp Val Asp Ala Ile
            100                 105                 110

Glu Gln His Lys Thr Glu Ser Gly Tyr Gly Ser Glu Ser Ser Leu Arg
            115                 120                 125

Arg His Gly Ser Met Val Ser Leu Val Ser Gly Ala Ser Gly Tyr Ser
        130                 135                 140

Ala Thr Ser Thr Ser Ser Phe Lys Lys Gly His Ser Leu Arg Glu Lys
145                 150                 155                 160

Leu Ala Glu Met Glu Thr Phe Arg Asp Ile Leu Cys Arg Gln Val Asp
                165                 170                 175

Thr Leu Gln Lys Tyr Phe Asp Val Cys Ala Asp Ala Val Ser Lys Asp
            180                 185                 190

Glu Leu Gln Arg Asp Lys Val Val Glu Asp Asp Glu Asp Phe Pro
            195                 200                 205

Thr Thr Arg Ser Asp Gly Asp Phe Leu His Asn Thr Asn Gly Asn Lys
        210                 215                 220

Glu Lys Leu Phe Pro His Val Thr Pro Lys Gly Ile Asn Gly Ile Asp
225                 230                 235                 240

Phe Lys Gly Glu Ala Ile Thr Phe Lys Ala Thr Thr Ala Gly Ile Leu
                245                 250                 255

Ala Thr Leu Ser His Cys Ile Glu Leu Met Val Lys Arg Glu Glu Ser
            260                 265                 270

Trp Gln Lys Arg His Asp Arg Glu Val Glu Lys Arg Arg Val Glu
        275                 280                 285

Glu Ala Tyr Lys Asn Val Met Glu Glu Leu Lys Lys Pro Arg Phe
    290                 295                 300

Gly Gly Pro Asp Tyr Glu Glu Gly Pro Asn Ser Leu Ile Asn Glu Glu
305                 310                 315                 320

Glu Phe Phe Asp Ala Val Glu Ala Ala Leu Asp Arg Gln Asp Lys Ile
                325                 330                 335

Glu Glu Gln Ser Gln Ser Glu Lys Val Arg Leu His Trp Pro Thr Ser
            340                 345                 350

Leu Pro Ser Gly Asp Thr Phe Ser Ser Val Gly Thr His Arg Phe Val
        355                 360                 365

Gln Lys Val Glu Glu Met Val Gln Asn His Met Asn Tyr Ser Leu Gln
    370                 375                 380

Asp Val Gly Gly Asp Ala Asn Trp Gln Leu Val Val Glu Glu Gly Glu
```

-continued

```
                385                 390                 395                 400
Met Lys Val Tyr Arg Arg Glu Val Glu Glu Asn Gly Ile Val Leu Asp
                    405                 410                 415

Pro Leu Lys Ala Thr His Ala Val Lys Gly Val Thr Gly His Glu Val
                420                 425                 430

Cys Asn Tyr Phe Trp Asn Val Asp Val Arg Asn Asp Trp Glu Thr Thr
                435                 440                 445

Ile Glu Asn Phe His Val Val Glu Thr Leu Ala Asp Asn Ala Ile Ile
            450                 455                 460

Val Tyr Gln Thr His Lys Arg Val Trp Pro Ser Gln Arg Asp Val
465                 470                 475                 480

Leu Tyr Leu Ser Ala Ile Arg Lys Ile Pro Ala Leu Thr Glu Asn Asp
                485                 490                 495

Pro Glu Thr Trp Ile Val Cys Asn Phe Ser Val Asp His Asp Ser Ala
            500                 505                 510

Pro Leu Asn Asn Arg Cys Val Arg Ala Lys Ile Asn Ile Ala Met Ile
            515                 520                 525

Cys Gln Thr Leu Val Ser Pro Pro Glu Gly Asp Gln Glu Ile Ser Arg
        530                 535                 540

Asp Asn Ile Leu Cys Lys Ile Thr Tyr Val Ala Asn Val Asn Pro Gly
545                 550                 555                 560

Gly Trp Ala Pro Ala Ser Val Leu Arg Ala Val Ala Lys Arg Glu Tyr
                565                 570                 575

Pro Lys Phe Leu Lys Arg Phe Ser Tyr Val Gln Glu Lys Thr Ala
                580                 585                 590

Gly Lys Pro Ile Leu Phe
        595
```

<210> SEQ ID NO 11
<211> LENGTH: 2283
<212> TYPE: DNA
<213> ORGANISM: Artificial Sequence
<220> FEATURE:
<223> OTHER INFORMATION: Description of Artificial Sequence: Bovine GPBP26
<220> FEATURE:
<221> NAME/KEY: CDS
<222> LOCATION: (421)..(2214)

<400> SEQUENCE: 11

```
cggcaggaag atggcggcct agcggaggtg tgagtggacc tgggtctctg cagctgggtt    60
ttccctcttc ccgtctttct cctctttccc tctccccga ggttggcatc gaggggggcca   120 aattcgggcg gcggcgccgg gcgcagcgca ggggtcacaa cgacggcgac ggctgacggt   180
tggaagggca ggcttccttc gcccctcgac ctccttcccc ggtccgcttg tgtcaggcg   240 cggcggcggc ggcggcggcg gcgcggcggg cggactccat ccctcctccc gctccctcct   300
gcaccggagc gggcactcct tccttcgcca tcccccgacc cttcacccgg gggactgggc   360
gcctccaccg gcgcagctca gggagcgggg gccggtctcc tgctcggctg tcgcgcctcc   420 atg tcg gat aac cag agc tgg aac tcg tcg ggc tcg gag gag gat ccg    468
Met Ser Asp Asn Gln Ser Trp Asn Ser Ser Gly Ser Glu Glu Asp Pro
1               5                   10                  15 gag acg gag tcc ggg ccg ccg gtg gag cgc tgc gga gtc ctc aac aag    516
Glu Thr Glu Ser Gly Pro Pro Val Glu Arg Cys Gly Val Leu Asn Lys
            20                  25                  30 tgg aca aac tat att cat ggg tgg cag gat cgc tgg gta gtt ttg aaa    564
Trp Thr Asn Tyr Ile His Gly Trp Gln Asp Arg Trp Val Val Leu Lys
```

-continued

```
                     35                  40                  45
aat aac act ctg agt tac tac aaa tct gaa gat gag aca gag tat ggc        612
Asn Asn Thr Leu Ser Tyr Tyr Lys Ser Glu Asp Glu Thr Glu Tyr Gly
         50                  55                  60 tgc aga gga tcc atc tgt ctt agc aag gct gtc atc acg cct cat gat        660
Cys Arg Gly Ser Ile Cys Leu Ser Lys Ala Val Ile Thr Pro His Asp
 65                  70                  75                  80 ttt gat gaa tgc cga ttt gat att agt gta aat gat agt gtt tgg tat        708
Phe Asp Glu Cys Arg Phe Asp Ile Ser Val Asn Asp Ser Val Trp Tyr
                     85                  90                  95 ctt cgt gct caa gat cca gat cac aga cag cag tgg ata gat gcc att        756
Leu Arg Ala Gln Asp Pro Asp His Arg Gln Gln Trp Ile Asp Ala Ile
                100                 105                 110 gaa cag cac aag act gaa tct gga tat gga tct gaa tcc agc ttg cgt        804
Glu Gln His Lys Thr Glu Ser Gly Tyr Gly Ser Glu Ser Ser Leu Arg
            115                 120                 125 cga cat ggc tcc atg gta tca ttg gta tcc gga gca agt ggc tat tct        852
Arg His Gly Ser Met Val Ser Leu Val Ser Gly Ala Ser Gly Tyr Ser
        130                 135                 140 gca aca tcc acc tcc tca ttc aag aag ggc cac agt tta cgt gag aaa        900
Ala Thr Ser Thr Ser Ser Phe Lys Lys Gly His Ser Leu Arg Glu Lys
145                 150                 155                 160 ctg gct gaa atg gaa acc ttt aga gat ata ctg tgt aga caa gtt gat        948
Leu Ala Glu Met Glu Thr Phe Arg Asp Ile Leu Cys Arg Gln Val Asp
                165                 170                 175 acc cta cag aag ttc ttt gat gcc tgt gct gat gct gtc tcc aag gat        996
Thr Leu Gln Lys Phe Phe Asp Ala Cys Ala Asp Ala Val Ser Lys Asp
            180                 185                 190 gaa ttt caa agg gat aaa gtg gta gaa gat gat gaa gat gac ttt cct       1044
Glu Phe Gln Arg Asp Lys Val Val Glu Asp Asp Glu Asp Asp Phe Pro
        195                 200                 205 acg aca cgt tct gat gga gac ttc ttg cat aat acc aat ggc aat aag       1092
Thr Thr Arg Ser Asp Gly Asp Phe Leu His Asn Thr Asn Gly Asn Lys
    210                 215                 220 gaa aag gta ttt cca cat gta aca cca aaa gga att aat ggt ata gac       1140
Glu Lys Val Phe Pro His Val Thr Pro Lys Gly Ile Asn Gly Ile Asp
225                 230                 235                 240 ttt aaa ggt gag gcg ata act ttt aaa gca act act gcc gga atc ctt       1188
Phe Lys Gly Glu Ala Ile Thr Phe Lys Ala Thr Thr Ala Gly Ile Leu
                245                 250                 255 gct aca ctt tct cat tgt att gag ctg atg gta aaa cgt gag gac agc       1236
Ala Thr Leu Ser His Cys Ile Glu Leu Met Val Lys Arg Glu Asp Ser
            260                 265                 270 tgg caa aag aga atg gac aag gaa act gag aag aga aga gtg gag             1284
Trp Gln Lys Arg Met Asp Lys Glu Thr Glu Lys Arg Arg Val Glu
        275                 280                 285 gaa gca tac aaa aat gcc atg aca gaa ctt aag aaa aaa tcc cac ttt       1332
Glu Ala Tyr Lys Asn Ala Met Thr Glu Leu Lys Lys Lys Ser His Phe
    290                 295                 300 gga gga cca gat tat gag gaa ggc cca aac agt ttg att aat gaa gag       1380
Gly Gly Pro Asp Tyr Glu Glu Gly Pro Asn Ser Leu Ile Asn Glu Glu
305                 310                 315                 320 gag ttc ttt gat gct gtt gaa gct gct ctt gac aga caa gat aaa ata       1428
Glu Phe Phe Asp Ala Val Glu Ala Ala Leu Asp Arg Gln Asp Lys Ile
                325                 330                 335 gaa gaa cag tcg cag agt gaa aag gtc agg tta cat tgg tct act tca       1476
Glu Glu Gln Ser Gln Ser Glu Lys Val Arg Leu His Trp Ser Thr Ser
            340                 345                 350 atg cca tct gga gat gcc ttt tct tct gtg ggg act cat aga ttt gtc       1524
```

```
                            -continued

Met Pro Ser Gly Asp Ala Phe Ser Ser Val Gly Thr His Arg Phe Val
            355                 360                 365
caa aag gtt gaa gag atg gtg cag aac cac atg acc tat tca ttg cag      1572
Gln Lys Val Glu Glu Met Val Gln Asn His Met Thr Tyr Ser Leu Gln
    370                 375                 380 gat gta ggt ggg gac gcc aac tgg cag ttg gtt gta gaa gaa ggg gag      1620
Asp Val Gly Gly Asp Ala Asn Trp Gln Leu Val Val Glu Glu Gly Glu
385                 390                 395                 400 atg aag gta tat aga aga gaa gta gaa gaa aat ggg att gtt ctg gat      1668
Met Lys Val Tyr Arg Arg Glu Val Glu Glu Asn Gly Ile Val Leu Asp
                405                 410                 415 cct ttg aaa gct acc cat gca gtt aaa ggc gtt aca gga cac gag gtc      1716
Pro Leu Lys Ala Thr His Ala Val Lys Gly Val Thr Gly His Glu Val
            420                 425                 430 tgc aat tac ttc tgg aat gtt gat gtt cgc aat gat tgg gaa aca act      1764
Cys Asn Tyr Phe Trp Asn Val Asp Val Arg Asn Asp Trp Glu Thr Thr
        435                 440                 445 ata gaa aac ttt cat gtg gtg gaa aca tta gct gat aat gca atc atc      1812
Ile Glu Asn Phe His Val Val Glu Thr Leu Ala Asp Asn Ala Ile Ile
    450                 455                 460 att tat caa acg cac aag aga gtg tgg cca gcc tct cag cgg gat gtc      1860
Ile Tyr Gln Thr His Lys Arg Val Trp Pro Ala Ser Gln Arg Asp Val
465                 470                 475                 480 tta tat ctg tct gcc att cga aag ata cca gct ttg aat gaa aat gac      1908
Leu Tyr Leu Ser Ala Ile Arg Lys Ile Pro Ala Leu Asn Glu Asn Asp
                485                 490                 495 ccg gag act tgg ata gtt tgt aat ttt tct gta gat cac agc agt gct      1956
Pro Glu Thr Trp Ile Val Cys Asn Phe Ser Val Asp His Ser Ser Ala
            500                 505                 510 cct cta aac aat cga tgt gtc cgt gcc aaa ata aac gtt gct atg att      2004
Pro Leu Asn Asn Arg Cys Val Arg Ala Lys Ile Asn Val Ala Met Ile
        515                 520                 525 tgt cag acc ttg gtg agc ccc cca gag gga aac cag gag att agc agg      2052
Cys Gln Thr Leu Val Ser Pro Pro Glu Gly Asn Gln Glu Ile Ser Arg
    530                 535                 540 gac aac att cta tgc aag att aca tac gtg gcc aat gta aac cct gga      2100
Asp Asn Ile Leu Cys Lys Ile Thr Tyr Val Ala Asn Val Asn Pro Gly
545                 550                 555                 560 gga tgg gcc cca gcc tca gtg tta cgg gca gtg gca aag cga gaa tat      2148
Gly Trp Ala Pro Ala Ser Val Leu Arg Ala Val Ala Lys Arg Glu Tyr
                565                 570                 575 cca aag ttt cta aag cgt ttt act tct tac gta caa gaa aaa act gca      2196
Pro Lys Phe Leu Lys Arg Phe Thr Ser Tyr Val Gln Glu Lys Thr Ala
            580                 585                 590 gga aaa cct att ttg ttc tagtattaac agtgactgaa gcaaggctgt             2244
Gly Lys Pro Ile Leu Phe
            595 gtgacattcc atgttggagg aaaaaaaaaa aaaaaaaa                            2283

<210> SEQ ID NO 12
<211> LENGTH: 598
<212> TYPE: PRT
<213> ORGANISM: Artificial Sequence
<220> FEATURE:
<223> OTHER INFORMATION: Description of Artificial Sequence: Bovine
      GPBP26

<400> SEQUENCE: 12

Met Ser Asp Asn Gln Ser Trp Asn Ser Gly Ser Glu Glu Asp Pro
 1               5                  10                  15

Glu Thr Glu Ser Gly Pro Pro Val Glu Arg Cys Gly Val Leu Asn Lys
```

-continued

```
                20                  25                  30
Trp Thr Asn Tyr Ile His Gly Trp Gln Asp Arg Trp Val Val Leu Lys
         35                  40                  45

Asn Asn Thr Leu Ser Tyr Tyr Lys Ser Glu Asp Glu Thr Glu Tyr Gly
         50                  55                  60

Cys Arg Gly Ser Ile Cys Leu Ser Lys Ala Val Ile Thr Pro His Asp
65                   70                  75                  80

Phe Asp Glu Cys Arg Phe Asp Ile Ser Val Asn Asp Ser Val Trp Tyr
                 85                  90                  95

Leu Arg Ala Gln Asp Pro Asp His Arg Gln Gln Trp Ile Asp Ala Ile
                100                 105                 110

Glu Gln His Lys Thr Glu Ser Gly Tyr Gly Ser Glu Ser Ser Leu Arg
            115                 120                 125

Arg His Gly Ser Met Val Ser Leu Val Ser Gly Ala Ser Gly Tyr Ser
        130                 135                 140

Ala Thr Ser Thr Ser Ser Phe Lys Lys Gly His Ser Leu Arg Glu Lys
145                 150                 155                 160

Leu Ala Glu Met Glu Thr Phe Arg Asp Ile Leu Cys Arg Gln Val Asp
                165                 170                 175

Thr Leu Gln Lys Phe Phe Asp Ala Cys Ala Asp Ala Val Ser Lys Asp
                180                 185                 190

Glu Phe Gln Arg Asp Lys Val Val Glu Asp Asp Glu Asp Asp Phe Pro
            195                 200                 205

Thr Thr Arg Ser Asp Gly Asp Phe Leu His Asn Thr Asn Gly Asn Lys
        210                 215                 220

Glu Lys Val Phe Pro His Val Thr Pro Lys Gly Ile Asn Gly Ile Asp
225                 230                 235                 240

Phe Lys Gly Glu Ala Ile Thr Phe Lys Ala Thr Thr Ala Gly Ile Leu
                245                 250                 255

Ala Thr Leu Ser His Cys Ile Glu Leu Met Val Lys Arg Glu Asp Ser
                260                 265                 270

Trp Gln Lys Arg Met Asp Lys Glu Thr Glu Lys Arg Arg Arg Val Glu
            275                 280                 285

Glu Ala Tyr Lys Asn Ala Met Thr Glu Leu Lys Lys Lys Ser His Phe
        290                 295                 300

Gly Gly Pro Asp Tyr Glu Glu Gly Pro Asn Ser Leu Ile Asn Glu Glu
305                 310                 315                 320

Glu Phe Phe Asp Ala Val Glu Ala Ala Leu Asp Arg Gln Asp Lys Ile
                325                 330                 335

Glu Glu Gln Ser Gln Ser Glu Lys Val Arg Leu His Trp Ser Thr Ser
            340                 345                 350

Met Pro Ser Gly Asp Ala Phe Ser Ser Val Gly Thr His Arg Phe Val
        355                 360                 365

Gln Lys Val Glu Glu Met Val Gln Asn His Met Thr Tyr Ser Leu Gln
        370                 375                 380

Asp Val Gly Gly Asp Ala Asn Trp Gln Leu Val Val Glu Glu Gly Glu
385                 390                 395                 400

Met Lys Val Tyr Arg Arg Glu Val Glu Asn Gly Ile Val Leu Asp
                405                 410                 415

Pro Leu Lys Ala Thr His Ala Val Lys Gly Val Thr Gly His Glu Val
                420                 425                 430

Cys Asn Tyr Phe Trp Asn Val Asp Val Arg Asn Asp Trp Glu Thr Thr
            435                 440                 445
```

```
Ile Glu Asn Phe His Val Val Glu Thr Leu Ala Asp Asn Ala Ile Ile
    450                 455                 460

Ile Tyr Gln Thr His Lys Arg Val Trp Pro Ala Ser Gln Arg Asp Val
465                 470                 475                 480

Leu Tyr Leu Ser Ala Ile Arg Lys Ile Pro Ala Leu Asn Glu Asn Asp
                485                 490                 495

Pro Glu Thr Trp Ile Val Cys Asn Phe Ser Val Asp His Ser Ser Ala
            500                 505                 510

Pro Leu Asn Asn Arg Cys Val Arg Ala Lys Ile Asn Val Ala Met Ile
        515                 520                 525

Cys Gln Thr Leu Val Ser Pro Pro Glu Gly Asn Gln Glu Ile Ser Arg
    530                 535                 540

Asp Asn Ile Leu Cys Lys Ile Thr Tyr Val Ala Asn Val Asn Pro Gly
545                 550                 555                 560

Gly Trp Ala Pro Ala Ser Val Leu Arg Ala Val Ala Lys Arg Glu Tyr
                565                 570                 575

Pro Lys Phe Leu Lys Arg Phe Thr Ser Tyr Val Gln Glu Lys Thr Ala
            580                 585                 590

Gly Lys Pro Ile Leu Phe
        595
```

```
<210> SEQ ID NO 13
<211> LENGTH: 78
<212> TYPE: DNA
<213> ORGANISM: Homo sapiens
<220> FEATURE:
<221> NAME/KEY: CDS
<222> LOCATION: (1)..(78)

<400> SEQUENCE: 13 ccc tat agt cgc tct tcc tcc atg tct tcc att gat cta gtc agt gcc    48
Pro Tyr Ser Arg Ser Ser Ser Met Ser Ser Ile Asp Leu Val Ser Ala
  1               5                  10                  15 tct gat gat gtt cac aga ttc agc tcc cag                            78
Ser Asp Asp Val His Arg Phe Ser Ser Gln
             20                  25

<210> SEQ ID NO 14
<211> LENGTH: 26
<212> TYPE: PRT
<213> ORGANISM: Homo sapiens

<400> SEQUENCE: 14

Pro Tyr Ser Arg Ser Ser Ser Met Ser Ser Ile Asp Leu Val Ser Ala
  1               5                  10                  15

Ser Asp Asp Val His Arg Phe Ser Ser Gln
             20                  25

<210> SEQ ID NO 15
<211> LENGTH: 2034
<212> TYPE: DNA
<213> ORGANISM: Artificial Sequence
<220> FEATURE:
<223> OTHER INFORMATION: Description of Artificial Sequence: GPBPR3
<220> FEATURE:
<221> NAME/KEY: CDS
<222> LOCATION: (10)..(990)

<400> SEQUENCE: 15 gaattcacc atg gcc cca cta gcc gac tac aag gac gac gat gac aag atg    51
          Met Ala Pro Leu Ala Asp Tyr Lys Asp Asp Asp Asp Lys Met
```

```
            1               5                   10
tcg gat aat cag agc tgg aac tcg tcg ggc tcg gag gag gat cca gag       99
Ser Asp Asn Gln Ser Trp Asn Ser Ser Gly Ser Glu Glu Asp Pro Glu
 15              20                  25                  30 acg gag tct ggg ccg cct gtg gag cgc tgc ggg gtc ctc agt aag tgg      147
Thr Glu Ser Gly Pro Pro Val Glu Arg Cys Gly Val Leu Ser Lys Trp
                 35                  40                  45 aca aac tac att cat ggg tgg cag gat cgt tgg gta gtt ttg aaa aat      195
Thr Asn Tyr Ile His Gly Trp Gln Asp Arg Trp Val Val Leu Lys Asn
             50                  55                  60 aat gct ctg agt tac tac aaa tct gaa gat gaa aca gag tat ggc tgc      243
Asn Ala Leu Ser Tyr Tyr Lys Ser Glu Asp Glu Thr Glu Tyr Gly Cys
             65                  70                  75 aga gga tcc atc tgt ctt agc aag gct gtc atc aca cct cac gat ttt      291
Arg Gly Ser Ile Cys Leu Ser Lys Ala Val Ile Thr Pro His Asp Phe
         80                  85                  90 gat gaa tgt cga ttt gat att agt gta aat gat agt gtt tgg tat ctt      339
Asp Glu Cys Arg Phe Asp Ile Ser Val Asn Asp Ser Val Trp Tyr Leu
 95                 100                 105                 110 cgt gct cag gat cca gat cat aga cag caa tgg ata gat gcc att gaa      387
Arg Ala Gln Asp Pro Asp His Arg Gln Gln Trp Ile Asp Ala Ile Glu
                115                 120                 125 cag cac aag act gaa tct gga tat gga tct gaa tcc agc ttg cgt cga      435
Gln His Lys Thr Glu Ser Gly Tyr Gly Ser Glu Ser Ser Leu Arg Arg
            130                 135                 140 cat ggc tca atg gtg tcc ctg gtg tct gga gca agt ggc tac tct gca      483
His Gly Ser Met Val Ser Leu Val Ser Gly Ala Ser Gly Tyr Ser Ala
            145                 150                 155 aca tcc acc tct tca ttc aag aaa ggc cac agt tta cgt gag aag ttg      531
Thr Ser Thr Ser Ser Phe Lys Lys Gly His Ser Leu Arg Glu Lys Leu
        160                 165                 170 gct gaa atg gaa aca ttt aga gac atc tta tgt aga caa gtt gac acg      579
Ala Glu Met Glu Thr Phe Arg Asp Ile Leu Cys Arg Gln Val Asp Thr
175                 180                 185                 190 cta cag aag tac ttt gat gcc tgt gct gat gct gtc tct aag gat gaa      627
Leu Gln Lys Tyr Phe Asp Ala Cys Ala Asp Ala Val Ser Lys Asp Glu
                195                 200                 205 ctt caa agg gat aaa gtg gta gaa gat gat gaa gat gac ttt cct aca      675
Leu Gln Arg Asp Lys Val Val Glu Asp Asp Glu Asp Asp Phe Pro Thr
            210                 215                 220 acg cgt tct gat ggt gac ttc ttg cat agt acc aac ggc aat aaa gaa      723
Thr Arg Ser Asp Gly Asp Phe Leu His Ser Thr Asn Gly Asn Lys Glu
            225                 230                 235 aag tta ttt cca cat gtg aca cca aaa gga att aat ggt ata gac ttt      771
Lys Leu Phe Pro His Val Thr Pro Lys Gly Ile Asn Gly Ile Asp Phe
        240                 245                 250 aaa ggg gaa gcg ata act ttt aaa gca act act gct gga atc ctt gca      819
Lys Gly Glu Ala Ile Thr Phe Lys Ala Thr Thr Ala Gly Ile Leu Ala
255                 260                 265                 270 aca ctt tct cat tgt att gaa cta atg gtt aaa cgt gag gac agc tgg      867
Thr Leu Ser His Cys Ile Glu Leu Met Val Lys Arg Glu Asp Ser Trp
                275                 280                 285 cag aag aga ctg gat aag gaa act gag aag aaa aga aga aca gag gaa      915
Gln Lys Arg Leu Asp Lys Glu Thr Glu Lys Lys Arg Arg Thr Glu Glu
            290                 295                 300 gca tat aaa aat gca atg aca gaa cga aaa aat ccc act ttg gag gac      963
Ala Tyr Lys Asn Ala Met Thr Glu Arg Lys Asn Pro Thr Leu Glu Asp
            305                 310                 315 cag att atg aag aag gcc cta aca gtc tgattaatga agaagagttc           1010
Gln Ile Met Lys Lys Ala Leu Thr Val
```

-continued

```
Gln Ile Met Lys Lys Ala Leu Thr Val
    320             325 tttgatgctg ttgaagctgc tcttgacaga caagataaaa tagaagaaca gtcacagagt    1070
gaaaaggtga gattacattg gcctacatcc ttgccctctg gagatgcctt ttcttctgtg    1130
gggacacata gatttgtcca aaagccctat agtcgctctt cctccatgtc ttccattgat    1190
ctagtcagtg cctctgatga tgttcacaga ttcagctccc aggttgaaga gatggtgcag    1250
aaccacatga cttactcatt acaggatgta ggcggagatg ccaattggca gttggttgta    1310
gaagaaggag aaatgaaggt atacagaaga gaagtagaag aaaatgggat tgttctggat    1370
cctttaaaag ctacccatgc agttaaaggc gtcacaggac atgaagtctg caattatttc    1430
tggaatgttg acgttcgcaa tgactgggaa acaactatag aaaactttca tgtggtggaa    1490
acattagctg ataatgcaat catcatttat caaacacaca gagggtgtg gcctgcttct    1550 cagcgagacg tattatatct ttctgtcatt cgaaagatac cagccttgac tgaaaatgac    1610
cctgaaactt ggatagtttg taattttttct gtggatcatg acagtgctcc tctaaacaac    1670
cgatgtgtcc gtgccaaaat aaatgttgct atgatttgtc aaaccttggt aagcccacca    1730
gagggaaacc aggaaattag cagggacaac attctatgca agattacata tgtagctaat    1790
gtgaaccctg gaggatgggc accagcctca gtgttaaggg cagtggcaaa gcgagagtat    1850
cctaaatttc taaaacgttt tacttcttac gtccaagaaa aaactgcagg aaagcctatt    1910
ttgttctagt attaacaggt actagaagat atgtttatc ttttttttaac tttatttgac    1970 taatatgact gtcaatacta aaatttagtt gttgaaagta tttactatgt tttttccgga    2030
attc                                                                2034
```

<210> SEQ ID NO 16
<211> LENGTH: 327
<212> TYPE: PRT
<213> ORGANISM: Artificial Sequence
<220> FEATURE:
<223> OTHER INFORMATION: Description of Artificial Sequence: GPBPR3

<400> SEQUENCE: 16

```
Met Ala Pro Leu Ala Asp Tyr Lys Asp Asp Asp Lys Met Ser Asp
 1               5                  10                  15

Asn Gln Ser Trp Asn Ser Ser Gly Ser Glu Glu Asp Pro Glu Thr Glu
            20                  25                  30

Ser Gly Pro Pro Val Glu Arg Cys Gly Val Leu Ser Lys Trp Thr Asn
        35                  40                  45

Tyr Ile His Gly Trp Gln Asp Arg Trp Val Val Leu Lys Asn Asn Ala
    50                  55                  60

Leu Ser Tyr Tyr Lys Ser Glu Asp Glu Thr Glu Tyr Gly Cys Arg Gly
65                  70                  75                  80

Ser Ile Cys Leu Ser Lys Ala Val Ile Thr Pro His Asp Phe Asp Glu
                85                  90                  95

Cys Arg Phe Asp Ile Ser Val Asn Asp Ser Val Trp Tyr Leu Arg Ala
            100                 105                 110

Gln Asp Pro Asp His Arg Gln Gln Trp Ile Asp Ala Ile Glu Gln His
        115                 120                 125

Lys Thr Glu Ser Gly Tyr Gly Ser Glu Ser Ser Leu Arg Arg His Gly
    130                 135                 140

Ser Met Val Ser Leu Val Ser Gly Ala Ser Gly Tyr Ser Ala Thr Ser
145                 150                 155                 160
```

```
Thr Ser Ser Phe Lys Lys Gly His Ser Leu Arg Glu Lys Leu Ala Glu
            165                 170                 175

Met Glu Thr Phe Arg Asp Ile Leu Cys Arg Gln Val Asp Thr Leu Gln
            180                 185                 190

Lys Tyr Phe Asp Ala Cys Ala Asp Ala Val Ser Lys Asp Glu Leu Gln
            195                 200                 205

Arg Asp Lys Val Val Glu Asp Glu Asp Phe Pro Thr Thr Arg
    210                 215                 220

Ser Asp Gly Asp Phe Leu His Ser Thr Asn Gly Asn Lys Glu Lys Leu
225                 230                 235                 240

Phe Pro His Val Thr Pro Lys Gly Ile Asn Gly Ile Asp Phe Lys Gly
                245                 250                 255

Glu Ala Ile Thr Phe Lys Ala Thr Thr Ala Gly Ile Leu Ala Thr Leu
                260                 265                 270

Ser His Cys Ile Glu Leu Met Val Lys Arg Glu Asp Ser Trp Gln Lys
            275                 280                 285

Arg Leu Asp Lys Glu Thr Glu Lys Lys Arg Arg Thr Glu Glu Ala Tyr
    290                 295                 300

Lys Asn Ala Met Thr Glu Arg Lys Asn Pro Thr Leu Glu Asp Gln Ile
305                 310                 315                 320

Met Lys Lys Ala Leu Thr Val
                325

<210> SEQ ID NO 17
<211> LENGTH: 1978
<212> TYPE: DNA
<213> ORGANISM: Artificial Sequence
<220> FEATURE:
<223> OTHER INFORMATION: Description of Artificial Sequence:
      FLAG-GPBPDNLS
<220> FEATURE:
<221> NAME/KEY: CDS
<222> LOCATION: (10)..(1860)

<400> SEQUENCE: 17 gaattcacc atg gcc cca cta gcc gac tac aag gac gac gat gac aag atg     51
          Met Ala Pro Leu Ala Asp Tyr Lys Asp Asp Asp Asp Lys Met
           1               5                  10 tcg gat aat cag agc tgg aac tcg tcg ggc tcg gag gag gat cca gag    99
Ser Asp Asn Gln Ser Trp Asn Ser Ser Gly Ser Glu Glu Asp Pro Glu
 15                  20                  25                  30 acg gag tct ggg ccg cct gtg gag cgc tgc ggg gtc ctc agt aag tgg   147
Thr Glu Ser Gly Pro Pro Val Glu Arg Cys Gly Val Leu Ser Lys Trp
                 35                  40                  45 aca aac tac att cat ggg tgg cag gat cgt tgg gta gtt ttg aaa aat   195
Thr Asn Tyr Ile His Gly Trp Gln Asp Arg Trp Val Val Leu Lys Asn
             50                  55                  60 aat gct ctg agt tac tac aaa tct gaa gat gaa aca gag tat ggc tgc   243
Asn Ala Leu Ser Tyr Tyr Lys Ser Glu Asp Glu Thr Glu Tyr Gly Cys
         65                  70                  75 aga gga tcc atc tgt ctt agc aag gct gtc atc aca cct cac gat ttt   291
Arg Gly Ser Ile Cys Leu Ser Lys Ala Val Ile Thr Pro His Asp Phe
     80                  85                  90 gat gaa tgt cga ttt gat att agt gta aat gat agt gtt tgg tat ctt   339
Asp Glu Cys Arg Phe Asp Ile Ser Val Asn Asp Ser Val Trp Tyr Leu
 95                 100                 105                 110 cgt gct cag gat cca gat cat aga cag caa tgg ata gat gcc att gaa   387
Arg Ala Gln Asp Pro Asp His Arg Gln Gln Trp Ile Asp Ala Ile Glu
                115                 120                 125
```

```
                                                    -continued cag cac aag act gaa tct gga tat gga tct gaa tcc agc ttg cgt cga    435
Gln His Lys Thr Glu Ser Gly Tyr Gly Ser Glu Ser Ser Leu Arg Arg
        130                 135                 140 cat ggc tca atg gtg tcc ctg gtg tct gga gca agt ggc tac tct gca    483
His Gly Ser Met Val Ser Leu Val Ser Gly Ala Ser Gly Tyr Ser Ala
            145                 150                 155 aca tcc acc tct tca ttc aag aaa ggc cac agt tta cgt gag aag ttg    531
Thr Ser Thr Ser Ser Phe Lys Lys Gly His Ser Leu Arg Glu Lys Leu
160                 165                 170 gct gaa atg gaa aca ttt aga gac atc tta tgt aga caa gtt gac acg    579
Ala Glu Met Glu Thr Phe Arg Asp Ile Leu Cys Arg Gln Val Asp Thr
175                 180                 185                 190 cta cag aag tac ttt gat gcc tgt gct gat gct gtc tct aag gat gaa    627
Leu Gln Lys Tyr Phe Asp Ala Cys Ala Asp Ala Val Ser Lys Asp Glu
                195                 200                 205 ctt caa agg gat aaa gtg gta gaa gat gat gaa gat gac ttt cct aca    675
Leu Gln Arg Asp Lys Val Val Glu Asp Asp Glu Asp Asp Phe Pro Thr
            210                 215                 220 acg cgt tct gat ggt gac ttc ttg cat agt acc aac ggc aat aaa gaa    723
Thr Arg Ser Asp Gly Asp Phe Leu His Ser Thr Asn Gly Asn Lys Glu
        225                 230                 235 aag tta ttt cca cat gtg aca cca aaa gga att aat ggt ata gac ttt    771
Lys Leu Phe Pro His Val Thr Pro Lys Gly Ile Asn Gly Ile Asp Phe
    240                 245                 250 aaa ggg gaa gcg ata act ttt aaa gca act act gct gga atc ctt gca    819
Lys Gly Glu Ala Ile Thr Phe Lys Ala Thr Thr Ala Gly Ile Leu Ala
255                 260                 265                 270 aca ctt tct cat tgt att gaa cta atg gtt aaa cgt gag gac agc tgg    867
Thr Leu Ser His Cys Ile Glu Leu Met Val Lys Arg Glu Asp Ser Trp
                275                 280                 285 cag aag aga ctg gat aag gaa act gag cac ttt gga gga cca gat tat    915
Gln Lys Arg Leu Asp Lys Glu Thr Glu His Phe Gly Gly Pro Asp Tyr
            290                 295                 300 gaa gaa ggc cct aac agt ctg att aat gaa gaa gag ttc ttt gat gct    963
Glu Glu Gly Pro Asn Ser Leu Ile Asn Glu Glu Glu Phe Phe Asp Ala
        305                 310                 315 gtt gaa gct gct ctt gac aga caa gat aaa ata gaa gaa cag tca cag   1011
Val Glu Ala Ala Leu Asp Arg Gln Asp Lys Ile Glu Glu Gln Ser Gln
    320                 325                 330 agt gaa aag gtg aga tta cat tgg cct aca tcc ttg ccc tct gga gat   1059
Ser Glu Lys Val Arg Leu His Trp Pro Thr Ser Leu Pro Ser Gly Asp
335                 340                 345                 350 gcc ttt tct tct gtg ggg aca cat aga ttt gtc caa aag ccc tat agt   1107
Ala Phe Ser Ser Val Gly Thr His Arg Phe Val Gln Lys Pro Tyr Ser
                355                 360                 365 cgc tct tcc tcc atg tct tcc att gat cta gtc agt gcc tct gat gat   1155
Arg Ser Ser Ser Met Ser Ser Ile Asp Leu Val Ser Ala Ser Asp Asp
            370                 375                 380 gtt cac aga ttc agc tcc cag gtt gaa gag atg gtg cag aac cac atg   1203
Val His Arg Phe Ser Ser Gln Val Glu Glu Met Val Gln Asn His Met
        385                 390                 395 act tac tca tta cag gat gta ggc gga gat gcc aat tgg cag ttg gtt   1251
Thr Tyr Ser Leu Gln Asp Val Gly Gly Asp Ala Asn Trp Gln Leu Val
    400                 405                 410 gta gaa gaa gga gaa atg aag gta tac aga aga gaa gta gaa gaa aat   1299
Val Glu Glu Gly Glu Met Lys Val Tyr Arg Arg Glu Val Glu Glu Asn
415                 420                 425                 430 ggg att gtt ctg gat cct tta aaa gct acc cat gca gtt aaa ggc gtc   1347
Gly Ile Val Leu Asp Pro Leu Lys Ala Thr His Ala Val Lys Gly Val
                435                 440                 445
```

-continued

```
aca gga cat gaa gtc tgc aat tat ttc tgg aat gtt gac gtt cgc aat    1395
Thr Gly His Glu Val Cys Asn Tyr Phe Trp Asn Val Asp Val Arg Asn
            450                 455                 460 gac tgg gaa aca act ata gaa aac ttt cat gtg gtg gaa aca tta gct    1443
Asp Trp Glu Thr Thr Ile Glu Asn Phe His Val Val Glu Thr Leu Ala
        465                 470                 475 gat aat gca atc atc att tat caa aca cac aag agg gtg tgg cct gct    1491
Asp Asn Ala Ile Ile Ile Tyr Gln Thr His Lys Arg Val Trp Pro Ala
    480                 485                 490 tct cag cga gac gta tta tat ctt tct gtc att cga aag ata cca gcc    1539
Ser Gln Arg Asp Val Leu Tyr Leu Ser Val Ile Arg Lys Ile Pro Ala
495                 500                 505                 510 ttg act gaa aat gac cct gaa act tgg ata gtt tgt aat ttt tct gtg    1587
Leu Thr Glu Asn Asp Pro Glu Thr Trp Ile Val Cys Asn Phe Ser Val
                515                 520                 525 gat cat gac agt gct cct cta aac aac cga tgt gtc cgt gcc aaa ata    1635
Asp His Asp Ser Ala Pro Leu Asn Asn Arg Cys Val Arg Ala Lys Ile
            530                 535                 540 aat gtt gct atg att tgt caa acc ttg gta agc cca cca gag gga aac    1683
Asn Val Ala Met Ile Cys Gln Thr Leu Val Ser Pro Pro Glu Gly Asn
        545                 550                 555 cag gaa att agc agg gac aac att cta tgc aag att aca tat gta gct    1731
Gln Glu Ile Ser Arg Asp Asn Ile Leu Cys Lys Ile Thr Tyr Val Ala
    560                 565                 570 aat gtg aac cct gga gga tgg gca cca gcc tca gtg tta agg gca gtg    1779
Asn Val Asn Pro Gly Gly Trp Ala Pro Ala Ser Val Leu Arg Ala Val
575                 580                 585                 590 gca aag cga gag tat cct aaa ttt cta aaa cgt ttt act tct tac gtc    1827
Ala Lys Arg Glu Tyr Pro Lys Phe Leu Lys Arg Phe Thr Ser Tyr Val
                595                 600                 605 caa gaa aaa act gca gga aag cct att ttg ttc tagtattaac aggtactaga    1880
Gln Glu Lys Thr Ala Gly Lys Pro Ile Leu Phe
            610                 615 agatatgttt tatctttttt taactttatt tgactaatat gactgtcaat actaaaattt    1940
agttgttgaa agtatttact atgtttttc cggaattc                              1978
```

<210> SEQ ID NO 18
<211> LENGTH: 617
<212> TYPE: PRT
<213> ORGANISM: Artificial Sequence
<220> FEATURE:
<223> OTHER INFORMATION: Description of Artificial Sequence:
      FLAG-GPBPDNLS

<400> SEQUENCE: 18

```
Met Ala Pro Leu Ala Asp Tyr Lys Asp Asp Asp Asp Lys Met Ser Asp
 1               5                  10                  15

Asn Gln Ser Trp Asn Ser Ser Gly Ser Glu Glu Asp Pro Glu Thr Glu
             20                  25                  30

Ser Gly Pro Pro Val Glu Arg Cys Gly Val Leu Ser Lys Trp Thr Asn
         35                  40                  45

Tyr Ile His Gly Trp Gln Asp Arg Trp Val Val Leu Lys Asn Asn Ala
     50                  55                  60

Leu Ser Tyr Tyr Lys Ser Glu Asp Glu Thr Glu Tyr Gly Cys Arg Gly
 65                  70                  75                  80

Ser Ile Cys Leu Ser Lys Ala Val Ile Thr Pro His Asp Phe Asp Glu
                 85                  90                  95

Cys Arg Phe Asp Ile Ser Val Asn Asp Ser Val Trp Tyr Leu Arg Ala
```

-continued

```
                100                 105                 110
Gln Asp Pro Asp His Arg Gln Gln Trp Ile Asp Ala Ile Glu Gln His
            115                 120                 125
Lys Thr Glu Ser Gly Tyr Gly Ser Glu Ser Ser Leu Arg Arg His Gly
    130                 135                 140
Ser Met Val Ser Leu Val Ser Gly Ala Ser Gly Tyr Ser Ala Thr Ser
145                 150                 155                 160
Thr Ser Ser Phe Lys Lys Gly His Ser Leu Arg Glu Lys Leu Ala Glu
                165                 170                 175
Met Glu Thr Phe Arg Asp Ile Leu Cys Arg Gln Val Asp Thr Leu Gln
            180                 185                 190
Lys Tyr Phe Asp Ala Cys Ala Asp Ala Val Ser Lys Asp Glu Leu Gln
    195                 200                 205
Arg Asp Lys Val Val Glu Asp Glu Asp Phe Pro Thr Thr Arg
210                 215                 220
Ser Asp Gly Asp Phe Leu His Ser Thr Asn Gly Asn Lys Glu Lys Leu
225                 230                 235                 240
Phe Pro His Val Thr Pro Lys Gly Ile Asn Gly Ile Asp Phe Lys Gly
                245                 250                 255
Glu Ala Ile Thr Phe Lys Ala Thr Thr Ala Gly Ile Leu Ala Thr Leu
            260                 265                 270
Ser His Cys Ile Glu Leu Met Val Lys Arg Glu Asp Ser Trp Gln Lys
    275                 280                 285
Arg Leu Asp Lys Glu Thr Glu His Phe Gly Gly Pro Asp Tyr Glu Glu
    290                 295                 300
Gly Pro Asn Ser Leu Ile Asn Glu Glu Glu Phe Phe Asp Ala Val Glu
305                 310                 315                 320
Ala Ala Leu Asp Arg Gln Asp Lys Ile Glu Glu Gln Ser Gln Ser Glu
                325                 330                 335
Lys Val Arg Leu His Trp Pro Thr Leu Pro Ser Gly Asp Ala Phe
            340                 345                 350
Ser Ser Val Gly Thr His Arg Phe Val Gln Lys Pro Tyr Ser Arg Ser
    355                 360                 365
Ser Ser Met Ser Ser Ile Asp Leu Val Ser Ala Ser Asp Asp Val His
370                 375                 380
Arg Phe Ser Ser Gln Val Glu Glu Met Val Gln Asn His Met Thr Tyr
385                 390                 395                 400
Ser Leu Gln Asp Val Gly Gly Asp Ala Asn Trp Gln Leu Val Val Glu
                405                 410                 415
Glu Gly Glu Met Lys Val Tyr Arg Arg Glu Val Glu Glu Asn Gly Ile
            420                 425                 430
Val Leu Asp Pro Leu Lys Ala Thr His Ala Val Lys Gly Val Thr Gly
    435                 440                 445
His Glu Val Cys Asn Tyr Phe Trp Asn Val Asp Val Arg Asn Asp Trp
    450                 455                 460
Glu Thr Thr Ile Glu Asn Phe His Val Val Glu Thr Leu Ala Asp Asn
465                 470                 475                 480
Ala Ile Ile Ile Tyr Gln Thr His Lys Arg Val Trp Pro Ala Ser Gln
                485                 490                 495
Arg Asp Val Leu Tyr Leu Ser Val Ile Arg Lys Ile Pro Ala Leu Thr
            500                 505                 510
Glu Asn Asp Pro Glu Thr Trp Ile Val Cys Asn Phe Ser Val Asp His
    515                 520                 525
```

-continued

```
Asp Ser Ala Pro Leu Asn Asn Arg Cys Val Arg Ala Lys Ile Asn Val
        530                 535                 540

Ala Met Ile Cys Gln Thr Leu Val Ser Pro Pro Glu Gly Asn Gln Glu
545                 550                 555                 560

Ile Ser Arg Asp Asn Ile Leu Cys Lys Ile Thr Tyr Val Ala Asn Val
                565                 570                 575

Asn Pro Gly Gly Trp Ala Pro Ser Val Leu Arg Ala Val Ala Lys
            580                 585                 590

Arg Glu Tyr Pro Lys Phe Leu Lys Arg Phe Thr Ser Tyr Val Gln Glu
        595                 600                 605

Lys Thr Ala Gly Lys Pro Ile Leu Phe
610                 615

<210> SEQ ID NO 19
<211> LENGTH: 1975
<212> TYPE: DNA
<213> ORGANISM: Artificial Sequence
<220> FEATURE:
<223> OTHER INFORMATION: Description of Artificial Sequence:
      FLAG-GPBPDSXY
<220> FEATURE:
<221> NAME/KEY: CDS
<222> LOCATION: (10)..(1857)

<400> SEQUENCE: 19 gaattcacc atg gcc cca cta gcc gac tac aag gac gac gat gac aag atg        51
          Met Ala Pro Leu Ala Asp Tyr Lys Asp Asp Asp Asp Lys Met
            1               5                  10 tcg gat aat cag agc tgg aac tcg tcg ggc tcg gag gag gat cca gag        99
Ser Asp Asn Gln Ser Trp Asn Ser Ser Gly Ser Glu Glu Asp Pro Glu
 15                  20                  25                  30 acg gag tct ggg ccg cct gtg gag cgc tgc ggg gtc ctc agt aag tgg       147
Thr Glu Ser Gly Pro Pro Val Glu Arg Cys Gly Val Leu Ser Lys Trp
                 35                  40                  45 aca aac tac att cat ggg tgg cag gat cgt tgg gta gtt ttg aaa aat       195
Thr Asn Tyr Ile His Gly Trp Gln Asp Arg Trp Val Val Leu Lys Asn
             50                  55                  60 aat gct ctg agt tac tac aaa tct gaa gat gaa aca gag tat ggc tgc       243
Asn Ala Leu Ser Tyr Tyr Lys Ser Glu Asp Glu Thr Glu Tyr Gly Cys
 65                  70                  75 aga gga tcc atc tgt ctt agc aag gct gtc atc aca cct cac gat ttt       291
Arg Gly Ser Ile Cys Leu Ser Lys Ala Val Ile Thr Pro His Asp Phe
 80                  85                  90 gat gaa tgt cga ttt gat att agt gta aat gat agt gtt tgg tat ctt       339
Asp Glu Cys Arg Phe Asp Ile Ser Val Asn Asp Ser Val Trp Tyr Leu
 95                 100                 105                 110 cgt gct cag gat cca gat cat aga cag caa tgg ata gat gcc att gaa       387
Arg Ala Gln Asp Pro Asp His Arg Gln Gln Trp Ile Asp Ala Ile Glu
                115                 120                 125 cag cac aag act gaa tct gga tat gga tct gaa tcc agc ttg cgt cga       435
Gln His Lys Thr Glu Ser Gly Tyr Gly Ser Glu Ser Ser Leu Arg Arg
            130                 135                 140 cat ggc aaa ggc cac agt tta cgt gag aag ttg gct gaa atg gaa aca       483
His Gly Lys Gly His Ser Leu Arg Glu Lys Leu Ala Glu Met Glu Thr
145                 150                 155 ttt aga gac atc tta tgt aga caa gtt gac acg cta cag aag tac ttt       531
Phe Arg Asp Ile Leu Cys Arg Gln Val Asp Thr Leu Gln Lys Tyr Phe
160                 165                 170 gat gcc tgt gct gat gct gtc tct aag gat gaa ctt caa agg gat aaa       579
Asp Ala Cys Ala Asp Ala Val Ser Lys Asp Glu Leu Gln Arg Asp Lys
```

-continued

| | | | | | | | | | | | | | | | |
|---|---|---|---|---|---|---|---|---|---|---|---|---|---|---|---|
| | 175 | | | | 180 | | | | 185 | | | | 190 | | |
| gtg | gta | gaa | gat | gat | gaa | gat | gac | ttt | cct | aca | acg | cgt | tct | gat | ggt | 627
| Val | Val | Glu | Asp | Asp | Glu | Asp | Asp | Phe | Pro | Thr | Thr | Arg | Ser | Asp | Gly |
| | | | 195 | | | | | 200 | | | | | 205 | | |
| gac | ttc | ttg | cat | agt | acc | aac | ggc | aat | aaa | gaa | aag | tta | ttt | cca | cat | 675
| Asp | Phe | Leu | His | Ser | Thr | Asn | Gly | Asn | Lys | Glu | Lys | Leu | Phe | Pro | His |
| | | | 210 | | | | | 215 | | | | | 220 | | |
| gtg | aca | cca | aaa | gga | att | aat | ggt | ata | gac | ttt | aaa | ggg | gaa | gcg | ata | 723
| Val | Thr | Pro | Lys | Gly | Ile | Asn | Gly | Ile | Asp | Phe | Lys | Gly | Glu | Ala | Ile |
| | | | 225 | | | | | 230 | | | | | 235 | | |
| act | ttt | aaa | gca | act | act | gct | gga | atc | ctt | gca | aca | ctt | tct | cat | tgt | 771
| Thr | Phe | Lys | Ala | Thr | Thr | Ala | Gly | Ile | Leu | Ala | Thr | Leu | Ser | His | Cys |
| | 240 | | | | | 245 | | | | | 250 | | | | |
| att | gaa | cta | atg | gtt | aaa | cgt | gag | gac | agc | tgg | cag | aag | aga | ctg | gat | 819
| Ile | Glu | Leu | Met | Val | Lys | Arg | Glu | Asp | Ser | Trp | Gln | Lys | Arg | Leu | Asp |
| 255 | | | | | 260 | | | | | 265 | | | | 270 | |
| aag | gaa | act | gag | aag | aaa | aga | aga | aca | gag | gaa | gca | tat | aaa | aat | gca | 867
| Lys | Glu | Thr | Glu | Lys | Lys | Arg | Arg | Thr | Glu | Glu | Ala | Tyr | Lys | Asn | Ala |
| | | | 275 | | | | | 280 | | | | | 285 | | |
| atg | aca | gaa | ctt | aag | aaa | aaa | tcc | cac | ttt | gga | gga | cca | gat | tat | gaa | 915
| Met | Thr | Glu | Leu | Lys | Lys | Lys | Ser | His | Phe | Gly | Gly | Pro | Asp | Tyr | Glu |
| | | | 290 | | | | | 295 | | | | | 300 | | |
| gaa | ggc | cct | aac | agt | ctg | att | aat | gaa | gaa | gag | ttc | ttt | gat | gct | gtt | 963
| Glu | Gly | Pro | Asn | Ser | Leu | Ile | Asn | Glu | Glu | Glu | Phe | Phe | Asp | Ala | Val |
| | | 305 | | | | | 310 | | | | | 315 | | | |
| gaa | gct | gct | ctt | gac | aga | caa | gat | aaa | ata | gaa | gaa | cag | tca | cag | agt | 1011
| Glu | Ala | Ala | Leu | Asp | Arg | Gln | Asp | Lys | Ile | Glu | Glu | Gln | Ser | Gln | Ser |
| | 320 | | | | | 325 | | | | | 330 | | | | |
| gaa | aag | gtg | aga | tta | cat | tgg | cct | aca | tcc | ttg | ccc | tct | gga | gat | gcc | 1059
| Glu | Lys | Val | Arg | Leu | His | Trp | Pro | Thr | Ser | Leu | Pro | Ser | Gly | Asp | Ala |
| 335 | | | | | 340 | | | | | 345 | | | | 350 | |
| ttt | tct | tct | gtg | ggg | aca | cat | aga | ttt | gtc | caa | aag | ccc | tat | agt | cgc | 1107
| Phe | Ser | Ser | Val | Gly | Thr | His | Arg | Phe | Val | Gln | Lys | Pro | Tyr | Ser | Arg |
| | | | 355 | | | | | 360 | | | | | 365 | | |
| tct | tcc | tcc | atg | tct | tcc | att | gat | cta | gtc | agt | gcc | tct | gat | gat | gtt | 1155
| Ser | Ser | Ser | Met | Ser | Ser | Ile | Asp | Leu | Val | Ser | Ala | Ser | Asp | Asp | Val |
| | | | 370 | | | | | 375 | | | | | 380 | | |
| cac | aga | ttc | agc | tcc | cag | gtt | gaa | gag | atg | gtg | cag | aac | cac | atg | act | 1203
| His | Arg | Phe | Ser | Ser | Gln | Val | Glu | Glu | Met | Val | Gln | Asn | His | Met | Thr |
| | | 385 | | | | | 390 | | | | | 395 | | | |
| tac | tca | tta | cag | gat | gta | ggc | gga | gat | gcc | aat | tgg | cag | ttg | gtt | gta | 1251
| Tyr | Ser | Leu | Gln | Asp | Val | Gly | Gly | Asp | Ala | Asn | Trp | Gln | Leu | Val | Val |
| | 400 | | | | | 405 | | | | | 410 | | | | |
| gaa | gaa | gga | gaa | atg | aag | gta | tac | aga | aga | gaa | gta | gaa | gaa | aat | ggg | 1299
| Glu | Glu | Gly | Glu | Met | Lys | Val | Tyr | Arg | Arg | Glu | Val | Glu | Glu | Asn | Gly |
| 415 | | | | | 420 | | | | | 425 | | | | 430 | |
| att | gtt | ctg | gat | cct | tta | aaa | gct | acc | cat | gca | gtt | aaa | ggc | gtc | aca | 1347
| Ile | Val | Leu | Asp | Pro | Leu | Lys | Ala | Thr | His | Ala | Val | Lys | Gly | Val | Thr |
| | | | 435 | | | | | 440 | | | | | 445 | | |
| gga | cat | gaa | gtc | tgc | aat | tat | ttc | tgg | aat | gtt | gac | gtt | cgc | aat | gac | 1395
| Gly | His | Glu | Val | Cys | Asn | Tyr | Phe | Trp | Asn | Val | Asp | Val | Arg | Asn | Asp |
| | | | 450 | | | | | 455 | | | | | 460 | | |
| tgg | gaa | aca | act | ata | gaa | aac | ttt | cat | gtg | gtg | gaa | aca | tta | gct | gat | 1443
| Trp | Glu | Thr | Thr | Ile | Glu | Asn | Phe | His | Val | Val | Glu | Thr | Leu | Ala | Asp |
| | 465 | | | | | 470 | | | | | 475 | | | | |
| aat | gca | atc | atc | att | tat | caa | aca | cac | aag | agg | gtg | tgg | cct | gct | tct | 1491
| Asn | Ala | Ile | Ile | Ile | Tyr | Gln | Thr | His | Lys | Arg | Val | Trp | Pro | Ala | Ser |
| 480 | | | | | 485 | | | | | 490 | | | | | |
| cag | cga | gac | gta | tta | tat | ctt | tct | gtc | att | cga | aag | ata | cca | gcc | ttg | 1539

-continued

```
Gln Arg Asp Val Leu Tyr Leu Ser Val Ile Arg Lys Ile Pro Ala Leu
495                 500                 505                 510 act gaa aat gac cct gaa act tgg ata gtt tgt aat ttt tct gtg gat    1587
Thr Glu Asn Asp Pro Glu Thr Trp Ile Val Cys Asn Phe Ser Val Asp
                515                 520                 525 cat gac agt gct cct cta aac aac cga tgt gtc cgt gcc aaa ata aat    1635
His Asp Ser Ala Pro Leu Asn Asn Arg Cys Val Arg Ala Lys Ile Asn
            530                 535                 540 gtt gct atg att tgt caa acc ttg gta agc cca cca gag gga aac cag    1683
Val Ala Met Ile Cys Gln Thr Leu Val Ser Pro Pro Glu Gly Asn Gln
        545                 550                 555 gaa att agc agg gac aac att cta tgc aag att aca tat gta gct aat    1731
Glu Ile Ser Arg Asp Asn Ile Leu Cys Lys Ile Thr Tyr Val Ala Asn
    560                 565                 570 gtg aac cct gga gga tgg gca cca gcc tca gtg tta agg gca gtg gca    1779
Val Asn Pro Gly Gly Trp Ala Pro Ala Ser Val Leu Arg Ala Val Ala
575                 580                 585                 590 aag cga gag tat cct aaa ttt cta aaa cgt ttt act tct tac gtc caa    1827
Lys Arg Glu Tyr Pro Lys Phe Leu Lys Arg Phe Thr Ser Tyr Val Gln
                595                 600                 605 gaa aaa act gca gga aag cct att ttg ttc tagtattaac aggtactaga      1877
Glu Lys Thr Ala Gly Lys Pro Ile Leu Phe
            610                 615 agatatgttt tatctttttt taactttatt tgactaatat gactgtcaat actaaaattt  1937
agttgttgaa agtatttact atgtttttc cggaattc                           1975
```

<210> SEQ ID NO 20
<211> LENGTH: 616
<212> TYPE: PRT
<213> ORGANISM: Artificial Sequence
<220> FEATURE:
<223> OTHER INFORMATION: Description of Artificial Sequence: FLAG-GPBPDSXY

<400> SEQUENCE: 20

```
Met Ala Pro Leu Ala Asp Tyr Lys Asp Asp Asp Asp Lys Met Ser Asp
1               5                   10                  15

Asn Gln Ser Trp Asn Ser Ser Gly Ser Glu Glu Asp Pro Glu Thr Glu
            20                  25                  30

Ser Gly Pro Pro Val Glu Arg Cys Gly Val Leu Ser Lys Trp Thr Asn
        35                  40                  45

Tyr Ile His Gly Trp Gln Asp Arg Trp Val Val Leu Lys Asn Asn Ala
    50                  55                  60

Leu Ser Tyr Tyr Lys Ser Glu Asp Glu Thr Glu Tyr Gly Cys Arg Gly
65                  70                  75                  80

Ser Ile Cys Leu Ser Lys Ala Val Ile Thr Pro His Asp Phe Asp Glu
                85                  90                  95

Cys Arg Phe Asp Ile Ser Val Asn Asp Ser Val Trp Tyr Leu Arg Ala
                100                 105                 110

Gln Asp Pro Asp His Arg Gln Gln Trp Ile Asp Ala Ile Glu Gln His
            115                 120                 125

Lys Thr Glu Ser Gly Tyr Gly Ser Glu Ser Ser Leu Arg Arg His Gly
        130                 135                 140

Lys Gly His Ser Leu Arg Glu Lys Leu Ala Glu Met Glu Thr Phe Arg
145                 150                 155                 160

Asp Ile Leu Cys Arg Gln Val Asp Thr Leu Gln Lys Tyr Phe Asp Ala
                165                 170                 175
```

-continued

```
Cys Ala Asp Ala Val Ser Lys Asp Glu Leu Gln Arg Asp Lys Val Val
            180                 185                 190
Glu Asp Glu Asp Asp Phe Pro Thr Thr Arg Ser Asp Gly Asp Phe
        195                 200                 205
Leu His Ser Thr Asn Gly Asn Lys Glu Lys Leu Phe Pro His Val Thr
    210                 215                 220
Pro Lys Gly Ile Asn Gly Ile Asp Phe Lys Gly Glu Ala Ile Thr Phe
225                 230                 235                 240
Lys Ala Thr Thr Ala Gly Ile Leu Ala Thr Leu Ser His Cys Ile Glu
            245                 250                 255
Leu Met Val Lys Arg Glu Asp Ser Trp Gln Lys Arg Leu Asp Lys Glu
            260                 265                 270
Thr Glu Lys Lys Arg Arg Thr Glu Glu Ala Tyr Lys Asn Ala Met Thr
            275                 280                 285
Glu Leu Lys Lys Ser His Phe Gly Gly Pro Asp Tyr Glu Glu Gly
    290                 295                 300
Pro Asn Ser Leu Ile Asn Glu Glu Phe Phe Asp Ala Val Glu Ala
305                 310                 315                 320
Ala Leu Asp Arg Gln Asp Lys Ile Glu Glu Gln Ser Gln Ser Glu Lys
            325                 330                 335
Val Arg Leu His Trp Pro Thr Ser Leu Pro Ser Gly Asp Ala Phe Ser
            340                 345                 350
Ser Val Gly Thr His Arg Phe Val Gln Lys Pro Tyr Ser Arg Ser Ser
        355                 360                 365
Ser Met Ser Ser Ile Asp Leu Val Ser Ala Ser Asp Asp Val His Arg
    370                 375                 380
Phe Ser Ser Gln Val Glu Glu Met Val Gln Asn His Met Thr Tyr Ser
385                 390                 395                 400
Leu Gln Asp Val Gly Gly Asp Ala Asn Trp Gln Leu Val Glu Glu
            405                 410                 415
Gly Glu Met Lys Val Tyr Arg Arg Glu Val Glu Glu Asn Gly Ile Val
            420                 425                 430
Leu Asp Pro Leu Lys Ala Thr His Ala Val Lys Gly Val Thr Gly His
            435                 440                 445
Glu Val Cys Asn Tyr Phe Trp Asn Val Asp Val Arg Asn Asp Trp Glu
    450                 455                 460
Thr Thr Ile Glu Asn Phe His Val Val Glu Thr Leu Ala Asp Asn Ala
465                 470                 475                 480
Ile Ile Ile Tyr Gln Thr His Lys Arg Val Trp Pro Ala Ser Gln Arg
            485                 490                 495
Asp Val Leu Tyr Leu Ser Val Ile Arg Lys Ile Pro Ala Leu Thr Glu
            500                 505                 510
Asn Asp Pro Glu Thr Trp Ile Val Cys Asn Phe Ser Val Asp His Asp
            515                 520                 525
Ser Ala Pro Leu Asn Asn Arg Cys Val Arg Ala Lys Ile Asn Val Ala
    530                 535                 540
Met Ile Cys Gln Thr Leu Val Ser Pro Pro Glu Gly Asn Gln Glu Ile
545                 550                 555                 560
Ser Arg Asp Asn Ile Leu Cys Lys Ile Thr Tyr Val Ala Asn Val Asn
            565                 570                 575
Pro Gly Gly Trp Ala Pro Ala Ser Val Leu Arg Ala Val Ala Lys Arg
            580                 585                 590
Glu Tyr Pro Lys Phe Leu Lys Arg Phe Thr Ser Tyr Val Gln Glu Lys
```

```
                595                 600                 605
Thr Ala Gly Lys Pro Ile Leu Phe
    610                 615

<210> SEQ ID NO 21
<211> LENGTH: 1915
<212> TYPE: DNA
<213> ORGANISM: Artificial Sequence
<220> FEATURE:
<223> OTHER INFORMATION: Description of Artificial Sequence:
      FLAG-GPBPDSXY/NLS
<220> FEATURE:
<221> NAME/KEY: CDS
<222> LOCATION: (10)..(1797)

<400> SEQUENCE: 21 gaattcacc atg gcc cca cta gcc gac tac aag gac gac gat gac aag atg         51
          Met Ala Pro Leu Ala Asp Tyr Lys Asp Asp Asp Asp Lys Met
            1               5                  10 tcg gat aat cag agc tgg aac tcg tcg ggc tcg gag gag gat cca gag           99
Ser Asp Asn Gln Ser Trp Asn Ser Ser Gly Ser Glu Glu Asp Pro Glu
 15                  20                  25                  30 acg gag tct ggg ccg cct gtg gag cgc tgc ggg gtc ctc agt aag tgg          147
Thr Glu Ser Gly Pro Pro Val Glu Arg Cys Gly Val Leu Ser Lys Trp
                 35                  40                  45 aca aac tac att cat ggg tgg cag gat cgt tgg gta gtt ttg aaa aat          195
Thr Asn Tyr Ile His Gly Trp Gln Asp Arg Trp Val Val Leu Lys Asn
             50                  55                  60 aat gct ctg agt tac tac aaa tct gaa gat gaa aca gag tat ggc tgc          243
Asn Ala Leu Ser Tyr Tyr Lys Ser Glu Asp Glu Thr Glu Tyr Gly Cys
         65                  70                  75 aga gga tcc atc tgt ctt agc aag gct gtc atc aca cct cac gat ttt          291
Arg Gly Ser Ile Cys Leu Ser Lys Ala Val Ile Thr Pro His Asp Phe
     80                  85                  90 gat gaa tgt cga ttt gat att agt gta aat gat agt gtt tgg tat ctt          339
Asp Glu Cys Arg Phe Asp Ile Ser Val Asn Asp Ser Val Trp Tyr Leu
 95                 100                 105                 110 cgt gct cag gat cca gat cat aga cag caa tgg ata gat gcc att gaa          387
Arg Ala Gln Asp Pro Asp His Arg Gln Gln Trp Ile Asp Ala Ile Glu
                115                 120                 125 cag cac aag act gaa tct gga tat gga tct gaa tcc agc ttg cgt cga          435
Gln His Lys Thr Glu Ser Gly Tyr Gly Ser Glu Ser Ser Leu Arg Arg
            130                 135                 140 cat ggc aaa ggc cac agt tta cgt gag aag ttg gct gaa atg gaa aca          483
His Gly Lys Gly His Ser Leu Arg Glu Lys Leu Ala Glu Met Glu Thr
        145                 150                 155 ttt aga gac atc tta tgt aga caa gtt gac acg cta cag aag tac ttt          531
Phe Arg Asp Ile Leu Cys Arg Gln Val Asp Thr Leu Gln Lys Tyr Phe
    160                 165                 170 gat gcc tgt gct gat gct gtc tct aag gat gaa ctt caa agg gat aaa          579
Asp Ala Cys Ala Asp Ala Val Ser Lys Asp Glu Leu Gln Arg Asp Lys
175                 180                 185                 190 gtg gta gaa gat gat gaa gat gac ttt cct aca acg cgt tct gat ggt          627
Val Val Glu Asp Asp Glu Asp Asp Phe Pro Thr Thr Arg Ser Asp Gly
                195                 200                 205 gac ttc ttg cat agt acc aac ggc aat aaa gaa aag tta ttt cca cat          675
Asp Phe Leu His Ser Thr Asn Gly Asn Lys Glu Lys Leu Phe Pro His
            210                 215                 220 gtg aca cca aaa gga att aat ggt ata gac ttt aaa ggg gaa gcg ata          723
Val Thr Pro Lys Gly Ile Asn Gly Ile Asp Phe Lys Gly Glu Ala Ile
        225                 230                 235
```

|     |     |     |     |     |     |     |     |     |     |     |     |     |     |     |     | |
|---|---|---|---|---|---|---|---|---|---|---|---|---|---|---|---|---|
| act | ttt | aaa | gca | act | act | gct | gga | atc | ctt | gca | aca | ctt | tct | cat | tgt | 771 |
| Thr | Phe | Lys | Ala | Thr | Thr | Ala | Gly | Ile | Leu | Ala | Thr | Leu | Ser | His | Cys | |
| | 240 | | | | 245 | | | | | 250 | | | | | | |
| att | gaa | cta | atg | gtt | aaa | cgt | gag | gac | agc | tgg | cag | aag | aga | ctg | gat | 819 |
| Ile | Glu | Leu | Met | Val | Lys | Arg | Glu | Asp | Ser | Trp | Gln | Lys | Arg | Leu | Asp | |
| 255 | | | | | 260 | | | | | 265 | | | | | 270 | |
| aag | gaa | act | gag | cac | ttt | gga | gga | cca | gat | tat | gaa | gaa | ggc | cct | aac | 867 |
| Lys | Glu | Thr | Glu | His | Phe | Gly | Gly | Pro | Asp | Tyr | Glu | Glu | Gly | Pro | Asn | |
| | | | | 275 | | | | | 280 | | | | | 285 | | |
| agt | ctg | att | aat | gaa | gaa | gag | ttc | ttt | gat | gct | gtt | gaa | gct | gct | ctt | 915 |
| Ser | Leu | Ile | Asn | Glu | Glu | Glu | Phe | Phe | Asp | Ala | Val | Glu | Ala | Ala | Leu | |
| | | | 290 | | | | | 295 | | | | | 300 | | | |
| gac | aga | caa | gat | aaa | ata | gaa | gaa | cag | tca | cag | agt | gaa | aag | gtg | aga | 963 |
| Asp | Arg | Gln | Asp | Lys | Ile | Glu | Glu | Gln | Ser | Gln | Ser | Glu | Lys | Val | Arg | |
| | | 305 | | | | | 310 | | | | | 315 | | | | |
| tta | cat | tgg | cct | aca | tcc | ttg | ccc | tct | gga | gat | gcc | ttt | tct | tct | gtg | 1011 |
| Leu | His | Trp | Pro | Thr | Ser | Leu | Pro | Ser | Gly | Asp | Ala | Phe | Ser | Ser | Val | |
| | 320 | | | | 325 | | | | | 330 | | | | | | |
| ggg | aca | cat | aga | ttt | gtc | caa | aag | ccc | tat | agt | cgc | tct | tcc | tcc | atg | 1059 |
| Gly | Thr | His | Arg | Phe | Val | Gln | Lys | Pro | Tyr | Ser | Arg | Ser | Ser | Ser | Met | |
| 335 | | | | | 340 | | | | | 345 | | | | | 350 | |
| tct | tcc | att | gat | cta | gtc | agt | gcc | tct | gat | gat | gtt | cac | aga | ttc | agc | 1107 |
| Ser | Ser | Ile | Asp | Leu | Val | Ser | Ala | Ser | Asp | Asp | Val | His | Arg | Phe | Ser | |
| | | | | 355 | | | | | 360 | | | | | 365 | | |
| tcc | cag | gtt | gaa | gag | atg | gtg | cag | aac | cac | atg | act | tac | tca | tta | cag | 1155 |
| Ser | Gln | Val | Glu | Glu | Met | Val | Gln | Asn | His | Met | Thr | Tyr | Ser | Leu | Gln | |
| | | | 370 | | | | | 375 | | | | | 380 | | | |
| gat | gta | ggc | gga | gat | gcc | aat | tgg | cag | ttg | gtt | gta | gaa | gaa | gga | gaa | 1203 |
| Asp | Val | Gly | Gly | Asp | Ala | Asn | Trp | Gln | Leu | Val | Val | Glu | Glu | Gly | Glu | |
| | | 385 | | | | | 390 | | | | | 395 | | | | |
| atg | aag | gta | tac | aga | aga | gaa | gta | gaa | gaa | aat | ggg | att | gtt | ctg | gat | 1251 |
| Met | Lys | Val | Tyr | Arg | Arg | Glu | Val | Glu | Glu | Asn | Gly | Ile | Val | Leu | Asp | |
| | 400 | | | | 405 | | | | | 410 | | | | | | |
| cct | tta | aaa | gct | acc | cat | gca | gtt | aaa | ggc | gtc | aca | gga | cat | gaa | gtc | 1299 |
| Pro | Leu | Lys | Ala | Thr | His | Ala | Val | Lys | Gly | Val | Thr | Gly | His | Glu | Val | |
| 415 | | | | | 420 | | | | | 425 | | | | | 430 | |
| tgc | aat | tat | ttc | tgg | aat | gtt | gac | gtt | cgc | aat | gac | tgg | gaa | aca | act | 1347 |
| Cys | Asn | Tyr | Phe | Trp | Asn | Val | Asp | Val | Arg | Asn | Asp | Trp | Glu | Thr | Thr | |
| | | | | 435 | | | | | 440 | | | | | 445 | | |
| ata | gaa | aac | ttt | cat | gtg | gtg | gaa | aca | tta | gct | gat | aat | gca | atc | atc | 1395 |
| Ile | Glu | Asn | Phe | His | Val | Val | Glu | Thr | Leu | Ala | Asp | Asn | Ala | Ile | Ile | |
| | | | 450 | | | | | 455 | | | | | 460 | | | |
| att | tat | caa | aca | cac | aag | agg | gtg | tgg | cct | gct | tct | cag | cga | gac | gta | 1443 |
| Ile | Tyr | Gln | Thr | His | Lys | Arg | Val | Trp | Pro | Ala | Ser | Gln | Arg | Asp | Val | |
| | | 465 | | | | | 470 | | | | | 475 | | | | |
| tta | tat | ctt | tct | gtc | att | cga | aag | ata | cca | gcc | ttg | act | gaa | aat | gac | 1491 |
| Leu | Tyr | Leu | Ser | Val | Ile | Arg | Lys | Ile | Pro | Ala | Leu | Thr | Glu | Asn | Asp | |
| | 480 | | | | 485 | | | | | 490 | | | | | | |
| cct | gaa | act | tgg | ata | gtt | tgt | aat | ttt | tct | gtg | gat | cat | gac | agt | gct | 1539 |
| Pro | Glu | Thr | Trp | Ile | Val | Cys | Asn | Phe | Ser | Val | Asp | His | Asp | Ser | Ala | |
| 495 | | | | | 500 | | | | | 505 | | | | | 510 | |
| cct | cta | aac | aac | cga | tgt | gtc | cgt | gcc | aaa | ata | aat | gtt | gct | atg | att | 1587 |
| Pro | Leu | Asn | Asn | Arg | Cys | Val | Arg | Ala | Lys | Ile | Asn | Val | Ala | Met | Ile | |
| | | | | 515 | | | | | 520 | | | | | 525 | | |
| tgt | caa | acc | ttg | gta | agc | cca | cca | gag | gga | aac | cag | gaa | att | agc | agg | 1635 |
| Cys | Gln | Thr | Leu | Val | Ser | Pro | Pro | Glu | Gly | Asn | Gln | Glu | Ile | Ser | Arg | |
| | | | 530 | | | | | 535 | | | | | 540 | | | |
| gac | aac | att | cta | tgc | aag | att | aca | tat | gta | gct | aat | gtg | aac | cct | gga | 1683 |
| Asp | Asn | Ile | Leu | Cys | Lys | Ile | Thr | Tyr | Val | Ala | Asn | Val | Asn | Pro | Gly | |
| | | 545 | | | | | 550 | | | | | 555 | | | | |

-continued

```
gga tgg gca cca gcc tca gtg tta agg gca gtg gca aag cga gag tat      1731
Gly Trp Ala Pro Ala Ser Val Leu Arg Ala Val Ala Lys Arg Glu Tyr
    560                 565                 570 cct aaa ttt cta aaa cgt ttt act tct tac gtc caa gaa aaa act gca      1779
Pro Lys Phe Leu Lys Arg Phe Thr Ser Tyr Val Gln Glu Lys Thr Ala
575                 580                 585                 590 gga aag cct att ttg ttc tagtattaac aggtactaga agatatgttt             1827
Gly Lys Pro Ile Leu Phe
                595
tatcttttt taactttatt tgactaatat gactgtcaat actaaaattt agttgttgaa     1887
agtatttact atgttttttc cggaattc                                       1915

<210> SEQ ID NO 22
<211> LENGTH: 596
<212> TYPE: PRT
<213> ORGANISM: Artificial Sequence
<220> FEATURE:
<223> OTHER INFORMATION: Description of Artificial Sequence:
      FLAG-GPBPDSXY/NLS

<400> SEQUENCE: 22

Met Ala Pro Leu Ala Asp Tyr Lys Asp Asp Asp Asp Lys Met Ser Asp
  1               5                  10                  15

Asn Gln Ser Trp Asn Ser Ser Gly Ser Glu Glu Asp Pro Glu Thr Glu
             20                  25                  30

Ser Gly Pro Pro Val Glu Arg Cys Gly Val Leu Ser Lys Trp Thr Asn
         35                  40                  45

Tyr Ile His Gly Trp Gln Asp Arg Trp Val Val Leu Lys Asn Asn Ala
     50                  55                  60

Leu Ser Tyr Tyr Lys Ser Glu Asp Glu Thr Glu Tyr Gly Cys Arg Gly
 65                  70                  75                  80

Ser Ile Cys Leu Ser Lys Ala Val Ile Thr Pro His Asp Phe Asp Glu
                 85                  90                  95

Cys Arg Phe Asp Ile Ser Val Asn Asp Ser Val Trp Tyr Leu Arg Ala
            100                 105                 110

Gln Asp Pro Asp His Arg Gln Trp Ile Asp Ala Ile Glu Gln His
        115                 120                 125

Lys Thr Glu Ser Gly Tyr Gly Ser Glu Ser Ser Leu Arg Arg His Gly
    130                 135                 140

Lys Gly His Ser Leu Arg Glu Lys Leu Ala Glu Met Glu Thr Phe Arg
145                 150                 155                 160

Asp Ile Leu Cys Arg Gln Val Asp Thr Leu Gln Lys Tyr Phe Asp Ala
                165                 170                 175

Cys Ala Asp Ala Val Ser Lys Asp Glu Leu Gln Arg Asp Lys Val Val
            180                 185                 190

Glu Asp Asp Glu Asp Asp Phe Pro Thr Thr Arg Ser Asp Gly Asp Phe
        195                 200                 205

Leu His Ser Thr Asn Gly Asn Lys Glu Lys Leu Phe Pro His Val Thr
    210                 215                 220

Pro Lys Gly Ile Asn Gly Ile Asp Phe Lys Gly Glu Ala Ile Thr Phe
225                 230                 235                 240

Lys Ala Thr Thr Ala Gly Ile Leu Ala Thr Leu Ser His Cys Ile Glu
                245                 250                 255

Leu Met Val Lys Arg Glu Asp Ser Trp Gln Lys Arg Leu Asp Lys Glu
            260                 265                 270

Thr Glu His Phe Gly Gly Pro Asp Tyr Glu Glu Gly Pro Asn Ser Leu
```

```
                275                 280                 285
Ile Asn Glu Glu Glu Phe Phe Asp Ala Val Ala Ala Leu Asp Arg
    290                 295                 300
Gln Asp Lys Ile Glu Glu Gln Ser Gln Ser Glu Lys Val Arg Leu His
305                 310                 315                 320
Trp Pro Thr Ser Leu Pro Ser Gly Asp Ala Phe Ser Ser Val Gly Thr
                325                 330                 335
His Arg Phe Val Gln Lys Pro Tyr Ser Arg Ser Ser Ser Met Ser Ser
                340                 345                 350
Ile Asp Leu Val Ser Ala Ser Asp Val His Arg Phe Ser Ser Gln
    355                 360                 365
Val Glu Glu Met Val Gln Asn His Met Thr Tyr Ser Leu Gln Asp Val
    370                 375                 380
Gly Gly Asp Ala Asn Trp Gln Leu Val Val Glu Gly Glu Met Lys
385                 390                 395                 400
Val Tyr Arg Arg Glu Val Glu Glu Asn Gly Ile Val Leu Asp Pro Leu
                405                 410                 415
Lys Ala Thr His Ala Val Lys Gly Val Thr Gly His Glu Val Cys Asn
                420                 425                 430
Tyr Phe Trp Asn Val Asp Val Arg Asn Asp Trp Glu Thr Thr Ile Glu
                435                 440                 445
Asn Phe His Val Val Glu Thr Leu Ala Asp Asn Ala Ile Ile Ile Tyr
    450                 455                 460
Gln Thr His Lys Arg Val Trp Pro Ala Ser Gln Arg Asp Val Leu Tyr
465                 470                 475                 480
Leu Ser Val Ile Arg Lys Ile Pro Ala Leu Thr Glu Asn Asp Pro Glu
                485                 490                 495
Thr Trp Ile Val Cys Asn Phe Ser Val Asp His Asp Ser Ala Pro Leu
                500                 505                 510
Asn Asn Arg Cys Val Arg Ala Lys Ile Asn Val Ala Met Ile Cys Gln
                515                 520                 525
Thr Leu Val Ser Pro Pro Glu Gly Asn Gln Glu Ile Ser Arg Asp Asn
    530                 535                 540
Ile Leu Cys Lys Ile Thr Tyr Val Ala Asn Val Asn Pro Gly Gly Trp
545                 550                 555                 560
Ala Pro Ala Ser Val Leu Arg Ala Val Ala Lys Arg Glu Tyr Pro Lys
                565                 570                 575
Phe Leu Lys Arg Phe Thr Ser Tyr Val Gln Glu Lys Thr Ala Gly Lys
                580                 585                 590
Pro Ile Leu Phe
        595

<210> SEQ ID NO 23
<211> LENGTH: 2038
<212> TYPE: DNA
<213> ORGANISM: Artificial Sequence
<220> FEATURE:
<223> OTHER INFORMATION: Description of Artificial Sequence: GPBP-D169A
<220> FEATURE:
<221> NAME/KEY: CDS
<222> LOCATION: (10)..(1920)

<400> SEQUENCE: 23 gaattcacc atg gcc cca cta gcc gac tac aag gac gac gat gac aag atg    51
          Met Ala Pro Leu Ala Asp Tyr Lys Asp Asp Asp Asp Lys Met
            1               5                  10
```

-continued

| | |
|---|---|
| tcg gat aat cag agc tgg aac tcg tcg ggc tcg gag gag gat cca gag<br>Ser Asp Asn Gln Ser Trp Asn Ser Ser Gly Ser Glu Glu Asp Pro Glu<br>15                    20                  25                    30 | 99 |
| acg gag tct ggg ccg cct gtg gag cgc tgc ggg gtc ctc agt aag tgg<br>Thr Glu Ser Gly Pro Pro Val Glu Arg Cys Gly Val Leu Ser Lys Trp<br>                  35                    40                  45 | 147 |
| aca aac tac att cat ggg tgg cag gat cgt tgg gta gtt ttg aaa aat<br>Thr Asn Tyr Ile His Gly Trp Gln Asp Arg Trp Val Val Leu Lys Asn<br>                  50                    55                  60 | 195 |
| aat gct ctg agt tac tac aaa tct gaa gat gaa aca gag tat ggc tgc<br>Asn Ala Leu Ser Tyr Tyr Lys Ser Glu Asp Glu Thr Glu Tyr Gly Cys<br>65                    70                    75 | 243 |
| aga gga tcc atc tgt ctt agc aag gct gtc atc aca cct cac gat ttt<br>Arg Gly Ser Ile Cys Leu Ser Lys Ala Val Ile Thr Pro His Asp Phe<br>        80                    85                    90 | 291 |
| gat gaa tgt cga ttt gat att agt gta aat gat agt gtt tgg tat ctt<br>Asp Glu Cys Arg Phe Asp Ile Ser Val Asn Asp Ser Val Trp Tyr Leu<br>95                  100               105              110 | 339 |
| cgt gct cag gat cca gat cat aga cag caa tgg ata gat gcc att gaa<br>Arg Ala Gln Asp Pro Asp His Arg Gln Gln Trp Ile Asp Ala Ile Glu<br>                  115               120              125 | 387 |
| cag cac aag act gaa tct gga tat gga tct gaa tcc agc ttg cgt cga<br>Gln His Lys Thr Glu Ser Gly Tyr Gly Ser Glu Ser Ser Leu Arg Arg<br>              130               135              140 | 435 |
| cat ggc tca atg gtg tcc ctg gtg tct gga gca agt ggc tac tct gca<br>His Gly Ser Met Val Ser Leu Val Ser Gly Ala Ser Gly Tyr Ser Ala<br>                  145               150              155 | 483 |
| aca tcc acc tct tca ttc aag aaa ggc cac agt tta cgt gag aag ttg<br>Thr Ser Thr Ser Ser Phe Lys Lys Gly His Ser Leu Arg Glu Lys Leu<br>160                    165               170 | 531 |
| gct gaa atg gaa aca ttt aga gcc atc tta tgt aga caa gtt gac acg<br>Ala Glu Met Glu Thr Phe Arg Ala Ile Leu Cys Arg Gln Val Asp Thr<br>175                    180               185              190 | 579 |
| cta cag aag tac ttt gat gcc tgt gct gat gct gtc tct aag gat gaa<br>Leu Gln Lys Tyr Phe Asp Ala Cys Ala Asp Ala Val Ser Lys Asp Glu<br>                  195               200              205 | 627 |
| ctt caa agg gat aaa gtg gta gaa gat gat gaa gat gac ttt cct aca<br>Leu Gln Arg Asp Lys Val Val Glu Asp Asp Glu Asp Asp Phe Pro Thr<br>              210               215              220 | 675 |
| acg cgt tct gat ggt gac ttc ttg cat agt acc aac ggc aat aaa gaa<br>Thr Arg Ser Asp Gly Asp Phe Leu His Ser Thr Asn Gly Asn Lys Glu<br>225                    230               235 | 723 |
| aag tta ttt cca cat gtg aca cca aaa gga att aat ggt ata gac ttt<br>Lys Leu Phe Pro His Val Thr Pro Lys Gly Ile Asn Gly Ile Asp Phe<br>240                    245               250 | 771 |
| aaa ggg gaa gcg ata act ttt aaa gca act act gct gga atc ctt gca<br>Lys Gly Glu Ala Ile Thr Phe Lys Ala Thr Thr Ala Gly Ile Leu Ala<br>255                    260               265              270 | 819 |
| aca ctt tct cat tgt att gaa cta atg gtt aaa cgt gag gac agc tgg<br>Thr Leu Ser His Cys Ile Glu Leu Met Val Lys Arg Glu Asp Ser Trp<br>                  275               280              285 | 867 |
| cag aag aga ctg gat aag gaa act gag aag aaa aga aga aca gag gaa<br>Gln Lys Arg Leu Asp Lys Glu Thr Glu Lys Lys Arg Arg Thr Glu Glu<br>              290               295              300 | 915 |
| gca tat aaa aat gca atg aca gaa ctt aag aaa aaa tcc cac ttt gga<br>Ala Tyr Lys Asn Ala Met Thr Glu Leu Lys Lys Lys Ser His Phe Gly<br>305                    310               315 | 963 |
| gga cca gat tat gaa gaa ggc cct aac agt ctg att aat gaa gaa gag<br>Gly Pro Asp Tyr Glu Glu Gly Pro Asn Ser Leu Ile Asn Glu Glu Glu<br>320                    325               330 | 1011 |

```
ttc ttt gat gct gtt gaa gct gct ctt gac aga caa gat aaa ata gaa    1059
Phe Phe Asp Ala Val Glu Ala Ala Leu Asp Arg Gln Asp Lys Ile Glu
335                 340                 345                 350 gaa cag tca cag agt gaa aag gtg aga tta cat tgg cct aca tcc ttg    1107
Glu Gln Ser Gln Ser Glu Lys Val Arg Leu His Trp Pro Thr Ser Leu
            355                 360                 365 ccc tct gga gat gcc ttt tct tct gtg ggg aca cat aga ttt gtc caa    1155
Pro Ser Gly Asp Ala Phe Ser Ser Val Gly Thr His Arg Phe Val Gln
370                 375                 380 aag ccc tat agt cgc tct tcc tcc atg tct tcc att gat cta gtc agt    1203
Lys Pro Tyr Ser Arg Ser Ser Ser Met Ser Ser Ile Asp Leu Val Ser
        385                 390                 395 gcc tct gat gat gtt cac aga ttc agc tcc cag gtt gaa gag atg gtg    1251
Ala Ser Asp Asp Val His Arg Phe Ser Ser Gln Val Glu Glu Met Val
400                 405                 410 cag aac cac atg act tac tca tta cag gat gta ggc gga gat gcc aat    1299
Gln Asn His Met Thr Tyr Ser Leu Gln Asp Val Gly Gly Asp Ala Asn
415                 420                 425                 430 tgg cag ttg gtt gta gaa gaa gga gaa atg aag gta tac aga aga gaa    1347
Trp Gln Leu Val Val Glu Glu Gly Glu Met Lys Val Tyr Arg Arg Glu
            435                 440                 445 gta gaa gaa aat ggg att gtt ctg gat cct tta aaa gct acc cat gca    1395
Val Glu Glu Asn Gly Ile Val Leu Asp Pro Leu Lys Ala Thr His Ala
                450                 455                 460 gtt aaa ggc gtc aca gga cat gaa gtc tgc aat tat ttc tgg aat gtt    1443
Val Lys Gly Val Thr Gly His Glu Val Cys Asn Tyr Phe Trp Asn Val
        465                 470                 475 gac gtt cgc aat gac tgg gaa aca act ata gaa aac ttt cat gtg gtg    1491
Asp Val Arg Asn Asp Trp Glu Thr Thr Ile Glu Asn Phe His Val Val
480                 485                 490 gaa aca tta gct gat aat gca atc atc att tat caa aca cac aag agg    1539
Glu Thr Leu Ala Asp Asn Ala Ile Ile Ile Tyr Gln Thr His Lys Arg
495                 500                 505                 510 gtg tgg cct gct tct cag cga gac gta tta tat ctt tct gtc att cga    1587
Val Trp Pro Ala Ser Gln Arg Asp Val Leu Tyr Leu Ser Val Ile Arg
            515                 520                 525 aag ata cca gcc ttg act gaa aat gac cct gaa act tgg ata gtt tgt    1635
Lys Ile Pro Ala Leu Thr Glu Asn Asp Pro Glu Thr Trp Ile Val Cys
                530                 535                 540 aat ttt tct gtg gat cat gac agt gct cct cta aac aac cga tgt gtc    1683
Asn Phe Ser Val Asp His Asp Ser Ala Pro Leu Asn Asn Arg Cys Val
        545                 550                 555 cgt gcc aaa ata aat gtt gct atg att tgt caa acc ttg gta agc cca    1731
Arg Ala Lys Ile Asn Val Ala Met Ile Cys Gln Thr Leu Val Ser Pro
560                 565                 570 cca gag gga aac cag gaa att agc agg gac aac att cta tgc aag att    1779
Pro Glu Gly Asn Gln Glu Ile Ser Arg Asp Asn Ile Leu Cys Lys Ile
575                 580                 585                 590 aca tat gta gct aat gtg aac cct gga gga tgg gca cca gcc tca gtg    1827
Thr Tyr Val Ala Asn Val Asn Pro Gly Gly Trp Ala Pro Ala Ser Val
            595                 600                 605 tta agg gca gtg gca aag cga gag tat cct aaa ttt cta aaa cgt ttt    1875
Leu Arg Ala Val Ala Lys Arg Glu Tyr Pro Lys Phe Leu Lys Arg Phe
                610                 615                 620 act tct tac gtc caa gaa aaa act gca gga aag cct att ttg ttc        1920
Thr Ser Tyr Val Gln Glu Lys Thr Ala Gly Lys Pro Ile Leu Phe
        625                 630                 635 tagtattaac aggtactaga agatatgttt tatctttttt taactttatt tgactaatat  1980
```

-continued gactgtcaat actaaaattt agttgttgaa agtatttact atgtttttc cggaattc    2038

<210> SEQ ID NO 24
<211> LENGTH: 637
<212> TYPE: PRT
<213> ORGANISM: Artificial Sequence
<220> FEATURE:
<223> OTHER INFORMATION: Description of Artificial Sequence: GPBP-D169A

<400> SEQUENCE: 24

```
Met Ala Pro Leu Ala Asp Tyr Lys Asp Asp Asp Lys Met Ser Asp
  1               5                  10                  15

Asn Gln Ser Trp Asn Ser Ser Gly Ser Glu Glu Asp Pro Glu Thr Glu
                 20                  25                  30

Ser Gly Pro Pro Val Glu Arg Cys Gly Val Leu Ser Lys Trp Thr Asn
             35                  40                  45

Tyr Ile His Gly Trp Gln Asp Arg Trp Val Val Leu Lys Asn Asn Ala
         50                  55                  60

Leu Ser Tyr Tyr Lys Ser Glu Asp Glu Thr Glu Tyr Gly Cys Arg Gly
 65                  70                  75                  80

Ser Ile Cys Leu Ser Lys Ala Val Ile Thr Pro His Asp Phe Asp Glu
                 85                  90                  95

Cys Arg Phe Asp Ile Ser Val Asn Asp Ser Val Trp Tyr Leu Arg Ala
            100                 105                 110

Gln Asp Pro Asp His Arg Gln Gln Trp Ile Asp Ala Ile Glu Gln His
        115                 120                 125

Lys Thr Glu Ser Gly Tyr Gly Ser Glu Ser Ser Leu Arg Arg His Gly
    130                 135                 140

Ser Met Val Ser Leu Val Ser Gly Ala Ser Gly Tyr Ser Ala Thr Ser
145                 150                 155                 160

Thr Ser Ser Phe Lys Lys Gly His Ser Leu Arg Glu Lys Leu Ala Glu
                165                 170                 175

Met Glu Thr Phe Arg Ala Ile Leu Cys Arg Gln Val Asp Thr Leu Gln
            180                 185                 190

Lys Tyr Phe Asp Ala Cys Ala Asp Ala Val Ser Lys Asp Glu Leu Gln
        195                 200                 205

Arg Asp Lys Val Val Glu Asp Glu Asp Phe Pro Thr Thr Arg
    210                 215                 220

Ser Asp Gly Asp Phe Leu His Ser Thr Asn Gly Asn Lys Glu Lys Leu
225                 230                 235                 240

Phe Pro His Val Thr Pro Lys Gly Ile Asn Gly Ile Asp Phe Lys Gly
                245                 250                 255

Glu Ala Ile Thr Phe Lys Ala Thr Thr Ala Gly Ile Leu Ala Thr Leu
            260                 265                 270

Ser His Cys Ile Glu Leu Met Val Lys Arg Glu Asp Ser Trp Gln Lys
        275                 280                 285

Arg Leu Asp Lys Glu Thr Glu Lys Lys Arg Arg Thr Glu Glu Ala Tyr
    290                 295                 300

Lys Asn Ala Met Thr Glu Leu Lys Lys Lys Ser His Phe Gly Gly Pro
305                 310                 315                 320

Asp Tyr Glu Glu Gly Pro Asn Ser Leu Ile Asn Glu Glu Phe Phe
                325                 330                 335

Asp Ala Val Glu Ala Ala Leu Asp Arg Gln Asp Lys Ile Glu Glu Gln
            340                 345                 350

Ser Gln Ser Glu Lys Val Arg Leu His Trp Pro Thr Ser Leu Pro Ser
```

-continued

```
               355                 360                 365
Gly Asp Ala Phe Ser Ser Val Gly Thr His Arg Phe Val Gln Lys Pro
        370                 375                 380
Tyr Ser Arg Ser Ser Ser Met Ser Ser Ile Asp Leu Val Ser Ala Ser
385                 390                 395                 400
Asp Asp Val His Arg Phe Ser Ser Gln Val Glu Glu Met Val Gln Asn
                405                 410                 415
His Met Thr Tyr Ser Leu Gln Asp Val Gly Gly Asp Ala Asn Trp Gln
            420                 425                 430
Leu Val Val Glu Glu Gly Glu Met Lys Val Tyr Arg Arg Glu Val Glu
        435                 440                 445
Glu Asn Gly Ile Val Leu Asp Pro Leu Lys Ala Thr His Ala Val Lys
    450                 455                 460
Gly Val Thr Gly His Glu Val Cys Asn Tyr Phe Trp Asn Val Asp Val
465                 470                 475                 480
Arg Asn Asp Trp Glu Thr Thr Ile Glu Asn Phe His Val Val Glu Thr
                485                 490                 495
Leu Ala Asp Asn Ala Ile Ile Ile Tyr Gln Thr His Lys Arg Val Trp
            500                 505                 510
Pro Ala Ser Gln Arg Asp Val Leu Tyr Leu Ser Val Ile Arg Lys Ile
        515                 520                 525
Pro Ala Leu Thr Glu Asn Asp Pro Glu Thr Trp Ile Val Cys Asn Phe
    530                 535                 540
Ser Val Asp His Asp Ser Ala Pro Leu Asn Asn Arg Cys Val Arg Ala
545                 550                 555                 560
Lys Ile Asn Val Ala Met Ile Cys Gln Thr Leu Val Ser Pro Pro Glu
                565                 570                 575
Gly Asn Gln Glu Ile Ser Arg Asp Asn Ile Leu Cys Lys Ile Thr Tyr
            580                 585                 590
Val Ala Asn Val Asn Pro Gly Gly Trp Ala Pro Ala Ser Val Leu Arg
        595                 600                 605
Ala Val Ala Lys Arg Glu Tyr Pro Lys Phe Leu Lys Arg Phe Thr Ser
    610                 615                 620
Tyr Val Gln Glu Lys Thr Ala Gly Lys Pro Ile Leu Phe
625                 630                 635
```

<210> SEQ ID NO 25
<211> LENGTH: 12482
<212> TYPE: DNA
<213> ORGANISM: Homo sapiens

<400> SEQUENCE: 25

```
tcgatcattt ccctcttcat attcagtgta tattgcacag atctctcaac aacacagcca    60
ttaaatagat attctccaag tgacacttac atcacacatg tttgagttta cgttacttgc   120
aaacataggg aaagaaagat acatgggata aactggtgca tgagaaatga gatcttagca   180
gttggttgaa ataatgaga acaactgagg caaactaaag aggaagaagg gcaagtggca   240
gcttaacagg agtaagatga tgagatgaag ggcagaatac cttcatggag aggaggcaaa   300
gagatataca tgtatgttc ttaggaacat aactgaagca aacaatgata ttatttctaa    360
ttatatataa acctgtgagt cagccttcca ggggcggcct gctaaggtag aatcattgga   420
atgatttggc cagggtttgg ataggagaga attggcagca gcgttaagat tgacccatga   480
taaataatgc tatgcaggta gcaggagtc tgactaggag caaaatcaac gaacttatcc     540
```

-continued

```
cttgcctaac atagtatctg tggagtcaga aagaagaggt taaattggga tatctgaggc      600
aagtatcagg atttgccatg tctgcggagt agtttcataa ttctaatggt tataagcact      660
aaggcgttca ctaagtgaat gttggtagtt ccaggttata ttatccattc ttgagttaca      720
aaatacactt taaaaccttc ccatcttaat attatatgtt tttttagtca cagagtgaaa      780
aggtgagatt acattggcct acatccttgc cctctggaga tgccttttct tctgtgggga      840
cacatagatt tgtccaaaag gtaagctaat gtcagagttt actaaaagta caccttgtat      900
tgttcttcat tgttggtgga aatatctttt atttgagacg gagtctcact ctgtcaccag      960
agtggagtgc agtggcgcga tctcggctca ctacagtctc cacctcccgg gttcaagaga     1020
ttctcgtgcc tcagcctccc tggtagctgg gattacaggc atgtaccacc acacccagct     1080 aattttttgta tttttaatgg agacagtttc accatggcca ggatggtctt gatctcctga     1140
ccttgtgatc cacccacctc agcctcccag agtgctggga ttacaggcgt gagccaccat     1200
gcccagccgg aaatatcttg tagtatataa gttttctccc cttttcatta atttaagtaa     1260
tgagactgtt tttggtttta tatattgtat tccatataca tcctccaaaa cagttagaaa     1320
ttttgttctg aaaataaagt tctttcattt ttatttaagg ggaaagttgg gggtgggcaa     1380
ataaggagtg gctagtccaa aatagttaac cagaagtata tccagttata ctaaatctct     1440
ctcttctttg gggttaaatg gtattacttt gtattattgg aagcactaca ttcttttttg     1500
gaatgatttt ggaacataat acataatagg tgcatgaagt cagcagttgc tgctgtgctt     1560
gtttcatata gtgctttgtt ttctcttccc tttatcttgt gtttggaagt tggtactgaa     1620
tgctctgttg tgcctttgtt ctgattactt ggttttttct ttgtctgtct ctggtagccc     1680
tatagtcgct cttcctccat gtcttccatt gatctagtca gtgcctctga tgatgttcac     1740
agattcagct cccaggtact gtatgaatgt atagagtgga cttgagtctt tctgtgctat     1800
atttcagcct gctttcccag ttcctagaaa tcttttggtt aggccactga ttttagtttt     1860
gaatttaaaa tagtaacatt aagcattaaa aaggtcttcc ttgtctacta aatagttcct     1920
ctgtcaggtt tgcatgtgtc ctttactatt cacagcttgg aattttgtca tataggaggt     1980
actccagaaa gattttcaaa ctgaattgaa acaaatagaa gatactgggt tttgtatatc     2040
atgtaatatc tgtttcttca gtcaggattt agcagttttg atggacgtgg tccatatgat     2100
atgttatagc agaaaagcag attttttacaa gtctcacttt aaagcctaaa gtaccccccaa     2160 ttaatattca acaaggaaat cacttttttaa taatatgttt catttccatt ataatactaa     2220
gctctattga gcagattgtg ttttccttat gcaaattacc tttggatatt ataaatgaat     2280
atttctgttc atatgctaaa tctatggaaa tttgttttaa ttttttagcat tggtaagggt     2340 ttaggaattt aagacaggaa gctggatgct tgcggtctct aaagtctgta ccctcaaaat     2400
aaaatcagat taccattgga agaagttttt tttagtgtca gcgttagttc tttttttaat     2460
tttcttaatc ttcacatctt tgccattcaa cttttttatct ttctggtgat tgcattttat     2520
tggactagat tatattatgt taatcttata ttaaagacct gagcactctg gtcagaatga     2580
ctcagtttaa accctggtta ggtgtatgat cccagtaagt tttctaactt ttttgtgctt     2640
catttttatg atttagctag aacctgacac ataataagtg ctcaataaat gttaccttgt     2700
attgctatta taacataatt tctttgagct aataaaagtt atctacatca ttattttttc     2760
ctctgtgaga gtattgctat aaaagttttt aaaagtcata gtttaaagag atttctatta     2820
tttttatgtt tataaataaa gtttacatta gttttttaacc tgcaatagag aagaatatta     2880
agactttaat ttttctgact tgtacagcgt ttttctcctt gaatactctt aagaaaaaga     2940
```

-continued

```
tttagcaatt ctggatcaga aatcatccat aaccaaatat accacagtat attttacctt    3000
ttgcttgtcc atttatgcat ttttttttaa ttttacttat ttattttcga gacagggtct    3060
tgctctgttg cccaggctgg agtgcagtgg cacgatctgg ctcactgca acctccatct    3120
cccaggttca gcaattctc ctgcctcagc ctcccaagta gctgggatta caggcacgca    3180
ccactatgcc cagctaattt ttgtattctt agtaaagacg gttttcacc atgttggcca    3240
ggctggtcta gcactcctga cctcgtgatc tgcccacctc ggcctcccaa agtgctggga    3300
ttacaggtgt gagccaccat gcccggccct gcgtatgttt taaaaagag actcatattc    3360
ataatgaatc tgtgacaaaa ctacataata ctgggagact ttggtttatt gtgctaagct    3420
ccacattgca ttaaaatcat atcacagact aatcaaaaat gcaggaatac ataggctata    3480
aatgaaagaa aatataatga cagcaaagaa agaatgtaag ccagtaataa agaatgccta    3540
agaattaggg gttcagaacc caaaccaggg ccctcactgt agtgctgtag aacagctgaa    3600
ttgcttttaa gtccaggtaa ctatatcact gagaagcagg tgcctatatt tttacaaaat    3660
tttgctgaca gcttacttct tcgtaatatt aatacccttt tgtaaaactc atgtatgtaa    3720
cttgagagaa atcttgctgg attttttct ctaatatatg gtgctcatga ttgatcagat    3780
cctgttttag cctttgatta tgtactgttt tatatgccag aagagtaaa aatgaagaaa    3840
ataacattaa ggtcttcaag tatttgttgt ccttgctaaa gcattagttg tcattagcag    3900
acgtggactc tagcaattca ctgttgtaat taaattgtgt gccttatgtt cagcagttcc    3960
tttataatag atgactaatt cccaattgat aagattttt gtttcagagg atgttacact    4020
gccttatcag ccattatcaa aggatctagc aagttgattc tgtatagtca cacttgagaa    4080
tatagcattg gatgtagatc tggagttaat attagttgag aaacattgtg ttatctggaa    4140
aactcttcca gttcaacaca gtgtaaaatt atagtagtga ctatacagta gtgttacatt    4200
ttacagttct cacaccctat agagactttt gtattaacaa aataagaggc tcaaaggtta    4260
ttcattaaca ttagaaacac ttatgttata ttacattgca tcggtctttt ctgttttttg    4320
tttttttttt tttttttgaga cggagtttcg cttttgttgc ccaggctgga gtgcaatggt    4380
acgatcttgg ctcactgcac cctctgcccc ctggattcaa gcgattctct tgcctcagcc    4440
acctgagtag ctgggattac aggcacctgc caccacaccc agctaatttt ttttcatttt    4500
tagtagagat ggggtttcac catgttggcc aggctggtct cgaactcctg acctcaggtg    4560
atctgcccgc ctcggcctcc caaagtgctg ggattacagg catgagccgc cacacctggc    4620
ctacatcgtt cttaatacac aaatatacat cagttactcc acagcgcttg atatgggagg    4680
taaccaaatt ctttgtttta taatatcttc ataattaatt aaaaaactaa gtcgacattt    4740
ttaatcacct ttaataattt gccaaaatat tatataagca taatataatc aattcttact    4800
tactccaaca aattttaaaa gtccagatac agataccata tctagttct tgatcattta    4860
tatcagctcc catacagaag ccttctaaat ctctggtaat ttcactttgc tgtttatata    4920
agtgttggct catgactacc ttgttcttct tgaaatgatg ttttatagcc ttgaattggc    4980
tgaaataatc aagtgtacaa ttgagagatg ccctgaaaac agcttaaaat aaaatatgta    5040
catctactag gaaattagta ccaacacatg aatctgtctg atgggcagat attaggaatg    5100
aagtcactcc agatctgaga aattaaagtt gtaaaggact gcaagttctg tgttttttgtt    5160
gttgttgttg ttgttgttgt tgtttgtttt tcattttttg tttttttgggt ttttttgaga    5220
cagagtctca ttctgtcacc caggctgtag tgcagtggca cgatctcaac tcactgcaac    5280
```

```
ctccgtctcc caggttcaag cgattctcct gtctcagctg ggattacagg cacacgctat    5340
cacacccagc taattttgt attttagta gagacagggt ttcaccatgt tagccaggct    5400
ggtctcgaac tcctgacctc aagtgatctg cccgtctcgg cctcccaaag tgctgggatt    5460
acaggcctga gacaccatgc ccagcatttt ttttttttt tttttttttt gtaaagagac    5520
aaggtttcac ttgtccaggc caagtgcagt ggcatgatca tagctctgta acctgacctc    5580
tgacctctga cttcctggac acaagtgatc ctcctgtctc tcagcctccc aagtagctgg    5640
gactacaggc attccaccac acccaactaa ttgttttat tttttgtaga gacagggcct    5700
tgctatgttg cccaggctgg caagttcttg aaataatggc tgtggccaca aactagaaaa    5760
taattttcag gtgtacagag aatagaaaga atttagattc ataaattgat cattttgttc    5820
acagttattt gcataacaca gttcacattt aaggtgtca ccttagaaat caaggggaa    5880 gaacatcatc ctctattgaa aagaaagaa atcaaggat gtacagtgaa tttgcagctt    5940
aatctatggg gagcatcatt gcaaaaaatg gttctgtgtg aggctctttc ccacccttg    6000 tccataggag cacattattg ttgtagtaat tatttcaccc ctctcccttt ttcagtgtac    6060
aagtgataca tgctaatttt aacagaactt gaaagtagaa taaattaaa ataatagttt    6120 actaatattc catttatctt ctctcatata tatgagataa atattaaggt gtatgtactt    6180
atccatatgt gcctgatttt ttaaaatcct tgtatatgca tctttgcacc cttatctaat    6240
tatttcctta gaatatattc ctagaagcat aattgtggga acaaaggcca tgaacatttt    6300
caagtgttta ttttattatt ttatttatt tttattaatt ttgatacagg ttttgcttt    6360 gttccccaga ctggagtgca gtggtgagat caccactcac tgcaccttga cctcctggac    6420
tcaagcgatc cacctgcctc agtctcctca gtagcggggg ctaaggacta caggcacatg    6480
ccatcatgcc cagctaattt ttttatttgt agcagagacg aggtctcact gtgttgccca    6540
ggctgctatt ttattatttt tttaagagat agggtctcat tctgtcttcc aggctagaat    6600
gcagtggcac aatcatagct cactgcaacc tcaagcgatc tttgcctcag cctgagtagc    6660
tgggactaca ggcatgggcc accactctca gctaattttt ttttcaattt tttatttttt    6720
gtagatatgg gggtctcact gtgttgccta ggctggtctt gaaccctag cctaaagtga    6780 tcttcccacc tcagcctccc aaagtgctag gattacaggc cacaggcctc agccaagttt    6840
taaaaatttt tactgccaaa ctcttcatta gaaagttga accagcttac attccaggc    6900 cagttttcta ttgatatagt agcactgaat attataattc agttaacttt tgtcaatacg    6960
gtaggctaaa agtgctatgt tcttagccat ctctcttttg ggttaacagt gcactatttt    7020
gttattaata attattctat ctaacaagcc ccctctatgg ttttgtggct ttgtagtaag    7080
catagttgta tttcctttt tgaggtggag tcttgctatg ttgcccaggc tggagtgcag    7140
tggcgcgatc tcggctcact gcaccctccg cctcccgggt tcaagtgatt ctcctgcctc    7200
agactcctga gtatctggga ctacaggcat gcaccaccac gcccagctaa tttttatat    7260 ttttagtaga gagggagtt caccgtgtta gccgggatgg tctctatctc ttgacctcgt    7320
ggtccgcgtg cctcagcctc ccaaaatgct gtgattacag gcatgagcca ccctgcctgg    7380
ccaacatttc ttttacatgc ataaaagaga tctgagctgt ttttgagccc ttctagactt    7440 tcttttttt ttttttttt tttttttttt tttttttttt tttttttaa gtagatgagg    7500 tcttgctatg ttgccgagac ttaacctcaa actcctaggc ccaagcaatc ctcccaagct    7560
gctgggacta caggcatgaa ccaccatgcc caacttagac ttttattgta ctatcaaaag    7620
gcaattttct tttcaaattt ctgggtaata gtgttagaaa aatcctactt ggtaacatcc    7680
```

-continued

```
agaaatggca tcatactgag tgattcaaat gtgagatgga agaaaaggtt agaattggag    7740
tgaacgtccc ctcttatctc aaatgtattt tatctccatt ttgtttcata gtttattagt    7800
ttgaagatgc tttgaatgtc acctaatcat tttcaactct aggtccagaa aaatcaaggg    7860
catgatttct gaaattacac ttagcctaat taaaacttag aaacactgtt caccttcttc    7920
aatgttttg actgagtctt tttcatttat aagtgacagg aggtgttact ataacattat     7980
ttcctagaat gtcaaatttt gagcctaata gcatggtaaa tttggctata tttgttgttt    8040
tttgtttttg tttttttttt aatgaaactt agtatttcct tgtttcccac ttcttttttt    8100
tttttttttt tttttttttt tgagacggag tctctctctg tcatccaggc tggagtgcaa    8160
tggcgtgatc ttggctcact gccacctccg cctcgcaggt tcacgctatt ctcctttcac    8220
agcctcctga gtagctggga ctacaggcac ccaccaccac gcccggccaa ttttttttgta   8280
tttttagtag agacggggtt ttaccatgtt aggcaggatg gtctcgaact cctgaccttg    8340
tgatctgccc gcctcagcct cccaaagtgc tgggattaca ggcgtgagcc accgcacctg    8400
gcctcccact tctttttaat atgtcgtgtc ataactgaac agtaaagtga gcagattatc    8460
aggttaaatc tgaagtgtca gtctggtcac cagtgcccaa gttactgccc ctatggtaat    8520
attggttact ttgtattttc ctacagcaaa cataaaattt gttatagtga gattttttacc   8580
tgtataccte tcttaacttt aatgttatta cctcaaggaa gatattatca tgaatgaaga    8640
ttccatgatg aaagttttgc agagtttatt gcagtaattt agtacttcat tagaatcttt    8700
agttttttag gagcacagta ctgaatgttt gtttctttgt tggaccttttt gaaaaccggt   8760
tttccattga tgcagtgtag ctgttacagg aatatcattt ttaaaacgtt tttatacagc    8820
atggctgaaa attgaacctg ggcctccctc gtggcctacc attgaaggaa cagcattttt    8880
tgcctatcta gaaagacaat gttaaatgtg ctatctatat attttttaac ttgtgctacc    8940
tactacgcgt ttatatttgt ggaatctgtt ttcttttgga caaaaccaca aatcaaaaac    9000
acctcatttc ttaggcattt gaaatcccta attcagaata atctcccaaa cagaaacaca    9060
actacctgca ttcttttttga caaaagagct aagtagcatt agaaaattat tttaaaccca   9120
attctgttttt ttaacagaat aaaattcttc tgttcttcac attcttcttt cataggtaac   9180
ctattgaaag tagggtttat ttgggggaag catttctttc tgtctcttat ctcataataa    9240
atacaggtgt gcttaactac tagtttccta cctcaaagat atactcaaat ctaaagatgt    9300
ttaagattttt gggatctgaa gagtaaacat ttctcctaat cacaatgtga cagagacaaa   9360
tgaatcaagc caatgctact tttatttatg catactaact ggaacttttc ttttttggaaa  9420
tcagatacat tttgtatgta ttagtaattt ggaatcctgc attggttatc ctcgccctcc    9480
caaagcagat tctgaaatta taaaggtgca caggttctcc atgcaacacc aaaagttata    9540
ttttccaagg ctttgtaaaa ttgtagaatg tcctgttaaa tttctgtcaa atcagtaact    9600
cacactgttt tgagaattat gaataaagga ataaatatt gttagtgttt atttagtaca    9660
aaagtagatt atagaatctc agcatttttg tcaaaaaatt tctttttgat gattgacaga    9720
tcaggagaca cttaaggcca tacctgcttt cagtaatcaa aaatgcattt aagatccaga    9780
aacttgaggt agcagaacat cactatcaca tataacatat cctttggtat agaaaattat    9840
attcccagag tgagtttctt ttttaaaacc attaatgagg ccaaggtggg aagatcactt    9900
gggaccagga gttcaagacc aagcctgggc cagatggcga gaccctgtct ctacaaaaaa   9960
ttaactggat gtggtggtgc actcctgtag tcccacctac tcagaggctg aggcaggagg  10020
```

```
atcccttgag cccaggaaat tgtagtggca gtgagctatg atcatactac tgtactgcag    10080
tctgggccac gaagtgagac cgtgtctctt aaaaaaaaaa aaatgttagg catggtggca    10140
caggcatata gttttagcta cttaggaggc tgaggcagga ggatcacttg agcccagaag    10200
ttcaagatta cagtgagtta tgattgtgcc gctgcactcc aacctgggtg acaaaataac    10260
cctgtctctg gcgggtaggg gggaagttga ttatttactt tgaaatatgt tcaaaactga    10320
ttcctgttct atattcctaa tgaacagaat agactttata taaaacaaat agttaaactt    10380
aaggataaaa ttttaatgga agtataaatat atatatcttc cagctcttct gtcttctaat    10440
gtatttatta cagaaaatga aattactttg tttccgcaat ctttgtatca cttcagttct    10500
ccaataaatc tgagaattct ggtagtgtga atattcagc tttctttgct tatttacata    10560
aaatgtataa ggacaatttg tgataattaa gagttacatt taaatatcag gaaaagtta    10620 taaatttaaa ttaaaaaatt ttaaaaggaa attattagaa attttaaaag aatgaactaa    10680
aaggtgatta tatgtaaatg cttgcatata tgaatattag cattgtcccc aaaataattt    10740
agaacaaaga aattggaatc aaataaataa aggtttgatt attttttaaat tggcttatat    10800 tccatgataa aagagaggtt tatcagtggc ataagaaagg ttttttcacct tttttgtatt    10860 gaaatctttg acatatacat atatatcttt gctcatcttt gtgtatcttt gctcgtatga    10920
gagcaaagat ataggcaaag atatgctctc tctctctatg tctttgttca taccaagacc    10980
ttcctgatat ctccacataa tcttaaatat aggaacatta gactggatga tctctgtgcc    11040 cccttttatct ctactcttcc attatttttat actttaacac atcatctctg ttttatgata    11100
taagaatgga atatttctttt ttttcctgaaa atgcttattt tggtcacttg atacacatta    11160
ggccaatatg tgttacttga gtgacccatc ttccttcttt tcatttctgt ctcctgtcat    11220
taacctggat atctggaatg tggactaaac tcttcaaaca ctatgtaaaa cctactaacc    11280
tttgtgcatt tggttgctca gctactaaga gcaccatttc tgaactgaag ttaactgaag    11340
accattctgt tttagagatt atgacatacc tttttggattc tcatgccttt tccctcccctt    11400 ctcaaggttg aagagatggt gcagaaccac atgacttact cattacagga tgtaggcgga    11460
gatgccaatt ggcagttggt tgtagaagaa ggagaaatga aggtaattcc ccctgaaatg    11520
ttatagattg ccaaaggcgt ctctgtttca gtcatattat cattactatt gatatgaata    11580
aggatagcac tttcaactta cctttaaaac aaattattac atgtgatcaa agcagtacca    11640
tatattgagc aataaaatgt ctttttgctt ttctggcttt gcctttacta aaggttttta    11700
tgattataat ataaatatat gattaaacct ttctgttttg actaggccat gaagaaaata    11760
aaatttagag aattagatat gaccaggtca caattagctg atggtcctgt atttggatat    11820
ttccttttgt tttgtttttt taacatactg aatgttgtgc ctagatgaca ctttgtttct    11880
ctcccttttt ggtctatacc ctccttcttt tcccttctct tactgcacct ttaattgata    11940
tttggacatt ggtcagttaa tcctggttac atccctaaac acatgacag aaaataagag    12000 cagggactga gagatacaga gatggattga aaagcaaaag caacattgaa ttttggattt    12060
tctcattcct aaggaactat gctaaataaa gatacaaaga taataagaca ctctccaagc    12120
taaagcttta gttaaggaaa aagaatattg acatttaaaa gatactattg gccaggcaca    12180
gtggctatgc ctgtaatccc agcactttta ggaggacatg gcaggcggat tacttgagct    12240
caggagttca agtcaaacct gggcaacacg tgaaaccccc gtctctacca aaatacaaa    12300 aattagctgg gtgcagtacc acacacttgt agtcccagct acccaggagg ctgggcaaaa    12360
gattccttga gccagggagg tcaaggctgc aatgagccgc gtttgtgcca ctgcactcta    12420
```

-continued

```
gcctgggtca caaagtgaga ccctgtgtga gatatatata tatatatata tatatatata    12480
ta                                                                   12482

<210> SEQ ID NO 26
<211> LENGTH: 21
<212> TYPE: PRT
<213> ORGANISM: Artificial Sequence
<220> FEATURE:
<223> OTHER INFORMATION: Description of Artificial Sequence: GPpep1

<400> SEQUENCE: 26

Lys Gly Lys Arg Gly Asp Ser Gly Ser Pro Ala Thr Trp Thr Thr Arg
  1               5                  10                  15

Gly Phe Val Phe Thr
             20

<210> SEQ ID NO 27
<211> LENGTH: 21
<212> TYPE: PRT
<213> ORGANISM: Artificial Sequence
<220> FEATURE:
<223> OTHER INFORMATION: Description of Artificial Sequence: GPpep1Ala9

<400> SEQUENCE: 27

Lys Gly Lys Arg Gly Asp Ala Gly Ser Pro Ala Thr Trp Thr Thr Arg
  1               5                  10                  15

Gly Phe Val Phe Thr
             20

<210> SEQ ID NO 28
<211> LENGTH: 50
<212> TYPE: DNA
<213> ORGANISM: Artificial Sequence
<220> FEATURE:
<223> OTHER INFORMATION: Description of Artificial Sequence: ON-GPBP-54m

<400> SEQUENCE: 28
tcgaattcac catggcccca ctagccgact acaaggacga cgatgacaag               50

<210> SEQ ID NO 29
<211> LENGTH: 50
<212> TYPE: DNA
<213> ORGANISM: Artificial Sequence
<220> FEATURE:
<223> OTHER INFORMATION: Description of Artificial Sequence: ON-GPBP-55c

<400> SEQUENCE: 29
ccgagcccga cgagttccag ctctgattat ccgacatctt gtcatcgtcg               50

<210> SEQ ID NO 30
<211> LENGTH: 32
<212> TYPE: DNA
<213> ORGANISM: Artificial Sequence
<220> FEATURE:
<223> OTHER INFORMATION: Description of Artificial Sequence:
      ON-HNC-B-N-14m

<400> SEQUENCE: 30
cgggatccgc tagctaagcc aggcaaggat gg                                  32

<210> SEQ ID NO 31
<211> LENGTH: 32
<212> TYPE: DNA
<213> ORGANISM: Artificial Sequence
```

-continued

```
<220> FEATURE:
<223> OTHER INFORMATION: Description of Artificial Sequence:
      ON-HNC-B-N-16c

<400> SEQUENCE: 31
cgggatccat gcataaatag cagttctgct gt                                    32

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: FLAG
      peptide

<400> SEQUENCE: 32

Asp Tyr Lys Asp Asp Asp Asp Lys
  1               5

<210> SEQ ID NO 33
<211> LENGTH: 18
<212> TYPE: PRT
<213> ORGANISM: Artificial Sequence
<220> FEATURE:
<223> OTHER INFORMATION: Description of Artificial Sequence:
      Hypothetical peptide

<400> SEQUENCE: 33

Pro Arg Ser Ala Arg Cys Gln Ala Arg Arg Arg Gly Gly Arg Thr
  1               5                  10                  15

Ser Ser

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence: ON-GPBP-11m

<400> SEQUENCE: 34
gcgggactca gcggccggat tttct                                            25

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: ON-GPBP-15m

<400> SEQUENCE: 35
acagctggca gaagagac                                                    18

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: ON-GPBP-20c

<400> SEQUENCE: 36
catgggtagc ttttaaag                                                    18

<210> SEQ ID NO 37
<211> LENGTH: 27
<212> TYPE: DNA
<213> ORGANISM: Artificial Sequence
```

```
<220> FEATURE:
<223> OTHER INFORMATION: Description of Artificial Sequence: ON-GPBP-22m

<400> SEQUENCE: 37
tagaagaaca gtcacagagt gaaaagg                                         27

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: ON-GPBP-53c

<400> SEQUENCE: 38
gaattcgaac aaaataggct ttc                                             23

<210> SEQ ID NO 39
<211> LENGTH: 17
<212> TYPE: DNA
<213> ORGANISM: Artificial Sequence
<220> FEATURE:
<223> OTHER INFORMATION: Description of Artificial Sequence: ON-GPBP-56m

<400> SEQUENCE: 39
ccctatagtc gctcttc                                                    17

<210> SEQ ID NO 40
<211> LENGTH: 17
<212> TYPE: DNA
<213> ORGANISM: Artificial Sequence
<220> FEATURE:
<223> OTHER INFORMATION: Description of Artificial Sequence: ON-GPBP-57c

<400> SEQUENCE: 40
ctgggagctg aatctgt                                                    17

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: ON-GPBP-62c

<400> SEQUENCE: 41
gtggttctgc accatctctt caac                                            24

<210> SEQ ID NO 42
<211> LENGTH: 41
<212> TYPE: DNA
<213> ORGANISM: Artificial Sequence
<220> FEATURE:
<223> OTHER INFORMATION: Description of Artificial Sequence: ON-GPBP-26

<400> SEQUENCE: 42
cacatagatt tgtccaaaag gttgaagaga tggtgcagaa c                         41

<210> SEQ ID NO 43
<211> LENGTH: 19
<212> TYPE: PRT
<213> ORGANISM: Artificial Sequence
<220> FEATURE:
<223> OTHER INFORMATION: Description of Artificial Sequence: GPIII
      derived peptide

<400> SEQUENCE: 43

Gln Arg Ala His Gly Gln Asp Leu Asp Ala Leu Phe Val Lys Val Leu
```

```
                    1               5                   10                  15
Arg Ser Pro

<210> SEQ ID NO 44
<211> LENGTH: 14
<212> TYPE: PRT
<213> ORGANISM: Artificial Sequence
<220> FEATURE:
<223> OTHER INFORMATION: Description of Artificial Sequence: GPIII-IV-V
      derived peptide

<400> SEQUENCE: 44

Gln Arg Ala His Gly Gln Asp Leu Glu Ser Leu Phe His Gln
  1               5                  10

<210> SEQ ID NO 45
<211> LENGTH: 685
<212> TYPE: DNA
<213> ORGANISM: Artificial Sequence
<220> FEATURE:
<223> OTHER INFORMATION: Description of Artificial Sequence: GPDV
<220> FEATURE:
<221> NAME/KEY: CDS
<222> LOCATION: (1)..(633)

<400> SEQUENCE: 45 ggt ttg aaa gga aaa cgt gga gac agt gga tca cct gca acc tgg aca         48
Gly Leu Lys Gly Lys Arg Gly Asp Ser Gly Ser Pro Ala Thr Trp Thr
  1               5                  10                  15 acg aga ggc ttt gtc ttc acc cga cac agt caa acc aca gca att cct         96
Thr Arg Gly Phe Val Phe Thr Arg His Ser Gln Thr Thr Ala Ile Pro
             20                  25                  30 tca tgt cca gag ggg aca gtg cca ctc tac agt ggg ttt tct ttt ctt        144
Ser Cys Pro Glu Gly Thr Val Pro Leu Tyr Ser Gly Phe Ser Phe Leu
         35                  40                  45 ttt gta caa gga aat caa cga gcc cac gga caa gac ctt gga act ctt        192
Phe Val Gln Gly Asn Gln Arg Ala His Gly Gln Asp Leu Gly Thr Leu
     50                  55                  60 ggc agc tgc ctg cag cga ttt acc aca atg cca ttc tta ttc tgc aat        240
Gly Ser Cys Leu Gln Arg Phe Thr Thr Met Pro Phe Leu Phe Cys Asn
 65                  70                  75                  80 gtc aat gat gta tgt aat ttt gca tct cga aat gat tat tca tac tgg        288
Val Asn Asp Val Cys Asn Phe Ala Ser Arg Asn Asp Tyr Ser Tyr Trp
                 85                  90                  95 ctg tca aca cca gct ctg atg cca atg aac atg gct ccc att act ggc        336
Leu Ser Thr Pro Ala Leu Met Pro Met Asn Met Ala Pro Ile Thr Gly
            100                 105                 110 aga gcc ctt gag cct tat ata agc aga tgc act gtt tgt gaa ggt cct        384
Arg Ala Leu Glu Pro Tyr Ile Ser Arg Cys Thr Val Cys Glu Gly Pro
        115                 120                 125 gcg atc gcc ata gcc gtt cac agc caa acc act gac att cct cca tgt        432
Ala Ile Ala Ile Ala Val His Ser Gln Thr Thr Asp Ile Pro Pro Cys
    130                 135                 140 cct cac ggc tgg att tct ctc tgg aaa gga ttt tca ttc atc atg aaa        480
Pro His Gly Trp Ile Ser Leu Trp Lys Gly Phe Ser Phe Ile Met Lys
145                 150                 155                 160 gcc tat tcc atc aac tgt gaa agc tgg gga att aga aaa aat aat aag        528
Ala Tyr Ser Ile Asn Cys Glu Ser Trp Gly Ile Arg Lys Asn Asn Lys
                165                 170                 175 tcg ctg tca ggt gtg cat gaa gaa aag aca ctg aag cta aaa aag aca        576
Ser Leu Ser Gly Val His Glu Glu Lys Thr Leu Lys Leu Lys Lys Thr
            180                 185                 190 gca gaa ctg cta ttt ttc atc cta aag aac aaa gta atg aca gaa cat        624
```

-continued

```
Ala Glu Leu Leu Phe Phe Ile Leu Lys Asn Lys Val Met Thr Glu His
        195                 200                 205 gct gtt att taggtatttt tctttaacca aacaatattg ctccatgatg              673
Ala Val Ile
    210 acttagtaca aa                                                        685

<210> SEQ ID NO 46
<211> LENGTH: 211
<212> TYPE: PRT
<213> ORGANISM: Artificial Sequence
<220> FEATURE:
<223> OTHER INFORMATION: Description of Artificial Sequence: GPDV

<400> SEQUENCE: 46

Gly Leu Lys Gly Lys Arg Gly Asp Ser Gly Ser Pro Ala Thr Trp Thr
  1               5                  10                  15

Thr Arg Gly Phe Val Phe Thr Arg His Ser Gln Thr Thr Ala Ile Pro
             20                  25                  30

Ser Cys Pro Glu Gly Thr Val Pro Leu Tyr Ser Gly Phe Ser Phe Leu
         35                  40                  45

Phe Val Gln Gly Asn Gln Arg Ala His Gly Gln Asp Leu Gly Thr Leu
     50                  55                  60

Gly Ser Cys Leu Gln Arg Phe Thr Thr Met Pro Phe Leu Phe Cys Asn
 65                  70                  75                  80

Val Asn Asp Val Cys Asn Phe Ala Ser Arg Asn Asp Tyr Ser Tyr Trp
                 85                  90                  95

Leu Ser Thr Pro Ala Leu Met Pro Met Asn Met Ala Pro Ile Thr Gly
            100                 105                 110

Arg Ala Leu Glu Pro Tyr Ile Ser Arg Cys Thr Val Cys Glu Gly Pro
        115                 120                 125

Ala Ile Ala Ile Ala Val His Ser Gln Thr Thr Asp Ile Pro Pro Cys
    130                 135                 140

Pro His Gly Trp Ile Ser Leu Trp Lys Gly Phe Ser Phe Ile Met Lys
145                 150                 155                 160

Ala Tyr Ser Ile Asn Cys Glu Ser Trp Gly Ile Arg Lys Asn Asn Lys
                165                 170                 175

Ser Leu Ser Gly Val His Glu Glu Lys Thr Leu Lys Leu Lys Lys Thr
            180                 185                 190

Ala Glu Leu Leu Phe Phe Ile Leu Lys Asn Lys Val Met Thr Glu His
        195                 200                 205

Ala Val Ile
    210

<210> SEQ ID NO 47
<211> LENGTH: 680
<212> TYPE: DNA
<213> ORGANISM: Artificial Sequence
<220> FEATURE:
<223> OTHER INFORMATION: Description of Artificial Sequence: GPDIII
<220> FEATURE:
<221> NAME/KEY: CDS
<222> LOCATION: (1)..(216)

<400> SEQUENCE: 47 ggt ttg aaa gga aaa cgt gga gac agt gga tca cct gca acc tgg aca    48
Gly Leu Lys Gly Lys Arg Gly Asp Ser Gly Ser Pro Ala Thr Trp Thr
  1               5                  10                  15 acg aga ggc ttt gtc ttc acc cga cac agt caa acc aca gca att cct    96
```

```
                Thr Arg Gly Phe Val Phe Thr Arg His Ser Gln Thr Thr Ala Ile Pro
                                20                  25                  30 tca tgt cca gag ggg aca gtg cca ctc tac agt ggg ttt tct ttt ctt              144
Ser Cys Pro Glu Gly Thr Val Pro Leu Tyr Ser Gly Phe Ser Phe Leu
         35                  40                  45 ttt gta caa gga aat caa cga gcc cac gga caa gac ctt gat gca ctg              192
Phe Val Gln Gly Asn Gln Arg Ala His Gly Gln Asp Leu Asp Ala Leu
     50                  55                  60 ttt gtg aag gtc ctg cga tcg cca tagccgttca cagccaaacc actgacattc             246
Phe Val Lys Val Leu Arg Ser Pro
 65                  70 ctccatgtcc tcacggctgg atttctctct ggaaaggatt ttcattcatc atgttcacaa            306
gtgcaggttc tgagggcacc gggcaagcac tggcctcccc tggctcctgc ctggaagaat            366
tccgagccag cccatttcta gaatgtcatg gaagaggaac gtgcaactac tattcaaatt            426
cctacagttt ctggctggct tcattaaacc cagaaagaat gttcagaaag cctattccat            486
caactgtgaa agctgggaa ttagaaaaaa taataagtcg ctgtcaggtg tgcatgaaga             546
aaagacactg aagctaaaaa agacagcaga actgctattt ttcatcctaa agaacaaagt            606
aatgacagaa catgctgtta tttaggtatt tttctttaac caaacaatat tgctccatga            666
tgacttagta caaa                                                              680

<210> SEQ ID NO 48
<211> LENGTH: 72
<212> TYPE: PRT
<213> ORGANISM: Artificial Sequence
<220> FEATURE:
<223> OTHER INFORMATION: Description of Artificial Sequence: GPDIII

<400> SEQUENCE: 48

Gly Leu Lys Gly Lys Arg Gly Asp Ser Gly Ser Pro Ala Thr Trp Thr
 1               5                  10                  15

Thr Arg Gly Phe Val Phe Thr Arg His Ser Gln Thr Thr Ala Ile Pro
                20                  25                  30

Ser Cys Pro Glu Gly Thr Val Pro Leu Tyr Ser Gly Phe Ser Phe Leu
         35                  40                  45

Phe Val Gln Gly Asn Gln Arg Ala His Gly Gln Asp Leu Asp Ala Leu
     50                  55                  60

Phe Val Lys Val Leu Arg Ser Pro
 65                  70

<210> SEQ ID NO 49
<211> LENGTH: 392
<212> TYPE: DNA
<213> ORGANISM: Artificial Sequence
<220> FEATURE:
<223> OTHER INFORMATION: Description of Artificial Sequence: GPDIII-IV-V
<220> FEATURE:
<221> NAME/KEY: CDS
<222> LOCATION: (1)..(204)

<400> SEQUENCE: 49 ggt ttg aaa gga aaa cgt gga gac agt gga tca cct gca acc tgg aca               48
Gly Leu Lys Gly Lys Arg Gly Asp Ser Gly Ser Pro Ala Thr Trp Thr
 1               5                  10                  15 acg aga ggc ttt gtc ttc acc cga cac agt caa acc aca gca att cct               96
Thr Arg Gly Phe Val Phe Thr Arg His Ser Gln Thr Thr Ala Ile Pro
                20                  25                  30 tca tgt cca gag ggg aca gtg cca ctc tac agt ggg ttt tct ttt ctt              144
Ser Cys Pro Glu Gly Thr Val Pro Leu Tyr Ser Gly Phe Ser Phe Leu
```

```
                 35                  40                  45
ttt gta caa gga aat caa cga gcc cac gga caa gac ctt gaa agc cta      192
Phe Val Gln Gly Asn Gln Arg Ala His Gly Gln Asp Leu Glu Ser Leu
         50                  55                  60 ttc cat caa ctg tgaaagctgg ggaattagaa aaataataa gtcgctgtca           244
Phe His Gln Leu
 65 ggtgtgcatg aagaaaagac actgaagcta aaaaagacag cagaactgct attttcatc    304 ctaaagaaca agtaatgac agaacatgct gttatttagg tattttctt taaccaaaca     364 atattgctcc atgatgactt agtacaaa                                       392

<210> SEQ ID NO 50
<211> LENGTH: 68
<212> TYPE: PRT
<213> ORGANISM: Artificial Sequence
<220> FEATURE:
<223> OTHER INFORMATION: Description of Artificial Sequence: GPDIII-IV-V

<400> SEQUENCE: 50

Gly Leu Lys Gly Lys Arg Gly Asp Ser Gly Ser Pro Ala Thr Trp Thr
 1               5                  10                  15

Thr Arg Gly Phe Val Phe Thr Arg His Ser Gln Thr Thr Ala Ile Pro
            20                  25                  30

Ser Cys Pro Glu Gly Thr Val Pro Leu Tyr Ser Gly Phe Ser Phe Leu
        35                  40                  45

Phe Val Gln Gly Asn Gln Arg Ala His Gly Gln Asp Leu Glu Ser Leu
    50                  55                  60

Phe His Gln Leu
 65

<210> SEQ ID NO 51
<211> LENGTH: 507
<212> TYPE: DNA
<213> ORGANISM: Artificial Sequence
<220> FEATURE:
<223> OTHER INFORMATION: Description of Artificial Sequence: GPDIII-V
<220> FEATURE:
<221> NAME/KEY: CDS
<222> LOCATION: (1)..(216)

<400> SEQUENCE: 51 ggt ttg aaa gga aaa cgt gga gac agt gga tca cct gca acc tgg aca      48
Gly Leu Lys Gly Lys Arg Gly Asp Ser Gly Ser Pro Ala Thr Trp Thr
 1               5                  10                  15 acg aga ggc ttt gtc ttc acc cga cac agt caa acc aca gca att cct      96
Thr Arg Gly Phe Val Phe Thr Arg His Ser Gln Thr Thr Ala Ile Pro
            20                  25                  30 tca tgt cca gag ggg aca gtg cca ctc tac agt ggg ttt tct ttt ctt      144
Ser Cys Pro Glu Gly Thr Val Pro Leu Tyr Ser Gly Phe Ser Phe Leu
        35                  40                  45 ttt gta caa gga aat caa cga gcc cac gga caa gac ctt gat gca ctg      192
Phe Val Gln Gly Asn Gln Arg Ala His Gly Gln Asp Leu Asp Ala Leu
    50                  55                  60 ttt gtg aag gtc ctg cga tcg cca tagccgttca cagccaaacc actgacattc    246
Phe Val Lys Val Leu Arg Ser Pro
 65                  70 ctccatgtcc tcacggctgg atttctctct ggaaaggatt ttcattcatc atgaaagcct   306
attccatcaa ctgtgaaagc tgggaattta gaaaaaataa taagtcgctg tcaggtgtgc   366
atgaagaaaa gacactgaag ctaaaaaaga cagcagaact gctattttc atcctaaaga   426
```

```
acaaagtaat gacagaacat gctgttattt aggtatttt ctttaaccaa acaatattgc    486
tccatgatga cttagtacaa a                                              507

<210> SEQ ID NO 52
<211> LENGTH: 72
<212> TYPE: PRT
<213> ORGANISM: Artificial Sequence
<220> FEATURE:
<223> OTHER INFORMATION: Description of Artificial Sequence: GPDIII-V

<400> SEQUENCE: 52

Gly Leu Lys Gly Lys Arg Gly Asp Ser Gly Ser Pro Ala Thr Trp Thr
 1               5                  10                  15

Thr Arg Gly Phe Val Phe Thr Arg His Ser Gln Thr Thr Ala Ile Pro
            20                  25                  30

Ser Cys Pro Glu Gly Thr Val Pro Leu Tyr Ser Gly Phe Ser Phe Leu
        35                  40                  45

Phe Val Gln Gly Asn Gln Arg Ala His Gly Gln Asp Leu Asp Ala Leu
    50                  55                  60

Phe Val Lys Val Leu Arg Ser Pro
65                  70

<210> SEQ ID NO 53
<211> LENGTH: 659
<212> TYPE: DNA
<213> ORGANISM: Artificial Sequence
<220> FEATURE:
<223> OTHER INFORMATION: Description of Artificial Sequence: HMBP-21
<220> FEATURE:
<221> NAME/KEY: CDS
<222> LOCATION: (37)..(627)

<400> SEQUENCE: 53
gaaaacagtg cagccacctc cgagagcctg gatgtg atg gcg tca cag aag aga    54
                                        Met Ala Ser Gln Lys Arg
                                         1               5 ccc tcc cag agg cac gga tcc aag tac ctg gcc aca gca agt acc atg   102
Pro Ser Gln Arg His Gly Ser Lys Tyr Leu Ala Thr Ala Ser Thr Met
             10                  15                  20 gac cat gcc agg cat ggc ttc ctc cca agg cac aga gac acg ggc atc   150
Asp His Ala Arg His Gly Phe Leu Pro Arg His Arg Asp Thr Gly Ile
         25                  30                  35 ctt gac tcc atc ggg cgc ttc ttt ggc ggt gac agg ggt gcg cca aag   198
Leu Asp Ser Ile Gly Arg Phe Phe Gly Gly Asp Arg Gly Ala Pro Lys
     40                  45                  50 cgg ggc tct ggc aag gta ccc tgg cta aag ccg ggc cgg agc cct ctg   246
Arg Gly Ser Gly Lys Val Pro Trp Leu Lys Pro Gly Arg Ser Pro Leu
 55                  60                  65                  70 ccc tct cat gcc cgc agc cag cct ggg ctg tgc aac atg tac aag gac   294
Pro Ser His Ala Arg Ser Gln Pro Gly Leu Cys Asn Met Tyr Lys Asp
                 75                  80                  85 tca cac cac ccg gca aga act gct cac tat ggc tcc ctg ccc cag aag   342
Ser His His Pro Ala Arg Thr Ala His Tyr Gly Ser Leu Pro Gln Lys
             90                  95                 100 tca cac ggc cgg acc caa gat gaa aac ccc gta gtc cac ttc ttc aag   390
Ser His Gly Arg Thr Gln Asp Glu Asn Pro Val Val His Phe Phe Lys
        105                 110                 115 aac att gtg acg cct cgc aca cca ccc ccg tcg cag gga aag ggg aga   438
Asn Ile Val Thr Pro Arg Thr Pro Pro Pro Ser Gln Gly Lys Gly Arg
    120                 125                 130
```

```
gga ctg tcc ctg agc aga ttt agc tgg ggg gcc gaa ggc cag aga cca      486
Gly Leu Ser Leu Ser Arg Phe Ser Trp Gly Ala Glu Gly Gln Arg Pro
135                 140                 145                 150 gga ttt ggc tac gga ggc aga gcg tcc gac tat aaa tcg gct cac aag      534
Gly Phe Gly Tyr Gly Gly Arg Ala Ser Asp Tyr Lys Ser Ala His Lys
                155                 160                 165 gga ttc aag gga gtc gat gcc cag ggc acg ctt tcc aaa att ttt aag      582
Gly Phe Lys Gly Val Asp Ala Gln Gly Thr Leu Ser Lys Ile Phe Lys
        170                 175                 180 ctg gga gga aga gat agt cgc tct gga tca ccc atg gct aga cgc          627
Leu Gly Gly Arg Asp Ser Arg Ser Gly Ser Pro Met Ala Arg Arg
            185                 190                 195 tgaaaaccca cctggttccg gaatcctgtc ct                                  659

<210> SEQ ID NO 54
<211> LENGTH: 197
<212> TYPE: PRT
<213> ORGANISM: Artificial Sequence
<220> FEATURE:
<223> OTHER INFORMATION: Description of Artificial Sequence: HMBP-21

<400> SEQUENCE: 54

Met Ala Ser Gln Lys Arg Pro Ser Gln Arg His Gly Ser Lys Tyr Leu
 1               5                   10                  15

Ala Thr Ala Ser Thr Met Asp His Ala Arg His Gly Phe Leu Pro Arg
            20                  25                  30

His Arg Asp Thr Gly Ile Leu Asp Ser Ile Gly Arg Phe Phe Gly Gly
        35                  40                  45

Asp Arg Gly Ala Pro Lys Arg Gly Ser Gly Lys Val Pro Trp Leu Lys
    50                  55                  60

Pro Gly Arg Ser Pro Leu Pro Ser His Ala Arg Ser Gln Pro Gly Leu
65                  70                  75                  80

Cys Asn Met Tyr Lys Asp Ser His His Pro Ala Arg Thr Ala His Tyr
                85                  90                  95

Gly Ser Leu Pro Gln Lys Ser His Gly Arg Thr Gln Asp Glu Asn Pro
            100                 105                 110

Val Val His Phe Phe Lys Asn Ile Val Thr Pro Arg Thr Pro Pro Pro
        115                 120                 125

Ser Gln Gly Lys Gly Arg Gly Leu Ser Leu Ser Arg Phe Ser Trp Gly
    130                 135                 140

Ala Glu Gly Gln Arg Pro Gly Phe Gly Tyr Gly Gly Arg Ala Ser Asp
145                 150                 155                 160

Tyr Lys Ser Ala His Lys Gly Phe Lys Gly Val Asp Ala Gln Gly Thr
                165                 170                 175

Leu Ser Lys Ile Phe Lys Leu Gly Gly Arg Asp Ser Arg Ser Gly Ser
            180                 185                 190

Pro Met Ala Arg Arg
        195

<210> SEQ ID NO 55
<211> LENGTH: 12
<212> TYPE: DNA
<213> ORGANISM: Homo sapiens

<400> SEQUENCE: 55
ttttagtcac ag                                                         12

<210> SEQ ID NO 56
```

```
<211> LENGTH: 12
<212> TYPE: DNA
<213> ORGANISM: Homo sapiens

<400> SEQUENCE: 56
caaaaggtaa gc                                                              12

<210> SEQ ID NO 57
<211> LENGTH: 12
<212> TYPE: DNA
<213> ORGANISM: Homo sapiens

<400> SEQUENCE: 57
tggtagccct at                                                              12

<210> SEQ ID NO 58
<211> LENGTH: 12
<212> TYPE: DNA
<213> ORGANISM: Homo sapiens

<400> SEQUENCE: 58
tcccaggtac tg                                                              12

<210> SEQ ID NO 59
<211> LENGTH: 12
<212> TYPE: DNA
<213> ORGANISM: Homo sapiens

<400> SEQUENCE: 59
ctcaaggttg aa                                                              12

<210> SEQ ID NO 60
<211> LENGTH: 12
<212> TYPE: DNA
<213> ORGANISM: Homo sapiens

<400> SEQUENCE: 60
atgaaggtaa tt                                                              12

<210> SEQ ID NO 61
<211> LENGTH: 72
<212> TYPE: PRT
<213> ORGANISM: Homo sapiens

<400> SEQUENCE: 61

Gly Leu Lys Gly Lys Arg Gly Asp Ser Gly Ser Pro Ala Thr Trp Thr
 1               5                  10                  15

Thr Arg Gly Phe Val Phe Thr Arg His Ser Gln Thr Thr Ala Ile Pro
                20                  25                  30

Ser Cys Pro Glu Gly Pro Val Pro Leu Tyr Ser Gly Phe Ser Phe Leu
            35                  40                  45

Phe Val Gln Gly Asn Gln Arg Ala His Gly Gln Asp Leu Asp Ala Leu
    50                  55                  60

Phe Val Lys Val Leu Arg Ser Pro
 65                 70

<210> SEQ ID NO 62
<211> LENGTH: 69
<212> TYPE: PRT
<213> ORGANISM: Homo sapiens

<400> SEQUENCE: 62
```

```
Met Ala Ser Gln Lys Arg Pro Ser Gln Arg His Gly Ser Lys Tyr Leu
 1               5                  10                  15

Ala Thr Ala Ser Thr Met Asp His Ala Arg His Gly Phe Leu Pro Arg
             20                  25                  30

His Arg Asp Thr Gly Ile Leu Asp Ser Ile Gly Arg Phe Phe Gly Gly
         35                  40                  45

Asp Arg Gly Ala Pro Lys Arg Gly Ser Gly Lys Val Pro Trp Leu Lys
     50                  55                  60

Pro Gly Arg Ser Pro
 65
```

<210> SEQ ID NO 63
<211> LENGTH: 5
<212> TYPE: PRT
<213> ORGANISM: Homo sapiens

<400> SEQUENCE: 63

```
Lys Arg Gly Asp Ser
 1               5
```

<210> SEQ ID NO 64
<211> LENGTH: 9
<212> TYPE: PRT
<213> ORGANISM: Homo sapiens

<400> SEQUENCE: 64

```
Gln Lys Arg Pro Ser Gln Arg His Gly
 1               5
```

<210> SEQ ID NO 65
<211> LENGTH: 735
<212> TYPE: DNA
<213> ORGANISM: Artificial Sequence
<220> FEATURE:
<223> OTHER INFORMATION: Description of Artificial Sequence: recombinant
      variant of human alpha III type IV collagen NC1
      domain
<220> FEATURE:
<221> NAME/KEY: CDS
<222> LOCATION: (1)..(732)

<400> SEQUENCE: 65

```
ggt ttg aaa gga aaa cgt gga gac gay gga tca cct gca acc tgg aca      48
Gly Leu Lys Gly Lys Arg Gly Asp Asp Gly Ser Pro Ala Thr Trp Thr
 1               5                  10                  15 acg aga ggc ttt gtc ttc acc cga cac agt caa acc aca gca att cct      96
Thr Arg Gly Phe Val Phe Thr Arg His Ser Gln Thr Thr Ala Ile Pro
             20                  25                  30 tca tgt cca gag ggg aca gtg cca ctc tac agt ggg ttt tct ttt ctt     144
Ser Cys Pro Glu Gly Thr Val Pro Leu Tyr Ser Gly Phe Ser Phe Leu
         35                  40                  45 ttt gta caa gga aat caa cga gcc cac gga caa gac ctt gga act ctt     192
Phe Val Gln Gly Asn Gln Arg Ala His Gly Gln Asp Leu Gly Thr Leu
     50                  55                  60 ggc agc tgc ctg cag cga ttt acc aca atg cca ttc tta ttc tgc aat     240
Gly Ser Cys Leu Gln Arg Phe Thr Thr Met Pro Phe Leu Phe Cys Asn
 65                  70                  75                  80 gtc aat gat gta tgt aat ttt gca tct cga aat gat tat tca tac tgg     288
Val Asn Asp Val Cys Asn Phe Ala Ser Arg Asn Asp Tyr Ser Tyr Trp
                 85                  90                  95 ctg tca aca cca gct ctg atg cca atg aac atg gct ccc att act ggc     336
Leu Ser Thr Pro Ala Leu Met Pro Met Asn Met Ala Pro Ile Thr Gly
            100                 105                 110
```

| | | | | | | | | | | | | | | | | |
|---|---|---|---|---|---|---|---|---|---|---|---|---|---|---|---|---|
| aga | gcc | ctt | gag | cct | tat | ata | agc | aga | tgc | act | gtt | tgt | gaa | ggt | cct | 384 |
| Arg | Ala | Leu | Glu | Pro | Tyr | Ile | Ser | Arg | Cys | Thr | Val | Cys | Glu | Gly | Pro | |
| | | 115 | | | | | 120 | | | | | 125 | | | | |
| gcg | atc | gcc | ata | gcc | gtt | cac | agc | caa | acc | act | gac | att | cct | cca | tgt | 432 |
| Ala | Ile | Ala | Ile | Ala | Val | His | Ser | Gln | Thr | Thr | Asp | Ile | Pro | Pro | Cys | |
| 130 | | | | | 135 | | | | | 140 | | | | | | |
| cct | cac | ggc | tgg | att | tct | ctc | tgg | aaa | gga | ttt | tca | ttc | atc | atg | ttc | 480 |
| Pro | His | Gly | Trp | Ile | Ser | Leu | Trp | Lys | Gly | Phe | Ser | Phe | Ile | Met | Phe | |
| 145 | | | | | 150 | | | | | 155 | | | | | 160 | |
| aca | agt | gca | ggt | tct | gag | ggc | acc | ggg | caa | gca | ctg | gcc | tcc | cct | ggc | 528 |
| Thr | Ser | Ala | Gly | Ser | Glu | Gly | Thr | Gly | Gln | Ala | Leu | Ala | Ser | Pro | Gly | |
| | | | | 165 | | | | | 170 | | | | | 175 | | |
| tcc | tgc | ctg | gaa | gaa | ttc | cga | gcc | agc | cca | ttt | cta | gaa | tgt | cat | gga | 576 |
| Ser | Cys | Leu | Glu | Glu | Phe | Arg | Ala | Ser | Pro | Phe | Leu | Glu | Cys | His | Gly | |
| | | 180 | | | | | 185 | | | | | 190 | | | | |
| aga | gga | acg | tgc | aac | tac | tat | tca | aat | tcc | tac | agt | ttc | tgg | ctg | gct | 624 |
| Arg | Gly | Thr | Cys | Asn | Tyr | Tyr | Ser | Asn | Ser | Tyr | Ser | Phe | Trp | Leu | Ala | |
| | | 195 | | | | | 200 | | | | | 205 | | | | |
| tca | tta | aac | cca | gaa | aga | atg | ttc | aga | aag | cct | att | cca | tca | act | gtg | 672 |
| Ser | Leu | Asn | Pro | Glu | Arg | Met | Phe | Arg | Lys | Pro | Ile | Pro | Ser | Thr | Val | |
| 210 | | | | | 215 | | | | | 220 | | | | | | |
| aaa | gct | ggg | gaa | tta | gaa | aaa | ata | ata | agt | cgc | tgt | cag | gtg | tgc | atg | 720 |
| Lys | Ala | Gly | Glu | Leu | Glu | Lys | Ile | Ile | Ser | Arg | Cys | Gln | Val | Cys | Met | |
| 225 | | | | | 230 | | | | | 235 | | | | | 240 | |
| aag | aaa | aga | cac | tga | | | | | | | | | | | | 735 |
| Lys | Lys | Arg | His | | | | | | | | | | | | | |

<210> SEQ ID NO 66
<211> LENGTH: 244
<212> TYPE: PRT
<213> ORGANISM: Artificial Sequence
<220> FEATURE:
<223> OTHER INFORMATION: Description of Artificial Sequence:
      recombinant variant of human alpha III type IV collagen NC1 domain

<400> SEQUENCE: 66

Gly Leu Lys Gly Lys Arg Gly Asp Asp Gly Ser Pro Ala Thr Trp Thr
 1               5                  10                  15

Thr Arg Gly Phe Val Phe Thr Arg His Ser Gln Thr Thr Ala Ile Pro
            20                  25                  30

Ser Cys Pro Glu Gly Thr Val Pro Leu Tyr Ser Gly Phe Ser Phe Leu
        35                  40                  45

Phe Val Gln Gly Asn Gln Arg Ala His Gly Gln Asp Leu Gly Thr Leu
    50                  55                  60

Gly Ser Cys Leu Gln Arg Phe Thr Thr Met Pro Phe Leu Phe Cys Asn
65                  70                  75                  80

Val Asn Asp Val Cys Asn Phe Ala Ser Arg Asn Asp Tyr Ser Tyr Trp
                85                  90                  95

Leu Ser Thr Pro Ala Leu Met Pro Met Asn Met Ala Pro Ile Thr Gly
            100                 105                 110

Arg Ala Leu Glu Pro Tyr Ile Ser Arg Cys Thr Val Cys Glu Gly Pro
        115                 120                 125

Ala Ile Ala Ile Ala Val His Ser Gln Thr Thr Asp Ile Pro Pro Cys
    130                 135                 140

Pro His Gly Trp Ile Ser Leu Trp Lys Gly Phe Ser Phe Ile Met Phe
145                 150                 155                 160

Thr Ser Ala Gly Ser Glu Gly Thr Gly Gln Ala Leu Ala Ser Pro Gly
                165                 170                 175

```
Ser Cys Leu Glu Glu Phe Arg Ala Ser Pro Phe Leu Glu Cys His Gly
        180                 185                 190

Arg Gly Thr Cys Asn Tyr Tyr Ser Asn Ser Tyr Ser Phe Trp Leu Ala
    195                 200                 205

Ser Leu Asn Pro Glu Arg Met Phe Arg Lys Pro Ile Pro Ser Thr Val
    210                 215                 220

Lys Ala Gly Glu Leu Glu Lys Ile Ile Ser Arg Cys Gln Val Cys Met
225                 230                 235                 240

Lys Lys Arg His

<210> SEQ ID NO 67
<211> LENGTH: 735
<212> TYPE: DNA
<213> ORGANISM: Artificial Sequence
<220> FEATURE:
<223> OTHER INFORMATION: Description of Artificial Sequence: recombinant
      variant of human alpha III type IV collagen NC1 domain
<220> FEATURE:
<221> NAME/KEY: CDS
<222> LOCATION: (1)..(732)
<220> FEATURE:
<221> NAME/KEY: misc_feature
<222> LOCATION: (27)
<223> OTHER INFORMATION: "n" can be a, g, c, or t

<400> SEQUENCE: 67 ggt ttg aaa gga aaa cgt gga gac gcn gga tca cct gca acc tgg aca     48
Gly Leu Lys Gly Lys Arg Gly Asp Ala Gly Ser Pro Ala Thr Trp Thr
 1               5                  10                  15 acg aga ggc ttt gtc ttc acc cga cac agt caa acc aca gca att cct     96
Thr Arg Gly Phe Val Phe Thr Arg His Ser Gln Thr Thr Ala Ile Pro
                20                  25                  30 tca tgt cca gag ggg aca gtg cca ctc tac agt ggg ttt tct ttt ctt    144
Ser Cys Pro Glu Gly Thr Val Pro Leu Tyr Ser Gly Phe Ser Phe Leu
            35                  40                  45 ttt gta caa gga aat caa cga gcc cac gga caa gac ctt gga act ctt    192
Phe Val Gln Gly Asn Gln Arg Ala His Gly Gln Asp Leu Gly Thr Leu
        50                  55                  60 ggc agc tgc ctg cag cga ttt acc aca atg cca ttc tta ttc tgc aat    240
Gly Ser Cys Leu Gln Arg Phe Thr Thr Met Pro Phe Leu Phe Cys Asn
65                  70                  75                  80 gtc aat gat gta tgt aat ttt gca tct cga aat gat tat tca tac tgg    288
Val Asn Asp Val Cys Asn Phe Ala Ser Arg Asn Asp Tyr Ser Tyr Trp
                85                  90                  95 ctg tca aca cca gct ctg atg cca atg aac atg gct ccc att act ggc    336
Leu Ser Thr Pro Ala Leu Met Pro Met Asn Met Ala Pro Ile Thr Gly
            100                 105                 110 aga gcc ctt gag cct tat ata agc aga tgc act gtt tgt gaa ggt cct    384
Arg Ala Leu Glu Pro Tyr Ile Ser Arg Cys Thr Val Cys Glu Gly Pro
        115                 120                 125 gcg atc gcc ata gcc gtt cac agc caa acc act gac att cct cca tgt    432
Ala Ile Ala Ile Ala Val His Ser Gln Thr Thr Asp Ile Pro Pro Cys
    130                 135                 140 cct cac ggc tgg att tct ctc tgg aaa gga ttt tca ttc atc atg ttc    480
Pro His Gly Trp Ile Ser Leu Trp Lys Gly Phe Ser Phe Ile Met Phe
145                 150                 155                 160 aca agt gca ggt tct gag ggc acc ggg caa gca ctg gcc tcc cct ggc    528
Thr Ser Ala Gly Ser Glu Gly Thr Gly Gln Ala Leu Ala Ser Pro Gly
                165                 170                 175 tcc tgc ctg gaa gaa ttc cga gcc agc cca ttt cta gaa tgt cat gga    576
Ser Cys Leu Glu Glu Phe Arg Ala Ser Pro Phe Leu Glu Cys His Gly
```

-continued

```
                180                 185                 190
aga gga acg tgc aac tac tat tca aat tcc tac agt ttc tgg ctg gct      624
Arg Gly Thr Cys Asn Tyr Tyr Ser Asn Ser Tyr Ser Phe Trp Leu Ala
            195                 200                 205 tca tta aac cca gaa aga atg ttc aga aag cct att cca tca act gtg      672
Ser Leu Asn Pro Glu Arg Met Phe Arg Lys Pro Ile Pro Ser Thr Val
    210                 215                 220 aaa gct ggg gaa tta gaa aaa ata ata agt cgc tgt cag gtg tgc atg      720
Lys Ala Gly Glu Leu Glu Lys Ile Ile Ser Arg Cys Gln Val Cys Met
225                 230                 235                 240 aag aaa aga cac tga                                                  735
Lys Lys Arg His
```

<210> SEQ ID NO 68
<211> LENGTH: 244
<212> TYPE: PRT
<213> ORGANISM: Artificial Sequence
<220> FEATURE:
<223> OTHER INFORMATION: Description of Artificial Sequence: recombinant
      variant of human alpha III type IV collagen NC1 domain

<400> SEQUENCE: 68

```
Gly Leu Lys Gly Lys Arg Gly Asp Ala Gly Ser Pro Ala Thr Trp Thr
 1               5                  10                  15

Thr Arg Gly Phe Val Phe Thr Arg His Ser Gln Thr Thr Ala Ile Pro
            20                  25                  30

Ser Cys Pro Glu Gly Thr Val Pro Leu Tyr Ser Gly Phe Ser Phe Leu
        35                  40                  45

Phe Val Gln Gly Asn Gln Arg Ala His Gly Gln Asp Leu Gly Thr Leu
    50                  55                  60

Gly Ser Cys Leu Gln Arg Phe Thr Thr Met Pro Phe Leu Phe Cys Asn
65                  70                  75                  80

Val Asn Asp Val Cys Asn Phe Ala Ser Arg Asn Asp Tyr Ser Tyr Trp
                85                  90                  95

Leu Ser Thr Pro Ala Leu Met Pro Met Asn Met Ala Pro Ile Thr Gly
            100                 105                 110

Arg Ala Leu Glu Pro Tyr Ile Ser Arg Cys Thr Val Cys Glu Gly Pro
        115                 120                 125

Ala Ile Ala Ile Ala Val His Ser Gln Thr Thr Asp Ile Pro Pro Cys
    130                 135                 140

Pro His Gly Trp Ile Ser Leu Trp Lys Gly Phe Ser Phe Ile Met Phe
145                 150                 155                 160

Thr Ser Ala Gly Ser Glu Gly Thr Gly Gln Ala Leu Ala Ser Pro Gly
                165                 170                 175

Ser Cys Leu Glu Glu Phe Arg Ala Ser Pro Phe Leu Glu Cys His Gly
            180                 185                 190

Arg Gly Thr Cys Asn Tyr Tyr Ser Asn Ser Tyr Ser Phe Trp Leu Ala
        195                 200                 205

Ser Leu Asn Pro Glu Arg Met Phe Arg Lys Pro Ile Pro Ser Thr Val
    210                 215                 220

Lys Ala Gly Glu Leu Glu Lys Ile Ile Ser Arg Cys Gln Val Cys Met
225                 230                 235                 240

Lys Lys Arg His
```

<210> SEQ ID NO 69
<211> LENGTH: 244
<212> TYPE: PRT

<213> ORGANISM: Homo sapiens

<400> SEQUENCE: 69

```
Gly Leu Lys Gly Lys Arg Gly Asp Ser Gly Ser Pro Ala Thr Trp Thr
1               5                   10                  15

Thr Arg Gly Phe Val Phe Thr Arg His Ser Gln Thr Thr Ala Ile Pro
            20                  25                  30

Ser Cys Pro Glu Gly Thr Val Pro Leu Tyr Ser Gly Phe Ser Phe Leu
        35                  40                  45

Phe Val Gln Gly Asn Gln Arg Ala His Gly Gln Asp Leu Gly Thr Leu
    50                  55                  60

Gly Ser Cys Leu Gln Arg Phe Thr Thr Met Pro Phe Leu Phe Cys Asn
65                  70                  75                  80

Val Asn Asp Val Cys Asn Phe Ala Ser Arg Asn Asp Tyr Ser Tyr Trp
                85                  90                  95

Leu Ser Thr Pro Ala Leu Met Pro Met Asn Met Ala Pro Ile Thr Gly
            100                 105                 110

Arg Ala Leu Glu Pro Tyr Ile Ser Arg Cys Thr Val Cys Glu Gly Pro
        115                 120                 125

Ala Ile Ala Ile Ala Val His Ser Gln Thr Thr Asp Ile Pro Pro Cys
    130                 135                 140

Pro His Gly Trp Ile Ser Leu Trp Lys Gly Phe Ser Phe Ile Met Phe
145                 150                 155                 160

Thr Ser Ala Gly Ser Glu Gly Thr Gly Gln Ala Leu Ala Ser Pro Gly
                165                 170                 175

Ser Cys Leu Glu Glu Phe Arg Ala Ser Pro Phe Leu Glu Cys His Gly
            180                 185                 190

Arg Gly Thr Cys Asn Tyr Tyr Ser Asn Ser Tyr Ser Phe Trp Leu Ala
        195                 200                 205

Ser Leu Asn Pro Glu Arg Met Phe Arg Lys Pro Ile Pro Ser Thr Val
    210                 215                 220

Lys Ala Gly Glu Leu Glu Lys Ile Ile Ser Arg Cys Gln Val Cys Met
225                 230                 235                 240

Lys Lys Arg His
```

<210> SEQ ID NO 70
<211> LENGTH: 26
<212> TYPE: DNA
<213> ORGANISM: Artificial Sequence
<220> FEATURE:
<223> OTHER INFORMATION: Description of Artificial Sequence:
    oligonucleotide ON-B-HNC-1c

<400> SEQUENCE: 70
cagggatccg ttctttagga tgaaaa                                          26

<210> SEQ ID NO 71
<211> LENGTH: 17
<212> TYPE: DNA
<213> ORGANISM: Artificial Sequence
<220> FEATURE:
<223> OTHER INFORMATION: Description of Artificial Sequence:
    oligonucleotide ON-HNC-3m

<400> SEQUENCE: 71
gaccctgtgg gccaaga                                                    17

<210> SEQ ID NO 72

```
<211> LENGTH: 28
<212> TYPE: DNA
<213> ORGANISM: Artificial Sequence
<220> FEATURE:
<223> OTHER INFORMATION: Description of Artificial Sequence:
      oligonucleotide ON-HNC-6c

<400> SEQUENCE: 72
cagggatccg agtgtctttt cttcatgc                                    28

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence:
      oligonucleotide ON-GP-F1

<400> SEQUENCE: 73
ggagacagtg gatcacctgc a                                           21

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence:
      oligonucleotide ON-GP-R1

<400> SEQUENCE: 74
tgctgtggtt tgactgtgtc g                                           21

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence:
      oligonucleotide ON-GP-3-F1

<400> SEQUENCE: 75
cggacaagac cttgatgcac t                                           21

<210> SEQ ID NO 76
<211> LENGTH: 19
<212> TYPE: DNA
<213> ORGANISM: Artificial Sequence
<220> FEATURE:
<223> OTHER INFORMATION: Description of Artificial Sequence:
      oligonucleotide ON-GP-3-R2

<400> SEQUENCE: 76
cagccgtgag gacatggag                                              19

<210> SEQ ID NO 77
<211> LENGTH: 19
<212> TYPE: DNA
<213> ORGANISM: Artificial Sequence
<220> FEATURE:
<223> OTHER INFORMATION: Description of Artificial Sequence:
      oligonucleotide ON-hGPBPc-F1

<400> SEQUENCE: 77
ctgaatccag cttgcgtcg                                              19

<210> SEQ ID NO 78
<211> LENGTH: 20
```

-continued

```
<212> TYPE: DNA
<213> ORGANISM: Artificial Sequence
<220> FEATURE:
<223> OTHER INFORMATION: Description of Artificial Sequence:
      oligonucleotide ON-hGPBPc-R1

<400> SEQUENCE: 78
gcagagtagc cacttgctcc                                                    20

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence:
      oligonucleotide ON-hGPBPe26-F1

<400> SEQUENCE: 79
cgctcttcct ccatgtcttc c                                                  21

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence:
      oligonucleotide ON-GPBPe26-R1

<400> SEQUENCE: 80
cctgggagct gaatctgtga a                                                  21

<210> SEQ ID NO 81
<211> LENGTH: 22
<212> TYPE: DNA
<213> ORGANISM: Artificial Sequence
<220> FEATURE:
<223> OTHER INFORMATION: Description of Artificial Sequence:
      oligonucleotide ON-GPBP-26-F1

<400> SEQUENCE: 81
gctgttgaag ctgctcttga ca                                                 22

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence:
      oligonucleotide ON-GPBP-26-R1

<400> SEQUENCE: 82
tggtattgct caaatttcgg c                                                  21

<210> SEQ ID NO 83
<211> LENGTH: 19
<212> TYPE: DNA
<213> ORGANISM: Artificial Sequence
<220> FEATURE:
<223> OTHER INFORMATION: Description of Artificial Sequence:
      oligonucleotide ON-GAPDH-F

<400> SEQUENCE: 83
gaaggtgaag gtcggagtc                                                     19

<210> SEQ ID NO 84
<211> LENGTH: 20
<212> TYPE: DNA
```

-continued

```
<213> ORGANISM: Artificial Sequence
<220> FEATURE:
<223> OTHER INFORMATION: Description of Artificial Sequence:
      oligonucleotide ON-GAPDH-R

<400> SEQUENCE: 84
gaagatggtg atgggatttc                                                 20
```

US 6,881,547 B1

METHODS AND REAGENTS FOR TREATING AUTOIMMUNE DISORDERS

CROSS REFERENCE

This application claims priority to U.S. Provisional Patent Application Ser. No. 60/265,249, filed Jan. 31, 2001.

FIELD OF THE INVENTION

The invention relates to the fields of protein kinases, autoimmune disease, autoimmune gets, and protein structure.

BACKGROUND OF THE INVENTION

The idea that common pathogenic events exist at least for some autoimmune disorders is suggested by the significant number of patients displaying more than one autoimmune disease, and also by the strong and common linkage that some of these diseases show to specific MHC haplotypes. The experimental observation that the autoantigen is the leading moiety in autoimmunity and that a limited number of self-components are autoantigenic, suggests that these self-components share biological features which are relevant for self/non-self recognition by the immune system. One possibility is that triggering events by altering these features result in abnormal proteolysis. In certain individuals expressing a particular MHC specificity, the resulting abnormal peptides could be recognized by non-tolerized T cells and trigger an immune response Type IV collagen (also referred to herein as collagen IV) networks scaffold the basement membranes, the laminar extracellular matrix structures often found between the cells and connective tissue. Six different type IV collagen α chains ($\alpha 1$–$\alpha 6$) exist, and three chains associate through the C terminal non-collagenous (NC1) domain to form a collagen IV molecule. In basement membranes, two type IV collagen molecules interact through their NC1 regions, yielding a hexameric globular quaternary structure ("hexamer"). Six disulfide bonds stabilize the native structure of each individual NC1 domain, and bonds generated by disulfide exchange between collagen IV molecules stabilize the "hexamer". Bacterial collagenase digestion of basement membrane degrades the collagenous portion of collagen IV and releases the "hexamer". Upon dissociation, this globular structure yields the individual NC1 domains as single polypeptides ("monomer") or disulfide-related oligomers (dimers and higher molecular weight aggregates).

Recent data indicates that the information required to form a collagen IV "hexamer" resides in the covalent structure of the "monomer" as the individual NC1 domains select their partners and form "hexamers" without the assistance of other cellular factors. However the structural features mediating "monomer" association and the mechanism regulating the intermolecular disulfide bridging is presently unknown.

The chain composition of the collagen IV network varies among basement membranes and different collagen IV networks have been shown to exist. In the kidney, the glomerular basement membrane (GBM) results from assembly of two connected but independent collagen IV networks, one containing $\alpha 1$–$\alpha 2$(IV) and the other made of $\alpha 3$–$\alpha 4$–$\alpha 5$ (IV). GBM plays a major role in plasma ultrafiltration since genetic and acquired diseases altering its collagen IV network impair renal function. In Alport syndrome, mutations in any of the $\alpha 3$, $\alpha 4$ or $\alpha 5$(IV) genes result in disruption of the corresponding collagen IV network and nephritis, whereas in Goodpasture (GP) disease an autoimmune response against the $\alpha 3$(IV)NC1 (also referred to as the GP antigen) cause linear deposits of autoantibodies along alveolar and glomerular BM, causing a rapidly progressive glomerulonephritis and often lung hemorrhage.

In GP disease, immunologically privileged epitopes buried in the GBM hexamer are exposed by an unknown pathogenic mechanism that engages the immune system in the deleterious production of antibodies. The human condition of this disorder and the exclusive involvement of the $\alpha 3$(IV)NC1 domain among six highly related domains, supported early comparative studies to identify biological features relevant in autoimmune pathogenesis. Accordingly, the human $\alpha 3$(IV)NC1 domain undergoes unique phosphorylation at $Ser^9$ by type A protein kinases (cPKA) and structural diversification by alternative exon splicing generating multiple related products (GPΔIII, GPΔIII/IV/V and GPΔV).

The data presented herein indicate that the human $\alpha 3$(IV) NC1 domain exists as multiple phosphorylation-dependent conformational isoforms (conformers) that are stabilized by disulfide bonds. Furthermore our data indicate that phosphorylation of $Ser^9$ induces conformational diversification of the $\alpha 3$(IV)NC1 domain, whereas the alternative products contain divergent C terminal ends that specifically induce cPKA phosphorylation of $Ser^9$ in the primary product, suggesting that in humans the levels of expression of alternatively spliced products by regulating $Ser^9$ phosphorylation control the conformational diversification process of the $\alpha 3$(IV)NC1 domain. All of the above suggests that $Ser^9$ phosphorylation, alternative exon splicing and pathogenesis are related phenomenon.

The data presented herein further identify GPBP and GPBPΔ26 as two alternatively spliced isoforms of a novel non-conventional protein kinase that binds to the N terminal region of the human Δ3(IV)NC1 and phosphorylates $Ser^9$. GPBP is a more active variant whose expression is highly restricted to histological structures targeted by common autoimmune responses including human alveolar and glomerular basement membranes. Each GPBP isoform likely represents a different strategy to perform the same function as we have found that for a particular tissue individuals expressing higher levels of GPBP express very little GPBPΔ26 and vice versa. An augmented expression of GPBP with respect to GPBPΔ26 has been associated with several autoimmune conditions including GP patients, cutaneous lupus erythematosus, pemphigus, pemphigoid and lichen planus, suggesting that GPBP expression and autoinmune pathogenesis are related processes. Our data herein (Example 5) further indicate that phosphorylation activates the $\alpha 3$(IV)NC1 domain for aggregation, a process that is catalyzed at least in part by GPBP and which comprises conformational isomerization reactions and disulfide-bond exchange.

Furthermore we show here that in GP kidneys, a relative increased in the level of expression of GPΔIII and GPBP co-exist with assembled "aberrant" conformers of the $\alpha 3$(IV)NC1 domain that conduct the autoimmune response, suggesting this human disease represents the legitimate response of the immune system against misfolded autoantigen which results from a coordinated increase in the expression of GPBP and GPΔIII.

Finally, we disclose that myelin basic protein (MBP), a known human autoantigen implicated in multiple sclerosis, contains a structurally related site ($Ser^8$) for cPKA and GPBP whose phosphorylation regulates conformation and is under the control of a related alternative splicing mechanism when cPKA is phosphorylating enzyme, suggesting that phosphorylation-dependent conformation is the biological condition that renders self-components potentially immunogenic.

Based on all of the above, there exists a need in the art for methods and reagents to identify drug candidates to modify GPBP activity to treat autoimmune disorders.

SUMMARY OF THE INVENTION

The present invention provides methods and reagents for identifying compounds to treat autoimmune diseases. In one aspect, the present invention provides methods for identifying compounds to treat an autoimmune condition, comprising identifying compounds that (a) reduce phosphorylation of a first target protein selected from the group consisting of GPBP, an α3 type IV collagen NC1 domain polypeptide comprising the amino acid sequence of SEQ ID NO:26, and a polypeptide comprising the amino acid sequence of SEQ ID NO:64 and (b) reduce formation of conformational isomers of a second target protein selected from the group consisting of an α3 type IV collagen NC1 domain polypeptide and myelin basic protein, wherein such compounds are candidates for treating an autoimmune condition. In a preferred embodiment, phosphorylation assays are conducted in vitro. In a further preferred embodiment, conformer formation assays are conducted in cultured cells. In another preferred embodiment, the method further comprises identifying compounds that reduce oligomerization of the second target protein. In a further embodiment, the autoimmune condition is selected from the group consisting of Goodpasture Syndrome, multiple sclerosis, systemic and cutaneous lupus erythematosus, pemphigus, pemphigoid and lichen planus.

In another aspect, the invention provides isolated type IV collagen α3 NC1 domain tI, conformational isomers, wherein the isolated conformational isomer has an amino acid sequence identical to that of wild type α3 type IV collagen NC1 domain, wherein the conformational isomer is stabilized by disulfide bonds, wherein the isolated conformational isomer has a molecular weight in a non-reducing sodium dodecyl sulfate gel selected from the group consisting of 22 kD, 23, kD, 25 kD, 27 kD, and 28 kD, and wherein the conformational isomer has a molecular weight of 29 kDa in a reducing sodium dodecyl sulfate gel.

In a further embodiment, the invention provides isolated type IV collagen α3 NC1 domain nucleic acids encoding a polypeptide consisting of an amino acid sequence selected from the group consisting of SEQ ID NO:66 and SEQ ID NO:68, as well as the corresponding isolated polypeptides.

BRIEF DESCRIPTION OF THE FIGURES

FIG. 1. Nucleotide and derived amino acid sequences of n4'. The denoted structural features are from 5' to 3' end: the cDNA present in the original clone (HeLa1) (dotted box), which contains the PH homology domain (in black) and the Ser-Xaa-Yaa repeat (in gray); the heptad repeat of the predictable coiled-coil structure (open box) containing the bipartite nuclear localization signal (in gray); and a serine-rich domain (filled gray box). The asterisks denote the positions of in frame stop codons.

FIG. 2. Distribution of GPBP in human tissues (Northern blot) and in eukaryotic species (Southern blot). A random primed $^{32}$P-labeled HeLa1 cDNA probe was used to identify homologous messages in a Northern blot of poly($A^+$)RNA from the indicated human tissues (panel A) or in a Southern blot of genomic DNA from the indicated eukaryotic species (panel B). Northern hybridization was performed under highly stringent conditions to detect perfect Few matching messages and at low stringency in the Southern to allow the detection of messages with mismatches. No appreciable differences in the quality and amount of each individual poly A+ RNA was observed by denaturing gel electrophoresis or when probing a representative blot from the same lot with human β-actin cDNA. The numbers denote the position and the sizes in kb of the RNA or DNA markers used.

FIG. 3. Experimental determination of the translation start site. In (A), the two cDNAs present in pc-n1' and pc-FLAG-n4' plasmids used for transient expression are represented as black lines. The relative position of the corresponding predicted (n4') or engineered (FLAG-n4') translation start site is indicated (Met). In (B), the extracts from control (−), pc-n4'(n4') or pc-FLAG-n4' (FLAG-n4') transfected 293 cells were subjected to SDS-PAGE under reducing conditions in 10% gels. The separated proteins were transferred to a PVDF membrane (Millipore) and blotted with the indicated antibodies. The numbers and bars indicate the molecular mass in kDa and the relative positions of the molecular weight markers, respectively.

FIG. 4. Characterization of rGPBP from yeast and 293 cells. In (A), 1 μg (lane 1) or 100 ng (lanes 2 and 3) of yeast rGPBP were analyzed by reducing SDS-PAGE in a 10% gel. The separated proteins were stained with Coomassie blue (lane 1) or transferred and blotted with anti-FLAG antibodies (lane 2) or Mab14, a monoclonal antibody against GPBP (lane 3). In (B), the cell extracts from GPBP-expressing yeast were analyzed as in A and blotted with anti-FLAG (lane 1), anti-PSer (lane 2), anti-PThr (lane 3) or anti-PTyr (lane 4) monoclonal antibodies respectively. In (C), 200 ng of either yeast rGPBP (lane 1), dephosphorylated yeast rGPBP (lane 2) or 293 cells-derived rGPBP (lane 3) were analyzed as in B with the indicated antibodies. In (D), similar amounts of $H_{13}{}^{32}PO_4$-labeled non-transfected (lanes 1), stable pc-n4' transfected (lanes 2) or transient pc-FLAG-n4' expressing (lanes 3) 293 cells were lysed, precipitated with the indicated antibodies and analyzed by SDS-PAGE and autoradiography. The molecular weight markers are represented with numbers and bars as in FIG. 3. The arrows indicate the position of the rGPBP.

FIG. 5. Recombinant GPBP contains a serine/threonine kinase that specifically phosphorylates the N-terminal region of the human GP antigen. To assess phosphorylation, approximately 200 ng of yeast rGPBP was incubated with [γ]$^{32}$P-ATP in the absence (A and B) or presence of GP antigen-derived material (C). In (A), the mixture was subjected to reducing SDS-PAGE (10% gel) and autoradiographed. In (B), the mixture was subjected to $^{32}$P phosphoamino acid analysis by two-dimensional thin-layer chromatography. The dotted circles indicate the position of ninhydrin stained phosphoamino acids. In (C), the phosphorylation mixtures of the indicated GP-derived material were analyzed by SDS-PAGE (15% gel) and autoradiography (GPpep1 and GPpep1Ala$^9$) or immunoprecipitated with Mab 17, a monoclonal antibody that specifically recognize GP antigen from human and bovine origin, and analyzed by SDS-PAGE (12.5%) and autoradiography (rGP, GP). The relative positions of rGPBP (A), rGP antigen and the native human and bovine GP antigens (C) are indicated by arrows. The numbers and bars refer to molecular weight markers as in previous Figures.

FIG. 6. In-blot renaturation of the serine/threonine kinase present in rGPBP. Five micrograms of rGPBP from yeast were in-blot renatured. The recombinant material was specifically identified by anti-FLAG antibodies (lane 1) and the in situ $^{32}$P-incorporation detected by autoradiography (lane 2). The numbers and bars refer to molecular weight markers as in previous Figures. The arrow indicates the position of the 89 kDa rGPBP polypeptide.

Figure 7:
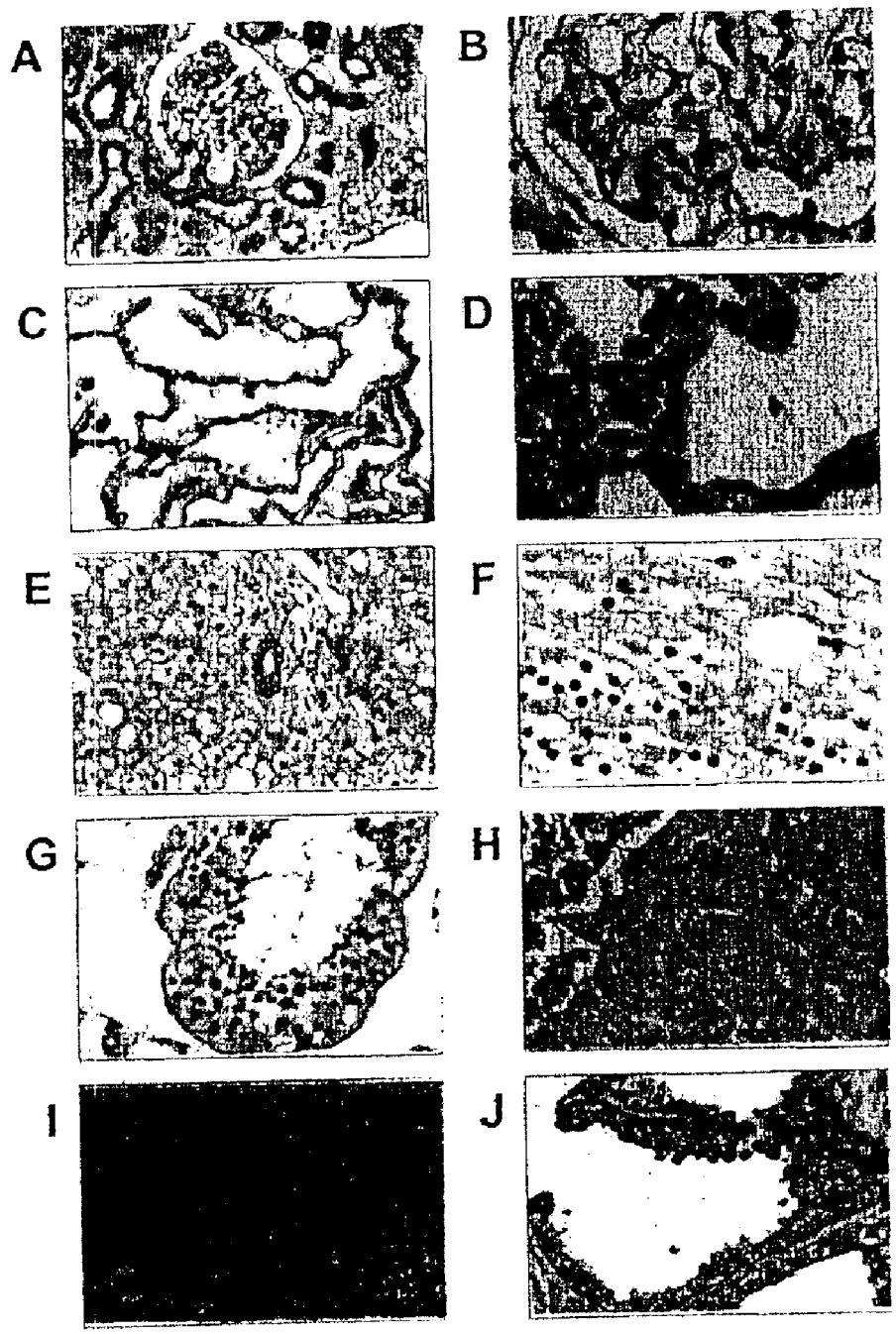

FIG. 7. Immunological localization of GPBP in human tissues. Rabbit serum against the N-terminal region of GPBP (1:50) was used to localize GPBP in human tissues. The tissues shown are kidney (A) glomerulus (B), lung (C), alveolus (D), liver (E), brain (F), testis (G), adrenal gland (H), pancreas (I) and prostate (J). Similar results were obtained using anti-GPBP affinity-purified antibodies or a pool of culture medium from seven different GPBP-specific monoclonal antibodies (anti-GPBP Mabs 3, 4, 5, 6, 8, 10 and 14). Rabbit pre-immune serum did not stain any tissue structure in parallel control studies. Magnification was 40× except in B and D where it was 100×.

Figure 8:
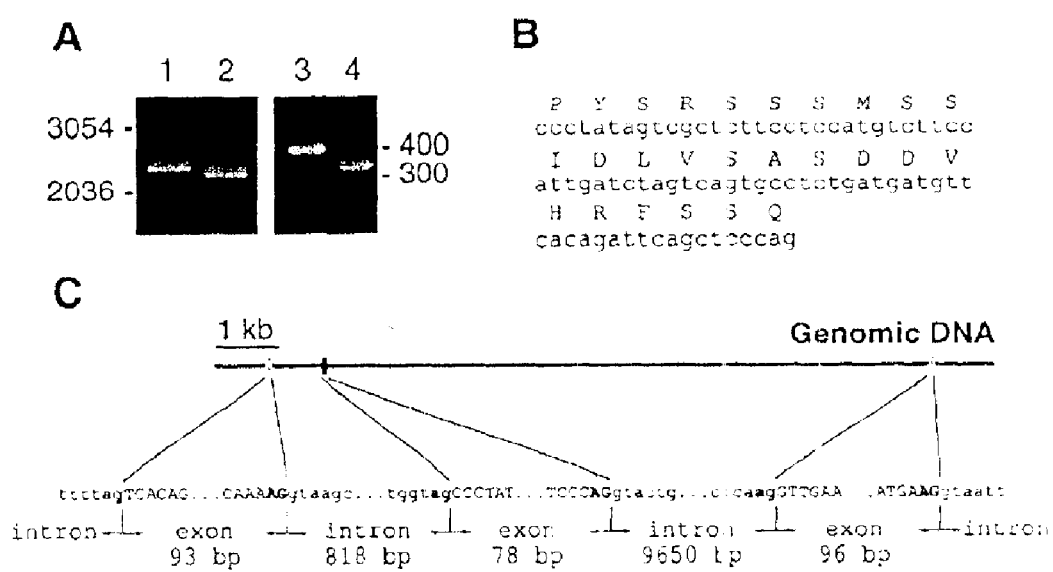

FIG. 8. GPBPΔ26 is a splicing variant of GPBP. (A) Total RNA from normal skeletal muscle was retrotranscribed using primer 53c and subsequently subjected to PCR with primers 11m-53c (lane 2) or 15m-62c (lane 4). Control amplifications of a plasmid containing GPBP cDNA using the same pairs of primers are shown in lanes 1 and 3. Numbers on the left and right refer to molecular weight in base pairs. The region missing in the normal muscle transcript was identified and its nucleotide sequence (lower case) and deduced amino acid sequence (upper case) are shown in (B). A clone of genomic DNA comprising the cDNA region of interest was sequenced and its structure is drawn in (C), showing the location and relative sizes of the 78-bp exon spliced out in GPBPΔ26 (black box), adjacent exons (gray boxes), and introns (lines). The size of both intron and exons is given and the nucleotide sequence of intron-exon boundaries (SEQ ID NOs:55–60) is presented, with consensus for 5' and 3' splice sites shown in bold case.

Figure 9:
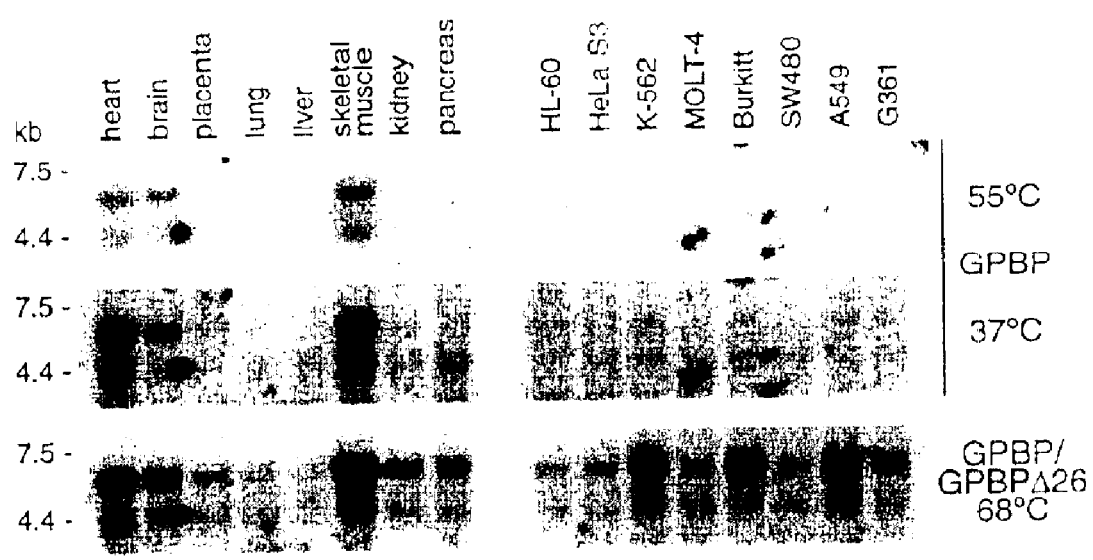

FIG. 9. Differential expression of GPBP and GPBPΔ26. Fragments representing the 78-bp exon (GPBP) or flanking sequences common to both isoforms (GPBP/GPBPΔ26) were $^{32}$P-labeled and used to hybridize human tissue and tumor cell line Northern blots (CLONTECH). The membranes were first hybridized with GPBP-specific probe, stripped and then reanalyzed with GPBP/GPBPΔ26 probe. Washing conditions were less stringent for GPBP-specific probe (0.1% SSPE, 37° C. or 55° C.) than for the GPBP/GPBPΔ26 (0.1% SSPE, 68° C.) to increase GPBP and GPBPΔ26 signals respectively. No detectable signal was obtained for the GPBP probe when the washing program was at 68° C. (not shown).

Figure 10:
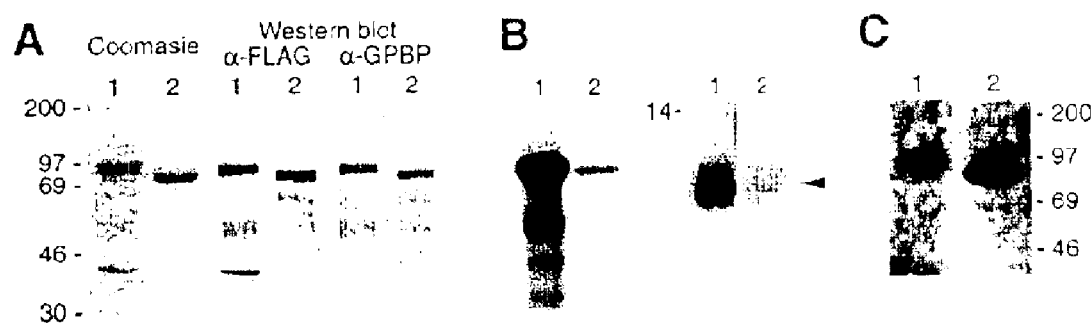

FIG. 10. GPBPΔ26 displays lower phosphorylating activity than GPBP. (A) Recombinantly-expressed, affinity-purified GPBP (rGPBP) (lanes 1) or rGPBPΔ26 (lanes 2) were subjected to SDS-PAGE under reducing conditions and either Coomasie blue stained (2 μg per lane) or blotted (200 ng per lane) with monoclonal antibodies recognizing the FLAG sequence (ca-FLAG) or GPBP/GPBPΔ26 (Mab14). (B) 200 ng of rGPBP (lanes 1) or rGPBPΔ26 (lanes 2) were in vitro phosphorylated without substrate to assay autophosphorylation (left), or with 5 nmol GPpep1 to measure trans-phosphorylation activity (right). An arrowhead indicates the position of the peptide. (C) 3 μg of rGPBP (lane 1) or rGPBPΔ26 (lane 2) were in-blot renatured as described under Material and Methods. The numbers and bars indicate the molecular mass in kDa and the relative position of the molecular weight markers, respectively.

Figure 11:
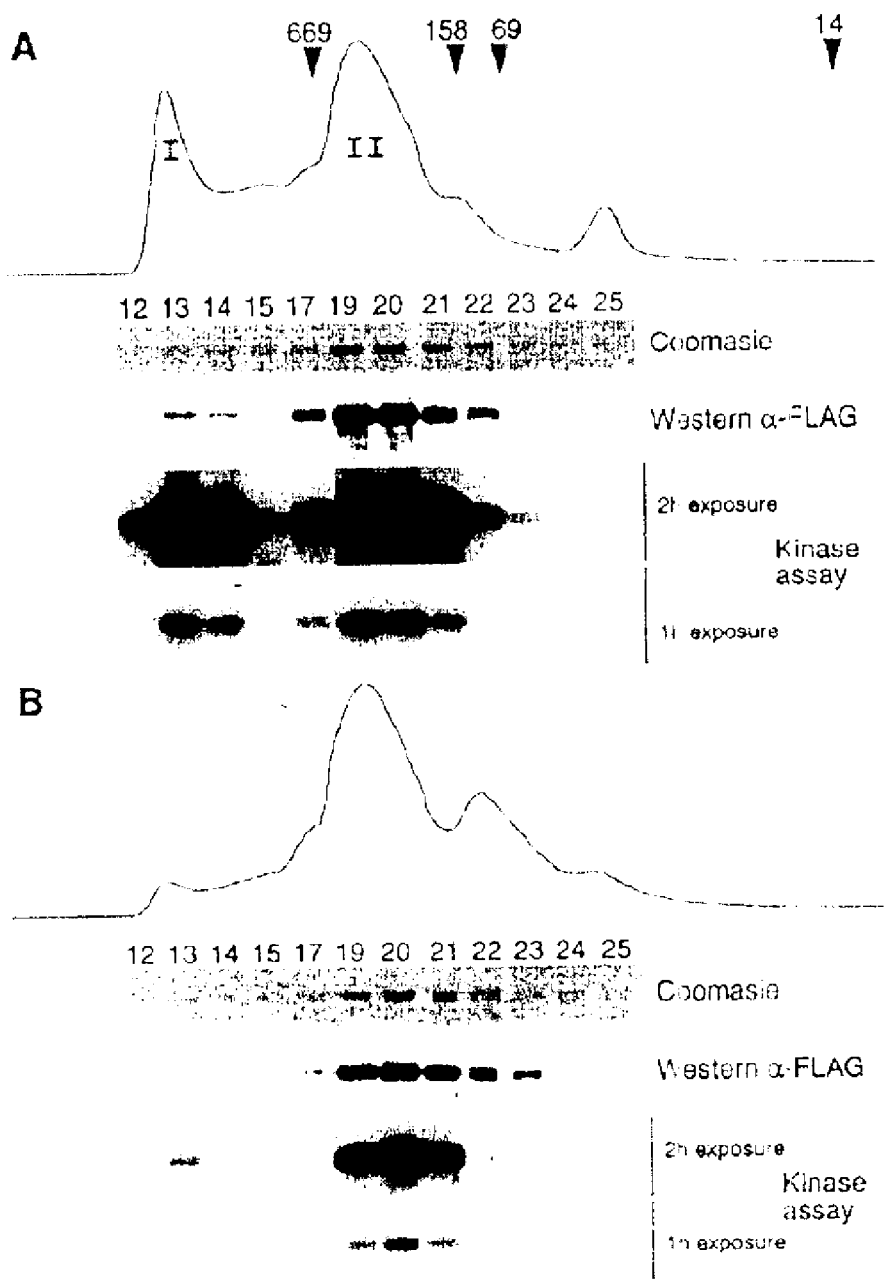

FIG. 11. rGPBP and rGPBPΔ26 form very active high molecular weight aggregates. About 300 μg of rGPBP (A) or rGPBPΔ26 (B) were subjected to gel filtration HPLC as described under Material and Methods. Vertical arrowheads and numbers respectively indicate the elution profile and molecular mass (kDa) of the molecular weight standards used. Larger aggregates eluted in the void volume (I), and the bulk of the material present in the samples eluted in the fractionation range of the column as a second peak between the 669 and 158 kDa markers (II). Fifteen microliters of the indicated minute fractions were subjected to SDS-PAGE and Coomasie blue staining. Five microliters of the same fractions were in vitro phosphorylated as described in Materials and Methods, and the reaction stopped by boiling in SDS sample buffer. The fractions were loaded onto SDS-PAGE, transferred to PVDF and autoradiographed for 1 or 2 hours using Kodak X-Omat films and blotted using anti-FLAG monoclonal antibodies (Sigma).

Figure 12:
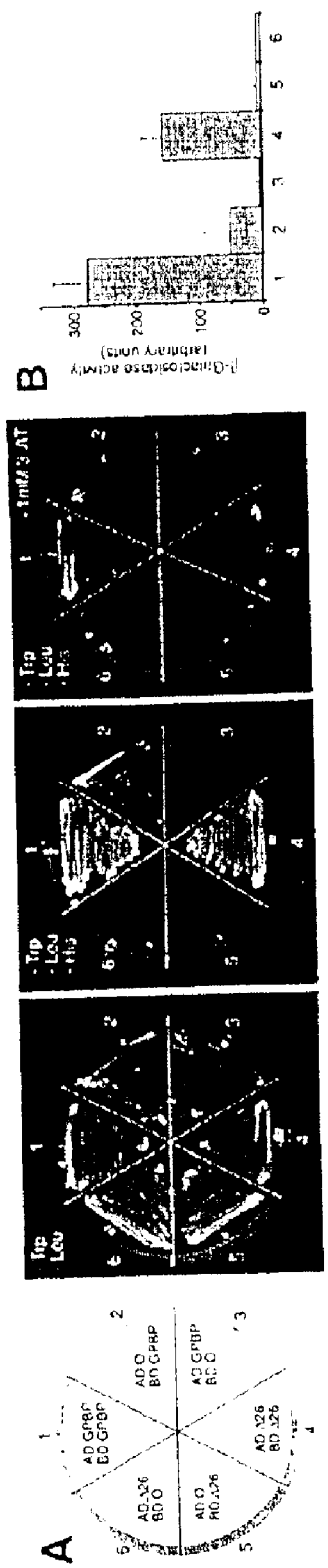

FIG. 12. Self-interaction of GPBP and GPBPΔ26 assessed by a yeast two-hybrid system. (A) Cell transfected for the indicated combinations of plasmids were selected on leucine-tryptophan-deficient medium (-Trp, -Leu), and independent transformants restreaked onto histidine-deficient plates (-Trp, -Leu, -His) in the presence or absence of 1 mM 3-amino-triazole (3-AT), to assess interaction. The picture was taken 3 days after streaking. (B) The bars represent mean values in β-galactosidase arbitrary units of four independent β-galactosidase in-solution assays.

Figure 13:
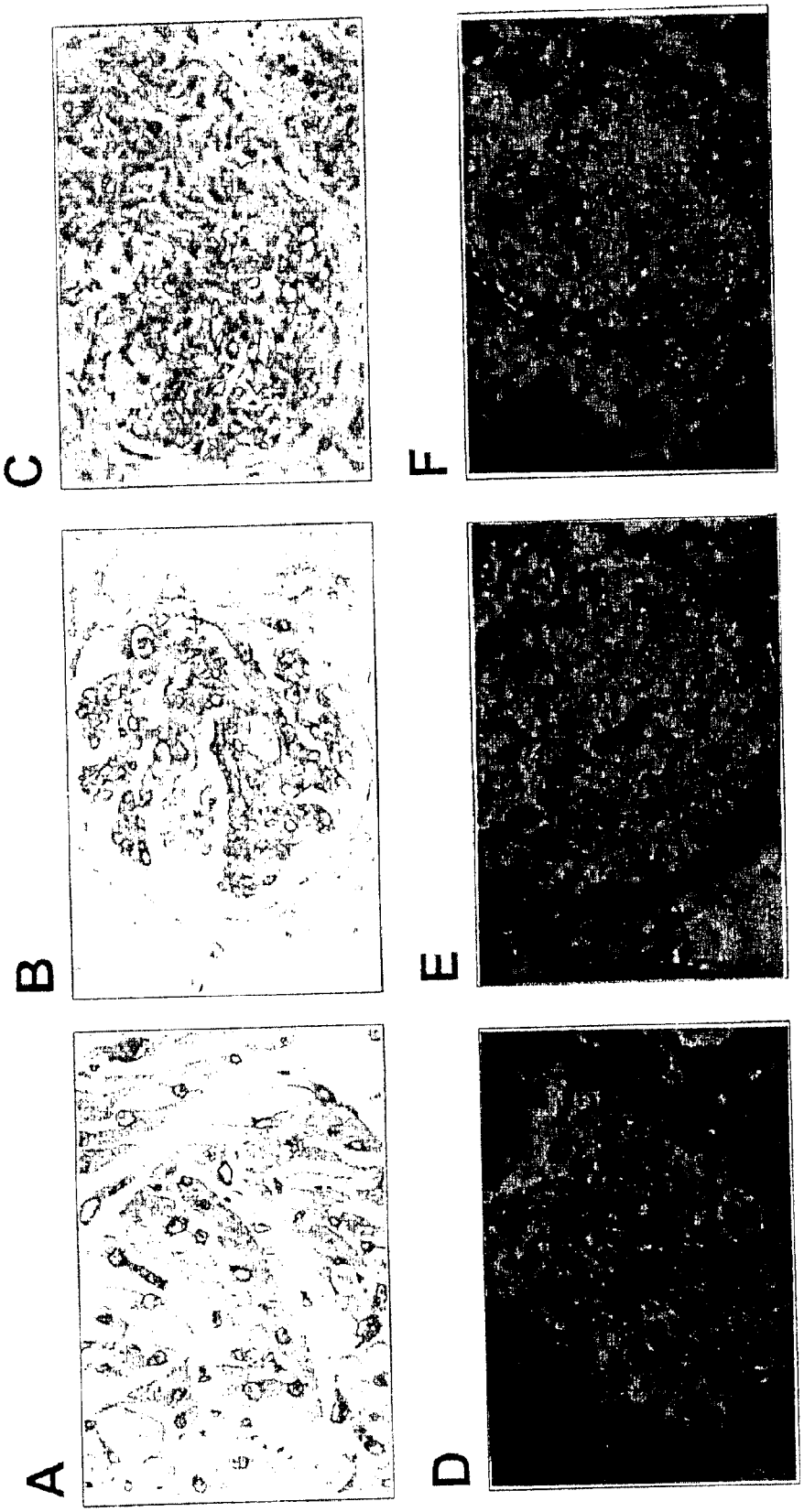

FIG. 13. GPBP is expressed associated with endothelial and glomerular basement membranes. Paraffin embedded sections of human muscle (A) or renal cortex (B, C) were probed with GPBP-specific antibodies (A,B) or with Mab189, a monoclonal antibody specific for the human α3(IV)NC1 (C). Frozen sections of human kidney (D-F) were probed with Mab17, a monoclonal antibody specific for the α3(IV)NC1 domain (D), GPBP-specific antibodies (E), or sera from a GP patient (F). Control sera (chicken pre-immune and human control) did not display tissue-binding in parallel studies (not shown).

Figure 14:
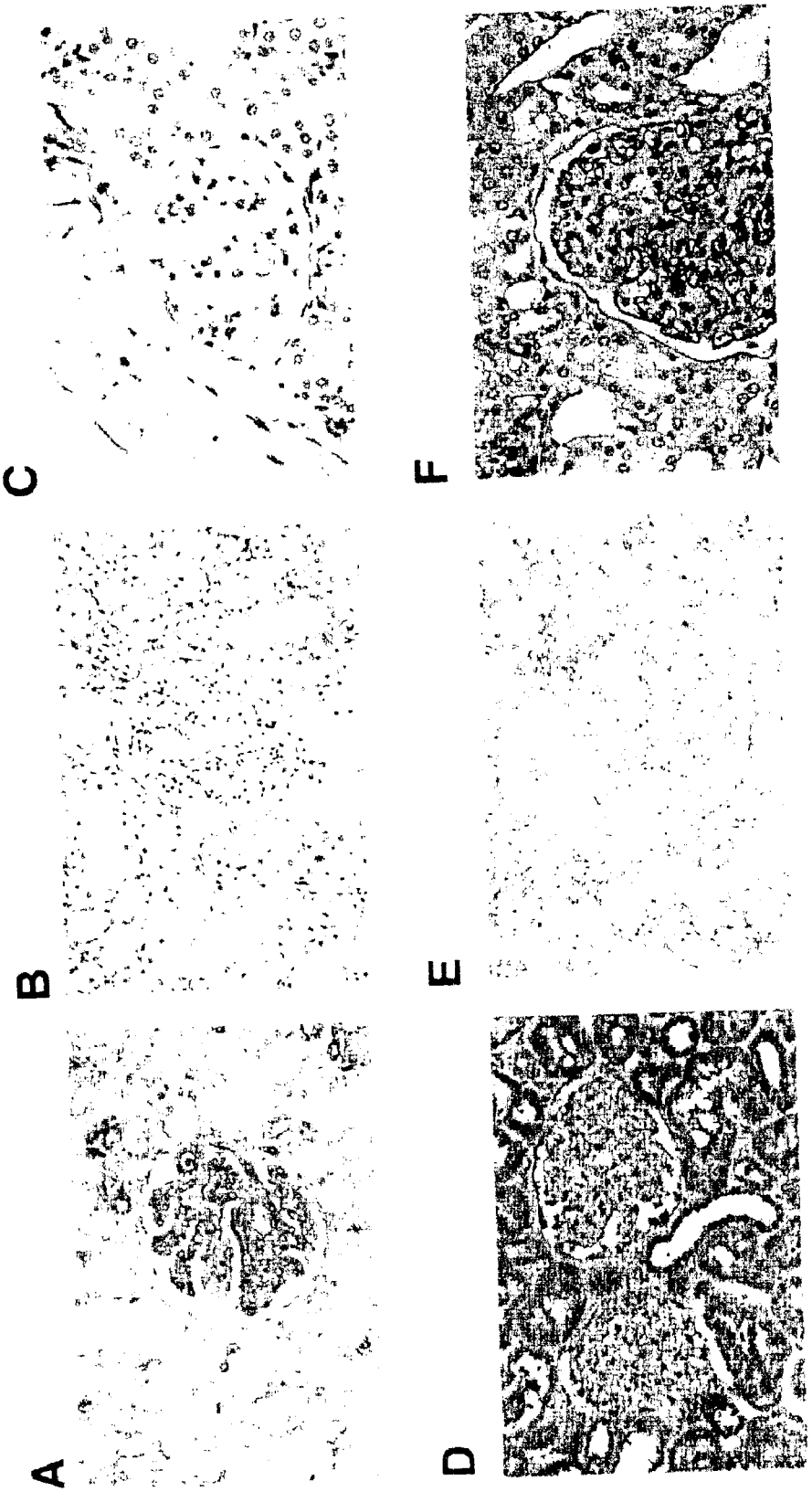

FIG. 14. GPBP is expressed in human but not in bovine and murine renal cortex. Cortex from human (A, D), bovine (B, E) or murine (C, F) kidney were paraffin embedded and probed with either GPBP-specific antibodies (A–C) or GPBP/GPBPΔ6-specific antibodies (D–F).

Figure 15:
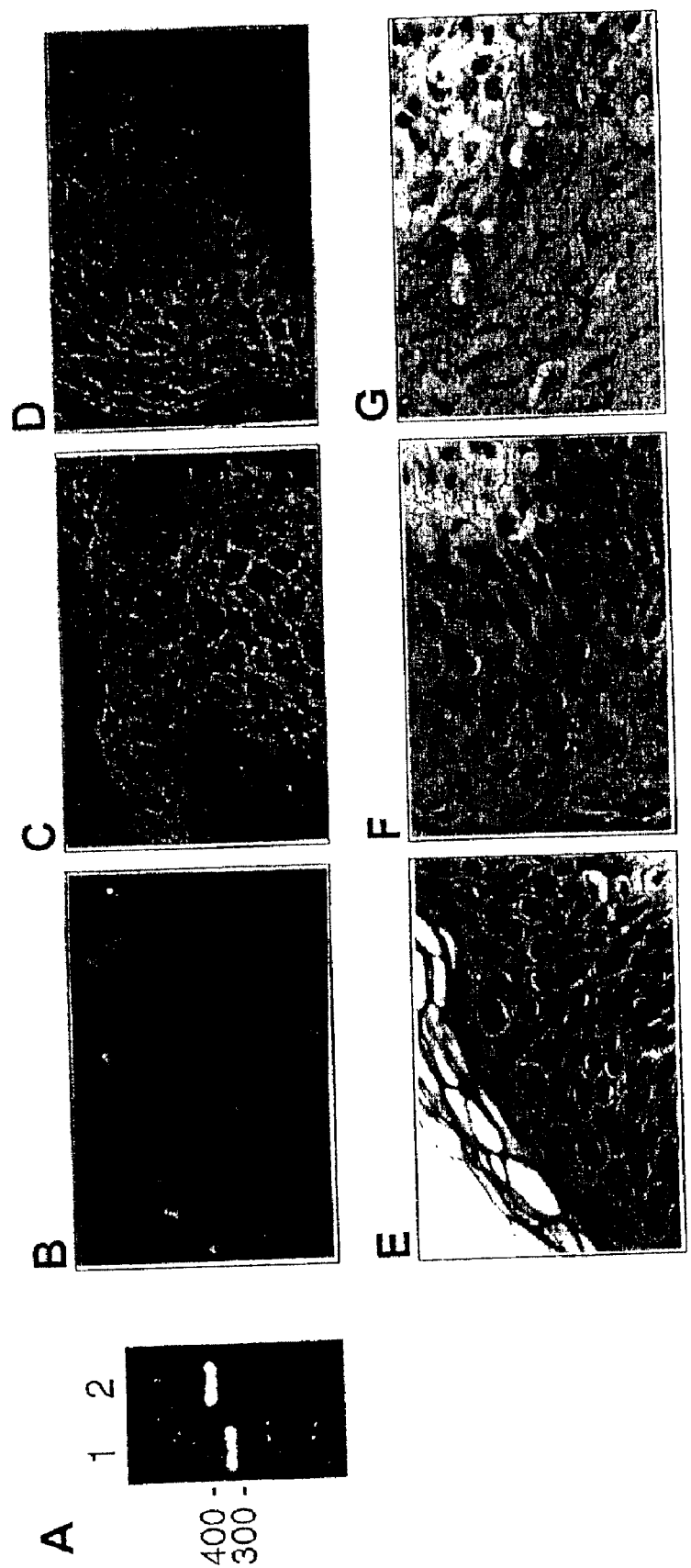

FIG. 15. GPBP is highly expressed in several autoimmune conditions. Skeletal muscle total RNA from a control individual (lane 1) or from a GP patient (lane 2) was subjected to RT-PCR as in FIG. 8, using the oligonucleotides 15m and 62c in the amplification program. Frozen (B–D) or paraffin embedded (E–G) human control skin (B, E) or skin affected by SLE (C, F) or lichen planus (D, G) were probed with GPBP-specific antibodies.

Figure 16:
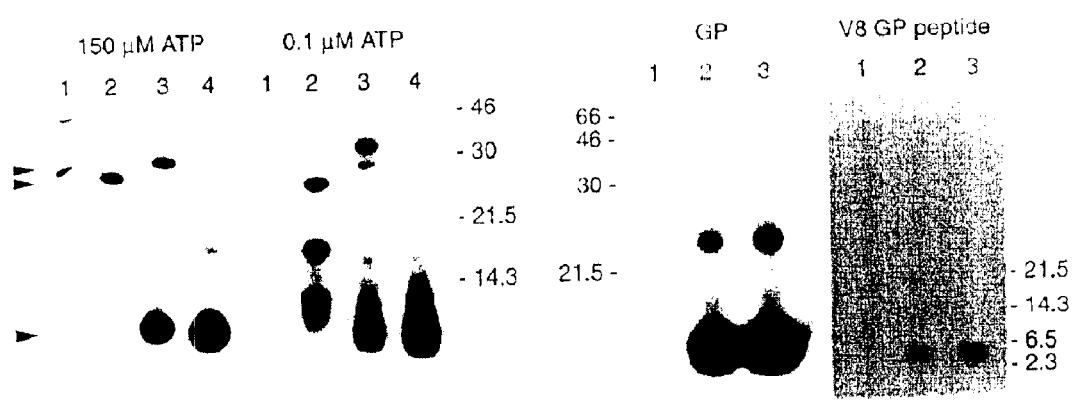

FIG. 16. Phosphorylation of GP alternative splicing products by PKA. In left panel, equimolecular amounts of rGP (lanes 1), rGPΔV (lanes 2), rGPΔIII (lanes 3) or rGPΔIII/IV/V (lanes 4), equivalent to 500 ng of the GP were phosphorylated at the indicated ATP concentrations. One-fifth of the total phosphorylation reaction mixture was separated by gel electrophoresis and transferred to PVDF, autoradiographed (shown) and the proteins blotted with M3/1, a specific monoclonal antibody recognizing all four species (shown) or using antibodies specific for each individual C-terminal region (not shown). Arrowheads indicate the position of each recombinant protein, from top to bottom, GP, GPΔV and, GPΔIII -GPΔIII/IV/V which displayed the same mobilities. Right panel: purified α3(IV) NC1 domain or hexamer was phosphorylated with PKA and 0.1 μM ATP in the absence (lanes 1) or in the presence of 10 nmol of peptides representing the C-terminal region of either GPΔIII (lanes 2) or GPΔIII/IV/V (lanes 3). Where indicated the phosphorylation mixtures of purified α3(IV)NC1 domain were V8 digested and immunoprecipitated with antibodies specific for the N terminus of the human α3(IV) NC1 domain (3). Bars and numbers indicate the position and sizes (kDa) of the molecular weight markers.

FIG. 17. Sequence alignment of GPΔIII and MBP. The phosphorylation sites for PKA (boxed) and the structural similarity for the sites at Ser 8 and 9 of MBP and GPΔIII respectively are shown (underlined). The identity (vertical bars) and chemical homology (dots) of the corresponding exon II (bent arrow) of both molecular species are indicated. The complete sequence of GPΔIII (SEQ ID NO:61) from the collagenase cleavage site (72-residues) is aligned with the 69-N terminal residues of MBP (SEQ ID NO:62) comprising the exon I and ten residues of the exon II.

Figure 18:
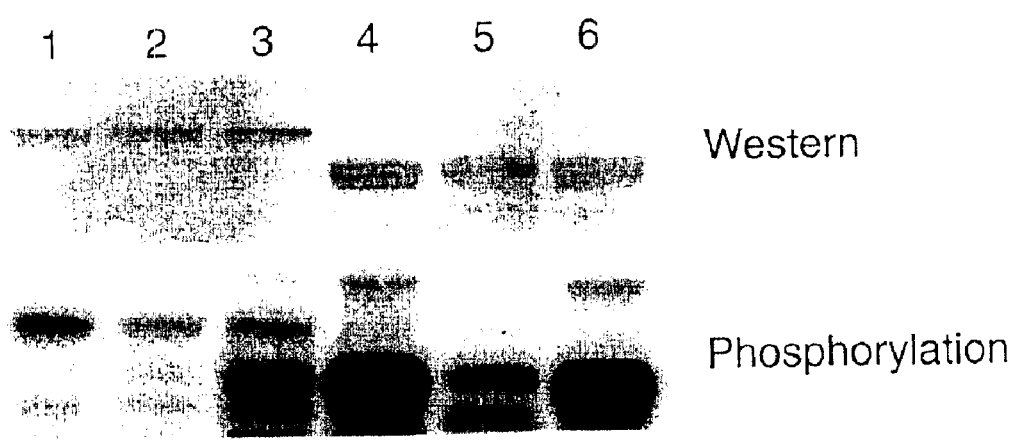

FIG. 18. Phosphorylation of recombinant MBP proteins by PKA. About 200 ng of rMBP (lane 1), or Ser to Ala mutants thereof in position 8 (lane 2) or 57 (lane 3), or rMPBΔII (lane 4) or Ser to Ala mutants thereof in position 8 (lane 5) or 57 (lane 6), were phosphorylated by PKA and 0.1 μM ATP. The mixtures were subjected to SDS-PAGE, transferred to PVDF and autoradiographed (Phosphorylation) and the individual molecular species blotted with monoclonal antibodies against human MBP obtained from Roche Molecular Biochemicals (Western).

Figure 19:
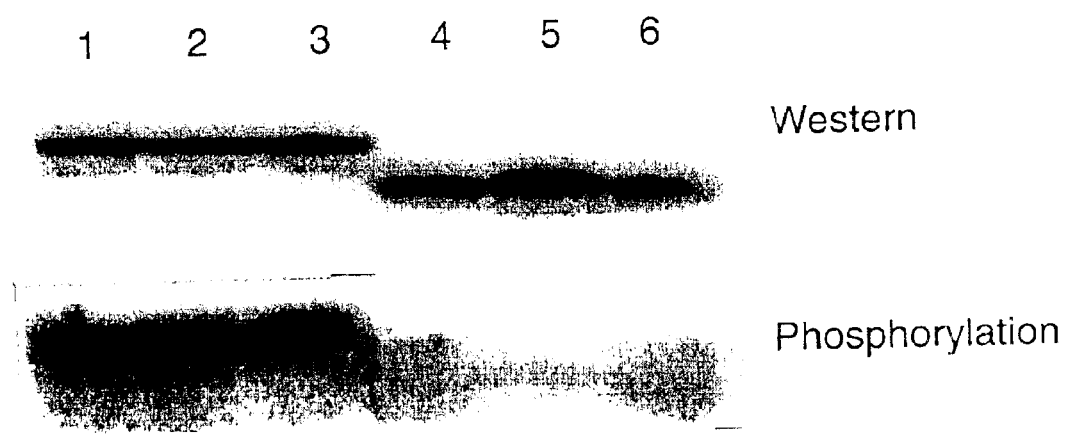

FIG. 19. Phosphorylation of recombinant MBP proteins by GPBP. About 200 ng of rMBP (lane 1), or Ser to Ala mutants thereof in positions 8 (lane 2) or 57 (lane 3), or rMPBΔII (lane 4), or Ser to Ala mutants thereof in positions 8 (lane 5) or 57 (lane 6), were subjected to SDS-PAGE, transferred to PVDF, and the area containing the proteins visualized with Ponceau and stripped out. The immobilized proteins were in situ phosphorylated with rGPBP as described in Materials and Methods, autoradiographed (Phosphorylation) and subsequently blotted as in FIG. 18 (Western).

Figure 20:
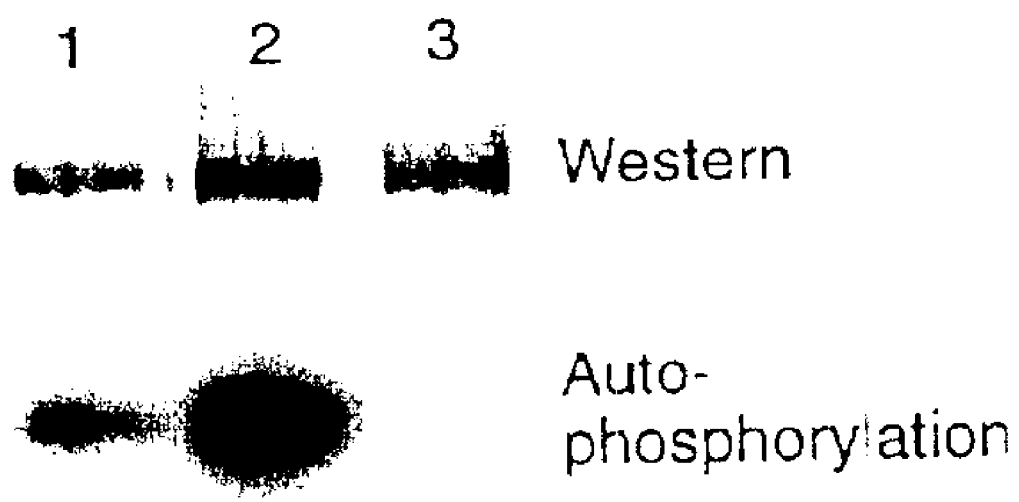

FIG. 20. Regulation of the GPBP by the C terminal region of GPΔIII. About 200 ng of RGPBP were in vitro phosphorylated with 150 μM ATP in the absence (lane 1) or in the presence of 5 nmol of GPΔIII-derived peptide synthesized either using Boc-(lane 2) or Fmoc-(lane 3) chemistry. The reaction mixtures were subjected to SDS-PAGE, transferred to PVDF and autoradiographed to assess autophosphorylation, and subsequently blotted with anti-FLAG monoclonal antibodies (Sigma) to determine the amount of recombinant material present (Western).

Figure 21:
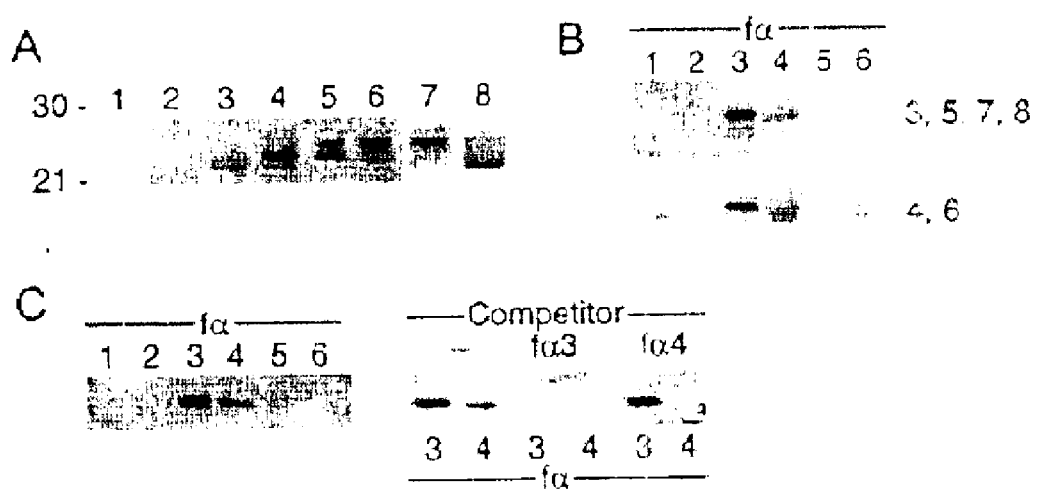

FIG. 21. The GP antibodies recognize multiple α3 polypeptides present in human renal cortex NC1. In A, "hexamer" from human renal cortex (2.5–3 μg) was dissociated by SDS-PAGE under non-reducing conditions and the "monomer" fraction subjected to Western-blot analysis using human normal serum (lane 1), serum containing p-ANCA autoantibodies (lane 2) or with representative individual GP sera (lanes 3–8). Similar negative results to those in lanes 1 and 2 were obtained with five normal sera and two other non-GP autoimmune sera. In B, 150 ng of FLAG-tagged recombinant proteins representing each individual human α(IV)NC1, fα1–fα6, were analyzed by SDS-PAGE and blotted with the individual GP sera used in A. Shown are the two patterns of reactivity observed. The numbers on the side refer to the lane number in A to identify individual GP sera. In C, the GP antibodies extracted from a patient kidney were used to blot 100 ng of either fα1–fα6 (left) or 50 ng of fα3 and fα4 (right) in the absence (−) or in the presence of 10 μg/ml of fα3 or fα4. No reactivity was observed when using control kidney extracts as blotting material (not shown). Numbers and bars at site of the composite in this and following figures indicate size in kDa and position of the rainbow molecular weight markers used (Amersham Bioscience).

Figure 22:
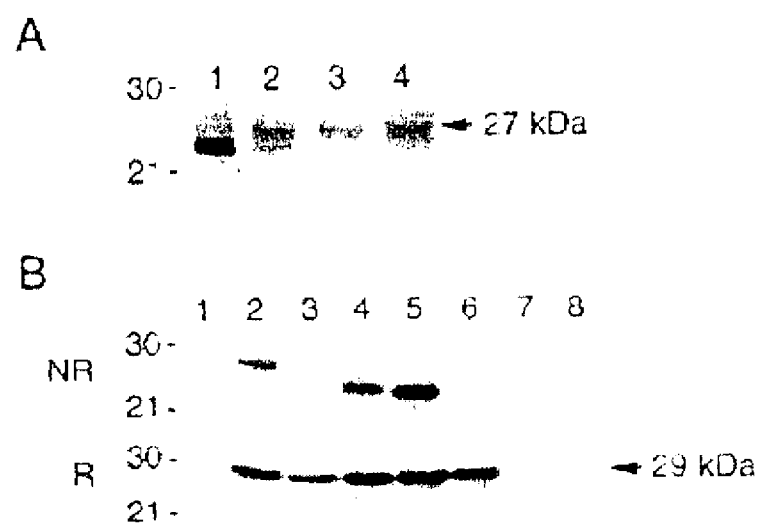

FIG. 22. Identification of the multiple α3(IV)NC1 polypeptides present in human collagen IV as conformational isoforms (conformers). In A, the human "monomers" isolated as in FIG. 21A were blotted using the following α3(IV)NC1 specific antibodies: Mab189, Mab175, MabM3/1 and Mab3 (lanes 1–4, respectively). In B, size-fractions of the human "monomers" isolated from a non-reducing fusible acrylamide SDS-PAGE gel (lanes 1–8) were re-analyzed under non reducing (NR) or reducing (R) conditions and blotted with Mab189. The position of the 27-kDa conformer in A, and the position of the 29-kDa reduced isoforms in B are indicated. Similar results to those shown in B were obtained with two other different α3(IV) NC1 specific Mab.

Figure 23:
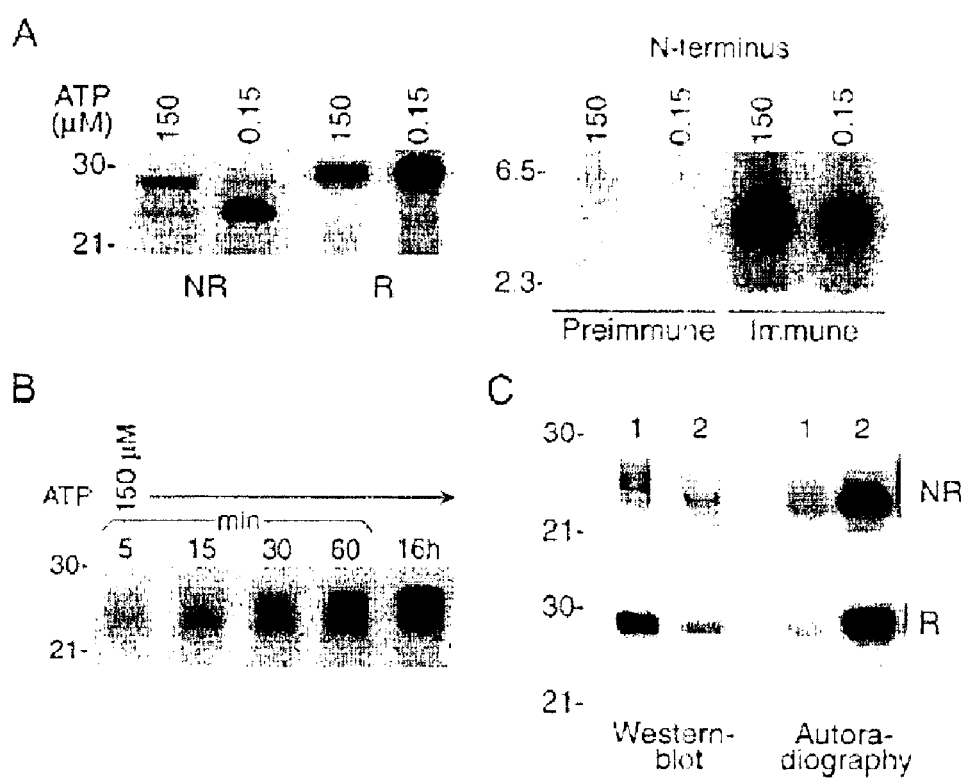

FIG. 23. The 22-kDa conformer is the preferred substrate for PKA in vitro. Human α3(IV)NC1 (27-kDa) was phosphorylated at the indicated ATP concentrations (A, B). In A, similar amounts of incorporated $^{32}$P were analyzed by SDS-PAGE under non-reducing (NR) or reducing (R) conditions and autoradiographed (left) or V8 protease-digested, precipitated with pre-immune or anti-GPpep1 serum and similarly analyzed under reducing conditions (right). In B, at the indicated incubation times identical amounts of phosphorylation mixtures were analyzed under non reducing conditions as in A. In C, two α3(IV)NC1 "monomer" pools, 27-kDa (lanes 1) or 22–25-kDa (lanes 2), were phosphorylated at 0.15 μM ATP and the mixtures subjected to SDS-PAGE under the indicated redox conditions, transferred and analyzed by autoradiography and Western-blot using Mab175.

Figure 24:
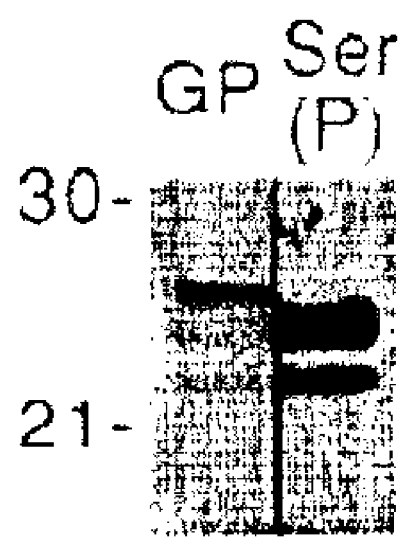

FIG. 24. The 22–25-kDa conformers are the preferred substrate for endogenous protein kinases. The "monomer" fraction of the human "hexamer" was analyzed by Western-blot using N terminal α3(IV)NC1 specific MabP1/2 (GP), and anti-phosphoserine antibodies [Ser(P)].

Figure 25:
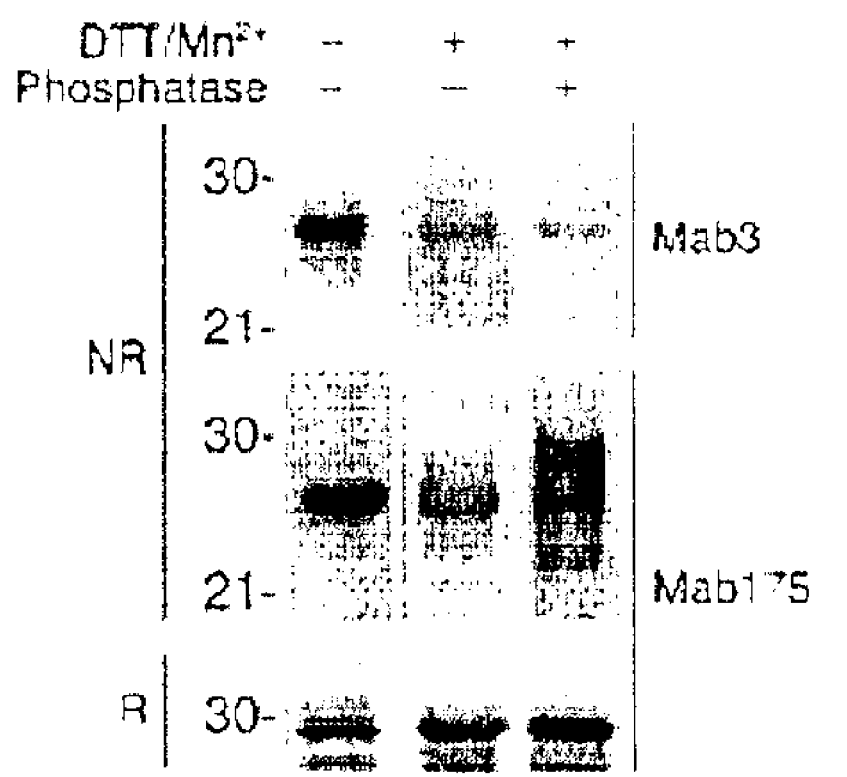

FIG. 25. The conformation of the α3(IV)NC1 domain depends on phosphorylation. Untreated or alkaline phosphatase-treated fα3 were allowed to rearrange disulfide-bonds in the presence of DTT and Mn$^{2+}$ until DTT was fully oxidized. Then the material was analyzed by Western-blot using the indicated α3(IV)-specific antibodies. In NR we loaded 550 and 275 ng for Mab3 and Mab175 studies, respectively, whereas R contained half of the amount used in the corresponding NR study. Approximately 200 ng and 100 ng of starting material were used for NR and R respectively in the control lanes.

Figure 26:
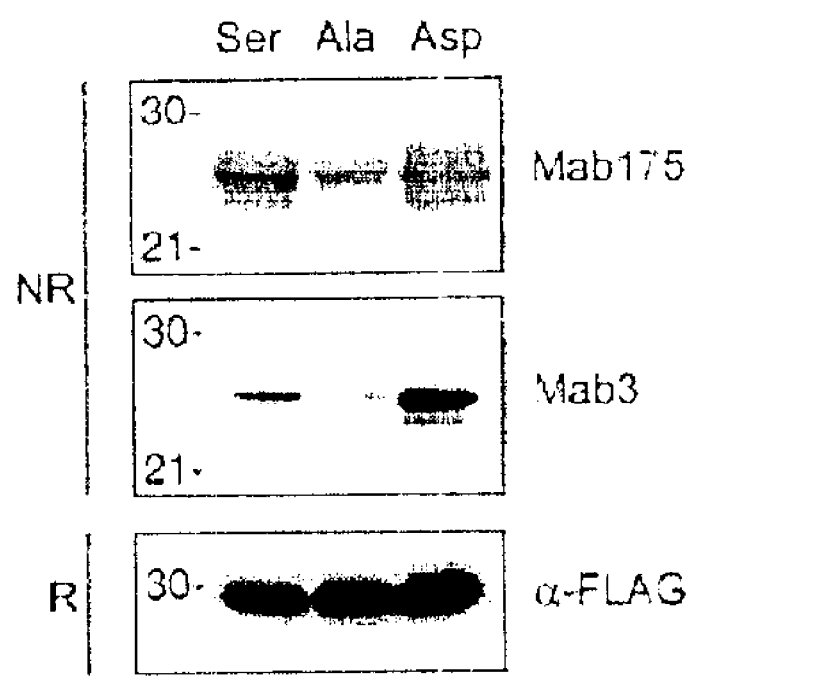

FIG. 26. Ser 9 (P) promotes conformational diversification of the human α3(IV)NC1 domain. Culture media (50 μl) from cells expressing human recombinant α3(IV)NC1 (Ser), or mutants thereof in which Ser 9 was replaced by Ala (Ala) or Asp (Asp) were analyzed by Western-blot using the indicated antibodies and redox conditions.

Figure 27:
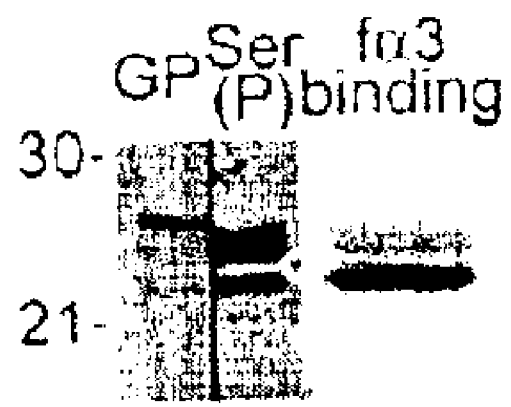

FIG. 27. The highly phosphorylated 22–25-kDa are the more interactive α3(IV)NC1 conformers. The "monomer" fraction of the human "hexamer" was analyzed by Western-blot using N terminal α3(IV)NC1 specific MabP1/2 (GP), anti-phosphoserine antibodies [Ser(P)] or fα3 and 0!FLAG antibodies (fα3 binding). In this and following figures, numbers and bars indicate size in kDa and position of molecular weight markers, respectively.

Figure 28:
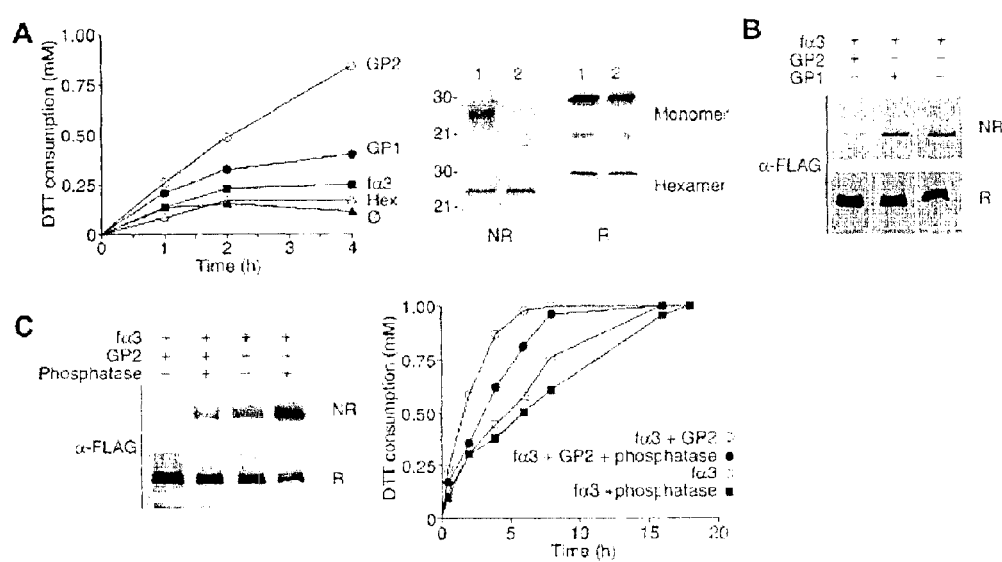

FIG. 28. Phosphorylation promotes the disulfide-based aggregation of the α3(IV)NC1 domain. In A, DTT oxidation in the absence (Ø) or in the presence of ~20 ng of non-assembled 27-kDa (GP1), 22–27-kDa (GP2) or fα3, or assembled (Hex) human α3(IV)NC1 was monitored (left). At right, 75 ng of non-assembled (Monomer) or assembled (Hexamer) human α3(IV)NC1 before (lanes 1) and after (lanes 2) a standard oligomerization assay were analyzed by SDS-PAGE under the indicated redox conditions, transferred and blotted with Mab175. With the exception of fα3 that contained residual non-oligomerized material similar results were obtained when assaying 27-kDa (shown) or 22–25-kDa (not shown) conformers. The amount of non disulfide-cross-linked α3(IV) material present in the "hexamer" (assembled "monomer") was estimated by SDS-PAGE and Western-blot analysis using Mab175. In B, human "monomers" (25 ng) at the indicated combinations were allowed to oligomerize, and the non-oligomerized fα3 was detected by Western-blot with α-FLAG. For a better detection of non-oligomerized fα3, in NR we loaded twice the amount of the reaction mixture loaded in R. In C, the indicated combinations were analyzed as in B and the DTT consumption monitored. Left to right samples in the blot composite correspond to the top to bottom curves in the graphic. The basal consumption of DTT in the presence or absence of alkaline phosphatase has been respectively subtracted in the graphic.

Figure 29:
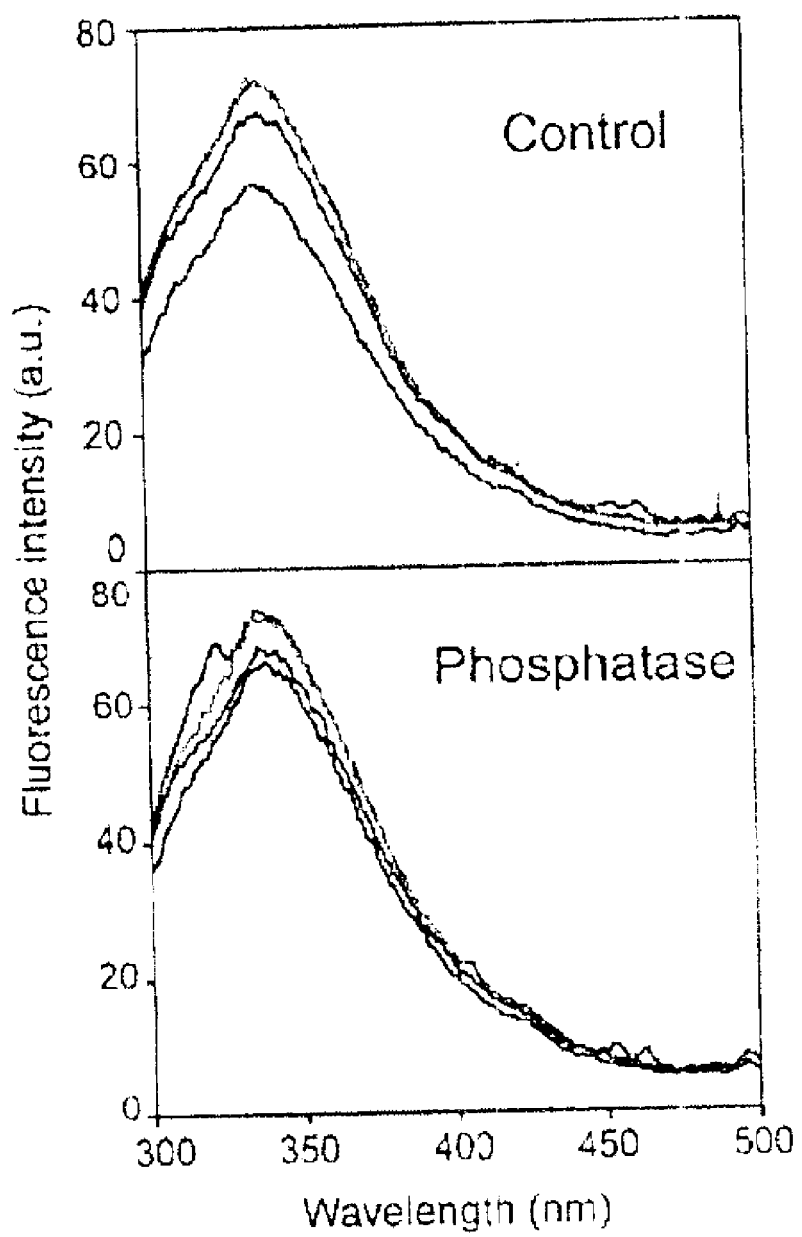

FIG. 29. The α3(IV)NC1 domain undergoes conformational changes during disulfide-based aggregation which depend on phosphorylation. One micromolar of fα3 (Control) or alkaline phosphatase-treated fα3 (Phosphatase) was excited at 280 nm and fluorescence emission spectrum determined prior (top black curves), immediately (second black curves from top) or 15 minutes after (gray curves) addition of 1 mM DTT. Subsequently, 5 mM Cl$_2$Mn was added and emission spectrum determined after 45 minutes (bottom black curves). Fluorescence intensity is expressed in arbitrary units (a.u.).

Figure 30:
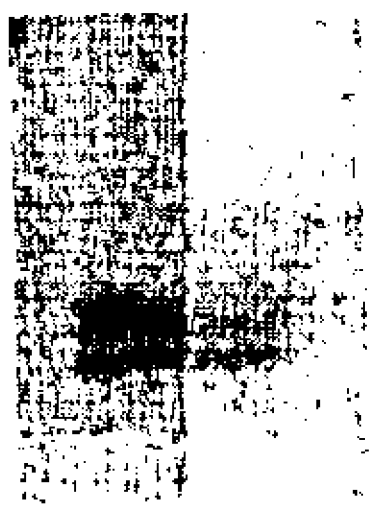

FIG. 30. GPBP preferentially binds to the highly phosphorylated 22–25-kDa α3(IV)NC1 conformers. The "monomer" fraction of the human "hexamer" was analyzed by Western-blot using anti-phosphoserine antibodies [Ser(P)] or GPBP and Mab14 (GPBP binding).

Figure 31:
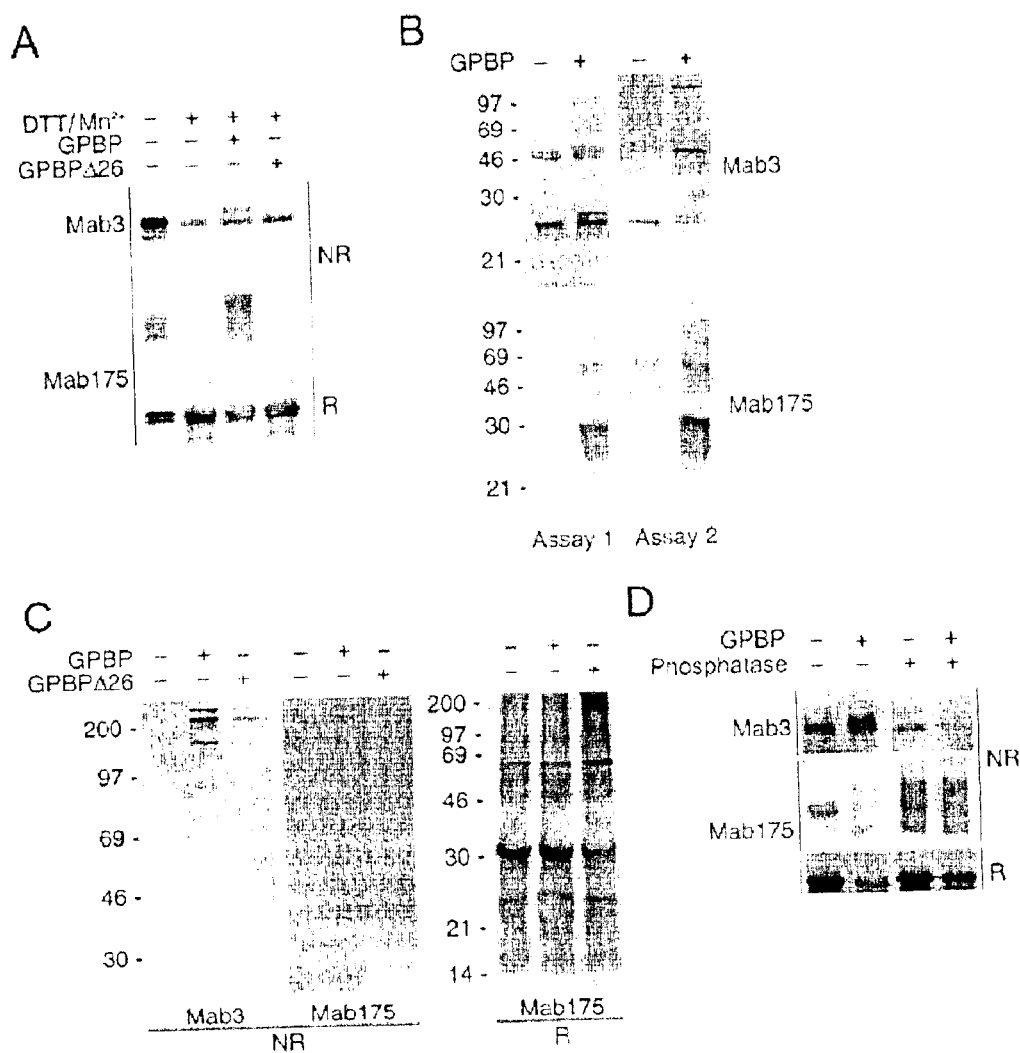

FIG. 31. GPBP catalyzes the conformational isomerization and disulfide-based aggregation of the α3(IV)NC1 domain. In A, similar amounts of bovine α3(IV)NC1 (300 ng) were allowed to oligomerize in the presence of RGPBP or rGPBPΔ26 (500 ng) or equivalent amounts of bovine serum albumin (BSA) until DTT was fully oxidized. The non-oligomerized material was analyzed by Western-blot performed under non-reducing (NR) or reducing (R) conditions using the indicated α3(IV)-specific antibodies. Shown are the regions comprised between 21- and 30-kDa. In B, samples from similar assays to that shown in A were analyzed by Western-blot performed under non-reducing conditions using the indicated antibodies. In C, a similar assay as in B was performed using recombinant material representing the human α3(IV)NC1 produced in bacteria. Similar amounts of the indicated samples were analyzed by Western-blot under non-reducing (NR) or reducing (R) conditions and blotted with the indicated antibodies. Similar results were obtained regardless the presence of DTT/Mn$^{2+}$ or ATP in the oligomerization mixture (not shown). In D, a similar assay to that in A was performed using untreated or phosphatase treated human recombinant fα3 and the indicated samples were similarly analyzed.

Figure 32:
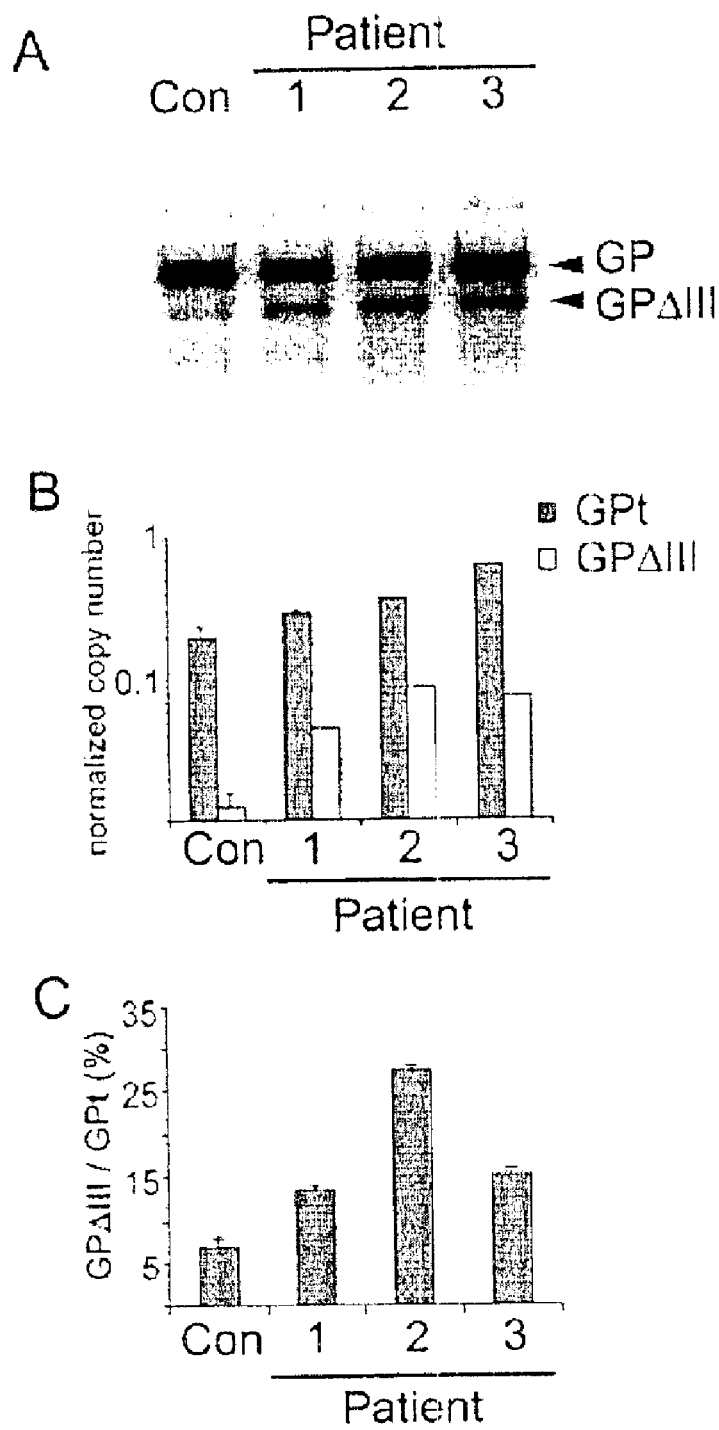

FIG. 32. Augmented expression of alternatively spliced products of the α3(IV)NC1 in GP kidneys. In A, the α3(IV) NC1-related transcripts from a control kidney (Con) or from three independent GP kidneys (Patient 1–3) were retrotranscribed and amplified by PCR. The resulting cDNAs were analyzed by agarose gel electrophoresis and stained with ethidium bromide. In the composite we indicate the two major products identified by nucleotide sequencing or endonuclease digestion, the α3(IV)NC1 primary product (GP) and the alternatively spliced variant GPΔIII. In B, we have expressed in a semi-logarithm plot the estimated mRNA copy number for all the α3(IV)NC1-related products (GPt) or for the alternatively spliced variant GPΔIII after normalization with the estimated mRNA copy number for GAPDH in control (Con) or GP (Patient) kidneys. The values represent the mean of five control kidneys or individual GP kidneys from three different PCR done in duplicate ±S.D. In C, the values in B are represented in lineal scale to show the mRNA copy number encoding GPΔIII per hundred mRNA copies derived from COL4A3.

Figure 33:
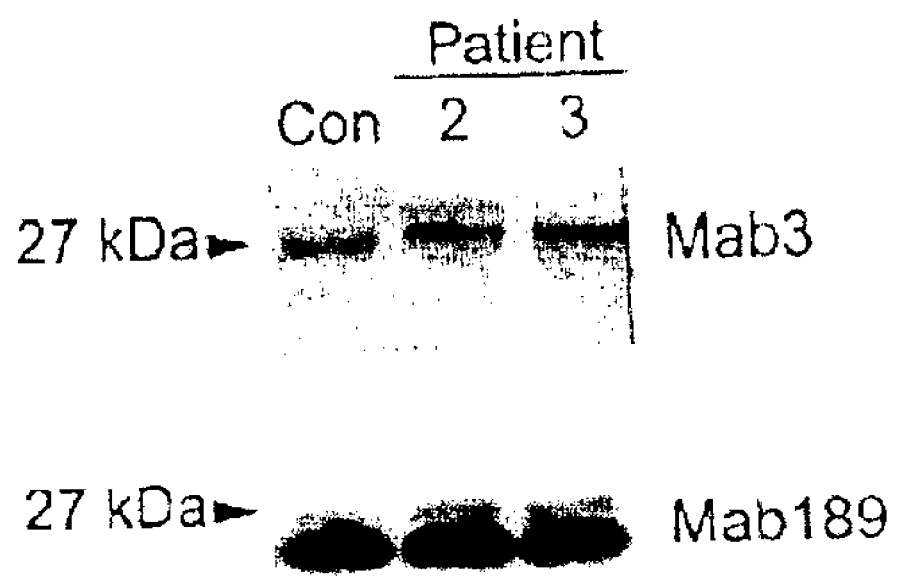

FIG. 33. Immunochemical characterization of the α3(IV) NC1 domain in GP kidneys. Similar amounts of collagen IV NC1 purified from control (Con) or from two independent GP kidneys (Patients 2 and 3) were subjected to SDS-PAGE under non-reducing conditions, transferred and the monomer region comprised between 21- and 30-kDa blotted with the indicated antibodies. The position of the 27-kDa conformer is denoted.

Figure 34:
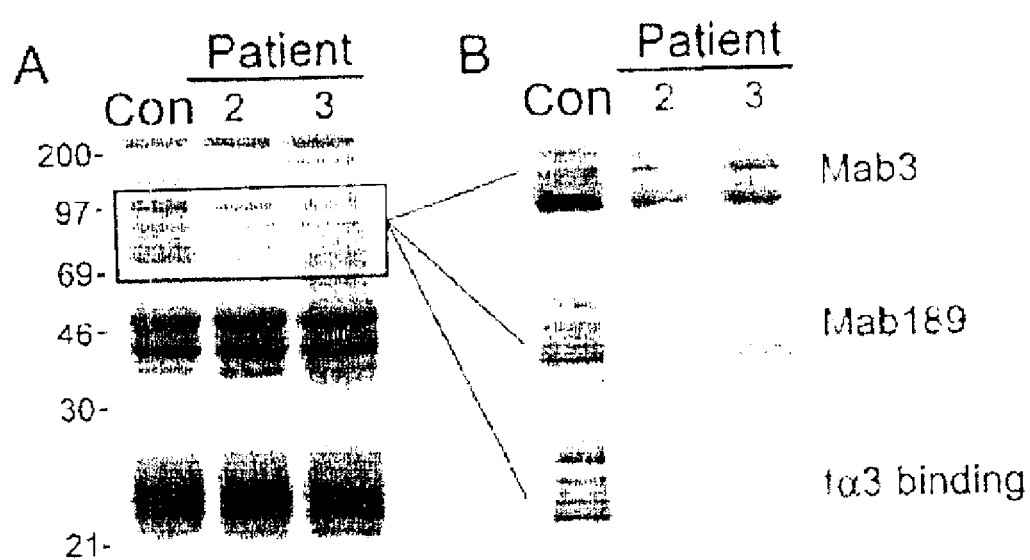

FIG. 34. Immunochemical characterization of the high molecular weight disulfide-based oligomers present in GP kidneys. A similar SDS-PAGE study to that shown in FIG. 33 was silver stained (A) or similarly transferred (B) and the region boxed either blotted with the indicated antibodies or with α-FLAG after probing with fα3 (fα3 binding). The numbers and bars at all site indicate here and in the following Figures the size (kDa) and position of the rainbow coloured protein molecular weight markers (Amersham Pharmacia Biotech). Reduction of the three samples resulted in similar amounts of monomer-sized material in all three samples (not shown).

Figure 35:
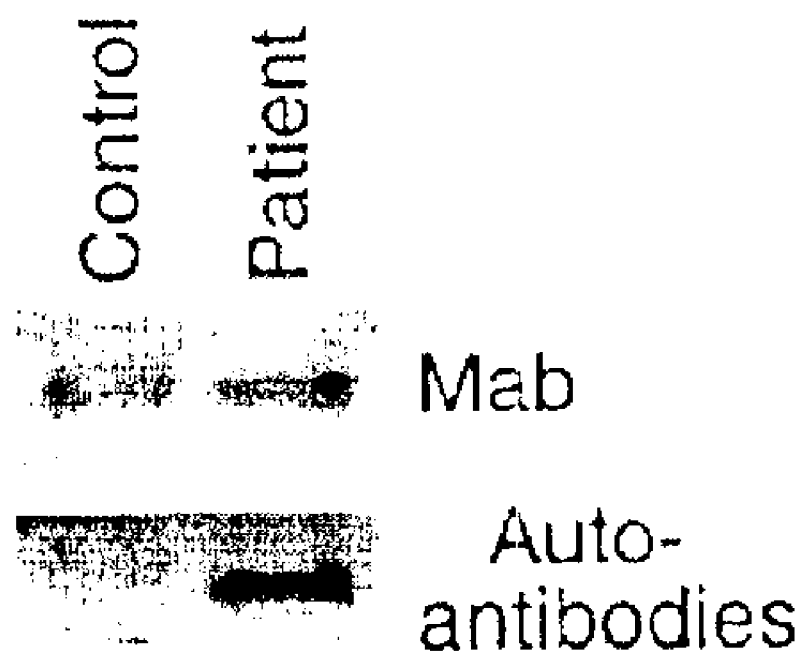

FIG. 35. The α3(IV)NC1 of disease-affected kidneys is preferentially recognized by the GP antibodies. Similar amounts of collagen IV NC1 extracted from a control or a GP kidney were SDS-PAGE analyzed as in FIG. 33 using the α3(IV)NC1 specific antibody Mab175 (Mab) or with the antibodies eluted from the corresponding patient kidney (Autoantibodies). Similar results were obtained when assaying the autoantibodies isolated from two different GP kidneys versus two independent control samples. Antibodies extracted from control kidneys displayed no reactivity in the region displayed (not shown).

Figure 36:
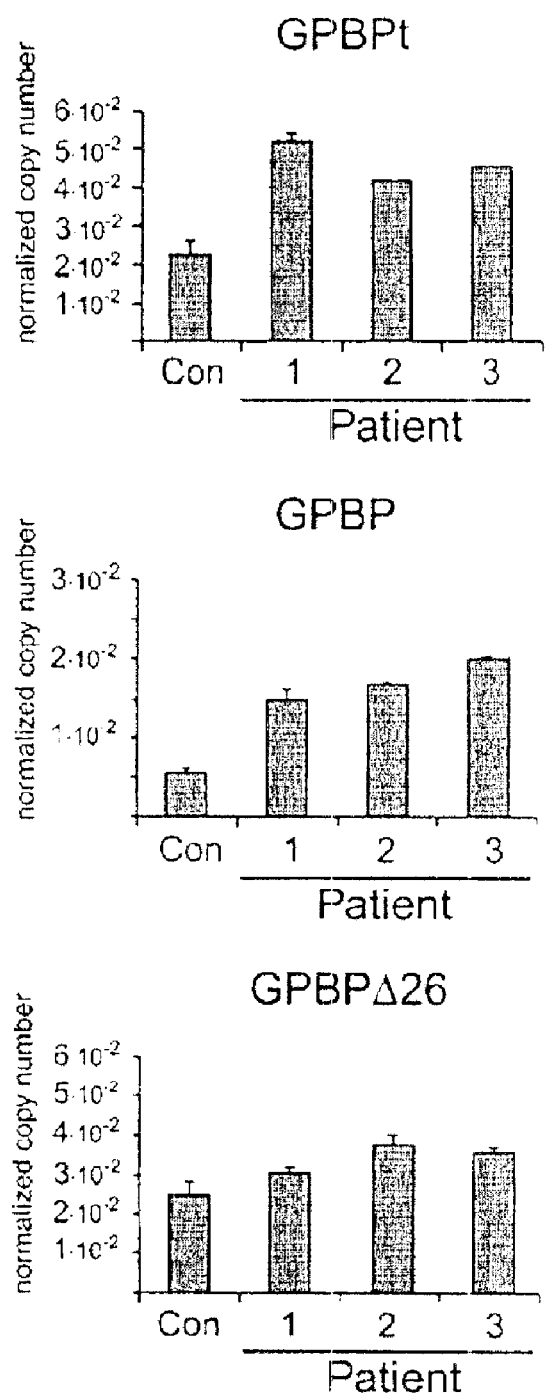

FIG. 36. Augmented expression of GPBP in GP kidneys. We express in lineal plots the estimated copy number for the mRNA transcribed from COL4A3BP (GPBPt) or for the mRNA encoding GPBP or GPBPΔ26, after normalization with the estimated mRNA copy number for GAPDH in control (Con) or GP kidneys (Patient). The values represent the mean of five control kidneys or individual GP kidneys obtained from three different PCR that were done in duplicate±S.D.

Figure 37:
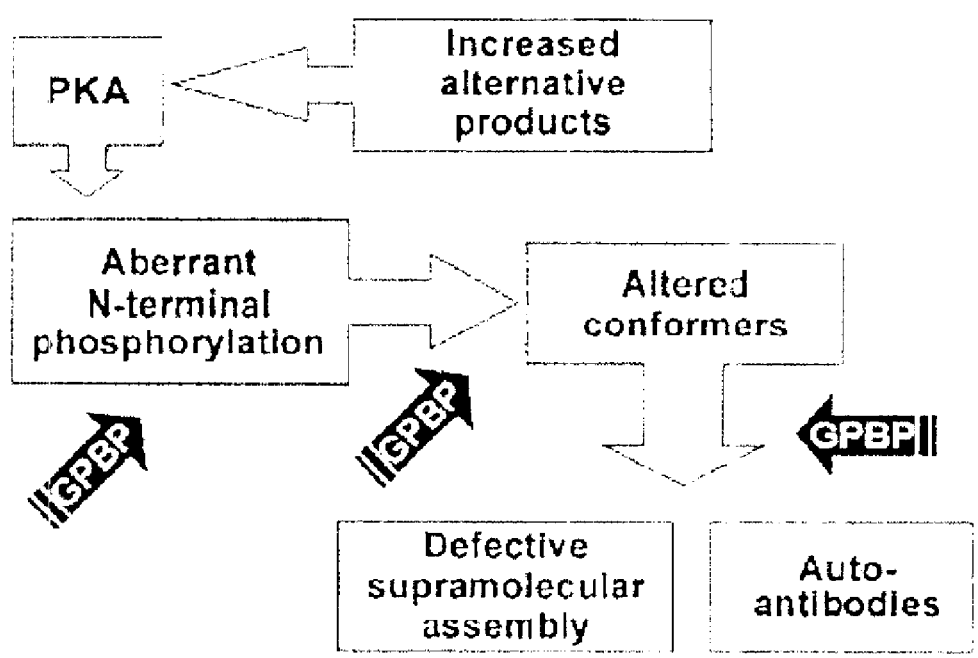

FIG. 37. A model for GP autoimmune response. Early in pathogenesis a coordinated induction of the transcriptional activity of the highly homologous promoters controlling COL4A3 and COL4A3BP result in augmented levels of GPγIII and GPBP respectively. GPΔIII, by inducing PKA action, would promote non-physiological phosphorylation of the N-terminal region of the α3(IV)NC1 domain alone or in collaboration with GPBP. Aberrant phosphorylation generates activated structures with a defective assembly program (altered conformers) that are efficiently assembled into the collagen IV network assisted by the increased levels of GPBP. The conformers with altered conformation by exposing immunologically privileged epitope(s) trigger an otherwise legitimate secondary antibody-mediated immune response.

DETAILED DESCRIPTION OF THE INVENTION

The abbreviations used herein are: BM, basement membrane; bp, base pair; DTT, dithiothreitol; DMEM, Dulbecco's modified Eagle's medium; EDTA, ethylenediamine tetraacetic acid; EGTA, ethylene glycol-bis(β-aminoethyl ether) N,N,N',N'-tetraacetic acid; GBM, glomerular basement membrane; GP, Goodpasture; rGPΔIII, rGPΔIII/IV/V and rGPΔV, recombinant material representing the alternative forms of the Goodpasture antigen resulting from splicing out exon III, exon III, IV and V or exon V, respectively; GPBP and rGPBP, native and recombinant Goodpasture antigen binding protein; GPBPΔ26 and rGPBPΔ26, native and recombinant alternative form of the GPBP; GSH and GSSG, glutathione reduced and oxidized respectively; HLA, human lymphocyte antigens; HPLC, high performance liquid as chromatography; Kb, thousand base pairs; kDa (or kD), thousand daltons; MBP, rMBP, native and recombinant 21 kDa myelin basic protein; MBPΔII and rMBPΔII, native and recombinant 18.5 kDa myelin basic protein that results from splicing out exon II; MBPΔV and MBPΔII/V, myelin basic protein alternative forms resulting from splicing out exon V and exons II and V, respectively; MHC, major histocompatibility complex; NC1, non-collagenous domain; PH, pleckstrin homology; PDI, protein disulfide isomerase; PKA, cPKA, cAMP-dependent protein kinase and catalytic subunit thereof; PMSF, phenylmethylsulfonyl fluoride; SDS-PAGE, sodium dodecylsulfate polyacrylamide gel electrophoresis; TBS, tris buffered saline.

Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); PCR Protocols: *A Guide to Methods and Applications* (Innis, et al. 1990. Academic Press, San Diego, Calif.), *Culture of Animal Cells: A Manual of Basic Technique*, $2^{nd}$ Ed. (R. I. Freshney. 1987. Liss, Inc. New York, N.Y.), *Gene Transfer and Expression Protocols*, pp. 109–128, ed. E. J. Murray, The Humana Press Inc., Clifton, N.J.), and the Ambion 1998 Catalog (Ambion, Austin, Tex.).

As used herein, the term "GPBP" refers to Goodpasture binding protein, and includes both monomers and oligomers thereof. Human (SEQ ID NO:2), mouse (SEQ ID NO:4), and bovine GPBP sequences (SEQ ID NO:6) are provided herein.

As used herein, the term "GPBPΔ26" refers to Goodpasture binding protein deleted for the 26 amino acid sequence shown in SEQ ID NO:14, and includes both monomers and oligomers thereof. Human (SEQ ID NO:8), mouse (SEQ ID NO:10), and bovine GPBP sequences (SEQ ID NO:12) are provided herein.

As used herein the term "GPBPpep1" refers to the 26 amino acid peptide shown in SEQ ID NO:14, and includes both monomers and oligomers thereof.

As used herein, the term "GP antigen" refers to the α3 NC1 domain of type IV collagen.

As used herein, the terms "an α3 NC1 domain of type IV collagen" and "α3(IV)NC1" includes all conformational isomers thereof, and oligomers thereof, and also includes the Cα3(IV)NC1 mutants, α3(IV)NC1Asp9 (SEQ ID NO: 66) and α3(IV)NC1AlA9 (SEQ ID NO: 68), conformational isomers thereof and oligomers thereof, described below.

As used herein, the term "α3(IV)NC1Ser9" means the wild type α3 NC1 domain of type IV collagen.

As used herein, the term "protein kinase A" refers to the cAP-dependent protein kinase.

As used herein, "MBP" refers to myelin basic protein.

As used herein, "test compound" refers to any substance that is tested for ability to produce the desired effects as discussed herein. It will be understood that such test compounds can be added to the various assays at a wide variety of concentrations in order to determine their effect on the results of the assay.

The inventor has discovered that GPBP, a non-conventional protein kinase that in vitro binds to and phosphorylates α3(IV)NC1, the autoantigen in Goodpasture disease, also possesses chaperone, chaperonine, and protein disulfide isomerase (PDI) activities. The present invention demonstrates that GPBP activity includes (1) aggregate disruption (typical chaperone activity); (2) folding catalysis into multiple conformations (atypical chaperonine activity, since typically chaperonines catalyzes only one conformation) and (3) intra and intermolecular disulfide-bond shuffling. The present invention has established the importance of these activities in the autoimmune process, as well as the general importance of autoantigen aberrant phosphorylation and conformational isomerization, which can be influenced by factors in addition to GPBP.

In one aspect, the present invention provides methods for identifying compounds to treat an autoimmune condition, comprising identifying compounds that (a) reduce phosphorylation of a first target protein selected from the group consisting of GPBP, an α3 type IV collagen NC1 domain polypeptide comprising the amino acid sequence of SEQ ID NO:26, and a polypeptide comprising the amino acid sequence of SEQ ID NO:64; and (b) reduce formation of conformational isomers of a second target protein selected from the group consisting of an α3 type IV collagen NC1 domain polypeptide and myelin basic protein, wherein such compounds are candidates for treating an autoimmune condition. Thus the first and second target proteins can be different (for example, when GPBP is the first target and an α3 type IV collagen NC1 domain polypeptide is the second target protein; or when GPpep1 is the first target and an α3 type IV collagen NC1 domain polypeptide is the second target), or they can be identical.

The phosphorylation assays can be conducted in vitro on isolated targets, or can comprise analyzing the effects of the one or more test compounds on phosphorylation in cultured cells, although in vitro assays are preferred. A preferred method for identifying compounds that reduce in vitro phosphorylation of the target protein comprises:

i) incubating the first target protein and ATP in the presence or absence of one or more test compounds under conditions that promote phosphorylation of the target protein in the absence of the one or more test compounds;

ii) detecting phosphorylation of the first target protein; and iii) identifying test compounds that reduce phosphorylation of the first target protein relative to phosphorylation of the first target protein in the absence of the one or more test compounds.

One of skill in the art is capable of determining suitable phosphorylation conditions for conducting the phosphorylation assay, and thus the present method is not limited by the details of the particular phosphorylation conditions employed. A non-limiting example of such suitable conditions for assaying phosphorylation of the first target comprises the use of 0.5 µg to 5 µg of the first target protein, Hepes buffer pH 7.5, and 5 mM MgCl$_2$, optionally including 1 mM DTF, depending on the first target protein.

In a further preferred embodiment, the first target protein is GPBP, and the assay comprises analyzing the effect(s) of the one or more test compounds on GPBP autophosphorylation. In such an embodiment, an exemplary amount of GPBP for use in the assay is between 50 to 200 ng. In an alternative embodiment, the first target protein is selected from the group consisting of an α3 type IV collagen NC1 domain polypeptide comprising the amino acid sequence of SEQ ID NO:26, and an MBP polypeptide comprising the amino acid sequence of SEQ ID NO:64, and the assay is conducted in the presence of GPBP to test for transphosphorylation of the first target protein by the protein kinase. In this embodiment, the first target protein can comprise a full length α3 type IV collagen NC1 domain polypeptide (including α3(IV)NC1Asp9 SEQ ID NO:66 or α3(IV)NC1Ala9 SEQ ID NO:68), full length MBP, or any fragments thereof containing the recited sequence.

For in vitro phosphorylation assays, detection of phosphorylation can be accomplished by any number of means, including but not limited to using $^{32}$P labeled ATP and carrying out autoradiography of a Western blot of the resulting protein products on a reducing or non-reducing gel, or by scintillation counting after a step to separate incorporated from unincorporated label.

Analysis of in vitro phosphorylation may further include identifying the effect of the one or more test compounds on phosphorylation of individual conformational isomers of the first target protein, when the first target protein is selected from the group consisting of an α3 type IV collagen NC1 domain polypeptide and MBP. Such identification can be accomplished, for example, by carrying out SDS-PAGE on the reaction products of the phosphorylation reaction, followed by Western blotting, autoradiography and immunodetection of the target protein.

Analysis of in vitro phosphorylation may further include identifying the effect of the one or more test compounds on Ser$^9$ phosphorylation of the α3 type IV collagen NC1 domain. Such identification can be accomplished, for example, by comparing the immunoreactive patterns of antibodies specifically reacting with the N terminus of the α3(IV)NC1 (including but not limited to anti-GPpep1, MabM3/1 and MabP1/2, disclosed herein) and antibodies specifically reacting with Ser(P), such as those commercially available from Sigma Chemical Co. (St. Louis, Mo.). Alternatively, V8 protease digestion and anti-GPpep1 precipitation followed by reducing SDS-PAGE on the precipitated products and autoradiography can be used.

The data presented herein demonstrate that phosphorylation at Ser$^9$ exerts a positive control over conformational isomerization of α3(IV)NC1, and efficiently changes the cohort of α3(IV)NC1 conformers produced by a cell. These findings indicate that Ser$^9$ is, at least in part, the structural feature that renders the α3(IV)NC1 domain immunogenic, and suggest that, during pathogenesis, a phosphorylation event lead the formation of conformers for which the immune system has not established a tolerance. Thus, determining the effect of test compounds on phosphorylation of the Ser$^9$ residue of α3 type IV collagen NC1 domain may be important in identifying especially useful candidate compounds for treating autoimmune disorders.

Alternatively, the effects of test compounds on phosphorylation of the first target protein can be analyzed in cultured cells. Such a method involves contacting cells that express a first target protein selected from the group consisting of an α3 type IV collagen NC1 domain polypeptide and MBP, under conditions to promote phosphorylation, detecting phosphorylation of the first target protein; and identifying test compounds that reduce phosphorylation of the first target protein relative to phosphorylation of the first target protein in the absence of the one or more test compounds. Appropriate cells for use are eukaryotic cells that express the appropriate first target protein. Methods of detecting phosphorylation are as described above.

As used herein, the phrase "reduce/reducing phosphorylation" means to lessen the phosphorylation of the target protein relative to phosphorylation of the target protein in the absence of the one or more test compounds. Such "reducing" does not require elimination of phosphorylation, and includes any detectable reduction in phosphorylation. Thus, a test compound that inhibits phosphorylation of the first target by, for example, as little as 10–20% would be considered a test compound that reduced phosphorylation. Such a compound may, for example, affect phosphorylation of Ser9, which is shown to exert a powerful control on conformational diversification, and thus to be a strong candidate for an inhibitor of autoimmunity. Alternatively, a test compound may inhibit phosphorylation of a first target protein, such as an α3 type IV collagen NC1 domain polypeptide comprising the amino acid sequence of SEQ ID NO:26 by 90%, but have little inhibitory effect on conformational isomerization of the second target protein, because reduction affects phosphorylation at sites other than Ser9. By performing assays both for phosphorylation inhibition of the first target protein, and conformer inhibition of the second target protein, it is possible to identify those compounds with the best potential for use as therapeutics for autoimmune disorders.

Similarly, inhibition of conformational isomerization of the second target protein can be carried out in vitro using isolated components, or can be carried out in cultured cells, although the use of cultured cells is preferred. In a preferred embodiment using cultured cells, identifying compounds that reduce formation of conformational isomers of the second target protein comprises:

i) providing cells expressing the second target protein;

ii) culturing the cells in the presence or absence of one or more test compounds, under conditions that promote conformational isomerization of the second target protein in the absence of the one or more test compounds;

iii) detecting conformational isomerization of the second target protein; and iv) identifying test compounds that reduce conformational isomerization of the second target protein relative to conformational isomerization of the second target protein in the absence of the one or more test compounds.

Appropriate cells for use are eukaryotic cells that express the appropriate second target protein. In a preferred embodiment, cell lines stably transfected to express the second target protein are used.

In this embodiment, detection of conformational isomers of, for example, the α3 type IV collagen NC1 domain polypeptide, and the effects of the test compounds thereon, generally involve immunodetection using Western blots of non-reducing SDS-PAGE gels containing the α3 type IV collagen NC1 domain polypeptide from the cells. The α3 type IV collagen NC1 domain polypeptide can be purified via standard techniques (such as using cells transfected with a recombinant second target protein that is linked to an epitope tag or other tag to facilitate purification), or cell extracts can be analyzed. In a most preferred embodiment, stable cell lines (such as those disclosed herein) expressing recombinant α3(IV)NC1 are used, which secrete the protein into the medium in a monomeric form, permitting running of serum-free media samples on SDS-PAGE gels and subsequent Western blot analysis and immunodetection. Preferably, immunodetection is carried out using, in parallel, an antibody that detects a native conformation of α3 type IV collagen NC1 domain polypeptide (including but not limited to Mab3 disclosed herein), and an antibody that detects all α3 type IV collagen NC1 domain polypeptide conformational isomers (including but not limited to Mab175 disclosed herein). Alternatively, serum free media or otherwise isolated proteins could be used to coat ELISA plates, followed by similar immunodetection using antibodies that selectively bind to native conformers and either aberrant conformers or all conformers, respectively, and analysis using plate readers.

In a preferred embodiment of an in vitro assay for inhibitors of conformational isomerization of the second target protein, the method comprises i) contacting in vitro the second target protein with GPBP in the presence or absence of one or more test compounds under conditions that promote GPBP-induced conformational isomerization of the second target protein in the absence of the one or more test compounds;

ii) detecting GPBP-induced conformational isomerization of the second target protein; and iii) identifying test compounds that reduce GPBP-induced conformational isomerization of the second target protein relative to GPBP-induced conformational isomerization of the second target protein in the absence of the one or more test compounds.

As used herein, the phrase "reduce/reducing conformational isomerization" means to lessen the formation of conformers of the target protein relative to conformer production under control conditions. Such "reducing" does not require elimination of conformer formation, and includes any detectable reduction in conformer formation. Furthermore, such "reduction in conformer formation" may entail a reduction in only one, or fewer than all conformational isomers; one can envision that such a reduction in production of specific conformers may be accompanied by an increase in the formation of other conformers. For example, we show in the examples to follow that, for the α3 type IV collagen NC1 domain polypeptide, a 27 kD conformer is the primary product, from which the remaining conformers derive. Thus, in a further preferred embodiment, the method comprises identifying those compounds that do not alter the formation of the 27-kDa conformer, but reduce formation of one or more of the other conformers. A preferred method for monitoring this inhibition of specific conformers is to use Mab3 antibody (described below), which only reacts with the 27-kDa conformer, in parallel with Mab175, which is equally reactive with all α3 type IV collagen NC1 domain conformers.

In a further preferred embodiment of the assays to identify inhibitors of conformational isomerization of the second target protein, the second target protein is an α3 type IV collagen NC1 domain polypeptide, and analysis of test compound effect on conformer formation of each of wild type α3(IV)NC1 and α3(IV)NC1Asp9 (SEQ ID NO:66) is carried out in parallel. α3(IV)NC1Asp9 is modified to replace Ser9 with Asp9, an amino acid residue that mimics an always phosphorylated residue, which is used herein as an example of an aberrant phosphorylation of α3(IV)NC1, that leads to the production of aberrant conformers, as demonstrated in the Examples to follow. In example 4, we show that α3(IV)NC1Asp$^9$ expressing cells produce a larger number of conformers than cells expressing α3(IV) NC1Ser9. Furthermore α3(IV)NC1Asp9 cells expresses a 27-kDa conformer that reacts more strongly with Mab3, as well as Goodpasture patient autoantibodies, than the 27-kDa conformer produced by α3(IV)NC1Ser9 expressing cells. It is most preferred to identify compounds that abolish these differences in conformer production between ct3(IV) NC1Asp9 and α3(IV)NC1Ser9, because this will indicate that the compound inhibits the production of an aberrant 27-kDa conformer from α3(1V)NC1Asp9, while maintaining appropriate conformer production for α3(IV)NC1Ser9.

In a further preferred embodiment, identifying compounds for treating an autoimmune disorder further comprises identifying compounds that reduce oligomerization of the second target protein. While not being limited by a specific mechanism, the inventor proposes that the ideal drug candidate for treating autoimmune disorders would inhibit the kinase and chaperoning activity of GPBP, but would not inhibit its chaperone (ie: aggregate-disrupting) activity, in order to minimize the possibility that inhibition of GPBP activity would lead to increased random aggregate formation. Even more preferably, the ideal drug candidate would, in fact, enhance the chaperone activity of GPBP, to minimize secondary effects derived from undesirable aggregation of conformers.

Both in vitro assays and assays utilizing cultured cells can be used for identifying compounds that reduce oligomerization of the second target protein, although in vitro methods are preferred. One embodiment of an in vitro assay comprises:

i) incubating in vitro the second target protein, GPBP, and a redox system in the presence or absence of one or more test compounds, under conditions to promote GPBP-induced-oligomerization of the second target protein in the absence of the one or more test compounds; and ii) identifying test compounds that reduce GPBP-induced oligomerization of the second target protein relative to GPBP induced oligomerization of the second target protein in the absence of the one or more test compounds.

In a preferred embodiment, the second target protein is an α3(IV)NC1 domain polypeptide. Any appropriate redox system can be used, such as DTT/Mn$^{2+}$, (exemplified in Material and Methods of Example 5 below), or with GSH/GSSG (glutathione reduced and oxidized respectively) at 1.0 mM/0.2 mM at pH 8.0 in a similar buffer.

One of skill in the art will be able to determine appropriate conditions for promoting GPBP-induced oligomerization of the second target protein, and thus the method is not limited to specific details of the conditions. A non-limiting example of such conditions is provided in Example 5 below.

Detection of oligomers, and the effect of test compounds thereon, is preferably carried out by Western blotting of a non-reducing SDS-PAGE gel of the isolated recombinant α3 type IV collagen NC1 domain polypeptides after incubation, and probing with antibodies that recognize the α3 type IV collagen NC1 domain polypeptides. Preferably, immunodetection is carried out using, in parallel, an antibody that detects a native conformation of α3 type IV collagen NC1 domain polypeptide (including but not limited to Mab3 disclosed herein), and an antibody that detects all α3 type IV collagen NC1 domain polypeptide conformational isomers (including but not limited to Mab175 disclosed herein).

In a preferred embodiment of the oligomerization assay using cultured cells, cells that express type IV collagen are contacted with the one or more test compounds, and the IFFY extracellular matrix produced by the cells is collagenase digested and analyzed for α3(IV)NC1 oligomers by Western blot analysis as described herein.

As used herein the phrase "reduce/reducing GPBP induced disulfide-mediated oligomerization of the α3 type IV collagen NC1 domain polypeptide" means to decrease the amount of GPBP induced disulfide-mediated oligomers of the α3 type IV collagen NC1 domain polypeptide relative to oligomerization under control conditions. Such "reducing" does not require elimination of oligomer formation, and includes any detectable reduction in oligomer formation, including reduction in only a single species of oligomer in the presence of increased in other species of oligomers.

In another aspect, the present invention provides isolated nucleic acids that encode 3(IV)NC1(Asp9) (SEQ ID NO:66) and α3(IV)NC1(Ala9) (SEQ ID NO:68). The production and use of these mutant α3(IV)NC1 domains are described below. The nucleic acid sequences are useful, for example, for the production of the respective encoded polypeptide.

An used herein, an "isolated nucleic acid sequence" refers to a nucleic acid sequence that is free of gene sequences which naturally flank the nucleic acid in the genomic DNA of the organism from which the nucleic acid is derived (i.e., genetic sequences that are located adjacent to the gene for the isolated nucleic molecule in the genomic DNA of the organism from which the nucleic acid is derived). An "isolated" nucleic acid sequence according to the present invention may, however, be linked to other nucleotide sequences that do not normally flank the recited sequence, such as a heterologous promoter sequence. It is not necessary for the isolated nucleic acid sequence to be free of other cellular material to be considered "isolated", as a nucleic acid sequence according to the invention may be part of an expression vector that is used to transfect host cells In another aspect, the present invention provides recombinant expression vectors comprising nucleic acid sequences that encode α3 NC1(Asp9) (SEQ ID NO:66) or α3NC1(Ala9) (SEQ ID NO:68). In one embodiment, the vectors comprise nucleic acid sequences consisting of the sequences shown in SEQ ID NO:65 or SEQ ID NO:67.

"Recombinant expression vector" includes vectors that operatively link a nucleic acid coding region or gene to any promoter capable of effecting expression of the gene product. The promoter sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The construction of expression vectors for use in transfecting prokaryotic cells is also well known in the art, and thus can be accomplished via standard techniques. (See, for example, Sambrook, Fritsch, and Maniatis, in: Molecular Cloning, A Laboratory Manual, Cold Spring Harbor Laboratory Press, 1989; *Gene Transfer and Expression Protocols*, pp. 109–128, ed. E. J. Murray, The Humana Press Inc., Clifton, N.J.), and the Ambion 1998 Catalog (Ambion, Austin, Tex.), The expression vector must be replicable in the host organism either as an episome or by integration into host chromosomal DNA. In a preferred embodiment, the expression vector comprises a plasmid. However, the invention is intended to include other expression vectors that serve equivalent functions, such as viral vectors.

The expression vector may encode additional sequences that are operably linked to the nucleic acid encoding that encode α3(IV)NC1(Asp9) (SEQ ID NO:66) and α3(IV)NC1(Ala9) SEQ ID NO:68). Such additional sequences can encode, for example, amino acid sequences useful for promoting purification of the protein, such as epitope tags and transport signals. Examples of such epitope tags include, but are not limited to FLAG (Sigma Chemical, St. Louis, Mo.), myc (9E10) (Invitrogen, Carlsbad, Calif.), 6-His (Invitrogen; Novagen, Madison, Wis.), and HA (Boehringer Manheim Biochemicals). Examples of such transport signals include, but are not limited to, export signals, secretory signals, nuclear localization signals, and plasma membrane localization signals. Other examples of additional sequences include, but are not limited to, polyadenylation signals to effect proper polyadenylation of the transcript, and termination signals.

In a further aspect, the present invention provides host cells that have been transfected with the recombinant expression vectors disclosed herein, wherein the host cells can be either prokaryotic or eukaryotic. The cells can be transiently or stably transfected. Such transfection of expression vectors into prokaryotic and eukaryotic cells can be accomplished via any technique known in the art, including but not limited to standard bacterial transformations, calcium phosphate co-precipitation, electroporation, or liposome mediated-, DEAE dextran mediated-, polycationic mediated-, or viral mediated transfection. (See, for example, *Molecular Cloning: A Laboratory Manual* (Sambrook, et al., 1989, Cold Spring Harbor Laboratory Press; *Culture of Animal Cells: A Manual of Basic Technique*, 2nd Ed. (R. I. Freshney. 1987. Liss, Inc. New York, NY), In a still further aspect, the present invention provides isolated polypeptides selected from the group consisting of α3(IV)NC1Asp9 (SEQ ID NO:66) and α3(IV)NC1Ala9 (SEQ ID NO:68). These polypeptides represent mutant α3(IV)NC1, which have been substitute at the Ser9 residue to mimic an always phosphorylated position 9 (Asp9), or an always un-phosphorylated position 9 (Ala9). As described herein, such α3(IV)NC1 mimics can be used, for example, in carrying out the drug discovery assays of the invention, as described above.

As used herein, "α3(IV)NC1Asp9" and "α3(IV)NC1Ala9" include all conformational isomers, as well as oligomers thereof.

The protein may comprise additional sequences useful for promoting purification of the protein, such as epitope tags and transport signals. Examples of such epitope tags include, but are not limited to FLAG (Sigma Chemical, St. Louis, Mo.), myc (9E10) (Invitrogen, Carlsbad, Calif.), 6-His (Invitrogen; Novagen, Madison, Wis.), and HA (Boehringer Manheim Biochericals). Examples of such transport signals include, but are not limited to, export signals, secretory signals, nuclear localization signals, and plasma membrane localization signals.

The experiments described below disclose the isolation of type IV collagen α3 NC1 domain conformational isomers ("conformers"). Thus, in a further embodiment, the present invention provides an isolated type IV collagen α3 NC1 domain conformational isomer, wherein the isolated conformational isomer has an amino acid sequence identical to that of wild type α3 type IV collagen NC1 domain (SEQ ID NO:69), wherein the conformational isomer is stabilized by disulfide bonds, wherein the isolated conformational isomer has a molecular weight in a non-reducing sodium dodecyl sulfate gel selected from the group consisting of 22 kD, 23, kD, 25 kD, 27 kD, and 28 kD, and wherein the conformational isomer has a molecular weight of 29 kDa in a reducing sodium dodecyl sulfate gel.

Isolation of the conformers can be accomplished by separation of the conformers on a non-reducing SDS-PAGE gel, cutting out of the relevant bands from the gel, and isolating the conformer away from the gel components. Alternatively, such conformers can be isolated by HPLC methods, such as those described in Example 4, below.

The invention further comprises an isolated, aberrant conformational isomer of α3(IV)NC1Asp9, wherein the isomer has the amino acid sequence of SEQ ID NO:66, wherein the conformational isomer is stabilized by disulfide bonds, wherein the isolated conformational isomer has a molecular weight in a non-reducing sodium dodecyl sulfate gel selected from the group consisting of 25 kD and 27 kD, and wherein the conformational isomer has a molecular weight of 29 kDa in a reducing sodium dodecyl sulfate gel.

As used herein, the term "isolated" means that the conformer is separated from its cellular environment, and purified away from any gel matrix, such as polyacrylamide. Such "isolated" conformers are substantially separated from other conformers, such that a particular "isolated conformer" constitutes at least 70% of the type IV collagen α3 NC1 domain polypeptide present in the isolated sample, more preferably 80%, even more preferably 90%, and even more preferably more than 95%. Such "isolated" conformers can be suspended in any appropriate buffer or pharmaceutical composition, and are useful, for example, for preparing antibodies to specific conformers, and for use in the drug discovery assays of the invention.

The present invention may be better understood with reference to the accompanying examples that are intended for purposes of illustration only and should not be construed to limit the scope of the invention, as defined by the claims appended hereto.

EXAMPLE 1

Characterization of GPBP

Here we report the cloning and characterization of a novel type of serine/threonine kinase that specifically binds to and phosphorylates the unique N-terminal region of the human GP antigen.

Materials and Methods

Synthetic polymers-Peptides. GPpep1, KGKRGDSGS-PATWTIRGFVFT (SEQ ID NO:26), representing residues 3–23 of the human GP antigen and GPpep1Ala⁹, KGKRGDAGSPATWTIRGFVFT (SEQ ID NO:27), a mutant Ser⁹ to Ala⁹ thereof, were synthesized by MedProbe and CHIRON. FLAG peptide, was from Sigma.

Oligonucleotides. The following as well as several other GPBP-specific oligonucleotides were synthesized by Genosys and GIBCO BRL:

ON-GPBP-54m: TCGAATTCACCATGGCCCCACTAGC-CGACTACAAGGACGACGATG ACAAG (SEQ ID NO: 28).

ON-GPBP-55c: CCGAGCCCGACGAGTTCCAGCTCT-GATTATCCGACATCTTGTCATCG TCG (SEQ ID NO:29).

ON—HNC-B-N-14m: CGGGATCCGCTAGCTAAGC-CAGGCAAGGATGG (SEQ ID NO:30).

ON-HNC-B-N-16c: CGGGATCCATGCATAAATAG-CAGTTCTGCTGT (SEQ ID NO:31).

Isolation and characterization of cDNA clones encoding human GPBP-Several human λ-gt11 cDNA expression libraries (eye, fetal and adult lung, kidney and HeLa S3, from CLONTECH) were probed for cDNAs encoding proteins interacting with GPpep1. Nitrocellulose filters (Millipore) prepared following standard immunoscreening procedures were blocked and incubated with 1–10 nmoles per ml of GPpep1 at 37° C. Specifically bound GPpep1 was detected using M3/1A monoclonal antibodies (7). A single clone was identified in the HeLa-derived library (HeLa1). Specificity of fusion protein binding was confirmed by similar binding to recombinant eukaryotic human GP antigen. The EcoRI cDNA insert of HeLa1 (0.5-kb) was used to further screen the same library and to isolate overlapping cDNAs. The largest cDNA (2.4-kb) containing the entire cDNA of HeLa1 (n4') was fully sequenced.

Northern and Southern blots-Pre-made Northern and Southern blots (CLONTECH) were probed with HeLa1 cDNA following manufacturer instructions.

Plasmid construction, expression and purification of recombinant proteins-GPBP-derived material. The original λ-gt11 HeLa1 clone was expressed as a lysogen in E. Coli Y1089 (8). The corresponding β-galactosidase-derived fusion protein containing the N-terminal 150 residues of GPBP was purified from the cell lysate using an APTG-agarose column (Boehringer). The EcoRI 2.4-kb fragment of n4' was subcloned in Bluescribe M13+vector (Stratagene) (BS-n4'), amplified and used for subsequent cloning. A DNA fragment containing (from 5' to 3'), an EcoRI restriction site, a standard Kozak consensus for translation initiation, a region coding for a tag peptide sequence (FLAG, DYKD-DDDK (SEQ ID NO:32)), and the sequence coding for the first eleven residues of GPBP including the predicted Meti and a Ban H restriction site, was obtained by hybridizing ON-GPBP-54m and ON-GPBP-55c, and extending with modified $T_7$ DNA polymerase (Amersham). The resulting DNA product was digested with EcoRI and BanII, and ligated with the BanII/EcoRI cDNA fragment of BS-n4' in the EcoRI site of pHIL-D2 (Invitrogen) to produce pHIL-FLAG-n4'.

This plasmid was used to obtain Mut$^s$ transformants of the GS115 strain of Pichia pastoris and to express FLAG-tagged recombinant GPBP (rGPBP) either by conventional liquid culture or by fermentation procedures (Pichia Expression Kit, Invitrogen). The cell lysates were loaded onto an anti-FLAG M2 column (Sigma), the unbound material washed out with Tris buffered saline (TBS, 50 mM Tris-HCl, pH 7.4, 150 mM NaCl) or salt-supplemented TBS (up to 2M NaCl), and the recombinant material eluted with FLAG peptide.

For expression in cultured human kidney-derived 293 cells (ATCC 1573-CRL), the 2.4- or 2.0-kb EcoRI cDNA insert of either BS-n4' or pHIL-FLAG-n4' was subcloned in pcDNA3 (Invitrogen) to produce pc-n4' and pc-FLAG-n4' respectively. When used for transient expression, 18 hours after transfection the cells were lysed with 3.5–4 μl/cm² of chilled lysis buffer (1% Nonidet P40 or Triton-X100, 5 mM EDTA and 1 mM PMSF in TBS) with or without 0.1% SDS, depending on whether the lysate was to be used for SDS-PAGE or FLAG-purification, respectively. For FLAG purification, the lysate of four to six 175 cm² culture dishes was diluted up to 50 ml with lysis buffer and purified as above.

For stable expression, the cells were similarly transfected with pc-n4' and selected for three weeks with 800 µg/ml of G418. For bacterial recombinant expression, the 2.0-kb EcoRI cDNA fragment of pHIL-FLAG-n4' was cloned in-frame downstream of the glutathione S-transferase (GST)-encoding cDNA of pGEX-5x-1 (Pharmacia). The resulting construct was used to express GST-GPBP fusion protein in DH5a cells (9).

GP antigen-derived material. Human recombinant GP antigen (rGP) was produced in 293 cells using the pRc/CMV-BM40 expression vector containing the α3-specific cDNA between ON—HNC-B-N-14m and ON-HNC-B-N-16c. The expression vector is a pRc/CMV (Invitrogen)-derived vector provided by Billy G. Hudson (Kansas University Medical Center) that contains cDNA encoding an initiation Met, a BM40 signal peptide followed by a tag peptide sequence (FLAG), and a polylinker cloning site. To obtain α3-specific cDNA, a polymerase chain reaction was performed using the oligonucleotides above and a plasmid containing the previously reported α3(IV) cDNA sequence (3) as template (clone C2). For stable expression of rGP, 293 cells were transfected with the resulting construct (fα3VLC) and selected with 400 µg/ml of G418. The harvested rGP was purified using an anti-FLAG M2 column.

All the constructs were verified by restriction mapping and nucleotide sequencing.

Cell culture and DNA transfection-Human 293 cells were grown in Dulbecco's modified Eagle's medium (DMEM) supplemented with 10% fetal calf serum. Transfections were performed using the calcium phosphate precipitation method of the Profection Mammnalian Transfection Systems (Promega). Stably transfected cells were selected by their resistance to G418. Foci of surviving cells were isolated, cloned and amplified.

Antibody production-Polyclonal antibodies against the N-terminal region of GPBP. Cells expressing HeLa1 λ-gt11 as a lysogen were lysed by sonication in the presence of Laemmli sample buffer and subjected to electrophoresis in a 7.5% acrylamide preparative gel. The get was stained with Coomassie blue and the band containing the fusion protein of interest excised and used for rabbit immunization (10). The anti-serum was tested for reactivity using APTG-affinity purified antigen. To obtain affinity-purified antibodies, the anti-serum was diluted 1:5 with TBS and loaded onto a Sepharose 4B column containing covalently bound affinity purified antigen. The bound material was eluted and, unless otherwise indicated, used in the immunochemical studies.

Monoclonal antibodies against GPBP. Monoclonal antibodies were produced essentially as previously reported (7) using GST-GPBP. The supernatants of individual clones were analyzed for antibodies against rGPBP.

In vitro phosphorylation assays-About 200 ng of rGPBP were incubated overnight at 30° C. in 25 mM P-glycerolphosphate (pH 7.0), 0.5 mM EDTA, 0.5 mM EGTA, 8 mM MgCl$_2$, 5 mM MnCl$_2$, 1 mM DTT and 0.132 µM γ-$^{32}$P-ATP, in the presence or absence of 0.5–1 µg of protein substrates or 10 nmoles of synthetic peptides, in a total volume of 50 µl.

In vivo phosphorylation assays-Individual wells of a 24-well dish were seeded with normal or with stably pc-n4' transfected 293 cells. When the cells were grown to the desired density, a number of wells of the normal 293 cells were transfected with pc-FLAG-n4'. After 12 hours, the culture medium was removed, 20 µCi/well of H$_3$$^{32}$PO4 in 100 µl of phosphate-free DMEM added, and incubation continued for 4 hours. The cells were lysed with 300 µl/well of TBS containing 1% Triton X-100, 2 mM EDTA, 1 mM PMSF, 50 mM NaF and 0.2 mM vanadate, and extracted with specific antibodies and Protein A-Sepharose. When anti-GPBP serum was used, the lysate was pre-cleared using pre-immune serum and Protein A-Sepharose.

In vitro dephosphorylation of rGPBP-About 1 µg of rGPBP was dephosphorylated in 100 µl of 10 mM Tris-acetate (pH 7.5), 10 mM magnesium acetate and 50 mM potassium acetate with 0.85 U of calf intestine alkaline phosphatase (Pharmacia) for 30 nun at 30° C.

Renaturation assays-In-blot renaturation assays were performed using 1–5 µg of rGPBP as previously described (11).

Nucleotide sequence analysis—cDNA sequence analyses were performed by the dideoxy chain termination method using [α]$^{35}$S-dATP, modified T$_7$ DNA polymerase (Amersham) and universal or GPBP-specific primers (8–10).

$^{32}$P-Phosphoamino acid analysis-Immunopurified rGPBP or HPLC gel-filtration fractions thereof containing the material of interest were phosphorylated, hydrolyzed and analyzed in one dimensional (4) or two dimensional thin layer chromatography (12). When performing two dimensional analysis, the buffer for the first dimension was formic acid:acetic acid:water (1:3.1:35.9) (pH 1.9) and the buffer for the second dimension was acetic acid:pyridine:water (2:0.2:37.8) (pH 3.5). Amino acids were revealed with ninhydrin, and $^{32}$P-phosphoamino acids by autoradiography.

Physical methods and immunochemical techniques-SDS-PAGE and Western-blotting were performed as in (4). Immunohistochemistry studies were done on human multi-tissue control slides (Biomeda, Biogenex) using the ABC peroxidase method (13).

Computer analysis-Homology searches were carried out against the GenBank and SwissProt databases with the BLAST 2.0 (14) at the NCB1 server, and against the TIGR Human Gene Index database for expressed sequence tags, using the Institute for Genomic Research server. The search for functional patterns and profiles was performed against the PROSITE database using the ProfileScan program at the Swiss Institute of Bioinformatics (15). Prediction of coiled-coil structures was done at the Swiss Institute for Experimental Cancer Research using the program Coils (16) with both 21 and 28 residue windows.

Results

Molecular cloning of GPBP-To search for proteins specifically interacting with the divergent N-terminal region of the human GP antigen, a 21-residue peptide (GPpep1; SEQ ID NO:26)), encompassing this region and flanking sequences, and specific monoclonal antibodies against it were combined to screen several human cDNA expression libraries. More than 5×10$^6$ phages were screened to identify a single HeLa-derived recombinant encoding a fusion protein specifically interacting with GPpep1 without disturbing antibody binding.

Using the cDNA insert of the original clone (HeLa1), we isolated a 2.4-kb cDNA (n4') that contains 408-bp of 5'-untranslated sequence, an open reading frame (ORF) of 1872-bp encoding 624 residues, and 109-bp of 3'-untranslated sequence (FIG. 1) (SEQ ID NO:1–2). Other structural features are of interest. First, the predicted polypeptide (hereinafter referred to as GPBP) has a large number of phosphorylatable (17.9%) and acidic (16%) residues unequally distributed along the sequence. Serine, which is the most abundant residue (9.3%), shows preference for two short regions of the protein, where it comprises nearly 40% of the amino acids, compared to an average of less than 7% throughout the rest of the polypeptide chain. It is also noteworthy that the more N-terminal, serine-rich region consists mainly of a Ser-Xaa-Yaa repeat. Acidic residues are preferentially located at the N-terminal three-quarters of the polypeptide, with nearly 18% of the residues being acidic. These residues represent only 9% in the most C-terminal quarter of the polypeptide, resulting in a polypeptide chain with two electrically opposite domains. At the N-terminus, the polypeptide contains a pleckstrin homology (PH) domain, which has been implicated in the recruitment of many signaling proteins to the cell membrane where they exert their biological activities (17). Finally, a bipartite nuclear targeting sequence (18) exists as an integral part of a heptad repeat region that meets all the structural requirements to form a coiled-coil (16).

Protein data bank searches revealed homologies almost exclusively within the approximately 100 residues at the N-terminal region harboring the PH domain. The PH domain of the oxysterol-binding protein is the most similar, with an overall identity of 33.5% and a similarity of 65.2% with GPBP. In addition, the *Caenorhabditis elegans* cosmid F25H2 (accession number Q93569) contains a hypothetical ORF that displays an overall identity of 26.5% and a similarity of 61% throughout the entire protein sequence, indicating that similar proteins are present in lower invertebrates. Several human expressed sequence tags (accession numbers AA287878, AA287561, AA307431, AA331618, AA040134, AA158618, AA040087, AA122226, AA158617, AA121104, AA412432, AA412433, AA282679 and N27578) possess a high degree of nucleotide identity (above 98%) with the corresponding stretches of the GPBP cDNA, suggesting that they represent human GPBP. Interestingly, the AA287878 EST shows a gap of 67 nucleotides within the sequence a corresponding to the GPBP 5'-untranslated region, suggesting that the GPBP pre-mRNA is alternatively spliced in human tissues (not shown).

The distribution and expression of the GPBP gene in human tissues was first assessed by Northern blot analysis (FIG. 2, panel A). The gene is expressed as two major mRNAs species between 4.4-kb and 7.5-kb in length and other minor species of shorter lengths. The structural relationship between these multiple mRNA species is not known and their relative expression varies between tissues. The highest expression level is seen in striated muscle (skeletal and heart), while lung and liver show the lowest expression levels.

Southern blot studies analysis of genomic DNA from different species indicated that homologous genes exist throughout phylogeny (FIG. 2, panel B). Consistent with the human origin of the probe, the hybridization intensities decreased in a progressive fashion as the origin of the genomic DNA moves away from humans in evolution.

Experimental determination of the translation start site— To experimentally confirm the predicted ORF, eukaryotic expression vectors containing either the 2.4-kb of cDNA of n4', or only the predicted ORF tagged with a FLAG sequence (FIG. 3A), were used for transient expression assays in 293 cells. The corresponding extracts were analyzed by immunoblot using GPBP- or FLAG-specific antibodies. The GPBP-specific antibodies bind to a similar major polypeptide in both transfected cells, but only the polypeptide produced by the engineered construct expressed the FLAG sequence (FIG. 3B). This located the translation start site of the n4' cDNA at the predicted Met and confirmed the proposed primary structure. Furthermore, the recombinant polypeptides displayed a molecular mass higher than expected (80 versus 71 kDa) suggesting that GPBP undergoes post-translational modifications.

Figure 4:
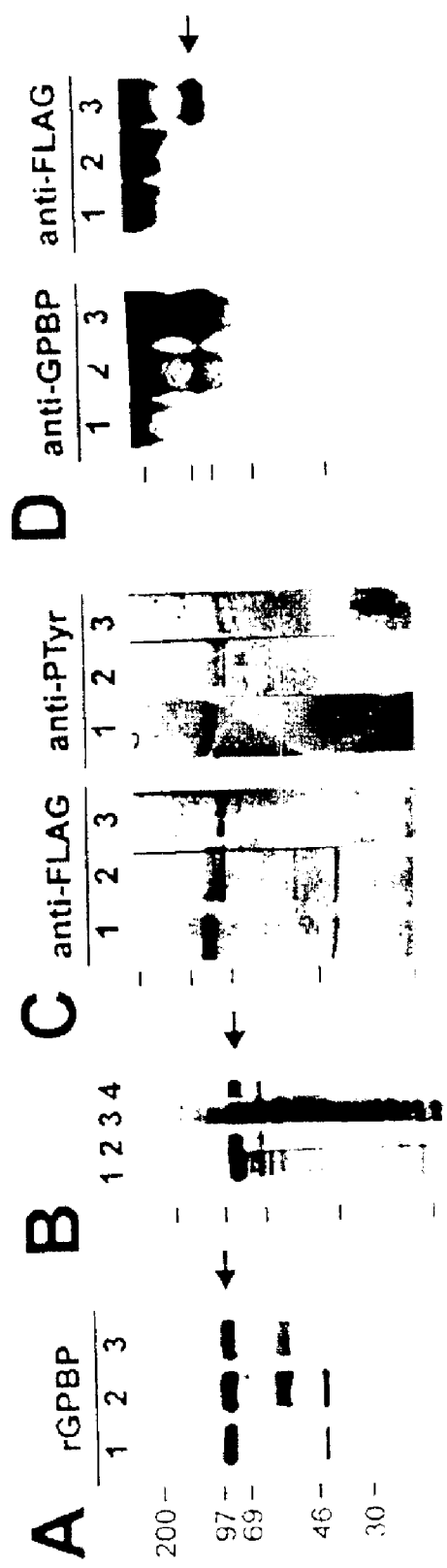

Expression and characterization of yeast rGPBP-Yeast expression and FLAG-based affinity-purification were combined to produce rGPBP (FIG. 4A). A major polypeptide of 89 kDa, along with multiple related products displaying lower $M_r$, were obtained. The recombinant material was recognized by both anti-FLAG and GPBP-specific antibodies, guaranteeing the fidelity of the expression system. Again, however, the $M_r$ displayed by the major product was notably higher than predicted and even higher than the $M_r$ of the 293 cell-derived recombinant material, supporting the idea that GPBP undergoes important and differential post-translational modifications. Since phosphorylatable residues are abundant in the polypeptide chain, we investigated the existence of phosphoamino acids in the recombinant materials. By using monoclonal or polyclonal (not shown) antibodies against phosphoserine (Pser), phosphothreonine (PThr) and phosphotyrosine (PNyr), we identified the presence of all three phosphoresidues either in yeast RGPBP (FIG. 4B) or in 293 cell-derived material (not shown). The specificity of the antibodies was further assessed by partially inhibiting their binding by the addition of 5–10 mM of the corresponding phosphoamino acid (not shown). This suggests that the phosphoresidue content varies depending upon the cell expression system, and that the $M_r$ differences are mainly due to phosphorylation. Dephosphorylated yeast-derived material consistently displayed similar $M_r$ to the material derived from 293 cells, and phosphoamino acid content correlates with SDS-PAGE mobilities (FIG. 4C). As an in vivo measurement, the phosphorylation of rGPBP in the 293 cells was assessed (FIG. 4D). Control cells (lanes 1) and cells expressing rGPBP in a stable (lanes 2) or transient (lanes 3) mode were cultured in the presence of $H_3{}^{32}PO_4$. Immunoprecipitated recombinant material contained $^{32}P$, indicating that phosphorylation of GPBP occurred in vivo and therefore is likely to be a physiological process.

Figure 5:
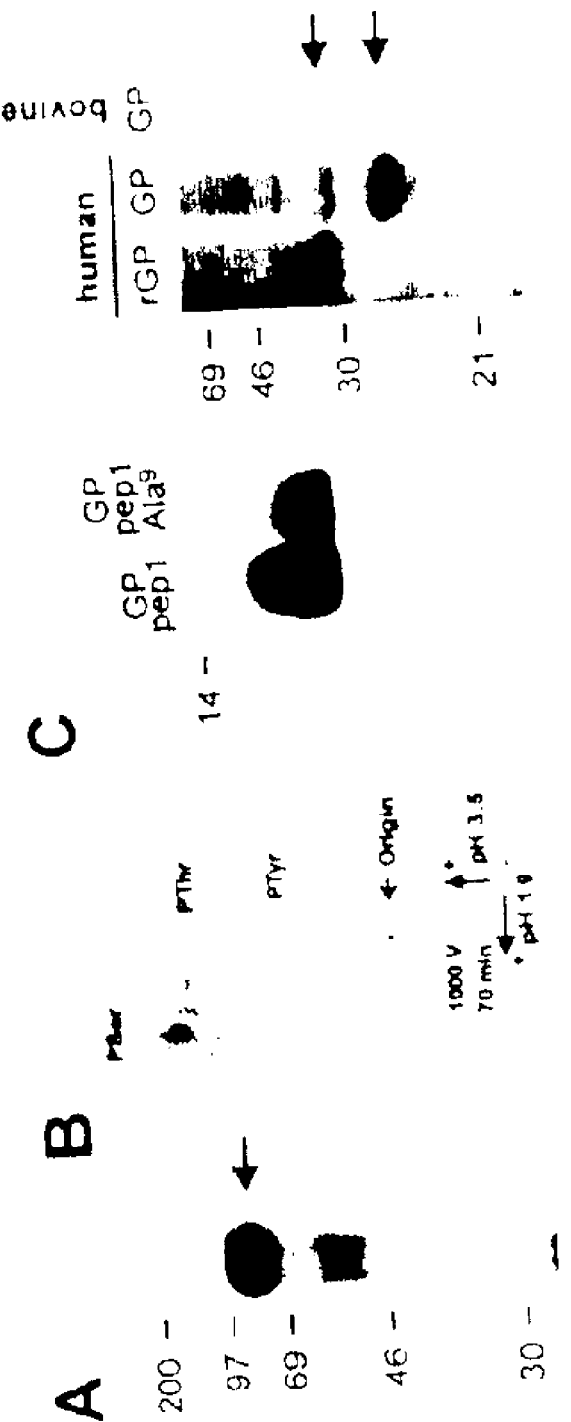

The rGPBP is a serine/threonine kinase that phosphorylates the N-terminal region of the human GP antigen-Although GPBP does not contain the conserved structural regions required to define the classic catalytic domain for a protein kinase, the recent identification and characterization of novel non-conventional protein kinases (19–27) encouraged the investigation of its phosphorylating activity. Addition of [$\gamma^{32}P$]ATP to rGPBP (either from yeast or 293 cells (not shown)) in the presence of $Mn^{2+}$ and $Mg^{2+}$ resulted in the incorporation of $^{32}P$ as PSer and PThr in the major and related products recognized by both anti-FLAG and specific antibodies (FIGS. 5A and B), indicating that the affinity-purified material contains a Ser/Thr protein kinase. To further characterize this activity, GPpep1, GPpep1Ala$^9$ (a GPpep1 mutant with Ser$^9$ replaced by Ala), native and recombinant human GP antigens, and native bovine GP antigen were assayed (FIG. 5C). Affinity-purified rGPBP phosphorylates all human-derived material to a different extent. However, in similar conditions, no appreciable $^{32}P$-incorporation was observed in the bovine-derived substrate. The lower $^{32}P$ incorporation displayed by GPpep1Ala9 when compared with GPpep1, and the lack of phosphorylation of the bovine antigen, indicates that the kinase present in rGPBP discriminates between human and bovine antigens, and that Ser$^9$ is a target for the kinase.

Figure 6:
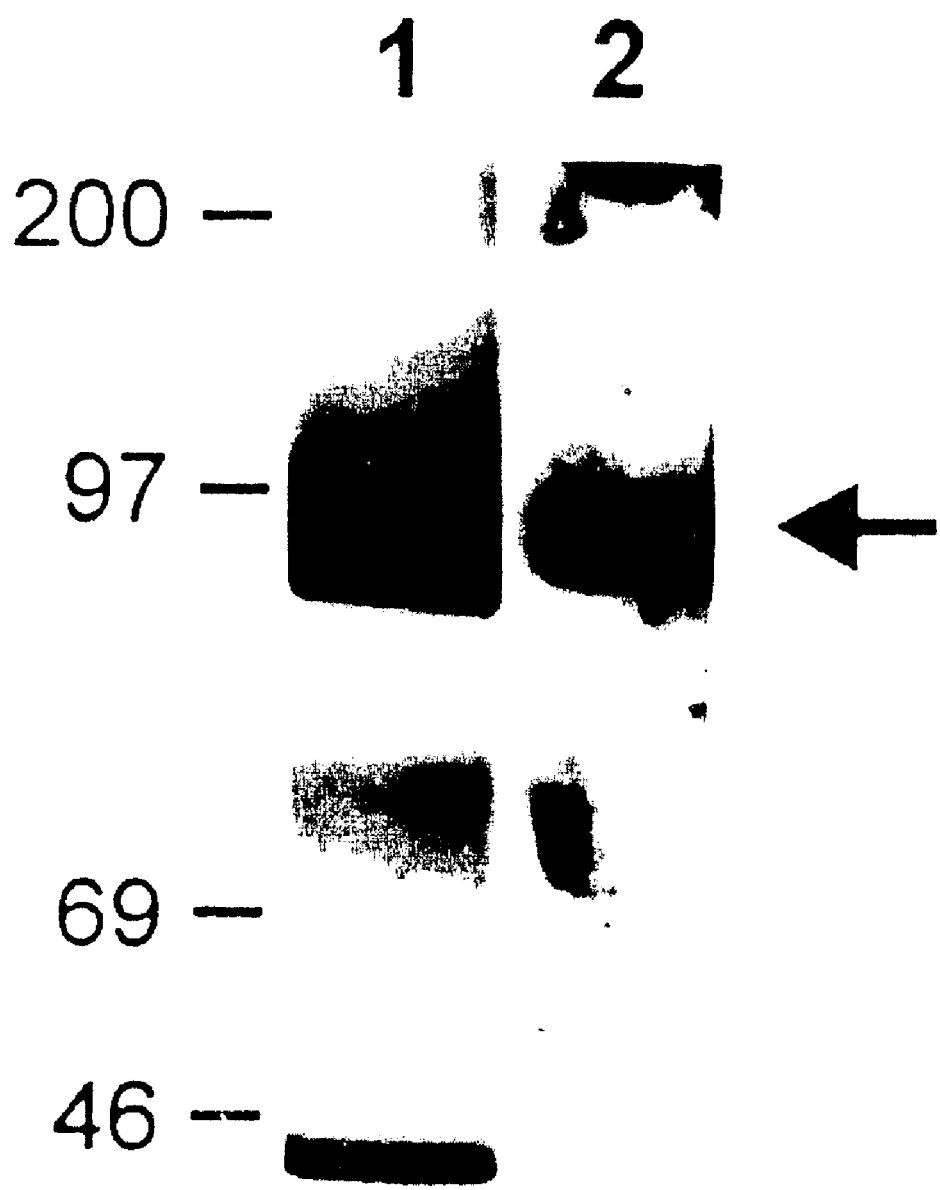

Although the purification system provides high quality material, the presence of contaminants with a protein kinase activity could not be ruled out. The existence of contaminants was also suggested by the presence of a FLAG-containing 40 kDa polypeptide, which displayed no reactivity with specific antibodies nor incorporation of $^{32}P$ in the phosphorylation assays (FIGS. 4A and 5A). To precisely identify the polypeptide harboring the protein kinase activity, we performed in vitro kinase renaturation assays after SDS-PAGE and Western-blotted (FIG. 6). We successfully combined the use of specific antibodies (lane 1) and autoradiographic detection of in situ $^{32}P$ incorporation (lane 2), and identified the 89 kDa rGPBP material as the primary polypeptide harboring the Ser/Thr kinase activity. The lack of $^{32}P$-incorporation in the rGPBP-derived products, as well as in the 40 kDa contaminant, further supports the specificity of the renaturation assays and locates the kinase activity to the 89 kDa polypeptide. Recently, it has been shown that traces of protein kinases intimately associated with a polypeptide can be released from the blot membrane, bind to, and phosphorylate the polypeptide during the labeling step (28). To assess this possibility in our system, we performed renaturation studies using a small piece of membrane containing the 89 kDa polypeptide, either alone or together with membrane pieces representing the different regions of the blot lane. We observed similar $^{32}P$-incorporation at the 89 kDa polypeptide regardless of the co-incubated pieces (not shown), indicating that if there are co-purified protein kinases in our sample they are not phosphorylating the 89 kDa polypeptide in the renaturation assays unless they co-migrate. Co-migration does not appear to be a concern, however, since RGPBP deletion mutants (GPBPΔ26 and R3; see below) displaying different mobilities also have kinase activities and could be similarly in-blot renatured (not shown).

Immunohistochemnical localization of the novel kinase—To investigate GPBP expression in human tissues we performed immunohistochemical studies using specific polyclonal (FIG. 7) or monoclonal antibodies (not shown). Although GPBP is widely expressed in human tissues, it shows tissue and cell-specificity. In kidney, the major expression is found at the tubule epithelial cells and the glomerular mesangial cells and podocytes. At the lung alveolus, the antibodies display a linear pattern suggestive of a basement membrane localization, along with staining of pneumocytes. Liver shows low expression in the parenchyma, but high expression in biliary ducts. Expression in the central nervous system is observed in the white matter, but not in the neurons of the brain. In testis, a high expression in the spermatogonium contrasts with the lack of expression in Sertoli cells. The adrenal gland shows a higher level of expression in cortical cells versus the medullar. In the pancreas, GPBP is preferentially expressed in Langerhans islets versus the exocrine moiety. In prostate, GPBP is expressed in the epithelial cells but not in the stroma (FIG. 7). Other locations with high expression of GPBP are striated muscle, epithelial cells of intestinal tract, and Purkinje cells of the cerebellum (not shown). In general, in tissues where GPBP is highly expressed the staining pattern is mainly diffuse cytosolic. However in certain locations there is, in addition, an important staining reinforcement at the nucleus (spermatogonium), at the plasma membrane (pneumocyte, hepatocyte, prostate epithelial cells, white matter) or at the extracellular matrix (alveolus) (FIG. 7).

Discussion

Our data show that GPBP is a novel, non-conventional serine/threonine kinase. We also present evidence that GPBP discriminates between human and bovine GP antigens, and targets the phosphorylatable region of human GP antigen in vitro. Several lines of evidence indicate that the 89 kDa polypeptide is the only kinase in the affinity purified rGPBP. First, we found no differences in auto- or trans-phosphorylation among rGPBP samples purified in the presence of 150 mM, 0.5 M, 1 M or 2 M salt (not shown), suggesting that rGPBP does not carry intimately bound kinases. Second, there is no FLAG-containing, yeast-derived kinase in our samples, since material purified using GPBP-specific antibodies shows no differences in phosphorylation (not shown). Third, a deletion mutant (GPBP26; see below) displays reduced auto- and trans-phosphorylation activities (not shown), demonstrating that the 89 kD polypeptide is the only portion of the rGPBP with the ability to carry out phosphate transfer.

Although GPBP is not homologous to other non-conventional kinases, they share some structural features including an N-terminal α-helix coiled-coil (26, 27), serine-rich motifs (24), high phosphoamino acids content (27), bipartite nuclear localization signal (27), and the absence of a typical nucleotide or ATP binding motif (24, 27).

Immunohistochemistry studies show that GPBP is a cytosolic polypeptide also found in the nucleus, associated with the plasma membrane and likely at the extracellular matrix associated with the basement membrane, indicating that it contains the structural requirements to reach all these destinations. The nuclear localization signal and the PH domain confer to it the potential to reach the nucleus and the cell membrane, respectively (17, 29, 30). Although GPBP does not contain the structural requirements to be exported, the 5'-end untranslated region of its mRNA includes an upstream ORF of 130 residues with an in-frame stop codon at the beginning (FIG. 1). A mRNA editing process inserting a single base pair (U) would generate an operative in-frame start site and an ORF of 754-residues containing an export signal immediately downstream of the edited Met (not shown). Polyclonal antibodies against a synthetic peptide representing part of this hypothetical extra-sequence (PRSARCQARRRRGGRTSS (SEQ ID NO:33)) display a linear vascular reactivity in human tissues suggestive of an extracellular basement membrane localization (data not shown).

Alternatively, a splicing phenomenon could generate transcripts with additional unidentified exon(s) that would provide the structural requirements for exportation. The multiple cellular localization, the high content in PTyr, and the lack of tyrosine kinase activity in vitro, suggest that GPBP is itself the target of specific tyrosine kinase(s) and therefore likely involved in specific signaling cascade(s).

As discussed above, specific serine phosphorylation, as well as pre-mRNA alternative splicing, are associated with the biology of several autoantigens, including the GP antigen, acetylcholine receptor and myelin basic protein (MBP) (4). The latter is suspected to be the major antigen in multiple sclerosis (MS), another exclusively human autoimmune disease in which the immune system targets the white matter of the central nervous system. GP disease and MS are human disorders that display a strong association with the same HLA class II haplotype (HLA DRB1*1501)(32, 33). This, along with the recent report of death by GP disease of a MS patient carrying this HLA specificity (34), supports the existence of common pathogenic events in these human disorders.

Phosphorylation of specific serines has been shown to change intracellular proteolysis (35–40). Conceivably, alterations in protein phosphorylation can affect processing and peptide presentation, and thus mediate autoimmunity. GP antigen-derived peptide presentation by the HLA-DR15 depends more on processing than on preferences of relatively indiscriminate DR15 molecules (41), suggesting that if processing is influenced by abnormal phosphorylation, the resulting peptides would likely be presented by this HLA. Our more recent data indicate that in both the GP and MBP systems, the production of alternative splicing products serves to regulate the phosphorylation of specific and structurally homologous PKA sites, suggesting that this or a closely related kinase is the in vivo phosphorylating enzyme. Alterations in the degree of antigen phosphorylation, caused either by an imbalance in alternative products, or by the action of an intruding kinase that deregulates phosphorylation of the same motifs, could lead to an autoimmune response in predisposed individuals. RGPBP phosphorylates the human GP antigen at a major PKA phosphorylation site in an apparently unregulated fashion, since the presence of specific alternative products of the GP antigen did not affect phosphorylation of the primary antigen by GPBP (not shown).

Although GPBP is ubiquitously expressed, in certain organs and tissues it shows a preference for cells and tissue structures that are target of common autoimmune responses: the Langerhans cells (type I diabetes); the white matter of the central nervous system (multiple sclerosis); the biliary ducts (primary biliary cirrhosis); the cortical cells of the adrenal gland (Addison disease); striated muscle cells (myasthenia gravis); spennatogonium (male infertility); Purkinje cells of the cerebellum (paraneoplasic cerebellar degeneration syndrome); and intestinal epithelial cells (pernicious anemia, autoimmuune gastritis and enteritis). All the above observations point to this novel kinase as an attractive candidate to be considered when envisioning a model for human autoimmune disease.

REFERENCES FOR THE BACKGROUND AND EXAMPLE 1

1 Saus, J. (1998) *Goodpasture's Syndrome*. Encyclopedia of Immunology, 2nd Ed., Delves, P. J., and Roitt, I. M. Eds., Academic Press Limited, London,UK
2 Leinonen, A., Mariyama, M., Mochizuki, T., Tryggvason, K., and Reeders, S. T. (1994) *J. Biol. Chem.* 269, 26172–26177
3 Quinones, S., Bernal, D., García-Sogo, M., Elena, S. F., and Saus, J. (1992) *J. Biol. Chem.* 267, 19780–19784
4 Revert, F., Penadés J. R., Plana, M., Bernal, D., Johansson, C., Itarte, E., Cervera, J., Wieslander, J., Quinones, S., and Saus, J. (1995) *J. Biol. Chem.* 270, 13254–13261
5 Bernal, D., Quinones, S., and Saus, J. (1993) *J. Biol. Chem.* 268, 12090–12094
6 Feng, L., Xia, Y., and Wilson, C. B. (1994) *J. Biol. Chem.* 269, 2342–2348
7 Penadés, J. R., Bernal, D., Revert, F., Johansson, C., Fresquet, V. J., Cervera, J., Wieslander, J., Quinones, S., and Saus, J. (1995) *Eur. J. Biochem.* 229, 754–760
8 Sambrook, J., Fritsch, E. F., and Maniatis, T. (1989) *Molecular Cloning: A Laboratory Manual*, 2 d Ed., Cold Spring Harbor Laboratory, Cold Spring Harbor, N.Y.
9 Coligan, J. E., Dunn, B. N., Ploegh, H. L., Speicher, D. W., and Winfield, P. T. (1995–97) *Current Protocols in Protein Science*, John Wiley & Sons Eds., New York, N. Y.
10 Ausubel, F. M., Brent, R., Kingston, R. E., Moore, D. D., Deidman, J. G., Smith, J. A., and Struhl, K. (1994–98) *Current Protocols in Molecular Biology*, John Wiley & Sons Eds., New York, N. Y.
11 Ferrel, J. E., and Martin, G. S. (1991) *Methods in Enzymology* 200,430–435
12 Boyle, W. J., van der Geer, P., and Hunter, T. (1991) *Methods in Enzymology* 201, 110–149
13 Hsu, S. M., Raine, L., and Fanger, H. (1981) *J. Histochem. Cytochem.* 29, 577–580
14 Altschul, S. F., Madden, T. L., Schaffer, A. A., Zhang, J., Zhang, Z., Miller, W., and Lipman, D. J. (1997) *Nucleic Acids Res.* 25, 3389–3402
15 Bairoch, A., Bucher, P., and Hofmann, K. (1997) *Nucleic Acids Res.* 25, 217–221
16 Lupas, A. (1996) *Trends Biochem. Sci.* 21, 375–382
17 Lemmon, M. A., Falasca, M., Ferguson, K. M., and Schlessinger, J. (1997) *Trends Cell Biol.* 7, 237–242
18 Boulikas, T. (1993) *Crit. Rev. Eukaryot. Gene Expr.* 3, 193–227
19 Csermely, P., and Kahn, C. R. (1991) *J. Biol. Chem.* 266, 4943–4950
20 Maru, Y., and Witte, O. N.(1991) *Cell* 67, 459–468
21 Beeler, J. F., LaRochelle, W. J., Chedid, M., Tronick, S. R., and Aaronson, S. A. (1994) *Mol. Cell. Biol.* 14, 982–988
22 Csermely, P., Miyata, Y., Schnaider, T., and Yahara, I. (1995) *J. Biol. Chem.* 270, 6381–6388
23 Dikstein, R., Ruppert, S., and Tjian, R. (1996) *Cell* 84, 781–790
24 Eichinger, L., Bomblies, L., Vandekerckhove, J., Schleicher, M., and Gettermans, J. (1996) EMBO J. 15, 5547–5556
25 Côté, G. P., Luo, X., Murphy, M. B., and Egelhoff, T. T.(1997) *J. Biol. Chem.* 272, 6846–6849
26 Ryazanov, A. G., Ward, M. D., Mendola, C. E., Pavur, K. S., Dorovkov, M. V., Wiedmann, M., Erdjument-Bromage, H., Tempst, P., Parmer, T. G., Prostko, C. R., Germino, F. J., and Hait, W. N. (1997) *Proc. Natl. Acad. Sci. USA* 94, 4884–4889
27 Fraser, R. A., Heard, D. J., Adam, S., Lavigne, A. C., Le Douarin, B., Tora, L., Losson, R., Rochette-Egly, C., and Chambon, P. (1998) *J. Biol. Chem.* 273, 16199–16204
28 Langelier, Y., Champoux, L., Hamel, M., Guilbault, C., Lamarche, N., Gaudreau, P., and Massie, B.(1998)*J. Biol. Chem.* 273, 1435–1443
29 Lemmon, M. A., and Ferguson, K. M. (1998) *Curr. Top. Microbiol. Immunol.* 228, 39–74
30 Rebecchi, M. J., and Scarlata, S. (1998) *Annu. Rev. Biophys. Biomol. Struct.* 27, 503–528
31 Roitt, I. (1994) *Autoimmune diseases in Essential Immunology*, 383–439, 8$^{th}$ Ed., Blackwell Scientific, Oxford, UK
32 Erlich, H., and Apple, R. (1998) MHC *disease associations. Encyclopedia of Immunology*, 2nd Ed., Delves, P. J., and Roitt, I. M. Eds., Academic Press Limited, London, UK
33 Phelps, R. G., Turner, A. N., and Rees, A. J.(1996)*J. Biol. Chem.* 271, 18549–18553
34 Henderson, R. D., Saltissi, D., and Pender, M. P.(1998) *Acta Neurol. Scand.* 98, 134–135
35 Litersky, J. M., and Johnson, G. V. W. (1992) *J. Biol. Chem.* 267, 1563–1568.
36 Brown, K., Gerstberger, S., Carlson, L., Franzoso, G., and Siebenlist, U. (1995) *Science* 267, 485–1488
37 Chen, Z. J., Parent, L., and Maniatis, T. (1996) *Cell* 84, 853–862
38 Aberle, H., Bauer, A., Stappert, J., Kispert, A., and Kemler, R. (1997) *EMBO J.* 16, 3797–3804
39 Regnier, C. H., Song, H. Y., Gao, X., Goeddel, D. V., Cao, Z., and Rothe, M. (1997) *Cell* 90, 373–383
40 Vlach, J., Hennecke, S., and Amati, B. (1997) *EMBO J.* 16, 5334–5344
41 Phelps, R. G., Jones, V. L., Coughlan, M., Turner, A. N., and Rees, A. J. (1998) *J. Biol. Chem.* 273, 11440–11447

EXAMPLE 2

GPBP Alternative Splicing

Here we report the existence of two isoforms of GPBP that are generated by alternative splicing of a 78-base pair (bp) long exon that encodes a 26-residue serine-rich motif. Both isoforms, GPBP and GPBPΔ26, exist as high molecular aggregates that result from polypeptide self-aggregation. The presence of the 26-residue peptide in the polypeptide chain results in a molecular species that self-interacts more efficiently and forms aggregates with higher specific activity. Finally, we present evidences supporting the observation that GPBP is implicated in human autoimmune pathogenesis.

Material and Methods.

Synthetic Polymers:

Peptides. GPpep1, KGKRGDSGSPATWTTRGFVFT (SEQ ID NO:26), is described in Example 1. GPBPpep1, PYSRSSSMSSIDLVSASDDVHRFSSQ (SEQ ID NO:14), representing residues 371–396 of GPBP was synthesized by Genosys.

Oligonucleotides. The following oligonucleotides were synthesized by Life Technologies, Inc., 5' to 3': ON-GPBP-11m, G CGG GAC TCA GCG GCC GGA MTT TCT (SEQ ID NO:34); ON-GPBP-15m, AC AGC TGG CAG AAG AGA C (SEQ ID NO:35); ON-GPBP-20c, C ATG GGT AGC T=T TAA AG (SEQ ID NO; 36); ON-GPBP-22m, TA GAA GAA CAG TCA CAG AGT GAA AAG G (SEQ ID NO;37); ON-GPBP-53c, GAATTC GAA CAA AAT AGG CTT TC (SEQ ID NO:38); ON-GPBP-56m, CCC TAT AGT CGC TCT TC (SEQ ID NO:39); ON-GPBP-57c, CTG GGA GCT GAA TCT GT (SEQ ID NO:40); ON-GPBP-62c, GTG GTT CTG CAC CAT CTC TTC AAC (SEQ ID NO:41); ON-GPBP-Δ26, CA CAT AGA TTT GTC CAA AAG GTT GAA GAG ATG GTG CAG AAC (SEQ ID NO:42).

Reverse transcriptase and polymerase chain rection (RT-PCR). Total RNA was prepared from different control and GP tissues as described in (15). Five micrograms of total RNA was retrotranscribed: using Ready-To-Go You-Prime First-Strand beads (Amersham Pharmacia Biotech) and 40 pmol of ON-GPBP-53c. The corresponding cDNA was subjected to PCR using the pairs of primers ON-GPBP-11m/ON-GPBP-53c or ON-GPBP-15m/ON-GPBP-62c. The identity of the products obtained with 15m-62c was further confirmed by Alu I restriction. To specifically amplify GPBP transcripts, PCR was performed using primers ON-GPBP-15m/ON-GPBP-57c.

Northern hybridization studies Pre-made human multiple-tissue and tumor cell-line Northern Blots (CLONTECH) were probed with a cDNA containing the 78-bp exon present only in GPBP or with a cDNA representing both isoforms. The corresponding cDNAs were obtained by PCR using the pair of primers ON-GPBP-56m and ON-GPBP-57c using GPBP as a template, or with primers ON-GPBP-22m and ON-GPBP-20c, using GPBPΔ26 as a template. The resulting products were random-labeled and hybridized following the manufacturers' instructions. Plasmid construction, expression and purification of recombinant proteins The plasmid pHEL-FLAG-n4', used for recombinant expression of FLAG-tagged GPBP in *Pichia pastoris* has been described elsewhere (4). The sequence coding for the 78-bp exon was deleted by site-directed mutagenesis using ON-GPBP-Δ26 to generate the plasmid pHIL-FLAG-n4'Δ26. Expression and affinity-purification of recombinant GPBP and GPBPΔ26 was done as in (4). Gel-filtration HPLC. Samples of 250 μl were injected into a gel filtration PE-TSK-G4000SW HPLC column equilibrated with 50 mM Tris-HCl pH 7.5, 150 mM NaCl. The material was eluted from the column at 0.5 ml/min, monitored at 220 nm and minute fractions collected. In vitro phosphorylation assays The auto-, trans-phosphorylation and in-blot renaturation studies were performed as in Example 1.

Antibodies and immunochemical techniques. Polyclonal antibodies were raised by in chicken against a synthetic peptide (GPBPpep1) representing the sequence coded by the 78-bp exon by (Genosys). Egg yolks were diluted 1:10 in water, the pH adjusted to 5.0. After 6 hours at 4C, the solution was clarified by centrifugation (25 min at 10000×g at 4° C.) and the antibodies precipitated by adding 20% (w/v) of sodium sulfate at 20.000×g, 20'. The pellets were dissolved in PBS (1 ml per yolk) and used for immunohistochemical studies. The production of antibodies against GPBP/GPBPΔ26 or against α3(IV)NC1 domain are discussed above (see also 4, 13).

Sedimentation velocity. Determination of sedimentation velocities were performed in an Optima XL-A analytical ultracentrifuge (Beckman Instruments Inc.), equipped with a VIS-UV scanner, using a Ti60 rotor and double sector cells of Epon-charcoal of 12 mm optical path-length. Samples of ca. 400 μl were centrifuged at 30,000 rpm at 20° C. and radial scans at 220 nm were taken every 5 min. The sedimentation coefficients were obtained from the rate of movement of the solute boundary using the program XLAVEL (supplied by Beckman). Sedimentation equilibrium. Sedimentation equilibrium experiments were done as described above for velocity experiments with samples of 70 μl, and centrifuged at 8,000 rpm. The experimental concentration gradients at equilibrium were analyzed using the program EQASSOC (Beckman) to determine the corresponding weight average molecular mass. A partial specific volumes of 0.711 $cm^3$/g for GPBP and 0.729 $cm^3$/g for GPBPΔ26 were calculated from the corresponding amino acid compositions. Physical methods and immunochemical techniques. SDS-PAGE and Western blotting were performed under reducing conditions as previously described (3). Immunohistochemistry studies were done on formalin fixed paraffin embedded tissues using the ABC peroxidase method (4) or on frozen human biopsies fixed with cold acetone using standard procedures for indirect immunofluorescence.

Two hybrid studies. Self-interaction studies were carried out in *Saccharomyces cerevisiae* (HF7c) using pGBT9 and pGAD424 (CLONTECH) to generate GAL4 binding and activation domain-fusion proteins, respectively. Interaction was assessed following the manufacture's recommendations. β-galactosidase activity was assayed with X-GAL (0.75 mg/ml) for in situ and with ortho-nitrophenyl β-D galactopyranoside (0.64 mg/ml) for the in-solution determinations.

Results

Identification of two spliced GPBP variants. To characterize the GPBP species in normal human tissues, we coupled reverse transcription to a polymerase chain reaction (RT-PCR) on total RNA from different tissues, using specific oligonucleotides that flank the full open reading frame of GPBP. A single cDNA fragment displaying lower size than expected was obtained from skeletal muscle-derived RNA (FIG. 8A), and from kidney, lung, skin, or adrenal gland-derived RNA (not shown). By combining nested PCR re-amplifications and endonuclease restriction mapping, we determined that all the RT-PCR products corresponded to the same molecular species (not shown). We fully sequenced the 2.2-Kb of cDNA from human muscle and found it identical to HeLa-derived material except for the absence of 78-nucleotides (positions 1519–1596), which encode a 26-residues motif (amino acids 371–396) (FIG. 8B). We therefore named this more common isoform of GPBP as GPBPΔ26.

To investigate whether the 78-bp represent an exon skipped transcript during pre-mRNA processing, we used this cDNA fragment to probe a human-derived genomic library and we isolated a ~14-Kb clone. By combining Southern blot hybridization and PCR, the genomic clone was characterized and a contiguous DNA fragment of 12482-bp was fully sequenced (SEQ ID 25). The sequence contained (from 5' to 3'), 767-bp of intron sequence, a 93-bp exon, an 818-bp intron, the 78-bp exon sequence of interest, a 9650-bp intron, a 96-bp exon and a 980-bp intron sequence (FIG. 8C). The exon-intron boundaries determined by comparing the corresponding DNA and cDNA sequences meet the canonical consensus for 5' and 3' splice sites (FIG. 8C) (5), thus confirming the exon nature of the 78-bp sequence. The GPBP gene was localized to chromosome 5q13 by fluorescence in situ hybridization (FISH) using the genomic clone as a probe (not shown).

The relative expression of GPBP in human-derived specimens was assessed by Northern blot analysis, using either the 78-bp exon or a 260-bp cDNA representing the flanking sequence of 78-bp (103-bp 5' and 157-bp 3') present in both GPBP and GPBPΔ26 (FIG. 9). The 78-bp containing the molecular species of interest were preferably expressed in striated muscle (both skeletal and heart) and brain, and poorly expressed in placenta, lung and liver. In contrast to GPBPΔ26, the GPBP was expressed at very low levels in kidney, pancreas and cancer cell lines.

All the above indicates that GPBP is expressed at low levels in normal human tissues, and that the initial lack of detection by RT-PCR of GPBP can be attributed to a preferential amplification of the more abundant GPBPΔ26. Indeed, the cDNA of GPBP could be amplified from human tissues (skeletal muscle, lung, kidney, skin and adrenal gland) when the specific RT-PCR amplifications were done using 78-bp exon-specific oligonucleotides (not shown). This also suggests that GPBPΔ26 mRNA is the major transcript detected in Northern blot studies when using the cDNA probe representing both GPBP and GPBPΔ26.

Recombinant expression and functional characterization of GPBPΔ26. To investigate whether the absence of the 26-residue serine-rich motif would affect the biochemical properties of GPBP, we expressed and purified both isoforms (rGPBP and rGPBPΔ26), and assessed their auto- and trans-phosphorylation activities (FIG. 10). As reported above for rGPBP (see also 4), rGPBPΔ26 is purified as a single major polypeptide and several related minor products (FIG. 10A). However, the number and relative amounts of the derived products vary compared to rGPBP, and they display $M_r$ on SDS-PAGE that cannot be attributed simply to the 26-residue deletion. This suggests that the 26-residue motif has important structural and functional consequences that could account for the reduced in-solution auto- and trans-phosphorylation activities displayed by rGPBPΔ26 (FIG. 10B). Interestingly, the differences in specific activity shown in the in-solution assays were not evident when autophosphorylation was assessed in-blot after SDS-PAGE and renaturation, suggesting that the 26-residue motif likely has important functional consequences at the quaternary structure level. Renaturation studies further showed that phosphate transfer activities reside in the major polypeptides representing the proposed open reading frames, and are not detectable in derived minor products.

rGPBP and rGPBP-26 exist as very active high molecular weight aggregates. Gel filtration analysis of affinity-purified RGPBP or rGPBPΔ26 yielded two chromatographic peaks (I and II), both displaying higher MW than expected for the individual molecular species, as determined by SDS-PAGE studies (89 kDa and 84 kDa, respectively) (FIG. 11). The bulk of the recombinant material eluted as a single peak between the 158 kDa and the 669 kDa molecular weight markers (peak II), while limited amounts of rGPBP and only traces of rGPBPΔ26 eluted in peak I (>1000 kDa). Aliquots of fractions representing each chromatographic profile were subjected to SDS-PAGE and stained, or incubated in the presence of $^{32}P[\gamma]$ ATP, and analyzed by immunoblot and autoradiography. Along with the major primary polypeptide, every chromatographic peak contained multiple derived products of higher or lower sizes indicating that the primary polypeptide associates to form high molecular weight aggregates that are stabilized by covalent and non-covalent bonds (not shown). The kinase activity also exhibited two peaks coinciding with the chromatographic profiles. However, peak I showed a much higher specific activity than peak II, indicating that these high molecular weight aggregates contained a much more active form of the kinase. Equal volumes of rGPBP fractions number 13 and 20 exhibited comparable phosphorylating activity, even though the protein content is approximately 20 times lower in fraction 13, as estimated by Western blot and Coomasie blue staining (FIG. 11A). The specific activities of rGPBP and rGPBPΔ26 at peak II are also different, and are consistent with the studies shown for the whole material, thus supporting the hypothesis that the presence of the 26-rediue serine-rich motif renders a more active kinase. These results also suggest that both rGPBP and rGPBPΔ26 exist as oligomers under native conditions, and that both high molecular weight aggregate formation and specific activity are greatly dependent on the presence of the 26-residue serine-rich motif. Analytical centrifugation analysis of rGPBP revealed that peak I contained large aggregates (over $10^7$ Da). Peak II of rGPBP contained a homogenous population of 220±10 kDa aggregates, likely representing trimers with a sedimentation coefficient of 11S. Peak II of rGPBPΔ26 however consisted of a more heterogenous population that likely contains several oligomeric species. The main population (ca. 80%) displayed a weight average molecular mass of 310±10 kDa and a coefficient of sedimentation of 14S.

GPBP and GPBPΔ26 self-interact in a yeast two-hybrid system. To assess the physiological relevance of the self-aggregation, and to determine the role of the 26-residue motif, we performed comparative studies using a two-hybrid interaction system in yeast. In this type of study, the polypeptides whose interaction is under study are expressed as a part of a fusion protein containing either the activation or the binding domains of the transcriptional factor GALA. An effective interaction between the two fusion proteins through the polypeptide under study would result in the reconstitution of the transcriptional activator and the subsequent expression of the two reporter genes, Lac Z and His3, allowing colony color detection and growth in a His-defective medium, respectively. We estimated the intensity of interactions by the growth-rate in histidine-defective medium, in the presence of different concentrations of a competitive inhibitor of the His3 gene product (3-AT), and a quantitative colorimetric liquid β-galactosidase assay. A representative experiment is presented in FIG. 12. When assaying GPBPΔ26 for self-interaction, a significant induction of the reporter genes was observed, while no expression was detectable when each fusion protein was expressed alone or with control fusion proteins. The insertion of the 26-residue motif in the polypeptide to obtain GPBP resulted in a notable increase in polypeptide interaction. All of the above data indicate that GPBPΔ26 self-associates in vivo, and that the insertion of the 26-residues into the polypeptide chain yields a more interactive molecular species.

GPBP is highly expressed in human but not in bovine and murine glomerulus and alveolus. We have shown that GPBP/GPBPΔ26 is preferentially expressed in human cells and tissues that are commonly targeted in naturally occurring autoimmune responses. To specifically investigate the expression of GPBP, we raised polyclonal antibodies against a synthetic peptide representing the 26-residue motif characteristic of this kinase isoform, and used it for immunohistochemical studies on frozen or formalin fixed paraffin embedded human tissues (FIG. 13). In general, these antibodies showed more specificity than the antibodies recognizing both isoforms for the tissue structures that are target of autoimmune responses such as the biliary ducts, the Langerhans islets or the white matter of the central nervous system (not shown). Nevertheless, the most remarkable finding was the presence of linear deposits of GPBP-selective antibodies around the small vessels in every tissue studied (A), suggesting that GPBP is associated with endothelial basement membranes. Consequently, at the glomerulus, the anti-GPBP antibodies displayed a vascular pattern closely resembling the glomerular basement membrane staining yielded either by monoclonal antibodies specifically recognizing the α3(IV)NC1 (compare 13B with 13C and 13D), or by circulating GP autoantibodies (compare 13E and 13F). These observations further supported the initial observation that GPBP is expressed in tissue structures targeted in natural autoimmune responses, suggesting that the expression of GPBP is a risk factor and makes the host tissue vulnerable to an autoimmune attack.

To further assess this hypothesis, we investigated the presence of GPBP and GPBPΔ26 in the glomerulus of two mammals that naturally do not undergo GP disease compared to human (FIG. 14). GPBP-specific antibodies failed to stain the glomerulus of both bovine or murine specimens (compare 14A with 14B and 14C) while antibodies recognizing the N-terminal sequence common to both GPBP and GPBPΔ26 stained these structures in all three species, although with different distributions and intensities (14D-14F). In bovine renal cortex, GPBPΔ26 was expressed at a lower rate than in human, but showed similar tissue distribution. In murine samples, however, GPBPΔ26 displayed a tissue distribution closely resembling that of GPBP in human glomerulus. Similar results were obtained when studying the alveolus in the three different species (not shown). To rule out that the differences in antibody detection was due to primary structure differences rather than to a differential expression, we determined the corresponding primary structures in these two species by cDNA sequencing. Bovine and mouse GPBP (SEQ ID NOS:3–6 and 9–12) displayed an overall identity with human material of 97.9% and 96.6% respectively. Furthermore, the mouse 26-residue motif was identical to human while bovine diverged only in one residue. Finally, and similarly to human, we successfully amplified GPBP cDNA from mouse or bovine kidney total RNA using oligonucleotides specific for the corresponding 78-bp exons, indicating that GPBP is expressed at very low levels not detectable by immunochemical techniques.

GPBP is highly expressed in several autoimmune conditions. We analyzed several tissues from different GP patients by specific RT-PCR to assess GPBP/GPBPΔ26 mRNA levels. As in control kidneys, the major expressed isoform in GP kidneys was GPBPΔ26. However, in the muscle of one of the patients, GPBP was preferentially expressed, whereas GPBPΔ26 was the only isoform detected in control muscle samples (FIG. 15A). Since we did not have kidney samples from this particular patient, we could not assess GPBP/GPBPΔ26 expression in the corresponding target organ. For similar reasons, we could not assess GPBP/GPBPΔ26 levels in the muscle of the patients in which kidneys were studied.

Muscle cells express high levels of GPBP/GPBPΔ26 (see Northern blot in FIG. 9), and they comprise the bulk of the tissue. In contrast, the expression of GPBP/GPBPΔ26 in the kidney was much less, and the glomerulus was virtually the only kidney structure expressing the GPBP isoform (see FIG. 13). The glomerulus is a relatively less abundant structure in kidney than the myocyte is in muscle, and the glomerulus is the structure targeted by immune attack in GP pathogenesis. These factors, together with the preferential amplification of the more abundant and shorter messages when performing RT-PCR studies, could account for the lack of detection of GPBP in both normal and GP kidneys, thus precluding the assessment of GPBP expression at the glomerulus during pathogenesis. Nevertheless, the increased levels of GPBP in a GP patient suggest that GPBP/GPBPΔ26 expression is altered during GP pathogenesis, and that augmented GPBP expression has a pathogenic significance in GP disease.

To investigate the expression of GPBP and GPBPΔ26 in autoimmune pathogenesis, we studied cutaneous autoimmune processes and compared them with control samples representing normal skin or non-autoimmune dermatitis (FIG. 15). Control samples displayed a limited expression of GPBP in the most peripheral keratinocytes (15B, 15E), while keratinocytes expanding from stratum basale to corneum expressed abundant GPBP in skin affected by systemic lupus erythematosus (SLE) (15C, 15F) or lichen planus (15D, 15G). GPBP was preferentially expressed in cell surface structures that closely resembled the blebs previously described in cultured keratinocytes upon UV irradiation and apoptosis induction (6). In contrast, antibodies recognizing both GPBP and GPBPΔ26 yielded a diffuse cytosolic pattern through the whole epidermis in both autoimmune affected or control samples (not shown). These data indicate that in both control and autoimmune-affected keratinocytes, GPBPΔ26 was expressed at the cytosol and that the expression did not significantly vary during cell differentiation. In contrast, mature keratinocytes were virtually the only GPBP expressing cells. However, bleb formation and expression of GPBP was observed in the early stages of differentiation in epidermis affected by autoimmune responses (15C, 15D, 15F, 15G). This further supports previous observations indicating that aberrant apoptosis at the basal keratinocytes is involved in the pathogenesis of autoimmune processes affecting skin (7), and suggests that apoptosis and GPBP expression are linked in this human cell system.

Discussion

Alternative pre-mRNA splicing is a fundamental mechanism for differential gene expression that has been reported to regulate the tissue distribution, intracellular localization, and function of different protein kinases (8–11). In this regard, and closely resembling GPBP, B-Raf exists as multiple spliced variants, in which the presence of specific exons renders more interactive, efficient and oncogenic kinases (12).

Although it is evident that rGPBPΔ26 still bears the uncharacterized catalytic domain of this novel kinase, both auto- and trans-phosphorylating activities are greatly reduced when compared to rGPBP. Gel filtration and two hybrid experiments provide some insights into the mechanisms that underlie such a reduced phosphate transfer activity. About 1–2% of rGPBP is organized in very high molecular weight aggregates that display about one third of the phosphorylating activity of rGPBP, indicating that high molecular aggregation renders more efficient quaternary structures. Recombinant GPBPΔ26, with virtually no peak I material, consistently displayed a reduced kinase activity. However, aggregation does not seem to be the only mechanism by which the 26-residues increases specific activity, since the rGPBPΔ26 material present in peak II also shows a reduced phosphorylating activity when compared to homologous fractions of rGPBP. One possibility is that rGPBP-derived aggregates display higher specific activities because of quaternary structure strengthening caused by the insertion of the 26-residue motif. The oligomers are kept together mainly by very strong non-covalent bonds, since the bulk of the material appears as a single polypeptide in non-reducing SDS-PAGE, and the presence of either 8 M urea or 6 M guanidine had little effect on chromatographic gel filtration profiles (not shown). How the 26-residue motif renders a more strengthened and active structure remains to be clarified. Conformational changes induced by the presence of an exon encoded motif that alter the activation status of the kinase have been proposed for the linker domain of the Src protein (24) and exons 8b and 10 of B-Raf (12). Alternatively, the 26-residue motif may provide the structural requirements such as residues whose phosphorylation may be necessary for full activation of GPBP.

We have reported (13) that the primary structure of the GP antigen (α3(IV)NC1) is the target of a complex folding process yielding multiple conformers. Isolated conformers are non-minimum energy structures specifically activated by phosphorylation for supramolecular aggregation and likely quaternary structure formation. In GP patients, the α3(IV)NC1 shows conformational alterations and a reduced ability to mediate the disulfide stabilization of the collagen IV network. The GP antibodies, in turn, demonstrate stronger affinity towards the patient α3(IV)NC1 conformers, indicating that conformationally altered material caused the autoimmune response. Therefore, it seems that in GP disease an early alteration in the conforming process of the α3(IV)NC1 could generate altered conformers for which the immune system is not tolerant, thus mediating the autoimmune response.

Other evidence (Raya et al., unpublished results) indicates that phosphorylation is the signal that drives the folding of the α3(IV)NC1 into non-minimum energy ends. In this scenario, three features of the human α3(IV)NC1 system are of special pathogenic relevance when compared to the corresponding antigen systems from species that, like bovine or murine, do not undergo spontaneous GP disease. First, the N-terminus of the human α3(IV)NC1 contains a motif that is phosphorylatable by PKA and also by GPBP (see above, and also 24). Second, the human gene generates multiples alternative products by alternative exon splicing (14,15). Exon skipping generates alternative products with divergent C-terminal ends that up-regulate the in vitro PKA phosphorylation of the primary α3(IV)NC1 product (See below Example 3). Third, the human GPBP is expressed associated with glomerular and alveolar basement membranes, the two main targets in GP disease. The phosphorylation-dependent conforming process is also a feature of non-pathogenic NC1 domains (13), suggesting that the phosphorylatable N-terminus, the alternative splicing diversification, and the expression of GPBP at the glomerular and alveolar basement membranes, are all exclusively human features that place the conformation process of α3(IV)NC1 in a vulnerable condition. The four independent GP kidneys studied expressed higher levels of GP antigen alternative products (15; Bernal and Saus, unpublished results), and an augmented expression of GPBP were found in a GP patient (see above). Both increased levels of alternative GP antigen products and GPBP are expected to have consequences in the phosphorylation-dependent conformational process of the α3(IV)NC1, and therefore with pathogenic potential.

GPBP is highly expressed in skin targeted by natural autoimmune responses. In the epidermis, GPBP is associated with cell surface blebs characteristic of the apoptosis-mediated differentiation process that keratinocytes undergo during maturation from basale to corneum strata (22, 23). Keratinocytes from SLE patients show a remarkably heightened sensitivity to UV-induced apoptosis (6, 18, 20), and augmented and premature apoptosis of keratinocytes has been reported to exist in SLE and dermatomyositis (7). Consistently, we found apoptotic bodies expanding from basal to peripheral strata of the epidermis in several skin autoimmune conditions including discoid lupus (not shown), SLE and lichen planus. Autoantigens, and modified versions thereof are clustered in the cell surface blebs of apoptotic keratinocytes (6,18,20). Apoptotic surface blebs present autoantigens (21), and likely release modified versions to the circulation (16–20). It has been suggested that the release of modified autoantigens from apoptotic bodies could be the immunizing event that mediates systemic autoimmune responses mediating SLE and scleroderma (18,19).

Our evidence indicates that both GPBP and GPBPΔ26 are able to act in vitro as protein kinases, with GPBP being a more active isoform than GPBPΔ26. Furthermore, recombinant material representing GPBP or GPBPΔ26 purified from yeast or from human 293 cells contained an associated proteolytic activity that specifically degrades the α3(IV)NC1 domain (unpublished results). The proteolytic activity operates on α3(IV)NC1 produced in an eukaryotic expression system, but not on recombinant material produced in bacteria (unpublished results), indicating that α3(IV)NC1 processing has some conformational or post-translational requirements not present in prokaryotic recombinant material. Finally, it has been reported that several autoantigens undergo phosphorylation and degradation in apoptotic keratinocytes (20). While not being limited to an exact mechanism, we propose, in light of all of the above data, that the machinery assembling GPBP at the apoptotic blebs likely performs a complex modification of the autoantigens that includes phosphorylation, conformational changes and degradation. Accordingly, recombinant protein representing autoantigens in SLE (P1 ribosomal phosphoprotein and Sm-D1 small nuclear ribonucleoproteins) and in dermatomyositis (hystidil-tRNA synthetase) were in vitro substrates of GPBP (unpublished results).

The down-regulation in cancer cell lines of GPBP, suggest that the cell machinery harboring GPBP/GPBPΔ26 is likely involved in signaling pathways inducing programmed cell death. The corresponding apoptotic pathway could be up regulated during autoimmune pathogenesis to cause an altered antigen presentation in individuals carrying specific MHC haplotypes; and down regulated during cell transformation to prevent autoimmune attack to the transformed cells during tumor growth.

REFERENCES FOR EXAMPLE 2

1. Saus, J. (1998) in *Goodpasture's Syndrome: Encyclopedia of Immunology* $2^{nd}$ edn. Vol. 2, eds. Delves, P. J., & Roitt, I. M., (Academic Press Ltd., London),pp. 1005–1011.
2. Quinones, S., Bernal, D., Garcia-Sogo, M., Elena S. F., & Saus, J. (1992) *J. Biol. Chem.* 267, 19780–19784.
3. Revert, F., Penadés, J. R., Plana, M., Bernal, D., Johansson, C., Itarte, E., Cervera, J., Wieslander, J., Quinones, S., & Saus, J.(1995) *J. Biol. Chem.* 270, 13254–13261.

4. Raya, A., Revert, F., Navarro, S., & Saus, J. (1999) *J. Biol. Chem.* 274, 12642–12649.
5. Green, M. R. (1986) *Ann. Rev. Genet.* 20, 671–708.
6. Casciola-Rosen, L. A., Anhalt, G. & Rosen, A. (1994) *J. Exp. Med.* 179:1317–1330.
7. Pablos, J. L:, Santiago, B., Galindo, M., Carreira, P. E., Ballestin, C.& Gomez-Reino, J. J. (1999) *J. Pathol.* 188: 63–68.
8. Srinivasan, M., Edman, C. F., & Schulman, H. (1994) *J. Cell. Biol.* 126, 839–852.
9. Naito, Y., Watanabe, Y., Yokokura, H., Sugita, R., Nishio, M., & Hidaka, H. (1997) *J. Biol. Chem.* 272, 32704–32708.
10. Bayer, K.-U., Löhler, J., & Harbers, K. (1996) *Mol. Cell. Biol.* 16, 29–36.
11. Madaule, P., Eda, M., Watanabe, N, Fujisawa, K., Matsuoka, T., Bito, H., Ishizaki, T., & Narumiya, S. (1998) *Nature* 394, 491–494.
12. Papin, C., Denouel-Galy, A., Laugier, D., Calothy, G., & Eychene, A. (1998) *J. Biol. Chem.* 273, 24939–24947.
13. Following examples
14. Penadés, J. R., Bernal, D., Revert, F., Johansson, C., Fresquet, V. J., Cervera, J., Wieslander, J., Quinones, S. & Saus, J. (1995) *Eur. J. Biochem.* 229, 754–760.
15. Bernal, D., Quinones, S., & Saus, J. (1993) *J. Biol. Chem.*, 268, 12090–12094.
16. Casciola-Rosen, L. A., Anhalt, G. J.& Rosen, A.(1995) *J. Exp. Med.* 182: 1625–1634.
17. Casiano, C. A., Martin, S. J., Green, D. R., & Tan, E. M. (1996) *J. Exp. Med.* 184: 765–770.
18. Casciola-Rosen, L., & Rosen, A. (1997) *Lupus* 6: 175–180.
19. Bolívar, J., Guelman, S., Iglesias, C., Ortíz, M., & Valdivia, M. (1998) *J. Biol. Chem.* 273: 17122–17127.
20. Utz, P. J., & Anderson, P. (1998) *Arthritis Rheum.* 41: 1152–1160.
21. Golan, T. D., Elkon, K. B., Ghavari, A. E.,& Krueger, J. G.(1992) *J. Clin. Invest,* 90: 1067–1076.
22. Polalowska, R. R., Piacentini, M., Bartlett, R., Goldsmith, L. A., & Haake, A. R. (1994) *Dev. Dinam.* 199: 176–188.
23. Maruoka, Y., Harada, H., Mitsuyasu et al. (1997) *Biochem. Biophys. Res. Commun.* 238: 886–890.
24. Xu, W., Harrison, S. C., & Eck, M. J. (1997) *Nature* 385, 595–602.

EXAMPLE 3

Regulation of Human Autoantigen Phosphorylation by Exon Splicing

Introduction

In GP disease, the immune system attack is mediated by autoantibodies against the non-collagenous C-terminal domain (NC1) of the α3 chain of collagen IV (the GP antigen) (1). The N-terminus of the human α3(IV)NC1 contains a highly divergent and hydrophilic region with a unique structural motif, KRGDS⁹ (SEQ ID NO:63) that harbors a cell adhesion signal as an integral part of a functional phosphorylation site for type A protein kinases (2,3). Furthermore, the gene region encoding the human GP antigen characteristically generates multiple mRNAs by alternative exon splicing (4,5). The alternative products diverge in the C-terminal ends and all but one share the N-terminal KRGDS⁹ (SEQ ID NO:63) (4,5).

Multiple sclerosis (MS) is an exclusive human neurological disease characterized by the presence of inflamatory demyelization plaques at the central nervous system. (6). Several evidences indicate that this disease is caused by an autoimmune attack mediated by cytotoxic T cells towards specific components of the white matter including the myelin basic protein (MBP) (7, 8). In humans, the MBP gene generates four products (MBP, MBPΔII, MBPΔV and MBPΔII/V) that result from alternative exon splicing during pre-mRNA processing (9). Among these, MBPΔII is the more abundant form in the mature central nervous system, while MBP form containing all the exons is virtually absent (9).

Several biological similarities exist between the autoimmune responses mediating GP disease and MS, namely: 1) both are human exclusive diseases and typically initiate after a viral flu-like disease; 2) a strong linkage exists to the same haplotype of the ILA-DR region of the class II MHC; 3) several products are generated by alternative splicing; and 4) the death of a MS patient by GP disease has recently been reported (10).

Materials and Methods

Synthetic polymers: GPΔIII derived peptide, QRAH-GQDLDALFVKVLRSP (SEQ ID NO:43) and GPΔIII/IV/V derived peptide, QRAHGQDLESLFHQL (SEQ ID NO:44) were synthesized using either Boc-(MedProbe) or Fmoc-(Chiron, Lipotec) chemistry.

Plasmid Construction and Recombinant Expression.

GP derived material: The constructs representing the different GP-spliced forms were obtained by subdloning the cDNAs used elsewhere to express the corresponding recombinant proteins (5) into the BardHI site of a modified pET15b vector, in which the extraneous vector-derived amino-terminal sequence except for the initiation Met was eliminated. The extra sequence was removed by cutting the vector with NcoI and Bam HI, filling-in of the free ends with Klenow, and re-ligation. This resulted in the reformation of both restriction sites and placed the BamHI site inmnediately downstream of the codon for the amino-terminal Met.

The recombinant proteins representing GP or GPΔV (SEQ ID NO:46) were purified by precipitation (5). Bacterial pellets containing the recombinant proteins representing GPΔIII (SEQ ID NO:48) or GPΔII/IV/V (SEQ ID NO:50) were dissolved by 8 M urea in 40 mM Tris-HCl pH 6.8 and sonication. After centrifugation at 40,000×g the supernatants were passed through a 0.22 μm filter and applied to resource Q column for FPLC. The effluent was acidified to pH 6 with HCl and applied to a resource S column previously equilibrated with 40 mM MES pH 6 for a second FPLC purification. The material in the resulting effluent was used for in vitro phosphorylation.

MBP-derived material: cDNA representing human MRPΔII (SEQ ID NO:51) was obtained by RT-PCR using total RNA from central nervous system. The cDNA representing human MBP was a generous gift from C. Campagnoni (UCLA). Both fragments were cloned into a modified version of pHIL-D2 (Invitrogen) containing a 6×His-coding sequence at the C-terminus to generate pHIL-MBPΔII-His and pHIL-MBP-His, respectively. These plasmids were used for recombinant expression in *Pichia pastoris* as described in (11). Recombinant proteins were purified using immobilized metal affinity chromatography (TALON resin, CLONTECH) under denaturant conditions (8M urea) and eluted with 300 mM imidazole following manufacturers' instructions. The affinity-purified material was then renatured by dilution into 80 volumes of 50 mM Tris-HCl pH 8.0, 10 mM CHAPS, 400 mM NaCl, 2 mM DTT, and concentrated 50 times by ultrafiltration through a YM10-type membrane (AMICON). The Ser to Ala mutants were produced by site-directed mutagenesis over native sequence-containing constructs using transformer mutagenesis kit from CLONTECH and the resulting proteins were similarly produced.

Phosphorylation studies. Phosphorylation studies were essentially done as described above (see also 3 and 11). In some experiments, the substrates were in-blot renatured and then, phosphorylated for 30 min at room temperature by overlaying 100 µl of phosphorylation buffer containing 0.5 µg of RGPBP. Digestion with V8 endopeptidase and immunoprecipitation were performed as described in (3).

Antibody production. Synthetic peptides representing the C-terminal divergent ends of GP☐III or GP☐III/IV/V comprised in SEQ ID NO:43 or SEQ ID NO:44 respectively were conjugated to a cytochrome C, BSA or ovoalbumine using a glutaraldehyde coupling standard procedure. The resulting protein conjugates were used for mouse immunization to obtain polyclonal antibodies specific for GPΔIII and monoclonal antibodies specific for GPΔIII/IV/V (Mab153). To obtain monoclonal antibodies specific for GPΔV (Mab5A) mouse were immunized using recombinant bacterial protein representing the corresponding alternative form comprising the SEQ ID NO:50. The production of monoclonal (M3/1, P1/2) or polyclonal (anti-GPpep1) antibodies against SEQ ID NO: 26 which represents the N-terminal region of the GP alternative forms have been previously described (3,5).

Boc-Based Peptide Synthesis.

Assembling. The peptide was assembled by stepwise solid phase synthesis using a Boc-Benzyl strategy. The starting resin used was Boc-Pro-PAM resin (0.56 meq/g, batch R4108). The deprotection/coupling procedure used was: TFA (1×1 min) TFA (1×3 min) DCM (flow flash) Isopropylalcohol (1×30 sec) DMF (3×1 min) COUPLING/DMF (1×10 min) DMF (1×1 min) COUPLING/DMF (1×10 min) DMF (2×1 min) DCM (1×1 min). For each step 10 ml per gram of peptide-resin were used. The coupling of all amino acids (fivefold excess) was performed in DMF in the presence of BOP, Hobt and DEEA. For the synthesis the following side-chain protecting groups were used: benzyl for serine; 2 chlorobenzyloxycarbonyl for lysine; cyclohexyl for aspartic and glutamic acid; tosyl for histidine and arginine.

Cleavage. The peptide was cleaved from the resin and fully deprotected by a treatment with liquid Hydrogen Fluoride (HF): Ten milliliters of HF per gram of peptide resin were added and the mixture kept at 0° C. for 45 min in the presence of p-cresol as scavengers. After evaporation of the HF, the crude reaction mixture is washed with ether, dissolved in TFA, precipitated with ether and dried.

Purification. Stationary phase: Silica C18, 15 µm, 120 A; Mobile phase: solvent A: water 0.1% TFA and solvent B: acetonitrile/A, 60/40 (v/v); Gradient: linear from 20 to 60% B in 30 min; Flow rate: 40 ml/min; and detection was U.V (210 nm). Fractions with a purity higher than 80% were pooled and lyophilized. Control of purity and identity was performed by analytical HPLC and ES/MS. The final product had 88% purity and an experimental molecular weight of 2192.9.

Fmoc-based peptide synthesis.

Assembling. The peptides were synthesized by stepwise linear solid phase on Pro-clorotrityl-resin (0.685 meq/g) with standard Fmoc/tBu chemistry. The deprotection/coupling procedure used was: Fmoc aa (0.66 g) HOBt (0.26 g) DIPCDI (0.28 ml) for 40 min following a control by Kaiser test. If the test was positive the time was extended until change to negative. Then DMF (31 min), piperidine/DMF 20% (11 min) piperidine/DMF 20% (15 min), and DMF (41 min). Side chain protectors were: Pmc (pentamethylcromane sulfonyl) for arginine, Bcc (tert-butoxycarbonyl) for lysine, tBu (tert-butyl) for aspartic acid and for serine and Trl (trityl) for histidine.

Cleavage. The peptide was cleaved and fully deprotected by treatment cleavage with TFA/water 90/10. Ten milliliters of TFA solution per gram of resin were added. Water acts as scavenger. After two hours, resin was filtered and the resulting solution was precipitated five times with cold diethylether. The final precipitated was dried.

Purification. Stationary phase: Kromasil C18 10 µm; Mobile phase: solvent A: water 0.1% TFA and solvent B: acetonitrile 0.1% TFA; Isocratic: 28% B; Flow rate: 55 ml/min; Detection: 220 nm. Fractions with the higher purity were pooled and lyophilized, and a second HPLC purification round performed. Control of purity and identity was performed by analytical HPLC and ES/MS. The final product had 97% purity and an experimental molecular weight of 2190.9.

Results

Regulation of the phosphorylation of the human GP antigen by alternative splicing. We produced bacterial recombinant proteins representing the primary antigen (GP) or the individual alternative products GPΔV (SEQ ID NO:46), GPΔIII (SEQ ID NO:48) and GPΔIII/IV/V (SEQ ID NO:50), and we tested their ability to be phosphorylated by PKA (FIG. 16, left panel). Using standard ATP concentrations (150 µM), all four recombinant antigens were phosphorylated but to very different extents. The alternative forms incorporated $^{32}$P more efficiently than the primary GP antigen, suggesting that they are better substrates. Because these antigens are expected to be in the extracellular compartment, we also assayed their phosphorylatability with more physiological ATP concentrations (0.1–0.5 μM). Under these conditions, the differences in $^{32}P$ incorporation between the primary and alternative products were more evident, indicating that at low ATP concentrations the primary GP antigen was a very poor substrate for the kinase. Among the three PKA phosphorylation sites present in the GP antigen, the N-terminal $Ser^9$ and $Ser^{26}$ are the major ones, and are common to all the alternative products assayed (3,5). Accordingly, the differences observed in phosphorylation for the full polypeptides also existed among the individual N-terminal regions, as determined after specific V8 digestion and immunoprecipitation (not shown). This strongly suggests that differences in phosphorylation might be due to the presence of different C-terminal sequences in the alternative products. Since GPΔIII and GPΔIII/IV/V displayed significantly higher $^{32}P$ incorporation rates than GPΔV, and they have shorter divergent C-terminal regions (5), we used synthetic peptides individually representing these C-terminal sequences (SEQ ID NO: 43, SEQ ID NO:44) to further examine their regulatory roles in the in vitro phosphorylation of the native antigen. Collagen IV is a trimeric molecule comprised of three interwoven αchains. In basement membranes, two collagen IV molecules assemble through their NC1 domains to yield a hexameric NC1 structure that can be solubilized by bacterial collagenase digestion (1). Dissociation of the hexamer structure releases the GP antigen in monomeric and disulfide-related dimeric forms (1). For the following set of experiments, we carried out phosphorylations in the presence of low, extracellular-like ATP concentrations using both monomeric or hexameric native GP antigen (FIG. 16, right panel). The presence of each specific peptide but not control peptides (not shown) induced the phosphorylation of a single polypeptide displaying an apparent MW of 22 kDa. By specific V8 digestion and immunoprecipitation, the corresponding polypeptide has been identified as the 22 kDa conformer of the α3(IV)NC1, identified below as the best substrate for the PKA.

Regulation of the phosphorylation of the MBP by alternative splicing. The MBP contains at its N terminal region two PKA phosphorylation sites (Ser$^8$, Ser57) that are structurally similar to the N terminus site (Ser$^9$) present in GP antigen products (FIG. 17). The Ser$^8$ site present in all the MBP proteins is located in a similar position than the Ser$^9$ in the GP-derived polypeptides. In addition, in the MBP and GPΔIII Ser$^8$ and Ser$^9$ respectively are at a similar distance in the primary structures of a highly homologous motif present in the corresponding exon 11 (bend arrow in FIG. 17). The GPΔIII-derived motif coincides with the C terminal divergent region that up-regulates PKA phosphorylation of Ser$^9$ in the GP antigen system FIG. 16). The regulatory-like sequence in MBP is located at exon II and its presence in the final products depends on an alternative exon splicing mechanism. Therefore, the MBP motif identified by structural comparison to GPΔIII may be also regulating PKA phosphorylation of Ser$^8$. We produced recombinant proteins representing MBP and MBPΔII (SEQ ID NO:54) and the corresponding Ser to Ala mutants to knock-out each of the two PKA phosphorylation sites (Ser$^8$ and Ser$^{57}$) present in exon I. Subsequently, we assessed its in vitro phosphorylation by PKA (FIG. 18). MBPΔII was a better substrate than MBP, and Ser$^8$ was the major phosphorylation site, indicating that, similarly to GP antigenic system, alternative exon splicing regulates the PKA phosphorylation of specific sites located at the N-terminal region common to all the MBP-derived alternative forms.

In similar experiments assessing GPBP phosphorylation of the recombinant MBP proteins, GPBP preferentially phosphorylated MBP, while little phosphorylation of MBPΔII was observed (FIG. 19). Furthermore, recombinant Ser to Ala mutants displayed no significant reduction in $^{32}$P incorporation, indicating that GPBP phosphorylates MBP/MBPΔII in an opposite way than PKA, and that these two kinases do not share major phosphorylation sites in MBP proteins.

From all these data we concluded that in the MBP system, alternative splicing regulates the phosphorylation of specific serines by either PKA or GPBP.

Synthetic peptides representing the C terminal region of GPΔIII influence GPBP phosphorylation. To assess the effect of the C terminal region of GPΔIII on GPBP activity, peptides representing this region were synthesized using two different chemistries (Boc or Fmoc), and separately added to a phosphorylation mixture containing GPBP (FIG. 20). Boc-based synthetic peptides positively influenced GPBP autophosphorylation while Fmoc-based inhibited GPBP autophosphorylation, suggesting that the regulatory sequences derived from the alternative products in either GP and MBP antigenic systems can influence the kinase activity of GPBP.

Discussion

We show (here and in the following examples) that the α3(IV)NC1 domain undergoes a complex structural diversification by two different mechanism: 1) alternative splicing (4,5) and 2) conformational isomerization of the primary product. Both mechanisms generate products that are distinguished by PKA, indicating that PKA phosphorylation is a critical event in the biology of the α3(IV)NC1 domain. Phosphorylation guides at least in part the folding, but also the supramolecular assembly of the α3(IV)NC1 domain in the collagen IV network (below). Altered conformers of the α3(IV)NC1 lead the autoimmune response mediating GP disease (See the following examples), suggesting that an alteration in antigen phosphorylation could be the primary event in the onset of the disease. Accordingly, we have found increased expression levels of GPΔIII in several GP kidneys (4 and Bernal and Saus, unpublished results), and an increased expression of GPBP has been detected in another Goodpasture patient (FIG. 15). Both increased expression of alternative GP antigen products and of GPBP are expected to have consequences in the phosphorylation steady state of α3(IV)NC1, and therefore in the corresponding conformational process. The discrimination among the different structural products by PKA strongly suggests that this kinase, or another structurally similar kinase, is involved in the physiological antigen conforming process, and that antigen phosphorylation by GPBP has a pathogenic significance. In pathogenesis, GPBP could be an intruding kinase, interfering in the phosphorylation-dependent conforming process. Accordingly, GPBP is expressed in tissue structures that are targeted by natural autoimmune responses, and an increased expression of GPBP is associated with several autoimmune conditions (See examples 1 and 2 above).

An alternative splicing mechanism also regulates the PKA phosphorylation of specific serines in the MBP antigenic system. MBP is also a substrate for GPBP suggesting that GPBP may play a pathogenic role in multiple sclerosis, and other autoimmune responses.

All of the above data identify GPBP as a potential target for therapeutics in autoimmune disease. In FIG. 20, we show that synthetic peptides representing the C terminal region of GPΔIII (SEQ ID NO:43) modulate the action of GPBP in vitro, and therefore we identified this and related sequences as peptide-based compounds to modulate the activity of GPBP in vivo. The induction of GP antigen phosphorylation by PKA was achieved when using Boc-based peptides, but not when using similar Fmoc-based peptides. Furthermore, Boc- but not Fmoc-based peptides were in vitro substrates of PKA (not shown), indicating that important structural differences exist between both products. Since both products displayed no significant differences in mass spectrometry, one possibility is that the different deprotection procedure used may be responsible for conformational differences in the secondary structure that may be critical for biological activity. Accordingly, Boc-based peptide loses its ability to induce PKA upon long storage at low temperatures.

REFERENCES FOR EXAMPLE 3

1. Saus, J. (1998) in *Goodpasture's Syndrome: Encyclopedia of Immunology* 2$^{nd}$ edn. Vol. 2, eds. Delves, P. J., & Roitt, I. M., (Academic Press Ltd., London),pp. 1005–1011.
2. Quinones, S., Bernal, D., García-Sogo, M., Elena S. F., & Saus, J. (1992) *J. Biol. Chem.* 267, 19780–19784.
3. Revert, F., Penadés, J. R., Plana, M., Bernal, D., Johansson, C., Itarte, E., Cervera, J., Wieslander, J., Quinones, S., & Saus, J.(1995) *J. Biol. Chem.*,270, 13254–13261.
4. Bernal, D., Quinones, S., & Saus, J. (1993) *J. Biol. Chem.*, 268, 12090–12094.
5. Penadés, J. R., Bernal, D., Revert, F., Johansson, C., Fresquet, V. J., Cervera, J., Wieslander, J., Quinones, S. & Saus, J. (1995) *Eur. J. Biochem.* 229, 754–760.
6. Raus, J. CM, en *Multiple Sclerosis : Encyclopedia of Immunology* 2$^{nd}$ edn. Vol. 3 (eds. Delves, P. J., & Roitt, I. M.) 1786–1789 (Academic Press Ltd., London, 1998).
7. Pette, M., Fujita, K., Wilkinson, D., Altmann, D. M., Trowsdale, J., Giegerich, G., Hinkkanen, A., Epplen, J. T., Kappos, L., and Wekerle, H. (1994) *Proc. Natl. Acad. Sci. USA* 87, 7968–7972

8. Tschida, T., Parker, K. C., Turner, R. V., McFarland, H. F., Coligan, J. E., and Biddison, W. E.(1994) *Proc. Natl. Acad. Sci USA* 91, 10859–10863.
9. Campagnoni, A. T. (1988) *J. Neurochem.* 51, 1–14.
10. Henderson, R. D., Saltissi, D., and Pender, M. P. (1998) *Acta Neurol. Scand.* 98, 134–135.
11. Raya, A., Revert, F., Navarro, S., and Saus, J. (1999). *J. Biol. Chem.* 274,12642–12649.

EXAMPLE 4

Here we show that the human α3(1V)NC1 domain exists as multiple phosphorylation-dependent conformational isoforms (conformers) that are stabilized by disulfide bonds. We present evidence supporting that phosphorylation of $Ser^9$ can lead to the formation of α3(IV)NC1 conformers for which tolerance has not been established.

MATERIALS AND METHODS FOR EXAMPLE 4

Production of native and recombinant NC1 material. Human collagen IV NC1 "hexamer" and "monomers" were prepared from renal cortex as previously described (21). The "monomers" were further analyzed by reverse-phase HPLC using a C18 column from Vydac and a 30–48% acetonitrile gradient developed during 36 min in the presence of 0.1% TFA. The most hydrophobic fractions containing α3(IV) NC1 domain with no detectable traces of other chains, as assessed by enzyme-linked immunosorbent assay (ELISA) and individual α(IV) chain specific antibodies, were pooled and concentrated (27-kDa). The more hydrophilic fractions, containing both α3 material and the other a chains, were re-analyzed by reverse-phase HPLC using a C4 column from Vydac and a 24–44% isopropanol gradient developed during 36 min in the presence of 0.2% TFA. Fractions containing mainly α3, but also α4 and α5 chains, were pooled and concentrated (22–25-kDa).

Recombinant FLAG-tagged α1(IV)NC1-α6(IV)NC1 (fα1–fα6) were prepared as reported in Ref. 22. A site-directed mutagenesis approach (Clontech) and the fα3 construct were used to obtain $fα3Ala^9$ and $fα3Asp^9$. The constructs were assessed by nucleotide sequencing, and used to generate stably transfected human kidney 293 (ATCC # CRL1573) cell lines as described in Ref. 23. Individual clones secreting similar levels of protein to the culture media, as estimated by Western blot analysis, were further selected and used for comparative studies. For these purposes, the individual cell lines were grown in Dubelcco's modified Eagle's medium supplemented with 10% fetal calf serum. When the culture reached ~80% confluence, the serum-containing media was removed and cells were brought to quiescence in serum-free medium supplemented with Ham's F-12 nutrient mixture. After 24 hours, the media were changed, and the media of an additional period of 24 hours were separately collected, centrifuged to remove cell debris and analyzed by Western-blot using α3(IV)NC1 specific antibodies.

Physical, chemical and immunocheniwcal methods. When indicated, SDS-electrophoresis was performed on a fusible acrylamide (National Diagnostics) following manufacturer instructions. After electrophoresis, the gel region between 21- and 30-kDa was split into eight horizontal slices of similar height. Each of these was further split in two, separately melted in the presence of reducing or non-reducing Laemmli sample buffer, and re-analyzed in SDS-PAGE for immunoblot purposes.

Otherwise indicated SDS-PAGE studies were carried out in the absence of a reducing agent and the immunoblots were performed following standard procedures using PVDF membranes (Millipore) and 27.5% methanol in the transfer buffer.

Reduction/Oxidation studies. In a standard assay, ~1 μg of recombinant human α3(IV)NC1 (fα3) in 25 mM β-glycerol phosphate (pH 7.0), 0.5 MM EDTA, 0.5 nM EGTA, 8 mM $MgCl_2$ was incubated with or without 2 units of calf intestine alkaline phosphatase (Pharmacia). After 1 hour at 30° C., 5 mM $MnCl_2$ and 1 mM DIT were added (redox conditions) and incubation continued until the DTT was fully oxidized ([DTT]<50 nM). To monitor the reaction, aliquots were taken at several times and DTT measured as described in Ref. 24. When the reaction was completed, the remaining material was analyzed by immunoblot. Phosphatase-treated materials were subjected to phosphorylation with the catalytic subunit of PKA to assess dephosphorylation effectiveness.

Phosphorylation, V8 protease digestion and immunoprecipitation assays. Phosphorylation with the catalytic subunit of the cAMP-dependent protein kinase (Promega), digestion with V8 protease (Sigma), and immunoprecipitation with anti-GPpep1 antibodies was performed essentially as previously described (17).

Antibodies. We have described the production and characterization of Mab3 antibodies (previously called Mab17), which recognize a conformational disulfide-dependent epitope in the α3(IV)NC1 (25). The epitope of Mab3 implicates residues 29–44 and more critically the two Ser and a Pro therein, and residues 139–153 (15,16). We have previously reported (17,20) the production of the antibodies specific for the N-terminus of the human α3(IV)NC1 domain (anti-GPpep1, MabM3/1 and MabP1/2). MabP/2 epitope implicates $Ser^9$, as substitution of this residue by Ala or Asp effectively abolishes antibody binding to the corresponding α3(IV)NC1 mutants. The remaining α3(IV)NC1-specific monoclonal antibodies, Mab175 and Mab189, were raised against bacterial randomly folded human recombinant α3(IV)NC1 (20). For these purposes, the α3(IV)NC1 was analyzed by SDS-PAGE under reducing conditions, stained with Coomassie blue, and the polyacrylamide band containing the material of interest excised and used for mice immunization following standard procedures. The two monoclonal antibodies showed similar binding to reduced α3(IV)NC1 material in Western blot studies (not shown) and recognize linear epitopes that involve residues 103–117 of the α3(IV)NC1 domain (15). However, whereas Mab175 reactivity does not vary significantly with antigen reduction or conformation (15), the binding of Mab189 to the α3(IV) NC1 varies among conformers (see FIG. 22 below). The residue number indicates its position from the collagenase digestion site (26). All the monoclonal antibodies used were monospecific in Western-blot studies using recombinant proteins representing each of the six α(IV)NC1 domains (not shown). The anti-FLAG (α-FLAG) and the anti-phosphoserine antibodies were from Sigma.

Individual sera from fifty GP patients, six healthy blood donors, or three autoimmune patients containing either rheumathoid factor, p-ANCA or ANCA autoantibodies, were used at 1:10 dilution in the immunoblot studies. Tissue-bound antibodies were acidextracted as described in Ref. 27 from a control and from a GP kidney and used in a 1:2 or 1:5 dilutions for immunoblot purposes.

Results

The GP antibodies recognize multiple α3(IV)NC1 conformers. The reactivity of the GP antibodies towards human "monomers" was assessed using 50 individual patient sera. The reactivity greatly varied among patients, resulting in multiple reactive patterns (FIG. 21A, lanes 3–8), whereas control or other non-GP autoimmune sera did not display significant reactivity (FIG. 21A, lanes 1–2,). Multiple polypeptides displaying $M_r$ between 22 and 28 kDa interacted with the GP antibodies. However, when representative individual patient sera were assayed for reactivity using recombinant material representing individual human α(IV) NC1 (fα1–fα6), fα3 displayed the major autoantibody binding (FIG. 21B), thus confirming the α3 nature of the multiple reactive polypeptides in the human "hexamer" and implicating the different α3(IV)NC1 polypeptides in pathogenesis.

To assess this the GP antibodies bound to the GBM of a patient kidney, and therefore with the highest affinity, were eluted and assayed for reactivity towards the recombinant proteins (FIG. 1C). The data indicated that all the pathogenic antibodies were α3(IV)NC1-specific.

Identification of multiple conformers of the human α3(IV)NC1. The structural diversification of the α3(IV) NC1 domain detected with the GP antibodies was confirmed by identifying multiple α3(IV)NC1 molecular species in human "hexamer" using monoclonal antibodies (Mab) (FIG. 22A). Under non-reducing conditions, four α3(IV)NC1 isoforms (22, 23, 25 and 28 kDa) in addition to the previously identified 27-kDa polypeptide were detected. However, all the isoforms yielded a single component with a $M_r$ of 29 kDa upon reduction, as determined by first isolating the non-reduced isoforms from a SDS-PAGE gel followed by a second SDS-PAGE analysis under reducing conditions (FIG. 22B). This indicates that, under non-reducing conditions, the differences in $M_r$ among the α3(IV)NC1 polypeptides reflect distinct conformations that are stabilized by disulfide bonds. In the study shown, we have used Mab189, a monoclonal antibody recognizing a linear epitope implicating residues 103–117 (15) which apparently is more exposed in the 23–25-kDa molecular species (lane 1 of FIG. 22A). As expected, these antibodies interacted differently with the various α3(IV)NC1 isoforms when blotting the SDS-PAGE study performed under non-reducing conditions (NR). Reduction of rit disulfide bonds, however, resulted in an increased reactivity in the molecular species in which specific disulfide bonds prevented efficient antibody binding in the non-reducing gels, and thus all the molecular species with the exception of that in lane 5 containing the 23-kDa material showed an increased reactivity under reducing conditions (R). These results reveal the existence of novel molecular species of the α3(IV)NC1 domain. They are designated as conformational isoforms (conformers) that are stabilized by individual disulfide bond distributions.

Differential phosphorylation of the α3(IV)NC1 conformers by PKA. We have shown that human α3(IV)NC1 undergoes phosphorylation by type A protein kinases (17). To assess the susceptibility of the different α3(IV)NC1 conformers to phosphorylation, purified α3(IV)NC1 from human renal cortex, mainly consisting of the 27-kDa conformer, was incubated with the catalytic subunit of the cAMP-dependent protein kinase in the presence of $[\gamma^{32}P]$ ATP (FIG. 23A, left). At 150 mM ATP, the major $^{32}P$ incorporation occurred in the 27-kDa conformer. However, when the ATP concentration was lowered to extracellular-like concentrations (0.15 mM), the 22-kDa conformer was preferentially labeled (NR). Both $^{32}P$-labeled conformers co-migrated when SDS-PAGE analysis was performed under reducing conditions (R), and V8 protease digestion at Glu36 coupled with N terminal immunoprecipitation supported that phosphorylation of the two conformers occurred at similar sites (FIG. 23A, right). At both ATP concentrations we always found a variable amount of labeled material in the 22–27-kDa region that, in the experiment shown, required a longer time of exposure to be evident (not shown). Although the 27-kDa conformer was the most phosphorylated species at 150 mM ATP, this appears to reflect the high relative abundance of this conformer (see FIG. 3C below) rather than its capacity for phosphorylation. Thus, when the time-course of the reaction was followed at this higher ATP concentration, the 22-kDa conformer was labeled first followed by the other conformers in the 22- and 27-kDa range. Finally, and only upon long periods of incubation did the 27-kDa conformer become more labeled (FIG. 23B). These results indicate that the 22–25-kDa conformers are better substrates for PKA at this ATP concentration.

This was independently confirmed by demonstrating that an α3(IV)NC1 fraction enriched in the 22–25-kDa species showed higher susceptibility to phosphorylation than the fraction which is enriched in the 27-kDa conformer (FIG. 23C). In both pools, the major phosphorylation occurred at the 22–25-kDa conformers and the amount of $^{32}P$ incorporated was consistent with the relative content in these molecular species. As expected, the multiple α3(IV)NC1 conformers present in either pool showed similar $M_r$ in SDS-PAGE analysis performed under reducing conditions, and autoradiographic and immunoreactive bands co-migrated.

To assess the physiological significance of these findings, we determined the presence of phosphoserine [Ser(P)] in the different human α3(IV)NC1 polypeptides by comparing the immunoreactive patterns of antibodies specifically reacting with the N terminus of the OQIVNCI (MabP1/2) and antibodies specifically reacting with Ser(P) (FIG. 24). Similarly to the in vitro phosphorylation, the α3(IV)NC1 polypeptides representing the previously unrecognized conformers (22–25 kDa) displayed the highest Ser(P) content, whereas the 27-kDa conformer was comparatively less phosphorylated. The different susceptibility of the various conformers to undergo phosphorylation both in vitro and in vivo further supports the existence of important differences at the tertiary structure, and suggest that phosphorylation and folding are related processes in the α3(IV)NC1 domain.

Phosphorylation regulates the conformation of the c3(IV) NC1 domain. The role of phosphorylation regulating the conformation of the α3(IV)NC1 domain was further investigated by assessing the ability of dephosphorylated domain to maintain its native structure. Untreated or alkaline phosphatase-treated human recombinant α3(IV)NC1 domain was allowed to rearrange its disulfide bonds in the presence of a DTT-metal-based redox system until DIT was fully oxidized. The material was then analyzed by SDS-PAGE and blotted either with Mab3, a monoclonal antibody binding to a native disulfide-dependent epitope present in the 27-kDa conformer (FIG. 22A) which overlaps with the major epitopes recognized by the GP autoantibodies (15,16), or by Mab175, a monoclonal antibody which reactivity does not vary significantly upon reduction or conformation (15) (FIG. 25).

During DTT consumption, most of the untreated material forms disulfide-bond high molecular weight aggregates, which do not enter into the running gel, and only a limited amount of material remains monomeric. Phosphatase treatment efficiently inhibited disulfide-based aggregation, and most of the material remains in a monomeric form. The untreated material that Fin remained in a monomeric form maintained both apparent molecular weight (27-kDa) and the relative reactivity with the two antibodies of the starting material, whereas monomeric phosphatase-treated material contained multiple molecular species between 22 and 29 kD, which were poorly reactive with Mab3. All the molecular species, however, displayed the same apparent mobility (29 kDa) under reducing conditions, thus confirming that they represented different disulfide-based conformers.

Therefore, it appears that upon dephosphorylation, the 27-kDa conformer was unable to keep its native conformation, recognized by Mab3 antibodies, but adopted multiple conformations (22–29 kDa conformers) during DTT consumption, and that disulfide-based aggregation of the α3(IV)NC1 is a specific phenomenon which requires phosphorylation and native conformation to occur.

The $Ser^9$ phosphorylation promotes conformational diversification of the α3(IV)NC1 domain. Phosphorylation at $Ser^9$ is a biological hallmark of the human α3(IV)NC1 when compared to other NC1 domains. To assess the implication of $Ser^9$ phosphorylation on the formation of multiple conformers of the α3(IV)NC1 domain, cell lines expressing α3(IV)NC1 (fαSer$^9$) or mutants thereof in which $Ser^9$ have been replaced by Ala (fα3Ala9) (SEQ ID NO:68) or Asp (fα3Asp$^9$) (SEQ ID NO:66) were generated. Although the two mutants are non-phosphorylatable at this site the Asp-based mutant is expected to mimic the Ser(P) derivative, because the acidic lateral chain Asp mimics Ser(P), whereas the Ala mutant is expected to represent the non phosphorylated counterpart, since, chemically, Ser is hydroxy-Alanine. The recombinant materials produced were separately collected and analyzed using Mab175 or Mab3 antibodies (FIG. 26). The studies with Mab175 revealed that the three materials mainly consisted of a major conformer of 27-kDa and a different number of conformers of lower and higher sizes which were more abundantly expressed in fα3Asp$^9$ than in f63Ser$^9$ whereas these were virtually absent in fα3Ala9. All three recombinant materials, however, displayed similar amounts of a ran single 29-kDa product under reducing conditions confirming that the different polypeptides were disulfide-bond stabilized α3(IV)NC1 conformers (α-FLAG). These results suggest that in vivo phosphorylation at $Ser^9$ promotes the assembly of multiple conformations of the α3(IV)NC1, and identifies $Ser^9$ as a major point of control for conformational diversification. The different reactive patterns shown by the three recombinant materials with Mab3 antibodies also indicate that the state of phosphorylation of $Ser^9$ can efficiently influence the exposure of specific conformation-dependent epitopes. Thus, the 27-kDa conformer of fα3Asp$^9$ was comparatively more reactive, and moved slightly faster in SDS-PAGE than fα3Ser$^9$ or fα3Ala$^9$ counterparts, and fα3Asp$^9$ contained a 25-kDa conformer also reactive with these antibodies that was not present in the other materials. These findings further support the phosphorylation-dependent nature of the α3(IV)NC1 conformers, but also reveal that a phosphorylation event involving $Ser^9$ can result in cellular production of conformers with different exposure of pathogenically relevant epitopes.

Discussion

Disulfide bond distribution represents the folding state of domains that are resident at the extracellular compartment (29). We have presented physical, chemical, immunochemical, biochemical and cell biological data supporting the existence of multiple disulfide bond-stabilized conformers of the α3(IV)NC1 domain in basement membrane collagen. The evidence presented in this example indicates that phosphorylation plays a critical role in the production of these multiple conformers, and suggest that differential phosphorylation is at least part of the strategy for cellular production of conformers. Differential phosphorylation of a single unique native structure could occur prior or during chain association, yielding multiple structures, each one stabilized by individual disulfide-bond distributions. Individual molecular species would have enciphered in their covalent structure the assembly partner and the final conformation that would be acquired once assembled and stabilized into a "hexamer". The multiple conformers produced by the cells expressing the phosphorylated version of the α3(IV)NC1 domain at $Ser^9$ (fα3Asp9) sharply contrasts with the limited structural diversification of the material representing the non-phosphorylated counterpart (fα3Ala$^9$). The molecular mechanism by which $Ser^9$ (P) promotes the assembly of the α3(IV)NC1 domain in multiple conformers is presently unknown. However, the presence of a cell adhesion motif as an integral part of the sequence that conforms the PKA recognition site (KRGDS$^9$) (SEQ ID NO:63) suggest that $Ser^9$ phosphorylation promotes cell attachment of the α3(IV)NC1 and induce conformational diversification through an integrin-mediated mechanism., The consequences on conforination derived from the presence of Asp$^9$ are unlikely to represent a physiological phenomenon, since the Mab3 reactive conformers of 25- and 27-kDa fz present in fα3Asp$^9$ are not produced by the cells expressing the native sequence (fα3Ser$^9$). More likely, the phenomenon represents the aberrant consequences of a permanently phosphorylated $Ser^9$ intruding in the phosphorylation-dependent conforming process. These findings, in addition to further implicating phosphorylation in conformation, reveal that a breakage in the homeostatic phosphorylation of $Ser^9$ can promote the formation of conformers for which the immune system has not established a tolerance and thus trigger the immune response mediating GP disease. Overall, our studies establish the phosphorylation-dependent nature of the α3(IV)NC1 folding system and point to $Ser^9$ phosphorylation as the biological feature that renders the human system vulnerable for autoimmune pathogenesis.

REFERENCES FOR EXAMPLE 4

1. Hudson, B. G., Reeders, S. T. & Tryggvason, K. (1993) J. Biol. Chem. 268, 26033–26036.
2. Bachinger, H. P., Fessler, L. I. & Fessler, J. H. (1982). J. Biol. Chem. 257, 9796–9803.
3. Netzer, K., Suzuki, K., Itoh, Y., Hudson, B. G. & Khalifah, R. G. (1998). Protein Sci. 7, 1340–1351.
4. Fessler, L. I. & Fessler, J. H. (1982) J. Biol. Chem. 257, 9804–9810.
5. Butkowski, R. J., Wieslander, J., Wisdom, B. J., Barr, J. F., Noelken, M. E. & Hudson, B. G.(1985) J. Biol. Chem. 260, 3739–3747.
6. Weber, S., Engel, J., Wiedemann, H., Glanville, R. W. & Timpl, R.(1984) Eur. J. Biochem. 139, 401–410.
7. Siebold, B., Deutzmann, R. & Kuhn, K. (1988) Eur. J. Biochem 176, 617–624.
8. Keppel, M. M., Fan, W. W., Cheong, H. I., & Michael, A. F. (1992) J. Biol. Chem. 267, 4137–4142.
9. Gunwar, S., Ballester, F., Noelken, M. E., Sado, Y., Ninomiya, Y.& Hudson, B. G. (1998) J. Biol. Chem. 273, 8767–75.
10. Borza, DB, Bondar, O., Ninomiya, Y., Sado, Y., Naito, I., Todd, P. & Hudson, BG (2001) J. Biol. Chem. 276, 28532–28540.
11. Boutaud, A., Borza, D., Bondar, O., Gunwar, S., Netzer, K.,Singh, N., Ninomiya, Y., Sado, Y., Noelken, M. E. & Hudson, B. G.(2000) J. Biol. Chem. 275, 30716–30724.
12. Saus, J. (1998) in *Goodpasture's Syndrome: Encyclopedia of Immunology* 2nd edn. Vol. 2, eds. Delves, P. J., and Roitt, I. M., Academic Press Ltd., London,pp. 1005–1011.

13. Kalluri, R.(1999) Kidney Int. 3, 1120–1122.
14. Shlomchik, M. J., Marshak-Rothstein, A., Wolfowicz, C. B., Rothsten, T. L.& Weigert, M. G. (1987) Nature 328, 805–811.
15. Borza, D. B., Netzer, K., Leinonen, A., Todd, P., Cervera, J., Saus, J. & Hudson, B. G. (2000) J. Biol. Chem. 275, 6030–6037.
16. David, M., Borza, D. B., Leinonen, A., Belmont, J. M.& Hudson, B. G.(2001) J. Biol. Chem. 276, 6370–6377.
17. Revert, F., Penades, J. R., Plana, M., Bernal, D., Johansson, C., Itarte, E., Cervera, J., Wieslander, J., Quinones, S. & Saus, J.(1995) J. Biol. Chem. 270, 13254–13261.
18. Bernal, D., Quinones, S.& Saus, J. (1993) J. Biol. Chem. 268, 12090–12094.
19. Feng, L., Xia, Y. & Wilson, C. B.(1994) J. Biol. Chem. 269, 2342–2348.
20. Penades, J. R., Bernal, D., Revert, F., Johansson, C., Fresquet, V. J., Cervera, J., Wieslander, J., Quinones, S. & Saus, J. (1995) Eur. J. Biochem. 229, 754–760.
21. Hellmark, T., Johansson, C. & Wieslander, J. (1994) Kidney Int. 46, 823–829.
22. Sado, Y., Boutaud, A., Kagawa, M., Naito, I., Ninomniya, Y. & Hudson, B. G. (1998) Kidney Int. 53, 664–671.
23. Raya, A., Revert, F., Navarro, S. & Saus, J. (1999) J. Biol. Chem. 274, 12642–12649.
24. Riddles, P. W., Robert, L. B. & Zerner, 13. (1983). Methods Enzymol. 91, 49–60.
25. Johansson, C., Butkowski, R. & Wieslander, J. (1991) Connect. Tissue Res. 25, 229–241.
26. Quinones, S., Bernal, D., García-Sogo, M., Elena S. F.& Saus, J. (1992) J. Biol. Chem. 267, 19780–19784.
27. Saxena, R., Bygren, P., Butkowski, R. & Wieslander, J. (1989) Clin. Exp. Immunol. 78, 31–36.
28. Kalluri, R., Wilson, C. B., Weber, M., Gunwar, S., Chonko, A. M., Neilson, E. G. & Hudson, B. G.(1995) J. Am. Soc.Nephrol. 4,1178–1185.
29. Creighton, T. E. (1997) Biol. Chem. 378, 731–744.

EXAMPLE 5

Here we show that the isolated α3(IV)NC1 conformers show a state of activation that depends on phosphorylation and which is required for "bexarner" assembly. GPBP exerts a complex catalysis over isolated α3(IV)NC1 conformers, which comprises conformational isomerization and specific intermolecular disulfide bond formation, suggesting that GPBP is a novel type of molecular enzyme that assists "hexamer" formation in vivo.

MATERIALS AND METHODS FOR EXAMPLE 5

Production of native and recombinant material. Human collagen IV NC1 "hexamer" and "monomers" were prepared from renal cortex as described in Example 4. Bovine testis α3(IV)NC1 "monomer" was prepared as described in Zashai et al., (1997). To produce prokaryotic human recombinant α3(IV)NC1, the cDNA used elsewhere to express the corresponding recombinant protein (Penades et al, 1995) was subcloned into the BarmHI site of a modified version of pET-15b vector (Novagen), in which the vector-derived N-terminal sequence except for the initiation Met was eliminated. The recombinant α3(IV)NC1 was purified by precipitation as described in Penades et al. (1995) and the final pellet was dissolved in 8M urea.

Recombinant FLAG-tagged α3(IV)NC1 (fα3) was prepared as previously reported in Sado et al., (1998).

Recombinant GPBP and GPBPΔ26 (rGPBP and rGPBPΔ26) were prepared as described in Raya et al. (1999).

Physical, chemical and immunochemical methods. Lnunoblot studies were performed as described in Example 4. For far-Western, after protein transfer the membrane was blocked with non-fat milk, incubated with 30 ng/μl of fα3 or recombinant GPBP and the bound recombinant material detected with α-FLAG or Mab14, respectively.

Steady-state fluorescence measurements were carried out at 25° C. on a Perkin-Elmer LS-50 spectrofluorimeter in Tris-buffered saline. The spectra were corrected by comparison to a quinine sulfate standard. The buffer was used as baseline in all the experiments and subtracted.

Unless indicated, SDS-PAGE studies were performed in the absence of a reducing agent.

DTT oxidation and oligomerization studies. In a standard assay, "monomer" or "hexamer" were reduced for 4 h with 2 mM DTT in 10 mM Tris pH 7.5 at 30° C. The mixtures were brought to 25 mM P-glycerol phosphate (pH 7.0), 0.5 nM EDTA, 0.5 mM EGTA, 8 mM $MgCl_2$, 5 mM $MnCl_2$ and 1 mM DTT (oligomerization buffer) in a final volume of 25–50 μl and incubation continued until the DTT was fully oxidized ([DTT]<50 nM). To monitor the reaction, aliquots of 2–5 μl were taken at several times and DTT measured as described in Riddles et al. (1983). In some experiments, when the reaction was completed, the remaining material was analyzed by immunoblot. For some purposes, "monomers" were first dephosphorylated with 2 units of calf intestine alkaline phosphatase (Pharmacia) in oligomerization buffer without $MnCl_2$ and DTT. After 1 h at 30° C., these components were added to reach oligomerization conditions and mixtures were monitored and analyzed as above. For some purposes alkaline phosphatase-treated fα3 were brought to the oligomerization conditions ($DTT/Mn^{2+}$) in the presence of Tris-buffered saline and the process monitored by fluorescence emission spectra. The untreated materials used in these assays were carried in parallel in the absence of alkaline phosphatase. Phosphatase-treated materials were subjected to phosphorylation with cAMP-dependent protein kinase as previously described (Revert et al, 1995) to assess dephosphorylation effectiveness. For other purposes when the material was brought to oligomerization conditions equivalent amounts of bovine serum albumin (BSA), rGPBP or rGPBPΔ26 were added and mixtures were similarly monitored and analyzed.

Antibodies. The production of monoclonal antibodies against GPBP (Mab 14) was described in Raya et al., (1999), for the other antibodies see details in Example 4.

Results

Phosphorylation promotes the supramolecular aggregation of the α3(IV)NC1 domain. At the endoplasmic reticulum, ATP is required to maintain the non-assembled monomers in a metastable conformation that is critical for physiological ofigomerization (Braakrnan et al., 1992). Consequently, ATP could be used to phosphorylate and to place the α3(IV)NC1 domain into a metastable condition required for "hexamer" formation. Upon dissociation, the "hexamer" yields the different α3(IV)NC1 conformers as individual polypeptides ("monomer") but also as disulfide-based oligomers (Fessler and Fessler, 1982; Weber et al., 1984; Butkowski et al, 1985; Siebold et al., 1988; Reddy et al., 1993), which, in turn, represent disassembled and partially assembled α3(IV) chains, respectively. Conceivably, the transition from the "hexameric" (assembled) to "monomeric" (disassembled) condition could return the individual α3(IV)NC1 species to a non-minimum energy condition that still may promote disulfide-based aggregation in vitro.

To explore this idea, we first dissociated human "hexamer" by SDS-PAGE and performed specific far-Western studies to assess "monomer-monomer" interactions. For these purposes, we used human recombinant FLAG-tagged α3(IV)NC1 domain (fα3) to probe in-blot renatured human "monomers" after SDS-PAGE, and FLAG-specific antibodies to detect fα3 binding (FIG. 27). Recombinant material preferentially bound to the 22–25-kDa polypeptides which were reactive with α3 (IV)NC1-specific antibodies and showed the highest Ser(P) content, suggesting that fα3 preferentially interacts with the 22–25-kDa conformers of the α3(IV)NC1 and that phosphorylation is a structural requirement for "monomer-monomer" interaction. Nevertheless, additional conformational requirements other than Ser(P) seem to mediate fα3 recognition since the 23–25 kDa conformers displayed relatively less fα3 binding than the 22-kDa conformer but contained similar amounts of Ser(P) as estimated by immunochemical (FIG. 27) and chemical techniques (not shown).

The ability to form disulfide-based aggregates of the isolated "monomers", in comparison with assembled counterparts present in the "hexamer", was first investigated by assessing spontaneous disulfide-based aggregation of disassembled (27-kDa and 22–25-kDa), unassembled (fα3), or assembled (hexamer) human α3(IV)-monomers in the presence of a DYT-metal-based redox system (FIG. 28A). DTT levels were measured at different incubation intervals and the kinetics of DTT oxidation for each individual sample was determined (left). The rate of DTT oxidation significantly varied between samples with 22–25-kDa the sample enriched with the lower-sized highly phosphorylatable conformers displaying the major catalytic activity followed by 27-kDa and fα3, whereas the "hexamer" did not oxidize DTT significantly. After DIT was fully oxidized (FIG. 28A, right), non-assembled (Monomer) but not assembled (Hexamer) "monomers" appeared organized as large disulfide-based aggregates (not shown in the composite) that, upon reduction, yielded monomeric material (compare lane 2 of Monomer in NR and R). These data suggest that the non-assembled, but not the assembled, α3(IV)NC1 conformers can form and break intermolecular disulfide bridges in a continuous fashion and cause DTT oxidation. The accessibility of DTT to the assembled α3 material was confirmed by demonstrating that DTT treatment of "hexamer" strongly inhibited the binding of Mab3an α3(IV) NC1-specific antibody recognizing a native disulfide-dependent conformational epitope present in the 27-kDa conformer (Borza et al., 2000) (not shown).

Differences in DTT oxidation rates could be attributed to the different capacity for disulfide-based aggregation displayed by each individual "monomeric" sample. This was confirmed by assessing the ability of each disassembled "monomeric" sample (27-kDa, 22–25-kDa) to disulfide-aggregate with recombinant fα3, which displayed the lowest DTI oxidation rate and contained an an engineered recognition site (FLAG) that allowed specific antibody detection (FIG. 28B). As expected, the 22–25-kDa conformers aggregated with fα3 to a greater extent than the 27-kDa conformer, and therefore upon DTr consumption, these samples contained significantly less monomeric fα3 (NR), indicating that samples enriched in conformers with lower apparent mass disulfide-aggregated more efficiently. The presence of fα3 disulfide-based aggregates was finally demonstrated by showing similar amounts of fα3 in all samples in parallel studies performed under reducing conditions (R). This, along with the higher phosphoserine content of these conformers (FIG. 27), suggests that phosphorylation mediates "monomer—monomer" recognition required for intermolecular disulfide-bond cross-linkage.

The role of phosphorylation mediating disulfide-based aggregation was further investigated by assessing fα3 aggregation of 22–25-krDa conformers in the presence or absence of alkaline phosphatase (FIG. 28C). Dephosphorylation significantly reduced DTT oxidation and aggregation, and a good correlation between the extent of aggregation and DTT oxidation rates was observed (compare left to right lanes in the blot with top to bottom curves in the graph), indicating that specific phosphorylation is the mechanism by which "monomers" become activated for disulfide-based oligomerization. Similar conclusions were obtained when we assayed alkaline phosphatase-free dephosphorylated fα3 material (not shown). Data from further experiments, including fluorescence spectroscopy of fα3 before and after alkaline phosphatase treatment (FIG. 29), suggested that disulfide-based aggregation and conformational changes occurred simultaneously and depend on phosphorylation.

GPBP catalyzes disuiride-based aggregation of the α3(IV)NC1 domain through specific conformational isomerization reactions. We have shown that GPBP is expressed associated with glomerular basement membranes, the main target of the GP autoantibodies, and that GPBP binds to recombinant material representing the human α3(IV)NC1 domain (see above). GPBP binding to human native NC1 material was tested over in-blot renatured human "monomers" after SDS-PAGE (FIG. 30). Interestingly, GPBP preferentially bound to 22–25-kDa polypeptides displaying the highest Ser(P) content, suggesting that, like fcα3 (FIG. 27), the non-conventional protein kinase displayed a preferential binding towards the 22–25 CL3(IV)NC1 conformers.

To investigate the role of GP13P in the supramolecular assembly of the α3(FV)NC1 domain, we assessed disulfide-mediated oligomerization of samples mainly consisting of the 27-kDa conformer in the presence of GPBP, or GPBPΔ26 (FIG. 31A). For these assays we have used fα3 mainly consisting of recombinant 27-kDa conformer and 27-kDa native material from a more reliable source than human kidney (bovine testis). We have found that bovine α3(IV)NC1 undergoes also conformational diversification and the corresponding 27-kDa conformer shows a phosphorylation-dependent metastability similar to human counterpart.

As shown above, in the absence of GPBP or GPBPΔ26, DTT consumption resulted in a reduction of monomeric material mainly due to disulfide-dependent molecular aggregation as the reactivity of Mab175, an α3(IV)NC1-specific antibody which reactivity does not vary significantly upon antigen reduction (Borza et al, 2000), towards monomeric molecular species largely increased upon sample reduction. Essentially the same results were obtained when blotting the samples that contained GPBPΔ26. In contrast, when GPBP was present in the reaction mixture during DTT consumption, the resulting material displayed different reactive patterns in the Western-blot studies. Thus, Mab3 reacted with a previously unidentified polypeptide of approximately 28-kDa, in addition to the 27-kDa conformer, indicating that during DTT consumption GPBP catalyzed specific conformational isomerization reactions over the 27-kDa conformer that still maintained the native disulfide bonds arrangement required for Mab3 recognition. Accordingly, after DIT consumption, GPBPΔ26 samples contained a relatively greater abundance of 27-kDa conformer than samples containing GPBP, suggesting that this conformer was the substrate, whereas the 28-kDa polypeptide was the product in the conformational isomerization reaction catalyzed by GPBP. Western-blot analysis using Mab175 antibodies revealed that, in the samples containing GPBP, most of the α3(IV)NC1 material existed as molecular species displaying M, from 22 to 29 kDa all of which yielded a single molecular species of 29 kDa upon reduction, indicating that GPBP impaired random monomer disulfide-aggregation and catalyzed multiple conformational isomerizations other than the 27- to 28-kDa monitored by Mab3. The catalysis performed by GPBP was ATP independent, required the presence of the DTT-metal-based redox system (not shown), and could be observed with both human recombinant (not shown) or bovine native (shown) α3(IV)NC1 materials.

The presence of α3(IV)NC1 Mab3-reactive material organized in high molecular weight oligomers was also investigated (FIG. 31B). GPBP and, to a lesser extent GPBPΔ26 (not shown), catalyzed the formation of multiple molecular species reactive with Mab3 or Mab175 at the dimer and higher oligomer regions that were not detectable in control samples, suggesting that GPBP also catalyzes specific disulfide-based aggregation. The ratio between Mab3 reactive material at the monomer and oligomer regions found in different assays (compare Assay 1 and Assay 2) suggests that conformational isomerization is a requirement for aggregation during GPBP catalysis. Thus, mixtures containing higher levels of Mab3 reactive material at the oligomer region displayed lower levels of Mab3 reactive monomer species and vice versa.

However, the most evident effect of GPBP over the α3(IV)NC1 material was to stabilize the different conformers in a monomeric form and to impair random disulfide-aggregation, suggesting that GPBP, and to a minor extent GPBPΔ26, are acting in the in vitro assays as molecular chaperones. Accordingly, GPBP and, to a lesser extent GPBPΔ26 disrupted disulfide-based high molecular weight aggregates characteristic of recombinant material representing human α3(IV)NC1 produced in bacteria which do not enter into the running gel of an SDS-PAGE analysis, and promoted the formation of lower molecular weight disulfide-based oligomers which reacted with Mab 3 (FIG. 31C). However, GPBP and GPBPΔ26 were unable to generate detectable levels of molecular species in monomer-trimer range. The disaggregating effect of GPBP on bacterial recombinant α3(IV)NC1 material did not vary significantly with the presence of ATP or DTT-metal-based redox system (not show).

Finally, we assessed the involvement of phosphate groups present in the α3(1V)NC1 in the overall process catalyzed by GPBP by comparing its action over alkaline phosphatase-treated or untreated fα3 (FIG. 31D). As shown in FIG. 25, upon DTT consumption phosphatase-treated fα3 showed reduced levels of material that maintained the native structure (Mab3), along with abundant non-oligomerized conformers between 22- to 29-kDa (Mabl75) that do not harbor the native conformation. As noted above, this indicates that, in the α3(IV)NC1 system, phosphorylation is critical for both the maintenance of the native conformation and the disulfide-aggregation, but also suggests that the native structure is required for effective aggregation. Consistently, the addition of GPBP to the phosphatase-treated samples resulted in a further reduction in the levels of monomeric material reactive with Mab3 which was not observed, at least to a similar extent, with the material only reactive with Mab175, supporting that native conformation is required for oligomerization and that GPBP catalyzes the reaction.

Discussion

Although it is widely accepted that the NC1 domain of individual chains plays a leading role in collagen formation (Fessler and Fessler, 1982; Ries et al., 1995; Boutaud et al., 2000), the precise mechanism mediating chain selection and assembly is unknown. As indicated herein, the individual NC1 domains are generated as phosphorylation-dependent metastable conformations that become stable once assembled in the "hexamer".

The mechanism by which α3(IV)NC1 conformers are generated remains to be established. However, the reduced ability of phosphatase-treated material to maintain the native structure and the high phosphoserine content of the non-conventional α3(IV)NC1 conformers, suggest that phosphorylation plays a critical role in the production of multiple non-minimum energy structures.

Phosphorylation also mediates at least in part the molecular recognition and DTT consumption in the oligomerization assays. The latter reveal the existence of a high turnover in the intermolecular disulfide bonds that likely reflects the search for the proper partner, but also suggests the existence of a machinery with the potential to assist disulfide-based cross-linking of the NC1 domain in vivo. We show here that GPBP catalyzes disulfide-based aggregation of the α3(IV) NC1 domain through a process that comprises specific conformational isomerization reactions in vitro, suggesting that GPBP catalyzes at least in part the intermolecular cross-linkage of the "hexamer" in vivo.

The information required to form a collagen IV "hexamer" resides in the covalent structure of the "monomer," as the individual NC1 domains select their partners to form "hexameric" structures without the assistance of other cellular factors (Boutaud et al., 2000). This suggests that GPBP catalysis is occurring, at least in part, after chain association and during disulfide stabilization of the collagen IV network, a process that occur necessarily outside of the cell kessler and Fessler, 1982). Consistently, GPBP is abundantly expressed associated with GBM (Raya et al, 2000), and recent data using confocal microscopy demonstrate that α3(IV)NC1 and GPBP co-localize at the human GBM (Burgues and Saus, unpublished observations).

At the endoplasmic reticulum, differential phosphorylation of a single unique native structure could occur prior or during chain association, yielding multiple metastable structures each one stabilized by individual disulfide-bond distributions. Individual molecular species would have enciphered in their covalent structure the assembly partner and the final conformation that will be acquired once assembled and stabilized into a "hexamer". In this model, GPBP could be the machinery assisting, deciphering and catalyzing the stabilization of the corresponding quaternary structures.

In the absence of AT?, GPBP catalyzed the formation of multiple conformers and specific i, oligomers of the α3(IV) NC1 domain, suggesting that the phosphorylated structure of this domain has enciphered multiple assembly programs that require GPBP assistance to be accomplished, and the kinase activity of GPBP could represent an auxiliary function required for specific in vivo folding-assembly reactions which are not occurring in the in vitro assays.

Humans have acquired an additional phosphorylation site for type A protein kinases at the N-terminal region of the α3(IV)NC1 domain (Ser$^9$) (Revert et al, 1995; Raya et al., 1999 and 2000), yielding a comparatively more phosphorylatable polypeptide (Revert et al., 1995; Raya et al., 1999) with a remarkable susceptibility to undergo autoimmune attack. Recent evidence indicates that phosphorylation of Ser$^9$ (P) regulates at least in part the conformational diversification perhaps operating through an integrin recognition motif adjacent to it. Interestingly we have found that the recombinant counterparts for the α-1,-2,-4,-5 and -6(IV) chains also show a phosphorylation-dependent metastability in the in vitro oligomerization assays, and that human α(IV)NC1 as well as bovine α3(IV)NC1 domains exist as multiple conformers (unpublished results). This indicates that the phosphorylation-dependent conformational diversification and "activation" for disulfide-aggregation are not a human α3(IV)NC1 exclusive conditions, and therefore cannot be considered the structural feature that renders this system vulnerable to pathogenesis. However, it is conceivable that vulnerability to pathogenesis of the human α3(IV) NC1 system comes from the potential intrusion in conformation of the human exclusive phosphorylation process at Ser$^9$. Accordingly we have presented evidences supporting that a phosphoryladon event involving Ser$^9$ can lead to the formation of α3( )NC1 conformers for which the immune system has not established a tolerance and trigger an autoimmune attack, which therefore can be envisioned as a legitimate response of the immune system against a misfolded autoantigen

REFERENCES FOR EXAMPLE 5

Bachinger, H. P., Fessler, L.I., and Fessler, J. H. (1982). Mouse procollagen IV: Characterization and supramolecular association. *J. Biol. Chem.* 257, 9796–9803.

Borza, D., Netzer, K., Leinonen, A., Todd, P., Cervera, J., Saus, J., and Hudson, B. G. (2000). The Goodpasture autoantigen: Identification of multiple cryptic epitopes on the NC1 domain of the α3(IV) collagen chain. *J. Biol. Chem.* 275, 6030–6037.

Boutaud, A., Borza, D., Bondar, O., Gunwar, S., Netzer, K., Singh, N., Ninoniya, Y., Sado, Y., Noelken, M. E. and Hudson, B. G.(2000). Type IV collagen of the glomerular basement membrane : Evidence that the chain specificity of network assembly is encoded by the non-collagenous NC1 domains. *J. Biol. Chem.* 275, 30716–30724.

Braakman, I., Helenius, J., and Helenius, A. (1992). Role of ATP and disulphide bonds during protein folding in the endoplasmnic reticulum. *Nature* 356, 260–262.

Butkowski, R. J., Wieslander, J., Wisdom, B. J., Barr, J. F., Noelken, M. E. and Hudson, B. G.(1985) Properties of the globular domain of type IV collagen and its relationship to the Goodpasture antigen. *J. Biol. Chem.* 260, 3739–3747.

David, M., Borza, D., Leinonen, A., Belmont, J. M., and Hudson, B. G.(2001). Hydrophobic amino acid residues are critical for the immunodomninant epitope of the Goodpasture autoantigen: A molecular basis for the cryptic nature of the epitope. *J. Biol. Chem.* 276, 6370–6377.

Fessler, L. I. and Fessler, J. H. (1982). Identification of the carboxyl peptides of mouse procollagen IV and its implications for the assembly and structure of basement membrane. *J. Biol. Chem.* 257, 9804–9810.

Kalluzi, R.(1999) Goodpasture syndrome. *Kidney Int.* 3, 1120–1122.

Penades, J. R., Bernal, D., Revert, F., Johansson, C., Fresquet, V. J., Cervera, J., Wieslander, J., Quinones, S. and Saus, J. (1995). Characterization and expression of multiple alternative spliced transcripts of the Goodpasture antigen gene region. *Eur. J. Biochem.* 229, 754–760.

Raya, A., Revert, F., Navarro, S., and Saus, J. (1999). Characterization of a novel type of serine/threonine kinase that specifically phosphorylates the human Goodpasture antigen. *J. Biol. Chem.* 274, 12642–12649.

Raya, A., Revert-Ros, F., Martinez-Martinez, P., Navarro, S., Rosello, E., Vieites, B., Granero, F., Forteza, J., and Saus, J. (2000). GPBP, the kinase that phosphorylates the Goodpasture antigen, is an alternatively spliced variant implicated in autoimmune pathogenesis. *J. Biol. Chem* 275, 40392–40399.

Reddy, G. K., Hudson, B. G., Bailey, A. J., and Noelken, M. E. (1993) Reductive cleavage of the disulfide bonds of thr collagen IV noncollagenous domain in aqueous sodium dodecyl sulfate: Absence of intermolecular nondisulfide cross-links *Biochem. Biophys. Res. Commun.* 190: 277–282.

Revert, F., Penadés, J. R., Plana, M., Bernal, D., Johansson, C., Itarte, E., Cervera, J., Wieslander, J., Quinones, S., and Saus, J.(1995). Phosphorylation of the Goodpasture antigen by type A protein kinases. *J. Biol. Chem.* 270, 13254–13261.

Riddles, P. W., Robert, L. B., and Zerner, B. (1983) Reassessment of Eliman's reagent. *Methods Enzymol.* 91, 49–60.

Ries, A., Engel, J., Lusting, A., and Kuhn, K. (1995). The function of the NC1 domains in type IV collagen. *J. Biol. Chem.* 270, 23790–23794.

Sado, Y., Boutaud, A., Kagawa, M., Naito, I., Ninomiya, Y. and Hudson, B. G. (1998). Induction of anti-GBM nephritis in rats by recombinant α3(IV)NC1 and α4(IV)NC1 of type IV collagen. *Kidney Int.* 53, 664–671.

Saus, J. (1998) in *Goodpasture's Syndrome: Encyclopedia of Immunology* 2$^{nd}$ edn. Vol. 2, eds. Delves, P. J., and Roitt, I. M., Academic Press Ltd., London,pp. 1005–1011.

Siebold, B., Deutzmann, R. and Kuhn, K. (1988). The arrangement of intra- and intermolecular disulfide bonds in the carboxylteroinal, non-collagenous aggregation and cross-linking domain of basement m embran e type IV collagen. *Eur. J. Biochem* 176, 617624.

Weber, S., Engel, J., Wiedemanni, H., Glanville, R. W. and Timpi, R.(1984). Subunit structure and assembly of the globular domain of basement membrane collagen type IV. *Eur. J. Biochem.* 139, 401–410.

Zahsai, T. Z, Enders, G. C., Gunwar, S., Brunmark, C., Wieslander, J., Kaluri, R., Zhou, J., Noelken, M., and Hudson, B. G.(1997). Semiiniferous tubule basement membrane: Composition and organization of type IV collagen chains, and the linkage of α3(IV) and α5(IV) chains. *J. Biol. Chem.* 272, 17023–17032.

EXAMPLE 6

Here we present evidence suggesting that in GP patients an augmented expression of both GPBP and GPΔIII results in the assembly at the glomerular basement membrane of aberrant non-tolerized α3(I)NC1 conformers that induce and conduct the autoimmune response. Our findings furter upprt pevius bsevations indicating that a phosphorylation event can lead the formation of α3(IV)NC1 conformers for which the immune system have not established a tolerance and therefore induce an immnune response.

MATERIALS AND METHODS FOR EXAMPLE 6

Synthetic oligonucleotides. The following oligonucleotides and other used for DNA sequencing were synthesized by Genosys, Life Technology Inc., Roche or Pharmacia:

ON-B-HNC-1c [5'-CAGGGATCCGTTQtTAGGATGAAAA-3'] (SEQ ID NO:70);

ON-HNC-3m [5'-GACCCTGTGGGCCAAGA-3'] (SEQ ID NO:71);

ON-HNC-6c [5'-GGAGGGATCCGAGTGTCTTTTCATGC-3'] (SEQ ID NO:72);

ON-GP-F1, [5'-GGAGACAGTGGATCACCTGCA-3'] (SEQ ID NO:73);
ON-GP-R1, [5'-TGCTGTGGTTTGACTGTGTCG-3'] (SEQ ID NO:74);
ON-GP-3–F1, [5'-CGGACAAGACCTTGATGCACT-3'] (SEQ ID NO:75);
ON-GP-3-R2, [5'-CAGCCGTGAGGACATGGAG-3'] (SEQ ID NO:76);
ON-hGPBPc-F1, [5'-CTGAATCCAGCTTGCGTCG-3'] (SEQ ID NO:77)
ON-hGPBPc-R1, [5'-GCAGAGTAGCCACITGCTCC-3'] (SEQ ID NO:78);
ON-GPBPe26-F1, [5'-CGCTCTTCCTCCATGTCTTCC-3'] (SEQ ID NO:79);
ON-GPBPe26-R1, [5'-CCTGGGAGCTGAATCTGTGAA-3'] (SEQ ID NO:80);
ON-GPBP-26-F1, [5'-GCTGTTGAAGCTGCTCTTGACA-3'] (SEQ ID NO:81);
ON-GPBP-26-R1, [5'-TGGTATTGCTCAAATTCGGC-3'] (SEQ ID NO:82);
ON-GAPDH-F, [5'-GAAGGTGAAGGTCGGAGTC-3'] (SEQ ID NO:83);
ON-GAPDH-R, [5'-GAAGATGGTGATGGGATTTC-3'] (SEQ ID NO:84).

Production of native and recombinant NC1 domain. These materials were prepared as described in the accompanying Examples.

RNA purification. Frozen human tissues were ground in the presence of liquid nitrogen and further disrupted with a Polytron-like device in the presence of either TRI-REAGENT™ (Sigma) and total RNA purified using manufacturer's recommendations, or with 4M guanidine thiocyanate 1% β-mercaptoethanol in 0.1 M Tris pH 7.5 and RNA purification carried out by standard CsCl gradient approach.

Reverse transcriptase coupled polymerase chain reaction studies (RT-PCR). To obtain the cDNA for the α3(IV)NC1 domain and for its alternatively spliced products, total RNA from each individual kidney (0.5 µg) was retro-transcribed using ON-B-HNC-1c. The corresponding single stranded cDNAs were subjected to PCR using ONHNC-3m and ON-HNC-6c. The products were further identified by nucleotide sequence or restriction map.

The mRNA levels for all the COL4A3 and COL4A3BP products (GPt and GPBPt), GPΔMII, GPBP, GPBPΔ26, or glyceraldehyde 3-phosphate dehydrogenase (GAPDH) in each individual human kidney was estimated by measuring the corresponding cDNAs in the reverse transcription mixtures obtained as above using a random hexamer priming and 5 µg of total RNA. This was accomplished by quantitative PCR using a SDS 7700 Applied Biosystems apparatus and the following primers: ON-GP-F1 and ON-OP-R1; ON-hGPBPc-F1 and ON-hGPBPc-R1; ON-GP-3-F1 and ON-GP-3-R2; ON-GPBPe26-F1 and ON-GPBPe26-R1; ON-GPBP-26-F1 and ON-GPBP-26-R1; or, ON-GAPDH-F and ON-GAPDH-R, respectively. PCR reactions were done using 5 µl of 1:100 and 1:1000 dilutions of the reverse transcriptase except for GAPDH for which determinations the dilutions used were 1:1000 and 1:10000. Standard curves for each PCR were done using the same oligonucleotides and different amounts of individual plasmids containing the corresponding cDNAs.

Immunochemnical studies. Immunoblot studies and in situ fα3 binding assays were performed as detailed in Example 5.

Antibodies. The production and specificity of the antibodies are detailed in the accompanying Examples 4 and 5. Tissue-bound antibodies were extracted from a control and from each of two GP kidneys from which NC1 hexamer was prepared for use.

Results

GPΔIII is expressed at higher levels in GP kidneys. We have made the observation that the mRNA level for GPΔIII was augmented with respect to the primary product in a GP kidney and that this could have pathogenic significance (Bernal et al, 1993). This was investigated in additional patient and control kidneys using two different PCR approaches coupled to reverse transcription (FIG. 32). First we used primers flanking the coding region of the α3(IV) NC1 domain and we amplified the cDNAs for the α3(IV) NC1 products of interest present in human kidney (FIG. 32A). As previously observed, control kidney expressed mainly the primary product with traces of GPΔIII, whereas GP kidneys expressed relatively higher levels of GPΔA, further supporting the initial observation that an increased expression of this alternative product has pathogenic relevance. Second, and for quantitative purposes, the individual reverse transcription mixtures were amplified using primers common to all the mRNA products derived from COL4A3 (GPt) or primers specific for the alternative variant under investigation (GPΔIII) (FIG. 32B, C). Quantitative studies revealed an overall augmented expression of the α3(IV) products in GP kidneys that was more evident for the alternative GPΔIII than for the primary product, reflecting that during pathogenesis, an augmented transcription of COM4A3 and a relative increase in the expression of GPΔIII. occur Identification of aberrant α3(IV)NC1 conformers in GP kidneys. Since GPΔIII positively regulates the phosphorylation of the primary α3(IV)NC1 product in vitro, and in this domain phosphorylation plays a critical role in conformation, we investigated the presence of disease associated α3(IV)NC1 conformers in GP kidneys. We have previously reported that there are not differences in the primary structure of patient α3(IV)NC1 that could account for its immunogenic condition, and therefore if there are structural differences between patient and control α3(IV) NC1 domains which account for the immunogenicity they must be post-translational (Bernal et al, 1993). Thus, after confirming by direct cDNA sequencing the fidelity of the primary structure of the α3(IV)NC1 domain in each individual patient kidney, we isolated the collagen IV NC1 domain ("hexarner") from patient kidneys 2 and 3, and also from control kidneys and we assessed the binding of α3(IV) NC1-specific antibodies, which reactivity largely depends on antigen conformation (FIG. 33). When the individual α(IV)NC1 domains present in the "hexamer" extracted from individual kidneys were blotted with Mab3, an antibody that recognizes a native disulfide-dependent epitope characteristic of the 27-kDa conformer of the α3(IV)NC1, the major reactive polypeptide in patient's material appeared slightly retarded with respect to control, and patient 2 contained an additional reactive polypeptide of 28-kDa not present in control or patient 3 "hexamer" (FIG. 33). Finally, when we assessed the reactivity of Mabl89, an antibody that reacts preferentially with the 23–25-kDa α3(IV)NC1 conformers, we found that these antibodies, in addition to interacting with the expected NC1 polypeptides in both control and patient materials, displayed an increased reactivity towards the patient 27-kDa α3(IV)NC1 conformer (FIG. 33). All these data rear reveal the presence of conformational differences between patient and control in the 27-kDa conformer of the α3(IV)NC1 domain.

The disulfide-bond cross-linkage of the NC1 domain is defective in GP kidneys. Since conformational differences are expected to be reflected in the quaternary structure ("hexamer"), the disulfide-based oligomeric subunits representing this structural level were analyzed in both patient and control "hexamers" (FIG. 34). WVhereas no major differences in the amount of material were evident between control and patient at the monomer region (between 21 and 30 kDa), patient material showed a relative higher content in dimers (46 kDa) and a reduction in the amount of aggregates of higher molecular mass (>69 kDa), revealing that in these patients the disulfide-based cross-linkage of collagen IV through the NC1 domain was impaired. Accordingly, the high molecular weight material in patient "hexamer" displayed a reduced reactivity towards Mab3 and Mab189 (FIG. 34B), suggesting that in GP "hexamer" there exists a defective disulfide-mediated cross-linkage of the α3(IV) NC1 conformers. This was also concluded when we assessed the binding of fα3 to the high molecular weight components of the "hexamer" (FIG. 34B). This recombinant form of the human α3(IV)NC1, which preferentially binds to the α13(IV)NC1 conformers of low apparent mass, exhibited a reduced binding to the high molecular weight components present in the patient "hexamer," further supporting that the disulfide bond cross-linkage of these α3(IV) NC1 conformers is highly impaired in GP patients. All these findings suggest that in GP patients there exists a defective disulfide bond cross-linkage of the "hexamer" that is caused by conformational alterations present in the NC1 domain of the α3(IV) chain.

The aberrant α3(IV)NC1 conformers conduct the immune response in GP disease. The conformational alterations present in the α3(IV)NC 1 of GP patients, however, does not significantly reduce the gross amount of cL3(IV) chain assembled into the collagen IV network since the reduced proportion of high molecular weight oligomers is compensated by a higher content in dimers (FIG. 34A). By modifying the B cell processing and peptide presentation, the aberrant conformers could promote a T cell mediated antigen-driven antibody response similar to that found in other autoimmune disorder (Shlomchik et al., 1987) and produce autoantibodies that, by somatic mutation, would develop a high specific reactivity for the aberrant conformation. To assess this, the autoantibodies bound to the glomerular basement membrane in the affected kidneys (and therefore with the highest affinity) were eluted and their reactivity towards control or patient antigen compared (FIG. 35). Antibodies eluted from the patient kidneys preferentially reacted with the corresponding patient 27-kDa antigen conformer, whereas Mab175, an α3(IV)NC1-specific antibody whose reactivity is not significantly affected by peptide conformation, showed similar amounts of 27-kDa conformer to be present in patient and control samples. Therefore, specific conformation(s) of the GP autoantigen found exclusively in the patients appears to conduct the immune response that mediates GP disease.

The expression of GPBP is augmented in GP kidneys. We have shown that GPBP redo phosphorylates the N terminal region of the α3(IV)NC1 domain including $Ser^9$ in vitro (Raya et al.,1999) and that $Ser^9$ phosphorylation determines the cohort of conformers produced by the cell (Example 4). Furthermore, GPBP is expressed associated with alveolar and glomerular basement membranes and an augmented expression of GPBP has been associated with different autoimmune conditions including a GP patient (Raya et al, 2000). Consequently, to investigate the implication of GPBP in GP pathogenesis, we estimated by reverse transcriptase coupled to quantitative PCR, the transcriptional activity of COL4A3BP, the gene encoding GPBP and GPBPΔ26, in both patient and control kidneys (FIG. 36). Quantitative studies revealed an augmented transcriptional activity for the corresponding gene in all three patient kidneys (GPBPt). However, when the levels of each of the two mRNA species derived from COLAA3BP were estimated, we found GPBP to be relatively higher expressed in patient than in control kidneys (GPBPΔ26 and GPBP), indicating that during pathogenesis the enhanced transcription of COL4A3BP is accompanied by a relative augmented expression of GPBP with respect to GPBPΔ26.

Discussion

The higher specificity of the pathogenic antibodies towards aberrant α3(IV)NC1 conformers present in disease-affected tissues indicates that this material is the antigen conducting the autoimmune response, and suggests that alterations in the tertiary structure of α3(IV)NC1 domain cause GP disease.

The data presented here and in the accompanying Examples support that phosphorylation activates the α3(IV) NC1 domain for disulfide bond-aggregation, a process that is catalyzed by GPBP, involves specific conformational isomerization reactions and which results in the assembly and stabilization of multiple conformers of this domain in the basement membrane. In the absence of ATP, GPBP catalyzes the formation of multiple conformers and specific oligomers of the a 3(M)NC1 domain in vitro (Example 5), suggesting that the phosphorylated structure of this domain has enciphered multiple assembly programs which require GPBP assistance to be accomplished. Consistently, alkaline phosphatase-treatcd α3(IV)NC1 did not aggregate efficiently and this material was unable to follow a disulfide bond-aggregation program in the presence of GPBP (Example 5).

In vitro, PKA and GPBP phosphorylate the human α3(M) NC1 domain at $Ser^9$, a site that is also targeted by the endogenous phosphorylation process (Revert et al, 1995; Raya et al., 1999). The evidence indicates that the homeostasis of $Ser^9$ phosphorylation is critical for physiological conformer production (Example 4). In addition to $Ser^9$, the N-terminal region of the human α3(IV)NC1 contains additional phosphorylation sites not present in other species ($Ser^{11}$ and $Thr^{14, 16,17}$), which are also targeted by the two kinases in vitro (Raya et al, 1999; Revert et al, unpublished observations) suggesting that N-terminal phosphorylability is critical for pathogenesis.

In a yeast two hybrid system, the fly counterpart of GPBP interacts with the corresponding fly cPKA. (Carine Rosse and Jacques Camonis, personal communication) Bovine cPKA phosphorylates GPBP in vitro (not shown). Finally, type A protein kinases and GPBP have been found associated with cell plasma membrane and endothelial basement membranes, respectively (Revert et al., 1995; Raya et al., 2000). All these suggest that the two kinases can interact and form stable complexes in vivo and which operate during the molecular and supramnolecular assembly of the collagen IV.

In addition to divergence at the N-terminal region of the cL3(IV)NC1 domain (Quinones et al, 1992), humans have developed a unique alternative splicing mechanism to regulate phosphorylation of $Ser^9$ by cPKA (herein), resulting in a comparatively more vulnerable polypeptide to undergo conformational alterations and an autoimmune attack.

The GP antibodies recognize a potent immunogenic region adjacent to the exclusive N-terminus that harbors also Mab3 epitope (Borza et al, 2000). The main epitope for the GP antibodies is maintained by disulfide bonds and depends on hydrophobic residues that require dissociation of the "hexamer" to be exposed (Netzer et al, 1999; Hellmark et al, 1999; Borza et al., 2000; David et al, 2001). Mab3 epitope is maintained by the same disulfide bonds but involves hydrophilic residues that are accessible in the "hexamer" (Saus et al, 1988; Johansson et al, 1991; Borza et al., 2000; David et al, 2001). Thus, during pathogenesis an aberrant N-terminal phosphorylation could result Fit in conformers with a higher exposure of the hydrophobic residues, which because of the disulfide bonds would still maintain the reactivity with Mab3. Consistently, permanently phosphorylated versions of the α3(IV)NC1 domain at Ser$^9$ show a relative higher specificity with Mab3 (Example 4) and with GP autoantibodies (not shown). Our data also indicate that a similar pathogenic mechanism is operating in every patient, therefore the resulting conformational alterations are expected to be highly similar among patients as no alterations in the primary structure of the patient α3(IV)NC1 have been found. This would account for the large cross-reaction among patient autoantibodies but also for the high affinity that tissue-bound autoantibodies from one patient display for the 27-kDa conformer of other patient in comparison with the affinity displayed towards control material (not shown).

COL4A3BP, the gene encoding GPBP and GPBPΔ26, and POLK the gene encoding for pol $K_1$ a member of the UmuC/DinB superfamily of DNA polymerases which can extend aberrant replication forks are transcribed in a divergent mode from a bidirectional promoter (Granero et al, unpublished results). This promoter shows high sequence homology with a number of other bi-directional promoters including that transcribing COL4A3 and COL4A, the genes encoding the α3 and α4 chains of collagen IV. The homology between promoters transcribing otherwvise unrelated structural genes reveals the existence of a convergent evolution phenomenon to coordinate their expression (Granero et al, unpublished results). Accordingly during pathogenesis we found a transcriptional induction of the two genes. Moreover, the signal(s) to coordinate the expression of these genes seems to reach the machinery regulating pre-mRNA processing, since GPΔIII and GPBP, which represent minor mRNA forms in each individual gene system, are the mRNA species more significantly increased.

Taking all these data together, it is plausible to think that during pathogenesis triggering events by increasing the expression of both GPΔIII and GPBP, cause an aberrant N-terminal phosphorylation generating activated α3(IV) NC1 structures with an altered disulfide bond-aggregation program. Subsequently, GPBP would catalyze its assembly into the collagen IV network resulting in the presence of altered conformers in the basement membrane. Finally, aberrant assembled α3(IV)NC1 conformers would induce and drive a T cell-dependent antibody-mediated immune response (FIG. 37).

We have shown above in an in vitro system that during GPBP catalysis, and prior disulfide bond-aggregation of the α3(IV)NC1 domain, the 27-kDa conformer undergoes conformational isomerization to generate a 28-kDa conformer similar to that found in Patient 2, suggesting that the Mab3-reactive 28-kDa conformer found in the "hexarner" of Patient 2 likely represents a trapped intermediate which derive from an aberrant 27-kDa conformer that is incapable to follow the correct disulfide bond-aggregation.

These and previous data which show that GPBP is abundantly expressed in structures that either are the target of common autoimmune responses or are undergoing an autoimmune attack (Raya et al, 1999 and 2000) reveal that GPBP plays a major role in human autoimmunity and suggest that the production of non-tolerized conformational versions of different autoantigens is operating in other autoimmune pathogenesis.

The molecular basis of the autoimmune responses has been elusive. The findings presented in this and the accompanying Examples lead to a new concept of the human autoimmune response, which is envisioned as a legitimate reaction of the immune system towards a non-physiologically folded but still assembled autoantigen.

REFERENCES FOR EXAMPLE 6

Bachinger, H. P., Fessler, L. I., and Fessler, J. H. (1982). Mouse procollagen IV: Characterization and supramolecular association. *J. Biol. Chem.* 257, 9796–9803.

Bernal, D., Quinones, S., and Saus, J. (1993). The human mRNA encoding the Goodpasture antigen is alternatively spliced. *J. Biol. Chem.,* 268, 12090–12094.

Borza, D., Netzer, K., Leinonen, A., Todd, P., Cervera, J., Saus, J., and Hudson, B. G. (2000). The Goodpasture autoantigen: Identification of multiple cryptic epitopes on the NC1 domain of the α3(1V) collagen chain. *J. Biol. Chem.* 275, 6030–6037.

Boutaud, A., Borza, D., Bondar, O., Gunwar, S., Netzer, K., Singh, N., Ninomiya, Y., Sado, Y., Noelken, M. E. and Hudson, B. G.(2000). Type IV collagen of the glomerular basement membrane : Evidence that the chain specificity of network assembly is encoded by the non-collagenous NC1 domains. *J. Biol. Chem.* 275, 30716–30724.

David, M., Borza, D., Leinonen, A., Belmont, J. M., and Hudson, B. G.(2001). Hydrophobic amino acid residues are critical for the immunodominant epitope of the Goodpasture autoantigen: A molecular basis for the cryptic nature of the epitope. *J. Biol. Chem.* 276, 6370–6377.

Dobson, C. M. (1999). Protein misfolding, evolution and disease. *TIBS* 24, 329–332.

Feng, L., xia, Y. and Wilson, C. B.(1994). Alternative splicing of the NC1 domain of the human α3(IV) collagen gene. Differential expression of mRNA transcripts that predict three protein variants with distinct carboxyl regions *J. Biol. Chem.* 269, 2342–2348.

Fessler, L. I. and Fessler, J. H. (1982). Identification of the carboxyl peptides of mouse procollagen IV and its implications for the assembly and structure of basement membrane. *J. Biol. Chem.* 257, 9804–9810.

Ghohestani, R. F., Hudson, B. G., Claudy, A., and Uitto, J. (2000). The α5 chain of type IV collagen is the target of IgG autoantibodies in a novel autoimmune disease with subepidermnal blisters and renal insufficiency. *J. Biol. Chem.* 275, 16002–16006.

Hellmark, T., Burkhardt, H., and Wieslander, J. (1999) Goodpasture disease: Characterization of a single conformational epitope as the target of pathogenic autoantibodies. *J. Biol. Chem.* 274, 25862–25868.

Johansson, C., Butkowski, R., and Wieslander, J. (1991). Characterization of monoclonal antibodies to the globular domain of collagen IV. *Connect. Tissue Res.* 25, 229–241.

Johansson, C., Butkowski, R., Swedenborg, P., Alm, P., and Wieslander, J. (1993). Characterization of a non-Goodpasture antibody to type IV collagen. *Nephrol Dial. Transplant.* 8, 1205–1210.

Merkel, F., Kalluri, R., Marx, M., Enders, U., Stevanovic, S., Giegerich, G., Neilson, E., Rammensee, H., Hudson, B. G., and Weber, M. (1996). Autoreactive T-cells in Goodpasture's syndrome recognize the N-terminal NC1 domain on α3 type IV collagen. *Kidney Int.* 49, 1127–1133.

Netzer, K., Suziki, K., Itoh, Y., Hudson, B. G. & Khalifah, R. G. (1998). Comparative analysis of the noncollagenous NC1 domain of type IV collagen: Identification of structural features important for assembly, function, and pathogenesis. *Protein Sci.* 7, 1340–1351.

Netzer, K., leinonen, A., Boutaud, A., Borza, D., Todd, P., Gunwar, S., Langeveld, J. P. M., and Hudson, B. G. (1999). The Goodpasture autoantigen: Mapping the major conformational epitope(s) of α3(IV) collagen to residues 17–31 and 127–141 of the NC1 domain. *J. Biol. Chem.* 274, 11267–11274.

Penadés, J. R., Bernal, D., Revert, F., Johansson, C., Fresquet, V. J., Cervera, J., Wieslander, J., Quinones, S. and Saus, J. (1995). Characterization and expression of multiple alternative spliced transcripts of the Goodpasture antigen gene region. *Eur. J. Biochem.* 229, 754–760.

Plemper, R. K., and Wolf, D. H.(1999). Retrograde protein translocation: ERADication of secretory proteins in health and disease. *TIBS* 24, 266–270.

Prusiner, S. (1998) Prions. *Proc. Natl. Acad. Sci. USA* 95, 13363–13383.

Quinones, S., Bernal, D., García-Sogo, M., Elena S. F., and Saus, J. (1992). Exon/intron structure of the human α3(IV) gene encompassing the Goodpasture antigen α3(IV)NC1). *J. Biol. Chem.* 267, 19780–19784.

Raya, A., Revert, F., Navarro, S., and Saus, J. (1999). Characterization of a novel type of serine/threonine kinase that specifically phosphorylates the human Goodpasture antigen. *J. Biol. Chem.* 274, 12642–12649.

Raya, A., Revert-Ros, F., Martinez-Martinez, P., Navarro, S., Roselló, E., Vieites, B., Granero, F., Forteza, J., and Saus, J. (2000). GPBP, the kinase that phosphorylates the Goodpasture antigen, is an alternatively spliced variant implicated in autoimmune pathogenesis. *J. Biol. Chem* 275, 40392–40399.

Revert, F., Penadés, J. R., Plana, M., Bernal, D., Johansson, C., Itarte, E., Cervera, J., Wieslander, J., Quinones, S., and Saus, J.(1995). Phosphorylation of the Goodpasture antigen by type A protein kinases. *J. Biol. Chem.* 270, 13254–13261.

Ries, A., Engel, J., Lusting, A., and Kuhn, K. (1995). The function of the NC1 domains in type IV collagen. *J. Biol. Chem.* 270, 23790–23794.

Saus, J., Wieslander, J., Langeveld, J. P., Quinones, S., and Hudson, B. G. (1988) Identification of the Goodpasture antigen as the α3(IV) chain of collagen IV. *J. Biol. Chem.* 263, 13374–13380.

Saus, J. (1998) in *Goodpasture's Syndrome: Encyclopedia of Immunology* 2$^{nd}$ edn. Vol. 2, eds. Delves, P. J., and Roitt, I. M., Academic Press Ltd., London, pp. 1005–1011.

Saus, J. (2000) Goodpasture antigen binding protein. PCT International published Application No. PCT/US00/04781.

Shlomchik, M. J., Marshak-Rothstein, A., Wolfowicz, C. B., Rothstein, T. L., and Weigert, M. G.(1987). The role of clonal selection and somatic mutation in autoimmunity. *Nature* 328, 805–811.

Siebold, B., Deutzmann, R. and Kuhn, K. (1988). The arrangement of intra- and intermolecular disulfide bonds in the carboxylterminal, non-collagenous aggregation and cross-linking domain of basement membrane type IV collagen. *Eur. J. Biochem* 176, 617–624.

Weber, S., Engel, J., Wiedemann, H., Glanville, R. W. and Timpl, R.(1984). Subunit structure and assembly of the globular domain of basement membrane collagen type IV. *Eur. J. Biochem.* 139, 401–410.

The present invention is not limited by the aforementioned particular preferred embodiments. It will occur to those ordinarily skilled in the art that various modifications may be made to the disclosed preferred embodiments without diverting from the concept of the invention. All such modifications are intended to be within the scope of the present invention.

I claim:

1. A method for identifying candidate compounds to treat Goodpasture Syndrome, comprising identifying compounds that:
   a) reduce autophosphorylation of GPBP; and
   b) reduce formation of conformational isomers α3 type IV collagen NC1 domain polypeptide;
   wherein such compounds are candidates for treating Goodpasture Syndrome.

2. The method of claim 1 wherein identifying compounds that reduce autophosphorylation of GPBP comprises:
   i) incubating the GPBP and ATP in vitro in the presence or absence of one or more test compounds under conditions that promote phosphorylation of the GPBP in the absence of the one or more test compounds;
   ii) detecting autophosphorylation of the GPBP; and
   iii) identifying test compounds that reduce autophosphorylation of the GPBP relative autophosphorylation of the GPBP in the absence of the one or more test compounds.

3. The method of claim 1 wherein identifying compounds that reduce formation of conformational isomers of the α3 type IV collagen NC1 domain polypeptide comprises:
   i) providing cells expressing the α3 type IV collagen NC1 domain polypeptide;
   ii) culturing the cells in the presence or absence of one or more test compounds, under conditions that promote conformational isomerization of the α3 type IV collagen NC1 domain polypeptide in the absence of the one or more test compounds;
   iii) detecting conformational isomerization of the α3 type IV collagen NC1 domain polypeptide; and
   iv) identifying test compounds that reduce conformational isomerization of the α3 type IV collagen NC1 domain polypeptide relative to conformational isomerization of the α3 type IV collagen NC1 domain polypeptide in the absence of the one or more test compounds.

4. The method of claim 1, wherein identifying compounds that reduce formation of conformational isomers of the α3 type IV collagen NC1 domain polypeptide comprises:
   i) contacting in vitro the α3 type IV collagen NC1 domain polypeptide with GPBP in the presence or absence of one or more test compounds under conditions that promote GPBP-induced conformational isomerization of the α3 type IV collagen NC1 domain polypeptide in the absence of the one or more test compounds;
   ii) detecting GPBP-induced conformational isomerization of the α3 type IV collagen NC1 domain polypeptide; and
   iii) identifying test compounds that reduce GPBP-induced conformational isomerization of the α3 type IV collagen NC1 domain polypeptide relative to GPBP-induced conformational isomerization of the α3 type IV collagen NC1 domain polypeptide in the absence of the one or more test compounds.

5. The method of claim 1, wherein the method further comprises identifying compounds that reduce oligomerization of the α3 type IV collagen NC1 domain polypeptide.

6. The method of claim 5, wherein identifying compounds that reduce oligomerization of the α3 type IV collagen NC1 domain polypeptide comprises:
   i) incubating in vitro the α3 type IV collagen NC1 domain polypeptide, GPBP, and a redox system, in the presence or absence of one or more test compounds, under conditions to promote GPBP-induced-oligomerization of the α3 type IV collagen NC1 domain polypeptide in the absence of the one or more test compounds; and
   ii) identifying test compounds that reduce GPBP-induced oligomerization of the α3 type IV collagen NC1 domain polypeptide relative to GPBP induced oligomerization of the α3 type IV collagen NC1 domain polypeptide in the absence of the one or more test compounds.

* * * * *